(12) United States Patent
Burton

(10) Patent No.: US 11,891,440 B2
(45) Date of Patent: Feb. 6, 2024

(54) ANTIBODIES WITH IMPROVED STABILITY TO INTESTINAL DIGESTION, POLYNUCLEOTIDES THEREOF AND METHODS OF USE THEREOF TO TREAT DISEASE

(71) Applicant: Circle33 LLC, Jackson, WY (US)

(72) Inventor: Randall Edward Burton, Billerica, MA (US)

(73) Assignee: CIRCLE33 LLC, Jackson, WY (US)

( * ) Notice: Subject to any disclaimer, the term of this patent is extended or adjusted under 35 U.S.C. 154(b) by 625 days.

(21) Appl. No.: 15/765,958

(22) PCT Filed: Sep. 29, 2016

(86) PCT No.: PCT/US2016/054304
§ 371 (c)(1),
(2) Date: Sep. 24, 2020

(87) PCT Pub. No.: WO2017/062253
PCT Pub. Date: Apr. 13, 2017

(65) Prior Publication Data
US 2022/0073602 A1 Mar. 10, 2022

Related U.S. Application Data

(60) Provisional application No. 62/237,270, filed on Oct. 5, 2015.

(51) Int. Cl.
*A61K 9/00* (2006.01)
*A61K 39/00* (2006.01)
*C07K 16/24* (2006.01)
*A61P 1/04* (2006.01)

(52) U.S. Cl.
CPC .......... *C07K 16/241* (2013.01); *A61K 9/0053* (2013.01); *A61P 1/04* (2018.01); *A61K 2039/505* (2013.01); *A61K 2039/54* (2013.01); *C07K 2317/20* (2013.01); *C07K 2317/21* (2013.01); *C07K 2317/522* (2013.01); *C07K 2317/524* (2013.01); *C07K 2317/526* (2013.01); *C07K 2317/53* (2013.01); *C07K 2317/565* (2013.01); *C07K 2317/76* (2013.01); *C07K 2317/94* (2013.01)

(58) Field of Classification Search
CPC .............. C07K 16/241; C07K 2317/20; C07K 2317/21; C07K 2317/522; C07K 2317/524; C07K 2317/526; C07K 2317/53; C07K 2317/565; C07K 2317/76; C07K 2317/94; A61K 9/0053; A61K 2039/505; A61K 2039/54; A61P 1/04
See application file for complete search history.

(56) References Cited

U.S. PATENT DOCUMENTS 9,079,955 B2 * 7/2015 Fox ...................... C07K 16/241
2012/0276092 A1 * 11/2012 Luo ........................ C07K 16/00
530/387.3

OTHER PUBLICATIONS

Morrison SL, et al. (Nov. 1984) PNAS 81(21):6851-6855. (doi: 10.1073/pnas.81.21.6851).*
Liu H and May K (Jan.-Feb. 2012) Mabs 4(1):17-23. ( doi: 10.4161/mabs.4.1.18347).*
Lee, E-C, et al. (Apr. 2014) Nature Biotechnology 32(4):356-367. (doi:10.1038/nbt.2825).*

* cited by examiner

*Primary Examiner* — Robert S Landsman
(74) *Attorney, Agent, or Firm* — HUESCHEN AND SAGE

(57) ABSTRACT

The present invention provides for recombinant antibodies having the features of ruminant early colostrum antibodies that impart resistance to proteases and intestinal digestion. It is a feature of the present invention that when administered to animals including humans, pharmaceutical compositions comprising the novel recombinant antibodies of the present invention, advantageously exhibit resistance to proteases and intestinal digestion. Thus, pharmaceutical compositions of the recombinant antibodies of the invention may be used to deliver antibody therapeutics particularly by oral delivery to the gastrointestinal tract when oral delivery is advantageous.

20 Claims, 32 Drawing Sheets
Specification includes a Sequence Listing.

1. Molecular weight markers
2. Colostral IgG
3. Serum IgG

```
                                    CH1                              hinge
                                     ┌──────────┴──────────┐         ┌────┴────┐
IgG1¹           VTVPGSTSGQTFTCNVAHPASSTKVDKAV .. DPTCKPSPCDCCPPPELPGGPSVF
IgG2 A1²        VTVPGSTSGQTFTCNVAHPASSTKVDKAVGVSSDCSKPNNQHC . VRE. . . .PSVF
IgG2 A2³        VTVPASSSGQTFTCNVAHPASSTKVDKAVGVSI D CSKCHNQPC . VRE. . . .PSVF
```

¹ IgG1ᵈ allotype from a monoclonal anti-testosterone antibody (Saini, et al., 2007, GenBank: CAA44699.1)
² IgG2 A1 allotype (Kacskovics and Butler, 1996, UniProt: S06611)
³ IgG2 A2 allotype (Kacskovics and Butler, 1996, GenBank: AAB37380.1)
Underlined residues are different from bovine IgG1

Figure 22

```
                                              Enzymatic and spontaneous
                                                  proteolysis sites
                                              ↓↓  ↓ ↓         ↓↓
Human IgG1       PSSSLGTQTYICNVNHKPSNTKVDKKVEPKSCDKTHTCPPCPAPELLGGPSVF
(AAH73766.1)
                 * *X    *X   * XX *    X * *        XX  X   X
Bovine IgG1      PGSTSGTQTFTCNVAHPASSTKVDKAVDPR . C . KT . TCDCCPPPELPGGPSVF
(AAB37381.2)
```

Figure 23

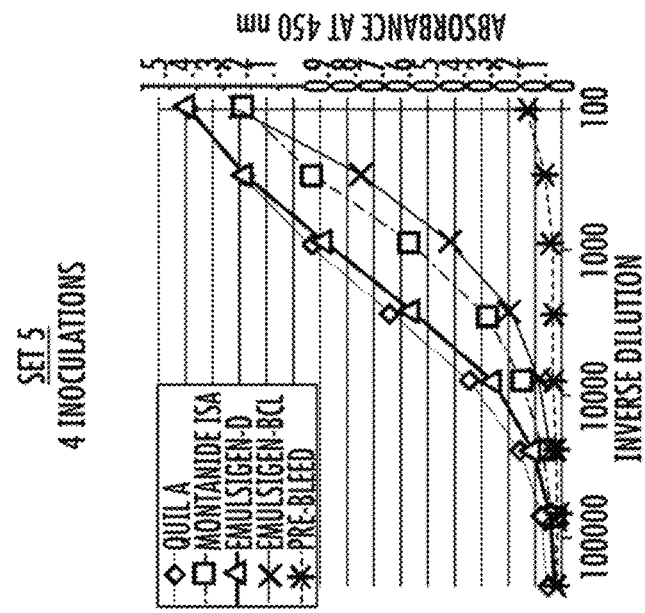
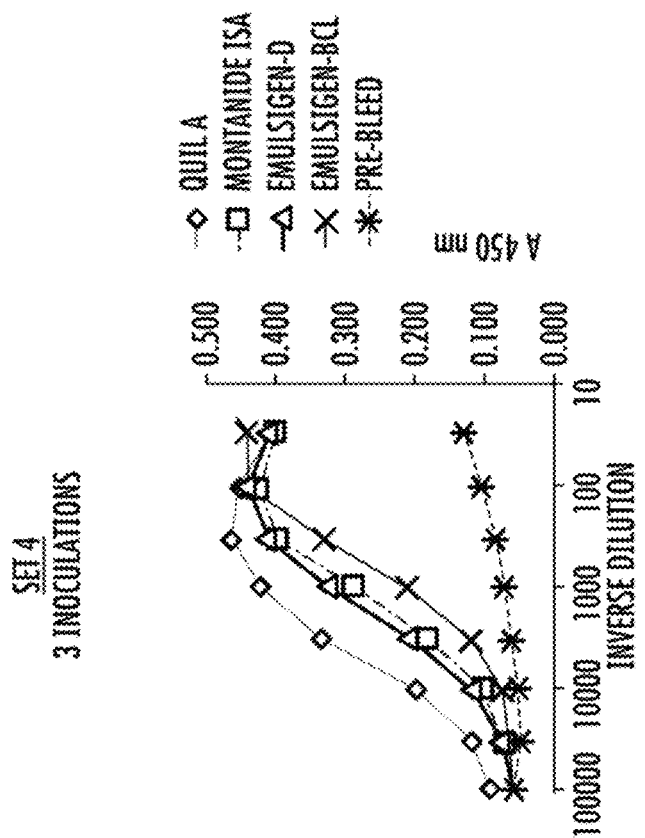
FIG. 26

ANTIBODIES WITH IMPROVED STABILITY TO INTESTINAL DIGESTION, POLYNUCLEOTIDES THEREOF AND METHODS OF USE THEREOF TO TREAT DISEASE

BACKGROUND

Orally administered bovine colostral antibodies have been used experimentally to treat and prevent infection and inflammation in the digestive tract (Jones et al., *Crit Rev Biotechnol* 2015; July 15: 1-15). In contrast to other types of antibodies, which are readily digested, bovine colostral antibodies naturally resist intestinal digestion, making them uniquely suited for oral, topical use in the digestive tract. Studies of bovine colostral antibodies have consistently shown that they survive in the human digestive tract (Jaison et al. *Nutrition Journal* 2015; 14:1-8). However, studies of digestion resistance for bovine antibodies isolated from serum have been inconsistent (Jaison et al., supra; Kuribayashi et al., Comparative *Medicine* 2009; 59:163-7), suggesting that bovine serum antibodies lack the digestion resistance of colostral antibodies. Despite the experimental success of colostral antibodies as orally administered drugs, they are naturally produced polyclonals and therefore cannot take advantage of routine methods used to design and manufacture recombinant monoclonal antibodies as drugs.

Bovine colostrum contains a mixture of immunoglobulins including IgG1, IgG2, IgM, and IgA. In addition to proteins, colostrum contains large quantities of lipids, sugars, and small molecules. In short, bovine colostrum is a complex mixture of bioactive substances, which makes it very difficult to elucidate the relevant factors that confer digestion resistance.

Immunoglobulins in bovine colostrum are transferred from the serum to the udder shortly before parturition. Most transfer of IgG occurs by active transport via mammary epithelial cells, which secrete substances into the colostrum. During transport through these cells, IgG can be modified by glycosylation or other means. This process adds to the complexity of efforts to identify factors that confer digestion resistance to bovine colostral antibodies. Further complicating these efforts are contradictory results of previous studies that assessed the protease resistance of bovine antibodies.

Numerous studies, dating back to 1997, have shown that different bovine antibody isotypes show distinct patterns of resistance to certain proteases, with some isotypes exhibiting greater resistance to certain proteases than others, but with inconsistent and contradicting results (Butler et al., *Biochim Biophys Acta* 1978; 535:125-37; Brock et al., *Annales de Recherches Veterinaires* 1978; 9:287-94). A study by de Rham et al. (*Int Archs Allergy Appl Immun* 1997; 55:61-9) showed no differences in protease resistance to trypsin or pepsin between colostral and serum IgG1. In contrast, later studies found profound differences in digestion resistance between bovine colostral and serum antibodies, with colostral antibodies being more resistant to protease digestion than serum antibodies (Jaison et al., supra; Kuribayashi et al., supra). These results suggest that another factor associated only with colostral antibodies must be responsible for digestion resistance. Over time, two main hypotheses emerged to explain the apparent protease resistance of bovine colostral antibodies.

One hypothesis was that a factor present in colostrum inhibited proteolysis. For instance, Piniero et al. (*Ann Rech Vet* 1978:9:287-94) isolated a trypsin inhibitor from bovine colostrum, and Quigley et al. (*J Dairy Sci* 1995; 78:1573-7) found that the amount of this trypsin inhibitor roughly correlated with the amount of immunoglobulin in the colostrum. The presence of this trypsin inhibitor, and possibly other protease inhibitors in the colostrum, could be responsible for the digestion resistance of bovine colostral antibodies.

Another hypothesis was that glycosylation specific to bovine colostral antibodies protected them from proteases. In one study, O-linked glycosylation associated with a jacalin-binding fraction of bovine colostral immunoglobulin resisted pepsin digestion, as compared with the fraction that did not bind jacalin (Porto et al., *J Dairy Sci* 2007; 90:955-62). Moreover, U.S. Pat. No. 8,647,626 also discloses glycosylation as conferring stability to bovine antibodies.

Collectively, studies to date point to the lack of a definitive understanding of the factors and/or molecular basis underlying the protease resistance of bovine colostral antibodies. Elucidating these determinants would enable the manufacture of uniform, digestion resistant, orally administratable, recombinant monoclonal antibody compositions, thereby addressing an unmet, longstanding need in the field of immunotherapy.

SUMMARY

The present invention is based, as least in part, on the identification of the structural features of ruminant early colostrum antibodies that impart resistance to proteases and intestinal digestion. When administered to animals, including humans, pharmaceutical compositions comprising recombinant antibodies as described herein advantageously exhibit resistance to proteases and intestinal digestion. Thus, these pharmaceutical compositions may be delivered to the gastrointestinal tract, particularly for the treatment of diseases of the digestive tract.

In one embodiment, the recombinant antibody retains at least the antigen binding CDRs or variable region (VR) from a parent (non-bovine) antibody, and includes all or a portion of a bovine IgG1 constant region (e.g., a bovine IgG1 CH1 and/or hinge domain). Such antibodies are referred to herein as "bovinized antibodies."

In another embodiment, the antibody comprises the variable region of a parent (non-bovine) antibody, and the constant region (i.e., CH1 domain, hinge region, CH2 domain, and CH3 domain) of a bovine IgG1 antibody. Such antibodies are referred to herein as "bovine chimeric antibodies."

In one aspect, provided herein are isolated recombinant monoclonal antibodies comprising (a) heavy and light chain CDR regions from a non-bovine antibody and (b) a constant region comprising all or a portion of a bovine IgG1 constant region (e.g., a bovine IgG1 constant region selected from any of SEQ ID NOs: 1-3). In one embodiment, the non-bovine antibody is a human antibody.

In one embodiment, the constant region comprises all or a portion of a bovine IgG1 hinge region. In another embodiment, the constant region comprises all or a portion of a bovine IgG1 CH1 domain. In another embodiment, the constant region comprises all or a portion of a bovine IgG1 CH2 domain. In another embodiment, the constant region comprises all or a portion of a bovine IgG1 CH3 domain. In another embodiment, the constant region further comprises a portion of a human constant region (e.g., a human IgG1 or IgG2 constant region).

In one aspect, provided herein are bovinized antibodies that incorporate one or more of the following structural features found in bovine IgG1 that impart protease resistance to the antibody:
1) a disulfide bond linking the N-terminus of the CH1 domain to the N-terminus of the hinge domain ("bovine CH1-hinge disulfide linkage"),
2) a disulfide bond linking the N-terminus of the CH1 domain to the C-terminus of the light chain ("bovine CH1-light chain disulfide linkage"),
3) a cluster of three disulfide bonds linking the hinge regions of two heavy chains together (bovine heavy chain-heavy chain disulfide linkage"), and/or
4) a hinge sequence that is less susceptible to common proteases ("bovinized hinge").

In one embodiment, the parent (non-bovine) antibody comprises a human IgG hinge, wherein sites within the hinge which are susceptible to enzymatic or spontaneous proteolysis are replaced with the equivalent bovine hinge region sequences. In another embodiment, the parent (non-bovine) antibody comprises a bovinized hinge region, in which some or all of the amino acid residues of the hinge region are replaced with the equivalent portion of the bovine IgG1 hinge region sequence.

In another aspect, provided herein are isolated recombinant monoclonal human antibodies, wherein the constant region of the antibodies comprise one or more of the following features found in bovine IgG1:
a) a disulfide bond linking the N-terminus of the CH1 domain to the N-terminus of the hinge region,
b) a disulfide bond linking the N-terminus of the CH1 domain to the C-terminus of the light chain, and
c) a cluster of three disulfide bonds linking the hinge regions of two heavy chains together.

In other words, the antibody has fully human sequences, except for one or more of these structural features that exist in bovine IgG1 (or structurally equivalent features of IgG1 from other ruminants or rabbit) which confer protease resistance.

In some embodiments, the antibodies described herein comprise a constant region comprising one or more of the following substitutions (Kabat numbering): threonine at position 252 is substituted with methionine; glycine at position 255 is substituted with arginine; glutamine at position 309 is substituted with leucine; threonine at position 314 is substituted with leucine; and glycine at position 315 is substituted with asparagine.

In some embodiments, the bovinized or fully bovine recombinant IgG1 monoclonal antibodies described herein bind to a biological antigen (e.g., TNF-α). In one embodiment, the antibody comprises the heavy and light chain variable region sequences of infliximab.

Bovinized antibodies described herein exhibit greater protease resistance relative to the parent antibody. In some embodiments, the bovinized antibodies also retain greater antigen-binding activity after protease digestion relative to the parent antibody. In some embodiments, the bovinized antibodies, upon being subjected to protease digestion in the GI tract, retain antigen-binding activity.

In another aspect, provided herein are fully bovine recombinant IgG1 monoclonal antibodies, as well as host cells that secrete the antibodies.

In another aspect, provided herein are bispecific bovinized antibodies or bispecific fully bovine recombinant IgG1 antibodies.

In another aspect, provided herein are immunoconjugates comprising the bovinized antibodies or fully bovine recombinant IgG1 monoclonal antibodies.

In another aspect, provided herein are nucleic acid molecules that encode the recombinant antibodies described herein. In another aspect, provided herein are expression vectors that comprise the nucleic acids. In yet another aspect, provided herein are host cells comprising the nucleic acids or expression vectors.

In another aspect, provided herein are pharmaceutical compositions containing (e.g., comprising, consisting of or consisting essentially of) the bovinized antibody or fully bovine recombinant IgG1 monoclonal antibodies or bovinized antibodies, and optionally a carrier (e.g., a pharmaceutically acceptable carrier), formulated for oral administration. In some embodiments, the composition further comprises a preservative. In some embodiments, the composition is lyophilized.

In another aspect, provided herein are methods for treating diseases (especially those involving the digestive tract) comprising administering the bovinized antibodies or fully bovine recombinant IgG1 monoclonal antibodies to a subject in need thereof. In one embodiment, the disease is ulcerative colitis. In another embodiment, the disease is Crohn's disease. In some embodiments, the antibodies bind specifically to TNF-α.

In another aspect, provided herein are kits comprising the bovinized antibodies or fully bovine recombinant IgG1 monoclonal antibodies described herein.

In another aspect, provided herein are methods of producing the bovinized antibodies or fully bovine recombinant IgG1 monoclonal antibodies described herein comprising expressing the antibodies in a host cell and isolating the antibodies from the cells.

BRIEF DESCRIPTION OF THE FIGURES

FIG. 22 is a schematic comparing the CH1-hinge region of bovine IgG1 (SEQ ID NO:95), and IgG2 A1 (SEO ID NO:96), and IgG2 A2 (SEQ ID NO:97).

FIG. 23 is a schematic comparing the CH1-hinge region of human IgG1 (SEQ ID NO:98), and bovine IgG1 (SEQ ID NO:99). Potential enzymatic and spontaneous proteolysis sites in human IgG1 are indicated.

FIG. 26 is a line graph showing titers of TNF-binding antibodies from pooled sera collected from calves immunized with the indicated adjuvants, as determined by ELISA.

DETAILED DESCRIPTION

Figure 1:
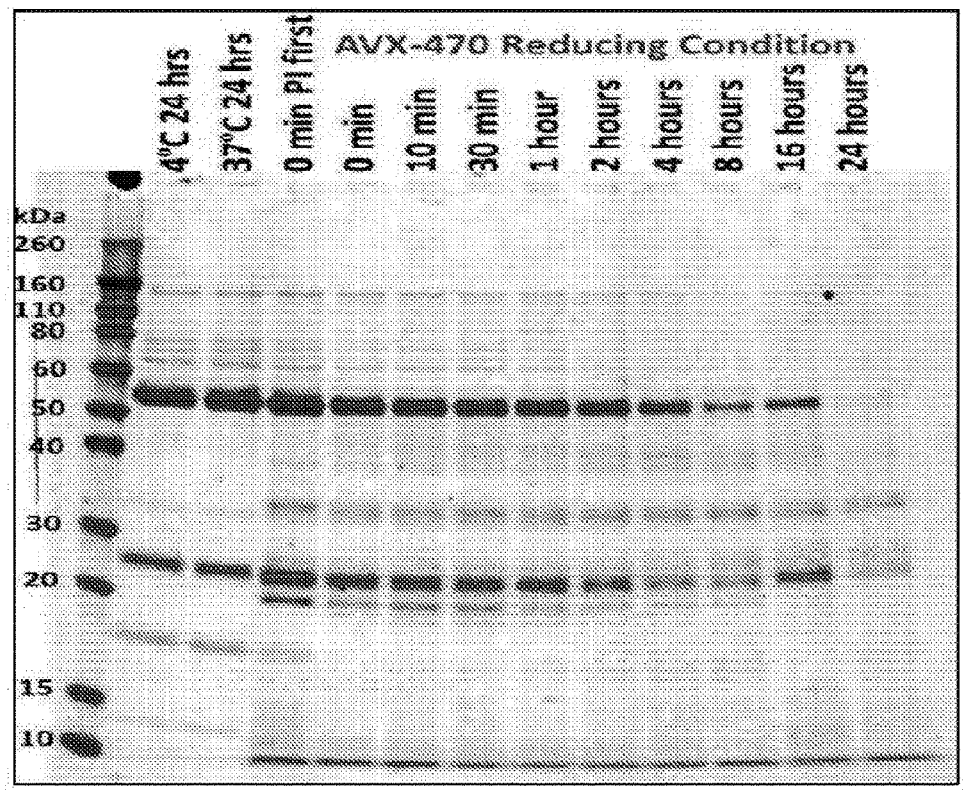
FIG. 1 is a reducing SDS-PAGE analysis of AVX-470 subjected to pancreatin digestion under conditions discussed in Example 2.
Figure 2:
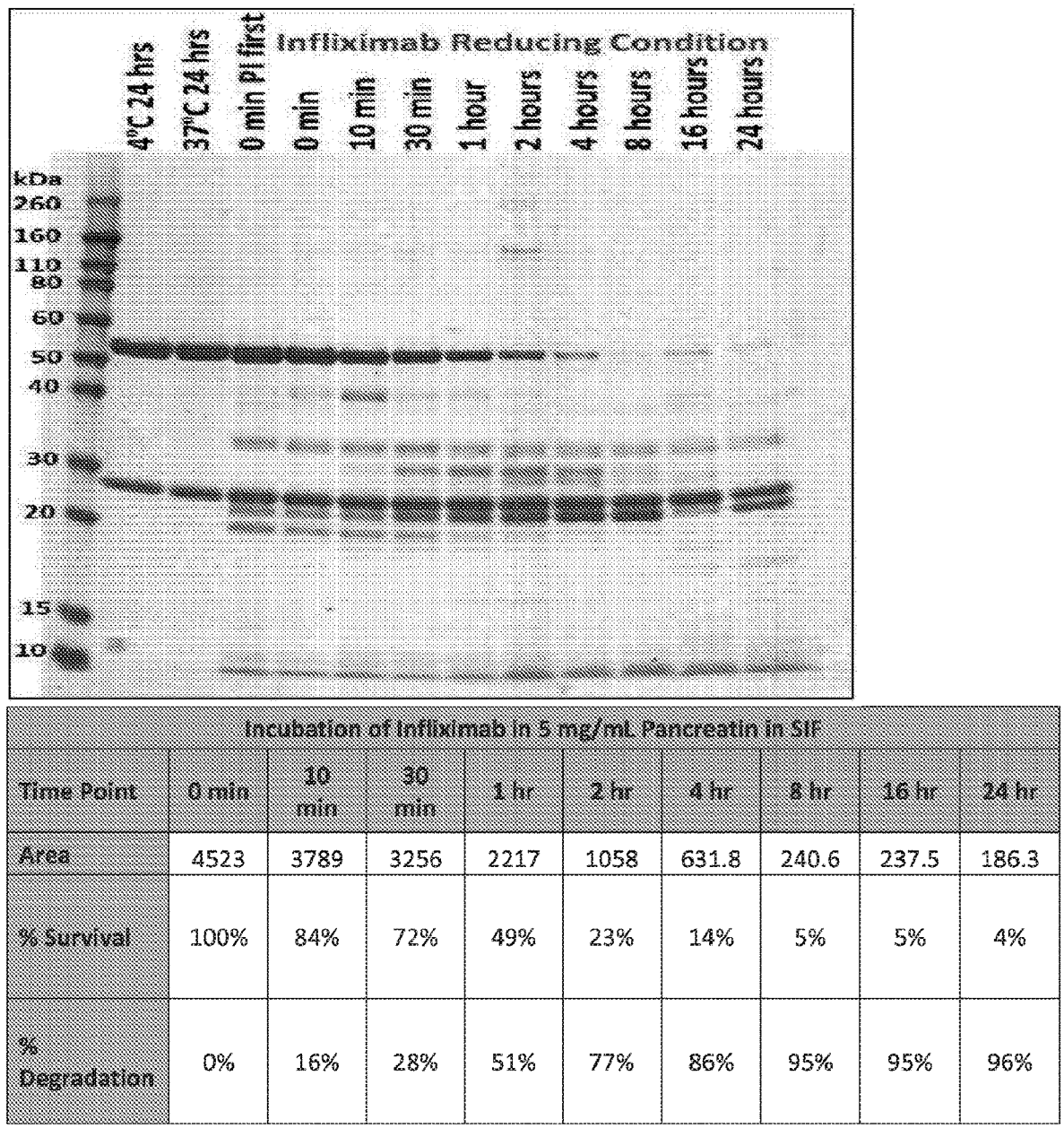
FIG. 2 is a reducing SDS-PAGE analysis of infliximab subjected to pancreatin digestion under conditions discussed in Example 2.
Figure 3:
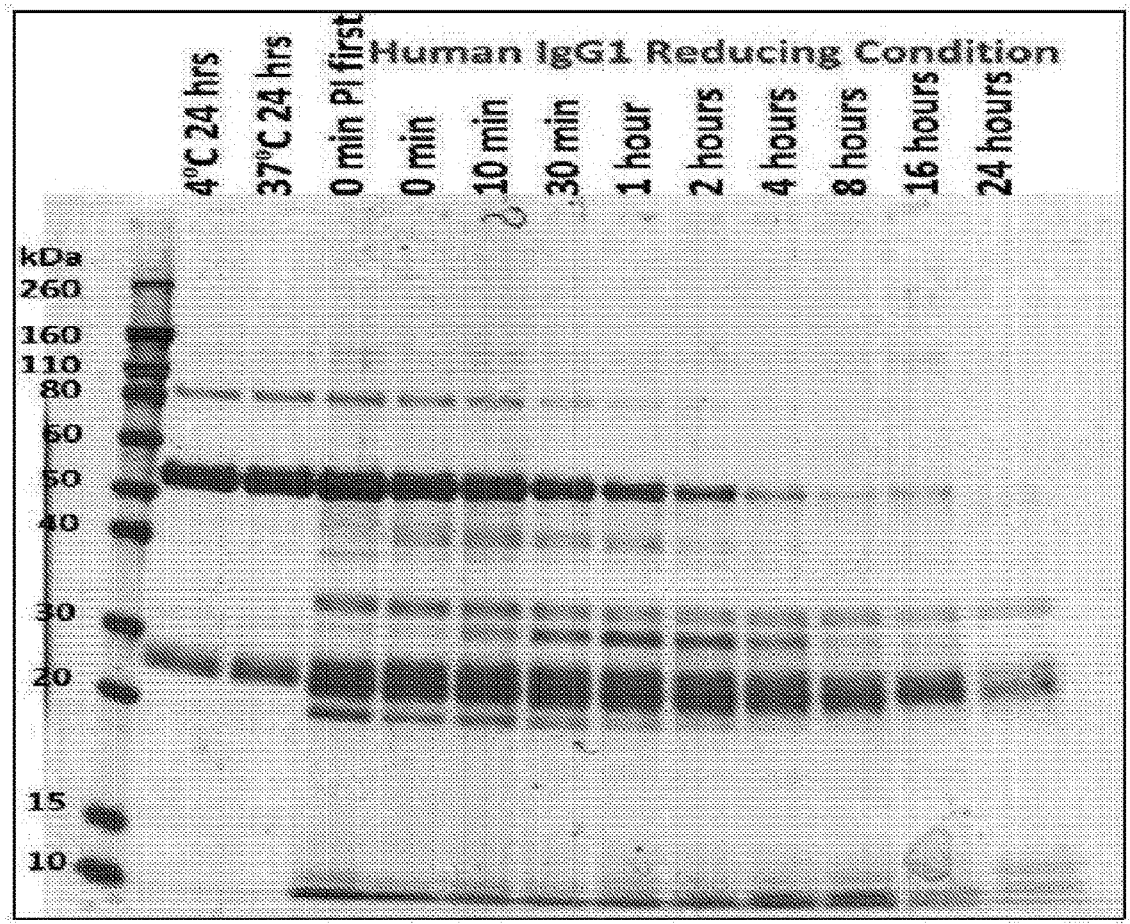
FIG. 3 is a reducing SDS-PAGE analysis of human IgG1 subjected to pancreatin digestion under conditions discussed in Example 2.
Figure 4:
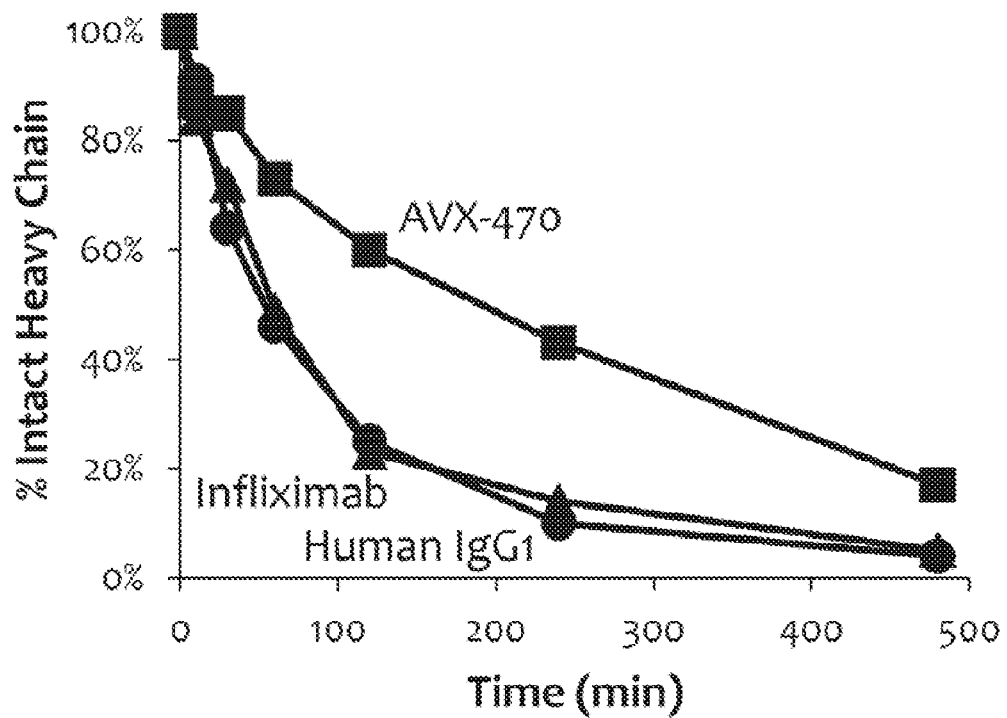
FIG. 4 is a line graph plotting the pancreatin-mediated degradation of the antibody heavy chain of AVX-470, infliximab, and human IgG1, as shown in FIGS. 1-3

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well-known and commonly employed in the art. Standard techniques are used for nucleic acid and peptide synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, N.Y.), which are provided throughout this document. The nomenclature used herein and the laboratory procedures used in analytical chemistry and organic syntheses described below are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

As used herein, the term "antibody" is referred to in the broadest sense and encompasses monoclonal antibodies (including full length monoclonal antibodies), polyclonal antibodies, multispecific antibodies (e.g., bispecific antibodies), and antibody fragments including antigen binding fragments. As used herein "antibody fragments" include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers and (ix) "diabodies" or "triabodies", multivalent or multispecific fragments constructed by gene fusion. The antibody fragments may be modified. For example, the molecules may be stabilized by the incorporation of disulphide bridges linking the VH and VL domains.

Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies and monoclonal antibodies. The use of the singular terms "a" or "an" or "the" antibody are not meant to be limited to a single antibody when it is clear that more than one antibody is present in the composition or preparation. In addition, unless indicated otherwise, the singular term for "antibody" may include a collection of antibodies that are not necessarily heterogenous in their structures or specificities unless indicated otherwise.

Antibodies are generally glycoproteins comprising at least two heavy (H) chains and two light (L) chains interconnected by disulfide bonds, i.e., covalent heterotetramers comprised of two identical Ig H chains and two identical L chains that are encoded by different genes. Each heavy chain is comprised of a heavy chain variable region (abbreviated herein as HCVR or $V_H$) and a heavy chain constant region. The heavy chain constant region of an IgG subclass of immunoglobulins, for example, is comprised of three domains, CH1, CH2 and CH3. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

The variable regions of the heavy and light chains contain a binding domain that interacts with an antigen. The constant regions of the antibodies may mediate the binding of the immunoglobulin to host tissues or factors, including various cells of the immune system (e.g., effector cells). Formation of a mature functional antibody molecule can be accomplished when two proteins are expressed in stoichiometric quantities and self-assemble with the proper configuration.

As used herein, the term "monoclonal antibody" refers to an antibody that displays a single binding specificity and affinity for a particular epitope or a composition of antibodies in which all antibodies display a single binding specificity and affinity for a particular epitope.

As used herein, an "isolated antibody" refers to an antibody that is substantially free of other antibodies having different antigenic specificities.

As used herein, "isotype" refers to the antibody class (e.g., IgG1, IgG2, IgG3, IgG4, IgM, IgA1, IgA2, IgD, and IgE antibody) that is encoded by the heavy chain constant region genes. In a preferred embodiment, the recombinant antibody of the invention antibody is an IgG antibody, e.g. IgG1, IgG2. In another preferred embodiment the recombinant antibody of the invention is an IgG1 antibody.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains CH2 and CH3 and the hinge between CH1 and CH2.

As used herein, the "hinge region" of an antibody refers to a stretch of peptide sequence between the CH1 and CH2 domains of an antibody. Hinge regions occur between Fab and Fc portions of an antibody. Hinge regions are generally encoded by unique exons, and contain disulfide bonds that link the two heavy chain fragments of the antibody. The amino acid sequence of a hinge region can be generally rich in proline, serine, and threonine residues. For example, the extended peptide sequences between the CH1 and CH2 domains of IgG, IgD, and IgA are rich in prolines. IgM and IgE antibodies include a domain of about 110 amino acids that possesses hinge-like features and are included in the term "hinge region" as used herein.

As used herein, the term "region equivalent to the hinge region of a ruminant antibody" is intended to include naturally occurring allelic variants of the hinge region of a ruminant (e.g., bovine) immunoglobulin of any isotype as well as variants having alterations which produce substitutions, additions, or deletions but which do not decrease substantially the ability of the immunoglobulin to resist enzyme digestion. Such variants can be selected according to general rules known in the art so as to have minimal effect on activity.

A CH1 domain is an immunoglobulin heavy chain constant region domain. Preferred are ruminant immunoglobulin CH1 domains such as a bovine, ovine or caprine with the bovine CH1 domains being preferred. The amino acid sequence of immunoglobulin CH1 domains of various species are known or are generally available to the skilled artisan (Kabat et al., Sequences of proteins of immunological interest Fifth Ed., U.S. Department of Health and Human Services, NIH Publication No. 91-3242). In a preferred embodiment, the CH1 domain is a bovine IgG1 CH1 domain. In further preferred embodiment, the immunoglobulin CH1 domain is of the d allotype.

As used herein, the term "region equivalent to CH1 domain of a ruminant antibody" is intended to include naturally occurring allelic variants of the CH1 domain of a ruminant (e.g., bovine) immunoglobulin of any isotype as well as variants having alterations which produce substitutions, additions, or deletions but which do not decrease substantially the ability of the immunoglobulin to resist enzyme digestion. Such variants can be selected according to general rules known in the art so as to have minimal effect on activity.

A CH2 domain is an immunoglobulin heavy chain constant region domain. According to the present invention, the CH2 domain is preferably the CH2 domain of one of the five immunoglobulins subtypes indicated above. Preferred are ruminant immunoglobulin CH2 domains such as a bovine, ovine or caprine with the bovine CH2 domains being preferred. The amino acid sequence of immunoglobulin CH2 domains of various species are known or are generally available to the skilled artisan (Kabat et al., Sequences of proteins of immunological interest Fifth Ed., U.S. Department of Health and Human Services, NIH Publication No. 91-3242). A preferred immunoglobulin CH2 domain within the context of the present invention is a bovine IgG and preferably from bovine IgG1, or IgG2, and more preferably a bovine IgG1. With respect to ruminant antibody molecules reference is made to the IgG class in which an N-linked oligosaccharide is attached to the amide side chain of Asn of the inner face of the CH2 domain of the Fc region. This site is equivalent to Asn 297 of the human IgG1 immunoglobulin molecule. It is characteristic of the recombinant antibody of the present invention that it contain or be modified to contain at least a CH2 domain.

As used herein, the term "region equivalent to CH2 domain of a ruminant antibody" is intended to include naturally occurring allelic variants of the CH2 domain of a ruminant (e.g., bovine) immunoglobulin of any isotype as well as variants having alterations which produce substitutions, additions, or deletions but which do not decrease substantially the ability of the immunoglobulin to resist enzyme digestion. Such variants can be selected according to general rules known in the art so as to have minimal effect on activity.

A CH3 domain is an immunoglobulin heavy chain constant region domain. According to the present invention, the CH3 domain is preferably the CH3 domain of one of the five immunoglobulins subtypes indicated above. Preferred are ruminant immunoglobulin CH3 domains such as a bovine, ovine or caprine with the bovine CH3 domains being preferred. The amino acid sequence of immunoglobulin CH3 domains of various species are known or are generally available to the skilled artisan (Kabat et al., Sequences of proteins of immunological interest Fifth Ed., U.S. Department of Health and Human Services, NIH Publication No. 91-3242). A preferred immunoglobulin CH3 domain within the context of the present invention is from bovine IgG CH3 domain, and preferably a bovine IgG1 CH3 domain or bovine IgG2 CH3 domain, and more preferably a bovine IgG1 CH3 domain.

As used herein, the term "region equivalent to CH3 domain of a ruminant antibody" is intended to include naturally occurring allelic variants of the CH3 domain of a ruminant (e.g., bovine) immunoglobulin of any isotype as well as variants having alterations which produce substitutions, additions, or deletions but which do not decrease substantially the ability of the immunoglobulin to resist enzyme digestion. Such variants can be selected according to general rules known in the art so as to have minimal effect on activity.

As used herein the term region equivalent to the Fc region of a ruminant antibody is intended to include naturally occurring allelic variants of the Fc region of a ruminant immunoglobulin of any isotype as well as variants having alterations which produce substitutions, additions, or deletions but which do not decrease substantially the ability of the immunoglobulin to resist enzyme digestion. Such variants can be selected according to general rules known in the art so as to have minimal effect on activity.

As used herein, the term "host cell" covers any kind of cellular system which can be engineered to generate the antibodies disclosed herein Host cells include cultured cells, e.g., mammalian cultured cells, such as CHO cells, HEK293T cells, BHK cells, NSO cells, SP2/0 cells, YO myeloma cells, P3X63 mouse myeloma cells, PER cells, PER.C6 cells or hybridoma cells, yeast cells, fungal cells, and insect cells, to name only a few, but also cells comprised within a transgenic animal or cultured tissue. In some embodiments, host cells are ruminant mammary epithelial cells including but not limited to: ruminant mammary epithelial cell lines such as Bovine cell lines BMEC+H (Bovine Mammary Epithelial Cells of the Hormone-adapted), HH2A (spontaneously immortalized bovine mammary epithelial cell line), ET-C (epithelial and myoepithelial-like characteristics) and Mac-T (Mammary Alveolar Cells).

An "isolated antibody" or "isolated antibodies", as used herein, is intended to refer to an antibody which is substantially free of other antibodies having different antigenic specificities. An isolated antibody may be substantially free of other cellular material and/or chemicals. The term "substantially" in any of the definitions herein generally means at least about 60%, at least about 70%, at least about 80%, or more preferably at least about 90%, and still more preferably at least about 95%. Isolated also means separation from ccontaminant components of the antibodies' natural environment that would typically interfere with diagnostic or therapeutic uses of the antibody, such as enzymes, hormones, and other materials. As is apparent to those of skill in the art, a non-naturally occurring antibody, does not require "isolation" to distinguish it from its naturally occurring counterpart. In addition, a "concentrated", "separated" or "diluted" antibody is distinguishable from its naturally occurring counterpart in that the concentration or number of molecules per volume is generally greater than that of its naturally occurring counterpart. In general, an antibody made by recombinant means and expressed in a host cell is considered to be "isolated."

As used herein, "specific binding" refers to antibody binding to a predetermined epitope, isoform or variant of an antigen. Typically, the antibody binds with an affinity that is at least two-fold greater than its affinity for binding to a non-specific antigen other than the predetermined antigen or a closely-related antigen. Therefore, the antibodies provided herein in some embodiments specifically bind a target antigen.

By "affinity" or "binding affinity" as used herein is meant the strength of interaction between an antibody and its target antigen. The strength of affinity is often reported with a equilibrium dissociation constant, $K_D$, which is obtained from the ratio of $k_d$ to $k_a$ (i.e., $k_d/k_a$) and is expressed as a molar concentration (M). $K_D$ values for antibodies can be determined using methods well established in the art (e.g., Biacore surface Plasmon resonance, flow cytometry, Scatchard analysis). Lower values of $K_D$ correspond to tighter binding and higher affinity. Higher values of $K_D$ correspond to weaker binding and lower affinity.

As used herein, "target antigen" refers to the molecule that is bound specifically by the variable region of a given antibody. A target antigen may be a protein, carbohydrate, lipid, or other chemical compound.

As used herein the term "bovine chimeric antibody" or "bovinized antibody" refers to a recombinant antibody that retains at least the antigen binding CDRs or variable region (VR) from a parent (non-bovine) antibody, and includes at least a portion of a bovine IgG1 constant region (e.g., a bovine IgG1 CH1 and/or hinge domain). For example, in one embodiment, a bovinized antibody comprises the variable regions and CH2 and CH3 domains of a parent antibody (e.g., a human antibody), and the hinge region and CH1 domain of a bovine IgG1 antibody. In another embodiment, a bovinized antibody comprises one or more amino acid residues in the parent antibody that are replaced with the equivalent residue(s) of a bovine constant region, e.g., a bovine IgG1 constant region. In yet another embodiment, the bovinized antibody comprises the variable region of a parent antibody, and the CH1 domain, hinge region, CH2 domain, and CH3 domain of a bovine IgG1 antibody (i.e., a "bovine chimeric antibody").

A "parent antibody" is used in the broadest sense and specifically covers monoclonal antibodies (including full length monoclonal antibodies), polyclonal antibodies, multispecific antibodies (e.g., bispecific antibodies), and antibody fragments including antigen binding fragments such as an Fc-fusion protein wherein the "parent antibody" is the basis for modification to generate a variant of the present invention also referred to herein as a "bovinized antibody". The term parent antibody may refer to the parent antibody itself, a composition comprising the parent antibody or the amino acid sequence or nucleic acid sequence that encodes the parent antibody.

The term "fully bovine recombinant monoclonal antibody" is intended to include recombinant antibodies having variable and constant regions derived from bovine germline immunoglobulin sequences. The fully bovine antibodies of the invention may include amino acid residues not encoded by the bovine germline immunoglobulin sequences (e.g., mutations introduced by random or site-specific mutagenesis in vitro or by somatic mutation in vivo). However, the term "fully bovine antibody", as used herein, is not intended to include antibodies in which CDR sequences derived from the germline of another mammalian species, such as a mouse have been grafted onto bovine framework sequences.

In some embodiments the antibody is a full-length antibody. In some embodiments the full-length antibody comprises a heavy chain and a light chain.

A "therapeutic recombinant antibody" as that term is used herein is a recombinant antibody that use useful in preventing or ameliorating a disease, disorder or conditions when administered to a subject in need of treatment.

The term "recombinant antibody", as used herein, is intended to include antibodies that are prepared, expressed, created or isolated by recombinant means including, but not limited to, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

"N-linked" oligosaccharides are those oligosaccharides that are linked to a peptide backbone through asparagine, by way of an asparagine-N-acetylglucosamine linkage. N-linked oligosaccharides are also called "N-linked glycans." All N-linked oligosaccharides have a common pentasaccharide core of $Man_3GlcNAc_2$. They differ in the presence of, and in the number of branches (also called antennae) of peripheral sugars such as N-acetylglucosamine, galactose, N-acetylgalactosamine, fucose and sialic acid. Optionally, this structure may also contain a core fucose molecule and/or a xylose molecule.

"O-linked" oligosaccharides are those oligosaccharides also referred to herein as "O-linked glycans" are linked to a peptide backbone through threonine, serine, hydroxyproline, tyrosine, or other hydroxy-containing amino acids.

The term "sialic acid" (SA) refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al., *JBC* 1986; 261:11550-7; Kanamori et al., *JBC* 1990; 65:21811-9). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 1992; 2:25-40; *Sialic Acids Chemistry, Metabolism and Function*, R. Schauer, Ed. (Springer-Verlag, New York (1992)).

The term "sialylated" or "sialylation" refers to the addition of sialyl acid groups to oligosaccharide groups present on a glycosylated peptide such as an antibody. Such addition may be by natural enzymatic processes taking place in, for example a cell or via chemical glycoengineering.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid nucleic acid encoding additional peptide sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides. The term "oligonucleotide" typically refers to short polynucleotides, generally no greater than about 50 nucleotides. Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a nucleic acid sequence encodes a protein if transcription and translation of mRNA corresponding to that nucleic acid produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that nucleic acid or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Homologous" as used herein, refers to the subunit sequence similarity between two polymeric molecules, e.g., between two nucleic acid molecules, e.g., two DNA molecules or two RNA molecules, or between two peptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCCS' and 3'TATGGC share 50% homology.

As used herein, "homology" is used synonymously with "identity." The determination of percent identity between two nucleotide or amino acid sequences can be accomplished using a mathematical algorithm. For example, a mathematical algorithm useful for comparing two sequences is the algorithm of Karlin and Altschul (PNAS 1990; 87:2264-8), modified as in Karlin and Altschul (PNAS 199390:5873-7). This algorithm is incorporated into the NBLAST and XBLAST programs of Altschul, et al. OMB 1990; 215:403-10), and can be accessed, for example at the National Center for Biotechnology Information (NCBI) world wide web site having the universal resource locator "www.ncbi.nlm.nih.gov/BLAST/". BLAST nucleotide searches can be performed with the NBLAST program (designated "blastn" at the NCBI web site), using the following parameters: gap penalty=5; gap extension penalty=2; mismatch penalty=3; match reward=I; expectation value 10.0; and word size=II to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (*Nucleic Acids Res* 1997; 25:3389-402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (eg., XBLAST and NBLAST) can be used. See www.ncbi.nlm.niftgov.

The percent identity between two sequences can be determined using techniques similar to those described above, with or without allowing gaps. In calculating percent identity, typically exact matches are counted.

A "heterologous nucleic acid expression unit" encoding a peptide is defined as a nucleic acid having a coding sequence for a peptide of interest operably linked to one or more expression control sequences such as promoters and/or repressor sequences wherein at least one of the sequences is heterologous, i.e., not normally found in the host cell.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a nucleic acid is able to promote transcription of the coding region.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter" is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

A "genetically engineered" or "recombinant" cell is a cell having one or more modifications to the genetic material of the cell. Such modifications are seen to include, but are not limited to, insertions of genetic material, deletions of genetic material and insertion of genetic material that is extrachromasomal whether such material is stably maintained or not.

As used herein, "native form" means the form of the peptide when produced by the cells and/or organisms in which it is found in nature. When the peptide is produced by a plurality of cells and/or organisms, the peptide may have a variety of native forms.

"Peptide" refers to a polymer in which the monomers are amino acids and are joined together through amide bonds, alternatively referred to as a peptide. Additionally, unnatural amino acids, for example, β-alanine, phenylglycine and homoarginine are also included. Amino acids that are not nucleic acid-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer thereof. The L-isomer is generally preferred. In addition, other peptidomimetics are also useful in the present invention. "Peptides" include, for example, oligopeptides, polypeptides, peptides, proteins, or glycoproteins.

As used herein, "polypeptide" refers to a chain comprising at least two consecutively linked amino acid residues, with no upper limit on the length of the chain. One or more amino acid residues in the protein may contain a modification such as, but not limited to, glycosylation, phosphorylation or a disulfide bond. A "protein" may comprise one or more polypeptides.

The present invention also provides for analogs of proteins or peptides which comprise a protein as identified above. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of peptides, e.g., acetylation, or carboxylation. Also included are modifications of glycosylation, e.g., those made by modifying the glycosylation patterns of a peptide during its synthesis and processing or in further processing steps; e.g., by exposing the peptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

It will be appreciated, of course, that the peptides may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

As used herein, the term "MALDI" is an abbreviation for Matrix Assisted Laser Desorption Ionization. During ionization, SA-PEG (sialic acid-poly(ethylene glycol)) can be partially eliminated from the N-glycan structure of the glycoprotein.

As used herein, a "ruminant" is any mammal of the suborder Ruminantia which include domestic animals such as camel, deer, cows (bovine), sheep (ovine) and goats (caprine).

As used herein, "early colostrum" or "early colostral" includes colostrum produced 1 day to 7 days after the ruminant gives birth. In a preferred embodiment early colostrum is the colostrum produced within 1 to 3 days after birth. In a most preferred embodiment, early colostrum is the colostrum produced within 24 to 36 hours after birth.

As used herein, the "digestive tract" consists of the mouth, pharynx, esophagus, stomach, small intestine (duodenum, jejunum, ileum), large intestine (cecum, colon, rectum) and anus. In one preferred embodiment, the digestive tract is a human digestive tract.

As used herein, the "oral cavity" includes the mouth, the pharynx and the esophagus. The term "oral degradation" of an antibody is used herein to mean degradation of an antibody in the oral cavity by endogenous or exogenous enzymes present in the oral cavity.

As used herein, the "gastrointestinal tract", or "GI tract" includes the stomach, small intestine (duodenum, jejunum, ileum), large intestine (cecum, colon, rectum) and anus.

As used herein, "intestinal digestion" refers to digestion in the small intestine and/or the large intestine.

As used herein, "intestinal degradation" of an antibody refers to degradation of an antibody in the small intestine and/or large intestine by endogenous or exogenous enzymes present in the small intestine and large intestine or due to exposure to acidic conditions during intestinal digestion.

As used herein, "enhanced" or "increased" ability to resist cleavage by proteases and/or enhanced or increased resistance to digestion or degradation during intestinal digestion in a mammal is intended to refer to a recombinant antibody or composition thereof that exhibits greater resistance to protease cleavage or intestinal digestion produced by the methods of the invention that impart the unique features of ruminant early colostral IgG antibodies that enable such antibodies to resist cleavage and digestion as compared to a recombinant antibody or composition thereof produced by a method that does not impart such features to the antibodies.

Proteases to which bovinized antibody variants of the invention have increased resistance may include, but are not limited to, simulated intestinal fluid, papain, pepsin, a matrix metalloproteinase including MMP-7, neutrophil elastase (HNE), stromelysin (MMP-3), macrophage elastase (MMP-12), trypsin, chymotrypsin, and other proteases as compared to antibodies that do not possess the features of the invention.

The term "antibody preparation" as used herein is used to define a composition comprising antibodies of the invention wherein contaminant components, such as materials which would interfere with diagnostic or therapeutic uses for the antibodies are substantially reduced. In an optional embodiment the antibody preparations of the invention will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

As used herein, "treatment" or "treating," or "palliating" or "ameliorating" is used interchangeably herein. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

A "therapeutic effect", as used herein, refers to a physiologic effect, including but not limited to the cure, mitigation, amelioration, or prevention of disease in humans or other animals, or to otherwise enhance physical or mental well being of humans or animals, wherein the such therapeutic effect is facilitated by a recombinant antibody of the invention. Determination of a therapeutically effective amount is well within the capability of those skilled in the art, especially in light of the detailed disclosure provided herein.

The terms "therapeutically effective amount" and "therapeutically effective dose", as used herein, refers to an amount of a recombinant antibody of the invention, either alone, or in combination with another therapeutic, that is capable of having any detectable, beneficial effect on any symptom, aspect, measured parameter or characteristics of a disease state or condition when administered in one or repeated doses to a subject. Such effect need not be absolute to be beneficial.

The term "therapeutically effective dose regimen", as used herein, refers to a schedule for consecutively administered doses of a recombinant antibody of the invention, either alone or as part of a combination with another therapeutic, wherein the doses are given in therapeutically effective amounts to result in sustained beneficial effect on any symptom, aspect, measured parameter or characteristics of a disease state or condition.

"Altering the features of an antibody or composition of antibodies" to impart the features of early colostral IgG in accordance with the methods described herein is intended to encompass instances where the alteration of the features of an individual antibody, a subset of the antibodies in the compositions or all of the antibodies in the composition have been made to impart the unique features of a ruminant early colostral IgG antibody (e.g., a bovine colostral IgG1 antibody). Antibody resistance to proteolysis may be measured by any of the standard proteolysis assays known in the art.

The terms "patient" and "subject" refer to any human or non-human animal that receives either prophylactic or therapeutic treatment. For example, the methods and compositions described herein can be used to treat a subject having a gastrointestinal disorder. The term "non-human animal" includes all vertebrates, e.g., mammals and non-mammals, such as non-human primates, sheep, dog, cow, chickens, amphibians, reptiles, etc.

As used herein, "cattle" refer to members of the subfamily Bovinae, and include the species *Bos indicus* and *Bos taurus*. As used herein, "cattle" is intended to encompass calves, mature cows, steers, and bulls.

Various aspects described herein are described in further detail in the following subsections.

Overview

Described herein are recombinant antibodies having an increased ability to resist cleavage by proteases and resist degradation during digestion in the digestive tract of a mammal (e.g., during human digestion), as well as methods for preparing the same.

Bovine antibodies, and particularly early colostral bovine IgG, are known to have a natural resistance to digestion in the human gastrointestinal tract (Warny et al., *Gut* 1999; 44:212-217). The basis of this resistance was previously unknown. The present invention is based, at least in part, on the discovery of the macromolecular basis that imparts to bovine IgG1 enhanced resistance to proteases and other digestive enzymes present in the gut in vitro and in vivo.

The initial secretion present in the mammary gland at or near the time of parturition is termed colostrum, which arises during a distinct physiological and functional stage of mammary gland development that is completely different from the gland's primary role of milk production. During colostrogenesis, the transfer of immunoglobulins from the maternal circulation into mammary secretions in domestic ruminants begins several weeks prior to parturition and ceases after parturition. During this time 500 g-3 kg of IgG are transferred into mammary secretions and early studies have established that the source of colostral immunoglobulin is the maternal circulation.

Colostrum is unique in its composition and function. In domestic ruminants the principal difference between colostrum and milk is the high concentration of colostral immunoglobulin, specifically IgG1. IgG1 is concentrated to levels 5-10 times that of serum where it accounts for greater than 90% of total colostral protein. The process by which immunoglobulin is transferred from maternal circulation into the mammary gland is the result of transcytosis, a process by which various macromolecules including immunoglobulins are transported across the interior bovine mammary epithelial cells. Immunoglobulins are captured in vesicles on the basal-lateral side of the mammary epithelium cell, drawn across the cell and ejected at the apical surface into colostrum.

As will be discussed in further detail below, described herein, for the first time, are several structural differences between the IgG found in bovine serum and colostrum, and in particular, between IgG isotypes, that impart protease resistance to bovine colostral antibodies. The antibodies described herein take advantage of these structural differences to generate protease-resistant antibodies.

Bovinized Antibodies

Provided herein are recombinant antibodies having unique structural features associated with bovine IgG1 antibodies that impart enhanced protease resistance and which can be orally administered for the treatment diseases of the digestive tract.

Accordingly, provided herein are recombinant antibodies that retain at least the antigen binding CDRs or variable region (VR) from a parent (non-bovine) antibody, and includes all or a portion of a bovine IgG1 constant region (e.g., a bovine IgG1 CH1 and/or hinge domain). Such antibodies are referred to herein as "bovinized antibodies." Also provided herein are bovinized antibodies which comprises the variable region of a parent antibody, and the constant region (i.e., CH1 domain, hinge region, CH2 domain, and CH3 domain) of a bovine IgG1 antibody. These antibodies are referred to as "bovine chimeric antibodies."

In one aspect, provided herein are bovinized antibodies that fully or partially replace one or more constant region domain(s) of a parent (i.e., non-bovine) antibody with the equivalent bovine IgG1 constant region domain(s).

Exemplary bovine IgG1 antibody constant regions are presented in Table 1.

TABLE 1

| Allotype | Accession ID | Sequence |
|---|---|---|
| IgG1a (SEQ ID NO: 1) | S82409 | ASTTAPKVYPLSSCCGDKSSSTVTLGCLVSSYMPEPVTVTWNSGALKSGVHTFPAVLQSSGL YSLSSMVTVPGSTSGTQTFTCNVAHPASSTKVDKAVDPRCKTTCDCCPPPELPGGPSVFIFP PKPKDTLTISGTPEVTCVVVDVGHDDPEVKFSWFVDDVEVNTATTKPREEQFNSTYRVVSAL RIQHQDWTGGKEFKCKVHNEGLPAPIVRTISRTKGPAREPQVYVLAPPQEELSKSTVSLTCM VTSFYPDYIAVEWQRNGQPESEDKYGTTPPQLDADGSYFLYSRLRVDRNSWQEGDTYTCVVM HEALHNHYTQKSTSKSAGK |

TABLE 1-continued

| Allotype | Accession ID | Sequence |
|---|---|---|
| IgG1b (SEQ ID NO: 2) | X16701 | ASTTAPKVYPLSSCCGDKSSSTVTLGCLVSSYMPEPVTVTWNSGALKSGVHTFPAVLQSSGL<br>YSLSSMVTVPGSTSGQTFTCNVAHPASSTKVDKAVDPTCKPSPCDCCPPPELPGGPSVFIFP<br>PKPKDTLTISGTPEVTCVVVDVGHDDPEVKFSWFVDDVEVNTATTKPREEQFNSTYRVVSAL<br>RIQHQDWTGGKEFKCKVHNEGLPAPIVRTISRTKGPAREPQVYVLAPPQEELSKSTVSLTCM<br>VTSFYPDYIAVEWQRNGQPESEDKYGTTPPQLDADSSYFLYSKLRVDRNSWQEGDTYTCVVM<br>HEALHNHYTQKSTSKSAGK |
| IgG1c (SEQ ID NO: 3) | DQ452014 | ASTTAPKVYPLSSCCGDKSSSTVTLGCLVSSYMPEPVTVTWNSGALKSGVHTFPAVLQSSGL<br>YSLSSMVTVPASSSGTQTFTCNVAHPASSTKVDKAVDPRCKRPCDCCPPPELPGGPSVFIFP<br>PKPKDTLTISGTPEVTCVVVDVGHDDPEVKFSWFVDNVEVNTATTKPREEQFNSTYRVVSAL<br>RIQHQDWTGGKEFKCKVHNEGLPAPIVRTISRTKGPAREPQVYVLAPPQEELSKSTVSLTCM<br>VTSFYPDYIAVEWQRNGQPESEDKYGTTPPQLDADSSYFLYSKLRVDRNSWQEGDTYTCVVM<br>HEALHNHYTQKSTSKSAGK |
| IgG1d (SEQ ID NO: 2) | X62916 | ASTTAPKVYPLSSCCGDKSSSTVTLGCLVSSYMPEPVTVTWNSGALKSGVHTFPAVLQSSGL<br>YSLSSMVTVPGSTSGQTFTCNVAHPASSTKVDKAVDPTCKPSPCDCCPPPELPGGPSVFIFP<br>PKPKDTLTISGTPEVTCVVVDVGHDDPEVKFSWFVDDVEVNTATTKPREEQFNSTYRVVSAL<br>RIQHQDWTGGKEFKCKVHNEGLPAPIVRTISRTKGPAREPQVYVLAPPQEELSKSTVSLTCM<br>VTSFYPDYIAVEWQRNGQPESEDKYGTTPPQLDADSSYFLYSKLRVDRNSWQEGDTYTCVVM<br>HEALHNHYTQKSTSKSAGK |

In one embodiment, provided are bovinized antibodies that incorporate 1, 2, 3, or all of the following structural features found in bovine IgG1 that impart protease resistance to the antibody:
1) a disulfide bond linking the N-terminus of the CH1 domain to the N-terminus of the hinge domain ("bovine CH1-hinge disulfide linkage"),
2) a disulfide bond linking the N-terminus of the CH1 domain to the C-terminus of the light chain ("bovine CH1-light chain disulfide linkage"),
3) a cluster of three disulfide bonds linking the hinge regions of two heavy chains together ("bovine heavy chain-heavy chain disulfide linkage"), and/or
4) a hinge sequence that is less susceptible to common proteases ("bovinized hinge").

In some embodiments, the bovinized antibody comprises the variable domain, CH2 domain, and CH3 domain of the parent antibody, and at least a portion (i.e., one or more amino acid residues) of a bovine IgG1 CH1 and/or hinge domain. In some embodiments, the CH1 domain of the antibody is at least 85% identical, for example, at least 90%, at least 95%, at least 98%, at least 99%, or at least 100% identical, to the bovine IgG1 CH1 and/or hinge domain.

In particular embodiments, the bovinized antibodies described herein comprise a CH1 domain from a parent antibody (e.g., a human CH1 domain), wherein the amino acid residues equivalent to Cys 127 and Cys 128 (according to Kabat numbering) in bovine IgG1 are replaced with cysteine in the parent antibody. For example, in one embodiment, the antibody comprises a human CH1 domain with S127C and/or S128C substitutions (numbering according to Kabat). In another embodiment, the antibody comprises a human CH1 domain with S127C and/or S128C amino acid substitutions, wherein 1, 2, 3, 4, 5, 6, 7, 8, 9, or 10 amino acids upstream (N-terminal) and/or 1, 2, 3, 4, 5, 6, 7, 8, 9, or 10 amino acids downstream (C-terminal) of amino acid residues 127 and 128 are replaced with the equivalent bovine IgG1 CH1 residues.

In other embodiments, the bovinized antibody comprises a bovinized hinge region. For example, in one embodiment, the antibody comprises a human IgG hinge, wherein sites within the hinge which are susceptible to enzymatic or spontaneous proteolysis are replaced with the equivalent bovine hinge region sequences. As shown in FIG. 23, the bovine IgG1 hinge region sequence differs from the human IgG1 hinge region sequence at sites known to be susceptible to protease digestion.

In further embodiments, the bovinized antibody comprises a bovinized hinge region, in which some or all of the amino acid residues of the hinge region are replaced with the equivalent portion of the bovine IgG1 hinge region sequence.

In still further embodiments, the bovinized antibody comprises a bovinized hinge region which comprises a bovine heavy chain-heavy chain linkage, wherein a cluster of three disulfide bonds link the hinge regions of two heavy chains together. Accordingly, in one embodiment, the antibody comprises a hinge of the parent antibody, wherein the amino acid residues equivalent to the underlined cysteine residues in the bovine hinge region below are replaced with cysteine (if not already cysteine) in the hinge of the parent antibody.

(SEQ ID NO: 4)
DKAVDPR<u>C</u>KPSPCD<u>CC</u>PPPELPGGP

In one embodiment, the antibody comprises a human hinge region sequence, wherein Pro241 (Kabat numbering) is replaced with a cysteine residue (i.e., a P241C substitution).

In some embodiments, the bovinized antibodies exhibit greater protease resistance relative to the parent antibody.

In some embodiments, the bovinized antibodies retain greater antigen-binding activity after protease digestion relative to the parent antibody.

In some embodiments, the bovinized antibodies, upon being subjected to protease digestion in the GI tract, retain antigen-binding activity. In certain embodiments, the bovinized antibodies remain bivalent upon digestion by proteases in the GI tract. In one embodiment, the bovinized antibodies are digested into F(ab')$_2$ fragments by proteases in the GI tract.

In some embodiments, the protease resistance of bovinized antibodies comprising a bovine IgG1 hinge is increased by partially incorporating bovine IgG3 hinge region sequences into the IgG1 hinge region. Without being bound by theory, pepsin cleavage can be prevented by adding a bovine IgG3 hinge domain having a putative O-glycosylation site to the bovine IgG1 constant region.

In certain embodiments, the antigen-binding region of the bovinized antibodies lack protease-sensitive sequences. Such determinations can be made by comparing the primary sequence of the variable region (e.g., the CDR regions) with known protease consensus sequences, or tested experimentally using pancreatin digestion methods described in the Examples.

In some embodiments, portions of the constant regions of other ruminants that share structural similarities with the bovine constant region that imparts protease stability can be incorporated into the recombinant antibodies described herein. For instance, Example 9 provides the CH1-hinge region sequences of other ruminant species which share structural similarities with the corresponding bovine sequences. In certain embodiments, these structurally similar sequences are derived from the rabbit IgG1 constant region.

In some embodiments, the bovinized antibody comprises one or more additional amino acid substitutions (e.g., 1, 2, 3, 4, or 5 amino acid substitutions) in the hinge or Fc region that increase or decrease antibody effector activity and/or FcRn binding activity.

Particular amino acid substitutions include those that generate an Fe variant that (a) has increased or decreased antibody-dependent cell-mediated cytotoxicity (ADCC). (b) increased or decreased complement mediated cytotoxicity (CDC), (c) has increased or decreased affinity for C1q and/or (d) has increased or decreased affinity for a Fc receptor relative to the parent Fc.

Although the passages below generally relate to substitutions and positions in the human Fc region, the skilled artisan could readily introduce corresponding substitutions at equivalent positions of the Fc regions of other species.

In some embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. See, e.g., U.S. Pat. Nos. 5,624,821 and 5,648,260.

In another example, one or more amino acids selected from amino acid residues 329, 331 and 322 can be replaced with a different amino acid residue such that the antibody has altered C1q binding and/or reduced or abolished complement dependent cytotoxicity (CDC). See, e.g., U.S. Pat. No. 6,194,551.

In another example, one or more amino acid residues within amino acid positions 231 and 239 are altered to thereby alter the ability of the antibody to fix complement. See, e.g., PCT Publication WO 94/29351.

In yet another example, the Fc region may be modified to increase antibody dependent cellular cytotoxicity (ADCC) and/or to increase the affinity for an Fcγ cry receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E.

Exemplary variants include 239D/332E, 236A/332E, 236A/239D/332E, 268F/324T, 267E/268F, 267E/324T, and 267E/268F/324T. Other modifications for enhancing FcγR and complement interactions include but are not limited to substitutions 298A, 333A, 334A, 326A, 247I, 339D, 339Q, 280H, 290S, 298D, 298V, 243L, 292P, 300L, 396L, 305I, and 396L. These and other modifications are reviewed in Strohl, 2009, Current Opinion in Biotechnology 20:685-691.

Fc modifications that increase binding to an Fcγ receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 3338, 340, 360, 373, 376, 379, 382, 388, 389, 398, 414, 416, 419, 430, 434, 435, 437, 438 or 439 of the Fc region, wherein the numbering of the residues in the Fc region is that of the EU index as in Kabat (WO00/42072).

Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, and 328, wherein numbering is according to the EU index. Exemplary substitutions include but are not limited to 234G, 235G, 236R, 237K, 267B, 269R, 325L, and 328R, wherein numbering is according to the EU index. An Fc variant may comprise 236R/328R. Other modifications for reducing FcγR and complement interactions include substitutions 297A, 234A, 235A, 237A, 318A, 228P, 236E, 268Q, 309L, 330S, 331S, 220S, 226S, 229S, 238S, 233P, and 234V, as well as removal of the glycosylation at position 297 by mutational or enzymatic means or by production in organisms such as bacteria that do not glycosylate proteins. See, e.g., Strohl, 2009, Current Opinion in Biotechnology 20:685-691.

Optionally, the Fc region may comprise a non-naturally occurring amino acid residue at additional and/or alternative positions known to one skilled in the art (see, e.g., U.S. Pat. Nos. 5,624,821; 6,277,375; 6,737,056; 6,194,551; 7,317,091; 8,101,720; PCT Patent Publications WO 00/42072; WO 01/58957; WO 02/06919; WO 04/016750; WO 04/029207; WO 04/035752; WO 04/074455; WO 04/099249; WO 04/063351; WO 05/070963; WO WO 05/092925 and WO 06/020114).

Fc variants that enhance affinity for an inhibitory receptor FcγR11b may also be used. Such variants may provide an Fc fusion protein with immunomodulatory activities related to FcγR11b$^+$ cells, including for example B cells and monocytes. In one embodiment, the Fc variants provide selectively enhanced affinity to FcγR11b relative to one or more activating receptors. Modifications for altering binding to FcγR11b include one or more modifications at a position selected from the group consisting of 234, 235, 236, 237, 239, 266, 267, 268, 325, 326, 327, 328, and 332, according to the EU index. Exemplary substitutions for enhancing FcγR11b affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcγR11b include 235Y/267E, 236D/267E, 239D/268D, 239D/267E, 267E/268D, 267E/268E, and 267E/328F.

In some embodiments, the hinge is a bovinized hinge, and comprises one or more of the amino acid substitutions described in Example 10.

In addition, IgG1 mutants containing L235V, F243L, R292P, Y300L and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al., 2007; Nordstrom et al., 2011). Other Fc mutants include: S298A/E333A/L334A, S239D/I332E, S239D/I332E/A330L, L235V/F243L/R292P/Y300L/P396L, and M428L/N434S.

Fc variants that enhance affinity for Protein A from *Staphylococcus areus* may also be used. Previous work (US Patent Application US20140154270A1) has shown that IgG from ruminant species binds to Protein A with poor affinity under conditions typically used for manufacturing. Variants of the bovine sequence may provide an Fc fusion protein that can be purified by methods commonly used in the manufacture of biological therapeutics. In some embodiments, the antibody can be modified at positions 250-255, 288, 307-317, or 430-436 to amino-acids found in IgG molecules known to bind Protein A with high affinity. In a subset of these embodiments, substitutions may be chosen to enhance Protein A binding while retaining weak binding to human FcRn. Without being bound by mechanism, these substitutions prevent the antibody from being transported from the gut into systemic circulation. Accordingly, in certain embodiments, the Fc domain contains one or more (i.e., 1, 2, 3, 4, or 5) of the following substitutions: T252M, G255R, Q309L, T314L, and G315N. In one embodiment, the Fc domain contains a T252M/G255R substitution. In another embodiment, the Fc domain contains a Q309L/T314L/G315N substitution. In yet another embodiment, the Fc domains contains a T252M/G255R/Q309L/T314L/G315N substitution.

In one embodiment, the parent antibody comprises a hinge region, or is altered to comprise a hinge region, that is at least 85%, such as at least 90%, at least 95%, at least 98%, at least 99%, or 100% identical to the equivalent portion of a hinge region comprising the amino acid sequence of bovine IgG1 (S22080): DKAVDPRCKPSPCDCCPP-PELPGGP (SEQ ID NO: 4). In another embodiment, the parent antibody comprises a hinge region, or is altered to comprise a hinge region, that is at least 85%, such as at least 90%, at least 95%, at least 98%, at least 99%, or 100% identical to the equivalent portion of a hinge region comprising the amino acid sequence of selected from the following hinge region amino acid sequences of Table 2:

TABLE 2

| SEQ ID | Species | Sequence |
|---|---|---|
| 5 | Bos Taurus (cow) | VDK--AVDP---RCK-TTCD-C-CPPPELPGGPSVF |
| 6 | Bos Taurus (cow) | VDK--AVDP---RCK-RPCD-C-CPPPELPGGPSVF |
| 7 | Bos Taurus (cow) | VDK--AVDP---TCKPSPCD-C-CPPPELPGGPSVF |
| 8 | Ovis aries (sheep) | VDK--RVEP---GCP-DPCKHCRCPPPELPGGPSVF |
| 8 | Ovis aries (sheep) | VDK--RVEP---GCP-DPCKHCRCPPPELPGGPSVF |
| 8 | Ovis aries (sheep) | VDK--RVEP---GCP-DPCKHCRCPPPELPGGPSVE |
| 9 | Lama glama (llama) | VDK--RVEPHG-GCT---CP--QCPAPELPGGPSVF |
| 9 | Vicugna pacos (alpaca) | VDK--RVEPHG-GCT---CP--QCPAPELPGGPSVF |
| 9 | Camelus dromedarius (Arabian camel) | VDK--RVEPHG-GCT---CP--QCPAPELPGGPSVF |
| 10 | Meriones unguiculatus (gerbil) | VDK--TVEPRGTKHICPDCP--KCPAPDLSGGPSVF |
| 11 | Felis catus (cat) | VDKTVRKTDHP-PGP-KPCDCPKCPPPEMLGGPSIF |

In one embodiment, the recombinant antibody comprises all or a portion of a hinge region that is at least 85%, such as at least 90%, at least 95%, at least 98%, at least 99%, or 100% identical to the amino acid sequence of the equivalent portion of a ruminant antibody hinge region (e.g., a bovine IgG1 hinge region) and optionally comprises all or a portion of a CH1 domain that is at least 85%, at least 90%, at least 95%, at least 98%, at least 99%, at least 100% identical to the amino acid sequence of the equivalent portion of a ruminant antibody (e.g., a bovine IgG1 hinge region) and further optionally comprises all or a portion of a CH1 domain that is at least 85%, at least 90%, at least 95%, at least 98%, at least 99%, at least 100% identical to the amino acid sequence of the equivalent portion of a ruminant antibody (e.g., a bovine IgG1 hinge region). Exemplary bovine hinge regions are presented in Table 3.

TABLE 3

| Allotype | Accession ID | Sequence |
|---|---|---|
| IgG1a (SEQ ID NO: 12) | S82409 | DPRCKTTCDCCP |
| IgG1b (SEQ ID NO: 13) | X16701 | DPTCKPSPCDCCP |
| IgG1c (SEQ ID NO: 14) | DQ452014 | DPRCKRPCDCCP |
| IgG1d (SEQ ID NO: 13) | X62916 | DPTCKPSPCDCCP |

In one embodiment, the parent antibody comprises or is altered to comprise a hinge region and a CH1 domain is at least 85%, such as at least 90%, at least 95%, at least 98%, at least 99%, or 100% identical to the equivalent portion of a bovine, CH1 domain amino acid sequence (e.g., a bovine IgG1 CH1 domain). Exemplary bovine IgG1 CH1 domains are presented in Table 4.

TABLE 4

| Allotype | Accession ID | Sequence |
|---|---|---|
| IgG1a (SEQ ID NO: 15) | S82409 | ASTTAPKVYPLSSCCGDKSSSTVTLGCLVSSYMPEPVTVTWNSGALKSGVHTFP AVLQSSGLYSLSSMVTVPGSTSGTQTFTCNVAHPASSTKVDKAV |
| IgG1b (SEQ ID NO: 16) | X16701 | ASTTAPKVYPLSSCCGDKSSSTVTLGCLVSSYMPEPVTVTWNSGALKSGVHTFP AVLQSSGLYSLSSMVTVPGSTSGQTFTCNVAHPASSTKVDKAV |
| IgG1c (SEQ ID NO: 17) | DQ452014 | ASTTAPKVYPLSSCCGDKSSSTVTLGCLVSSYMPEPVTVTWNSGALKSGVHTFP AVLQSSGLYSLSSMVTVPASSSGTQTFTCNVAHPASSTKVDKAV |
| IgG1d (SEQ ID NO: 16) | X62916 | ASTTAPKVYPLSSCCGDKSSSTVTLGCLVSSYMPEPVTVTWNSGALKSGVHTFP AVLQSSGLYSLSSMVTVPGSTSGQTFTCNVAHPASSTKVDKAV |

In one embodiment, the parent antibody comprises or is altered to comprise a hinge region and a CH2 domain is at least 85%, such as at least 90%, at least 95%, at least 98%, at least 99%, or 100% identical to the equivalent portion of a bovine, CH2 domain amino acid sequence (e.g., a bovine IgG1 CH2 domain). Exemplary bovine IgG1 CH2 domains are presented in Table 5.

TABLE 5

| Allotype | Accession ID | Sequence |
|---|---|---|
| IgG1a (SEQ ID NO: 18) | S82409 | PPELPGGPSVFIFPPKPKDTLTISGTPEVTCVVVDVGHDDPEVKFSWFVDDVEV NTATTKPREEQFNSTYRVVSALRIQHQDWTGGKEFKCKVHNEGLPAPIVRTISR TK |
| IgG1b (SEQ ID NO: 18) | X16701 | PPELPGGPSVFIFPPKPKDTLTISGTPEVTCVVVDVGHDDPEVKFSWFVDDVEV NTATTKPREEQFNSTYRVVSALRIQHQDWTGGKEFKCKVHNEGLPAPIVRTISR TK |
| IgG1c (SEQ ID NO: 19) | DQ452014 | PPELPGGPSVFIFPPKPKDILTISGTPEVTCVVVDVGHDDPEVKFSWFVDNVEV NTATTKPREEQFNSTYRVVSALRIQHQDWTGGKEFKCKVHNEGLPAPIVRTISR TK |
| IgG1d (SEQ ID NO: 18) | X62916 | PPELPGGPSVFIFPPKPKDTLTISGTPEVTCVVVDVGHDDPEVKFSWFVDDVEV NTATTKPREEQFNSTYRVVSALRIQHQDWTGGKEFKCKVHNEGLPAPIVRTISR TK |

In one embodiment, the parent antibody comprises or is altered to comprise a hinge region and a CH3 domain is at least 85%, such as at least 90%, at least 95%, at least 98%, at least 99%, or 100% identical to the equivalent portion of a bovine, CH3 domain amino acid sequence (e.g., a bovine IgG1 CH3 domain). Exemplary bovine IgG1 CH3 domains are presented in Table 6.

TABLE 6

| Allotype | Accession ID | Sequence |
|---|---|---|
| IgG1a (SEQ ID NO: 20) | S82409 | GPAREPQVYVLAPPQEELSKSTVSLTCMVTSFYPDYIAVEWQRNGQPESEDKYG TTPPQLDADGSYFLYSRLRVDRNSWQEGDTYTCVVMHEALHNHYTQKSTSKSAG K |

TABLE 6-continued

| Allotype | Accession ID | Sequence |
|---|---|---|
| IgG1b (SEQ ID NO: 21) | X16701 | GPAREPQVYVLAPPQEELSKSTVSLTCMVTSFYPDYIAVEWQRNGQPESEDKYGTTPPQLDADSSYFLYSKLRVDRNSWQEGDTYTCVVMHEALHNHYTQKSTSKSAGK |
| IgG1c (SEQ ID NO: 21) | DQ452014 | GPAREPQVYVLAPPQEELSKSTVSLTCMVTSFYPDYIAVEWQRNGQPESEDKYGTTPPQLDADSSYFLYSKLRVDRNSWQEGDTYTCVVMHEALHNHYTQKSTSKSAGK |
| IgG1d (SEQ ID NO: 21) | X62916 | GPAREPQVYVLAPPQEELSKSTVSLTCMVTSFYPDYIAVEWQRNGQPESEDKYGTTPPQLDADSSYFLYSKLRVDRNSWQEGDTYTCVVMHEALHNHYTQKSTSKSAGK |

In some embodiments, the parent antibody comprises or is altered to comprise a fusion between a VL domain with specific binding to a desired antigen and a bovine CL domain. In a preferred embodiment, the parent antibody contains a CL domain corresponding to the encoded protein from the bovine IGLC1, IGLC2, IGLC3 or IGLC4 loci.

In one embodiment, the recombinant antibodies are capable of surviving digestion and reaching their target antigens in the digestive tract. In another embodiment, the recombinant antibodies are therapeutic antibodies that are bovinized as described herein or variants of existing therapeutic antibodies modified to increase resistance to cleavage by proteases and resist degradation during digestion in the digestive tract of a mammal, such as during human digestion.

In one embodiment, the recombinant parent antibody is specific for a target antigen. In some embodiments, the target antigen is a biological antigen (e.g., a human protein, a human peptide, or other antigenic molecule specific to humans), such as the antigens described further herein. In other embodiments, the target antigen is not a synthetic antigen, such as a dye. In one embodiment, the antibody is not an anti-dansyl antibody. In one embodiment, the recombinant parent antibody is targeted to an antigen not normally present in a ruminant in the absence of immunization of the ruminant with the target antigen. In one embodiment, the recombinant parent antibody is specific for a target antigen that is a protein, peptide, or other antigenic molecule derived from another mammal.

In certain embodiments, the target antigen is a therapeutic target antigen and the bovinized antibody facilitates a therapeutic effect on a subject when administered to the subject.

Table 7 provides a partial list of various therapeutic fusion proteins that are suitable as parent antibodies for the production of the bovinized antibodies described herein.

TABLE 7

| Agent | Vendor | Cell Source |
|---|---|---|
| Monoclonal Antibodies | | |
| Actemra ® Tocilizumab | Genentech Inc. | CHO cells |
| Avastin ® Bevacizumab | Genentech Inc., Hoffmann-La Roche Ltd. | CHO cells |
| Campath ® (US), Mabcampath ® (EU) Alemtuzumab | Genzyme Corp. | CHO cells |
| Herceptin ® Trastuzumab | F. Hoffmann-La Roche Ltd, Genentech Inc. | CHO cells |
| Humira ® Adalimumab | Abbott Laboratories | CHO cells |
| Rituxan ® Rituximab | Genentech | CHO cells |
| Simponi ® Golimumab | Centocor Ortho Biotech Inc., Johnson & Johnson Co., Schering-Plough Corp. | CHO cells |
| Stelara ™ Ustekinumab | Centocor Ortho Biotech Inc. | CHO cells |
| Vectibix ® Panitumumab | Amgen | CHO cells |
| Xolair ® Omalizumab | Genentech Inc., Novartis Pharmaceuticals Corp. Tanox Inc. | CHO cells |
| Zevalin ® Ibritumomab tiuxetan | Biogen Idec., Schering AG | CHO cells |
| Bexxar ® Tositumomab-I31 | GlaxoSmithKline | Hybridoma, mammalian |
| Soliris ® Eculizumab | Alexion Pharmaceuticals, Inc | Murine myeloma cell line |
| ilaris ® Canakinumab | Novartis Pharmaceuticals Corp. | Murine Sp2/0-Ag14 fused hybridoma cell line |
| Mylotarg ® Gemtuzumab ozogamicin | Wyeth Pharmaceuticals | NSO mouse myeloma cells |
| Arzerra ® Ofatumumab | GlaxoSmithKline | NSO mouse myeloma cells |
| Synagis ® Palivizumab | Abbott Laboratories, MedImmune Inc. | NSO mouse myeloma cells |
| Tysabri ® Natalizumab | Élan Pharmaceuticals, Biogen Idec. | NSO mouse myeloma cells |
| Erbitux ® Cetuximab | ImClone Systems Merck & Co., Inc., Bristol-Myers Squibb | Sp2/0 mouse myeloma cells |
| Remicade ® Infliximab | Centocor Ortho Biotech Inc. | Sp2/0 mouse myeloma cells |
| Reopro ® Abciximab | Centocor Ortho Biotech Inc., Eli Lilly & Co. | Sp2/0 mouse myeloma cells |
| Simulect ® Basiliximab | Novartis Pharmaceuticals Corp. | Sp2/0 mouse myeloma cells |
| Zenapax ® Daclizumab | F. Hoffmann-La Roche Ltd., PDL (Protein Design Labs) BioPharma | Sp2/0 mouse myeloma cells |

TABLE 8 provides a non-limiting list of fusion proteins that are suitable parent antibodies for bovinization in accordance with the invention.

| | | |
|---|---|---|
| Amevive ® Alefacept | Astellas Pharma Inc. | CHO cells |
| Arcalyst ® Rilonacept | Regeneron Pharmaceuticals Inc. | CHO cells |
| Enbrel ® Etanercept | Amgen, Wyeth Pharmaceutical | CHO cells |
| Orencia ® Abatacept | Bristol-Myers-Squibb | CHO cells |
| Hormones | | |
| Follistim ® Follitropin beta | Schering-Plough Corp. | CHO cells |
| Gonal-F ® Follitropin alfa | EMD Serono, Inc. | CHO cells |
| Luveris ® Luteinizing hormone | EMD Serono, Inc. | CHO cells |
| OP-1 Putty Osteogenic Protein-1 (BMP-7) | Stryker Biotech | CHO cells |
| Ovidrel ® Choriogonadotropin α | EMD Serono, Inc. | CHO cells |
| Thyrogen ® Thyrotropin alfa | Genzyme Corp | CHO cells |
| Serostim ®, Saizen ®, Zorbtive ™ Somatropin | EMD Serono, Inc. | Murine cell line (mouse C127) |
| Cytokines | | |
| Aranesp ® Darbepoetin alfa | Amgen | CHO cells |
| Avonex ® Interferon beta-1a | Biogen Idec, Inc. | CHO cells |
| Neorecormon ® Epoetin beta | Hoffmann-La Roche Ltd. | CHO cells |
| Procrit ®, Epogen ® Epoetin alfa | Amgen, Centocor Ortho Biotech Inc. | CHO cells |
| Rebif ® Interferon beta-1a | Pfizer, Inc., EMD Serono, Inc. | CHO cells |
| Clotting Factors | | |
| Helixate FS Coagulation factor VIII | ZLB Behring | BHK cells |
| Kogenate FS Coagulation factor VIII | Genentech | BHK cells |
| NovoSeven ®, Coagulation Factor VIIa | Novo Nordisk | BHK cells |
| Advate ® Antihemophilic factor | Baxter International Inc. | CHO cells |
| BeneFIX ® Coagulation Factor IX | Wyeth Pharmaceuticals | CHO cells |
| ReFacto ® Antihemophilic Factor | Wyeth Pharmaceuticals | CHO cells |
| Xyntha ® Coagulation factor VIII | Wyeth Pharmaceuticals | CHO cells |
| Xigris ® Drotrecogin alfa (Activated Protein C) | Eli Lilly & Co. | HEK293 |
| Enzymes | | |
| Activase ®, Cathflo Activase ®, Actilyse ® Alteplase | Genentech, Boehringer Ingelheim Pharma KG | CHO cells |
| Aldurazyme ® Laronidase | Genzyme Corp | CHO cells |
| Cerezyme ® Imiglucerase | Genzyme Corp. | CHO cells |
| Fabrazyme ® agalsidase-β | Genzyme Corp | CHO cells |
| Hylenex ®, Cumulase ® Hyaluronidase | MediCult A/S, MidAtlantic Diagnostics, Inc., Halozyme Baxter Healthcare | CHO cells |
| Myozyme ® Alglucosidase alfa | Genzyme Corp | CHO cells |

TABLE 8-continued provides a non-limiting list of fusion proteins that are suitable parent antibodies for bovinization in accordance with the invention.

| | | |
|---|---|---|
| Naglazyme ® N-acetylgalactosamine 4-sulfatase | BioMarin Pharmaceutical Inc. | CHO cells |
| Pulmozyme ® Human DNase | Genentech, Hoffmann-La Roche Ltd. | CHO cells |
| TNKase ® Tenecteplase | Genentech | CHO cells |
| Elaprase ® Idursulfase | Shire Pharmaceuticals | human cell line (HT-1080) |

Bovinized antibodies can be prepared using standard recombinant technologies. Antibody fragments for example, which contain specific binding sites of the target protein of interest, may be generated by known techniques. For example, such fragments include, but are not limited to, F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., *Science* 1989; 246:1275-81) to allow rapid and easy identification of monoclonal Fab fragments with the desired specificity to the target protein of interest.

Also provided herein are antibodies (bovinized antibodies and fully bovine recombinant monoclonal IgG1 antibodies) which bind to the same epitope on a target of interest as a reference antibody (e.g., a therapeutic antibody), or competes with a reference antibody for binding to a target of interest. Whether a particular antibody binds to the same epitope on a target antigen as a reference antibody, or competes with binding to the same epitope on a target antigen as a reference antibody, can be readily determined by the skilled artisan using art-recognized epitope mapping and competition assays, respectively.

The antibodies described herein (bovinized antibodies and fully bovine recombinant monoclonal IgG1 antibodies) may be used to generate bispecific molecules. For instance, the antibodies can be derivatized or linked to another functional molecule, e.g., another peptide or protein (e.g., another antibody or ligand for a receptor) to generate a bispecific molecule that binds to at least two different binding sites or target molecules using methods known in the art.

In another aspect, provided herein are immunoconjugates comprising the antibodies (bovinized antibodies and fully bovine recombinant monoclonal IgG1 antibodies) described herein conjugated to a therapeutic moiety, e.g., a cytotoxin, drug, or radioisotope. Exemplary cytotoxins include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestostexone, glucocorticoids, procaine, tetracaine, lidocaine, propranolol, and puromycin and analogs or homologs thereof.

Suitable therapeutic agents for forming immunoconjugates include, e.g., akylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), antibiotics (e.g., dactinomycin (formerly actinomycin), bleomycin, mithramycin, and anthramycin (AMC)), antimetabolites (e.g., methotrexate, 6-mercaptopurine, 6-thioguanine, cytarabine, fludarabin, 5-fluorouracil decarbazine), anthracyclines (e.g., daunorubicin (formerly daunomycin) and doxorubicin), and anti-mitotic agents (e.g., vincristine and vinblastine).

The antibodies (bovinized antibodies and fully bovine recombinant monoclonal IgG1 antibodies) described herein can be conjugated to a radioisotope, e.g., iodine-131, yttrium-90 or indium-111, to generate cytotoxic radiopharmaceuticals for treating cancers. The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL, 1"), interleukin-2 ("IL-2"), interleukin-6 ("IL-6"), granulocyte macrophage colony stimulating factor ("GM-CSF"), granulocyte colony stimulating factor ("G-CSF"), or other growth factors. Methods for conjugating therapeutic moieties to antibodies are well known in the art.

In some embodiments, the antibodies described herein are administered systemically. In a preferred embodiment, the antibody is not immunogenic in the subject being treated.

Such antibodies can be designed to avoid increasing the predicted risk for T cell epitopes, for example, as assessed using art-recognized algorithms and databases (see, e.g., Vita et al., *Nucleic Acids Res* 2015; 43:D405-12; Vita et al., *Nucleic Acids Res* 38:D854-62, Nielsen et al., *Protein Sci* 2003; 12:1007-17; Bui et al., *Immunogenetics* 2005; 57:304-14; Lundegaard et al., *J Immunol Methods* 2011; 374:226-34). In certain embodiments, mutations are made in the Fc region of the antibodies described herein to increase resistance to host proteases, as described in, e.g., U.S. Pat. No. 8,871,204, CA2,822,366, and US2013/0011386.

Fully Bovine Recombinant Monoclonal IgG1 Antibodies

Also provided herein are fully bovine recombinant monoclonal IgG1 antibodies and related oral compositions. Such antibodies can be generated by immunizing cattle (calves or mature cows, steers or bulls) with an antigen of interest, using the methods described in Example 11. In certain embodiments, cattle are immunized with DNA encoding the antigen of interest. General methods for immunizing animals with genetic vaccines (e.g., DNA vaccines) are known in the art (see, e.g., U.S. Pat. No. 8,927,508, WO2003/012117, WO2003/048371, WO1997/040839).

In certain embodiments, cattle (e.g., Holstein breed) are injected (e.g., subcutaneously) with the antigen of interest formulated together with an adjuvant. Any art-recognized adjuvant can be used. Suitable adjuvants include, but are not limited to, Emulsigen-D, Carbigen, Quil A, and Seppic ISA. In a preferred embodiment, the adjuvant is Quil A.

In some embodiments, cattle are inoculated with antigen 1, 2, 3, 4, 5, or 6 times, or more, to induce a specific immune response. In some embodiments, inoculations can be performed in 1, 2, 3, 4, or 5 week intervals. In one embodiment, cattle are inoculated 4 times at 2-3 week intervals.

In one embodiment, the antigen for immunization is injected into the area drained by the target superficial lymph node (targeted for harvesting lymphocytes).

In some embodiments, cattle are immunized 1, 2, 3, 4, or 5 days prior to removal of the target lymph nodes for subsequent hybridoma production.

The optimal concentration of target antigen used in the immunizations can be readily determined by the skilled artisan.

In a preferred embodiment, the antigen is TNFα, which is formulated together with Quil A adjuvant.

Once lymph nodes (or the spleen) are harvested from immunized cattle, lymphocytes are isolated and fused with an immortalized cell line using a suitable fusing agent, e.g., polyethylene glycol (PEG), in order to form a hybridoma cell (see, e.g., Goding (1986) Monoclonal Antibodies: Principles and Practice, Academic Press, pp. 59-103). Other suitable methods for generating hybridomas are described, for example, in U.S. Pat. Nos. 5,026,646, 5,087,693, Tucker et al. (Hybridoma 1984; 3:171-6), Kennedy et al., *Journal of General Virology* 1988; 69:3023-32), Srikumaran et al. (*Veterinary Immunology and Immunopathology* 1984; 5:323-42), and Raybould et al. (*American Journal of Veterinary Research* 1985; 46:426-7), and Levings et al. (*Veterinary Immunology and Immunopathology* 2014; 159:58-73).

Immortalized cell lines may be transformed mammalian cells, particularly myeloma cells of rodent, bovine, and human origin. Rat or mouse myeloma cell lines may be used. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or APRT), the culture medium for the hybridomas typically will include hypoxanthine, aminopterin, and thymidine ("HAT medium"), which substances prevent the growth of HGPRT-deficient cells.

Immortalized cell lines suitable for use are those that fuse efficiently, support stable high level expression of antibody by the selected antibody-producing cells, and are sensitive to a medium such as FIAT medium. Preferred immortalized cell lines are murine myeloma lines, which can be obtained, for instance, from the Salk Institute Cell Distribution Center, San Diego, Calif, and the American Type Culture Collection, Manassas, Va.

The medium in which the hybridoma cells are cultured can then be assayed for the presence of monoclonal antibodies directed against the target of interest (e.g., TNF). The binding specificity of monoclonal antibodies produced by the hybridoma cells can be determined by immunoprecipitation or by an in vitro binding assay, such as radioimmunoassay (RIA) or enzyme-linked immunosorbent assay (ELISA). Such techniques and assays are well known in the art. The binding affinity of the monoclonal antibody can be determined by using art-recognized assays, such as Scatchard analysis and Biacore surface plasmon resonance assays.

After the desired hybridoma cells are identified, the clones may be subcloned by limiting dilution procedures and grown by standard methods. Suitable culture media include, for example, Dulbecco's Modified Eagle's Medium and RPMI-1640 medium. Alternatively, the hybridoma cells may be grown in vivo as ascites in a mammal.

In certain embodiments, the hybridoma cells are screened for the secretion of target-specific monoclonal IgG1 antibodies. The antibody isotype can be determined using standard sequencing procedures known in the art.

The fully bovine recombinant monoclonal IgG1 antibodies secreted by the subclones may be isolated or purified from the culture medium or ascites fluid by conventional immunoglobulin purification procedures, such as, protein A-Sepharose, hydroxylapatite chromatography, gel electrophoresis, dialysis, or affinity chromatography.

The monoclonal antibodies purified from hybridoma culture or ascites fluid can also be made using standard recombinant DNA methods known in the art. DNA encoding the bovine monoclonal antibodies can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. Other suitable host cells include fungal cells (*aspergillus*), insect cells yeast cells, bacterial cells, and other art-recognized host cells.

In certain embodiments, fully bovine recombinant monoclonal IgG1 antibodies are generated through art—recognized single B cell sequencing and cloning methods, as described in Example 14. See also, e.g., US2011/0312505, US2012/030855, Murugan et al., *Eur J Immunol* 2015; 45:2698; 700, Liao et al., *J Virol Methods* 2009; 158:171-9; Busse et al., *Eur Immunol* 2014; 44:597-603, the contents of all of which are herein incorporated by reference.

In one embodiment, the fully bovine recombinant monoclonal IgG1 antibodies are formulated with a preservative. In another embodiment, the fully bovine recombinant monoclonal IgG1 antibodies are lyophilized.

Nucleic Acid Molecules

Also provided herein are nucleic acid molecules that encode the bovinized and fully bovine recombinant monoclonal IgG1 antibodies described herein. Once an antibody having increased resistance to proteases is identified, the coding nucleic acid sequence can be identified and isolated using art-recognized techniques.

The nucleic acids may be present in whole cells (e.g., hybridomas, ascites fluid, stable cell lines), in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and may or may not contain intronic sequences. In a certain embodiments, the nucleic acid is a cDNA molecule.

Nucleic acids described herein can be obtained using standard molecular biology techniques. For antibodies expressed by hybridomas, cDNAs encoding the light and heavy chains of the antibody made by the hybridoma can be obtained by standard PCR amplification or cDNA cloning techniques.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region or VL chain can be converted to a full-length heavy chain or light chain gene by operatively linking the VH-encoding DNA or VL-encoding DNA to another DNA molecule encoding heavy chain or light chain constant regions. Nucleotide sequences for these regions are known in the art, and DNA fragments encompassing these regions can be obtained by standard PCR amplification. Also provided are nucleic acid molecules with conservative substitutions (i.e., substitutions that do not alter the resulting amino acid sequence upon translation of nucleic acid molecule), e.g., for codon optimization.

Methods of Production

Also provided herein are host cell expression systems for producing the bovinized and fully bovine recombinant monoclonal antibodies described herein. Such host cell expression systems may be engineered to comprise a recombinant nucleic acid molecule encoding the bovinized antibodies or bovine monoclonal antibodies described herein, operatively linked to an art-recognized regulatory sequences, which include promoters, enhancers, and other expression control elements (e.g., polyadenylation signals) that control the transcription or translation of the antibody chain genes. Exemplary regulatory sequences are described, for example, in Goeddel (Gene Expression Technology. Methods in Enzymology 185, Academic Press, San Diego, CA (1990)). It will be appreciated by those skilled in the art that the design of the expression vector, including the selection of regulatory sequences, may depend on factors such as the choice of host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, recombinant expression vectors may include additional sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.), and allows for the establishment of stable cell lines (which can be stored for later use). Typically, the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

To express heavy and light chains of antibodies, expression vector(s) encoding the heavy and light chains is transfected into a host cell using art-recognized techniques. Transfection, as used herein, is intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

In general, any type of cultured cell line can be used as a background to engineer the host cell lines of the present invention including but not limited to CHO cells (e.g., dhfr-CHO cells used with a DHFR selectable marker), BHK cells, NS0 myeloma cells, COS cells, SP2/0 cells, YO myeloma cells, P3X63 mouse myeloma cells, PER cells, PER.C6 cells or hybridoma cells, yeast cells (e.g., *Pichia pastoris, S. cerevisiae*), bacterial cells (e.g., *E. coli*), fungal cells (e.g., *Aspergillus niger, Aspergillus niger* var. *awamori*), insect cells (SF9, SF21, High Five™), or plant cells (e.g., tobacco). In certain embodiments, host cell systems capable of glycosylating the recombinantly produced antibody are used. In further embodiments, these host cells are used for large-scale production of antibodies. Methods for large-scale production of antibodies are also known in the art (and are described in Example 19), e.g., in *Aspergillus* (Ward et al., *Appl Environ Microb* 2004; 70:2567-576), yeast (e.g., *Pichia pastoris, S. cerevisiae*), mammalian cells (Sinacore et al., *Biotechnol Bioeng* 1996; 52: 518-28; Li et al. *mAbs* 2010; 2:466-77; Wurm et al., *Nat Biotechnol* 2004; 22:1393-8; Birch et al., *Adv Drug Delivery Rev* 2006; 58:671-85; Jayapal et al., *Chem Eng Prog* 2007; 103:40-7; Mammalian Cell Culture for Biopharmacuetical Production. Chapter 12 of Manual of Industrial Microbiology and Biotechnology, 3$^{rd}$ Edition. pp. 157-178 (2010)), and insect cells (Liang et al., *J Immunol Methods* 2001; 247; 119-30; Tan and Lam, Biotechnol Appl Biochem 1999; 30:59-64; U.S. Pat. No. 7,795,015). In certain embodiments, where purity of the antibody is not absolutely essential, e.g., for oral administration, fungal cells (e.g., *Aspergillus* species) are suitable for rapid gram-scale production of antibodies.

For methods of producing the antibodies described herein, stable expression is generally preferred to transient expression because it typically achieves more reproducible results and also is more amenable to large scale production. Rather than using expression vectors which contain viral origins of replication, host cells can be transformed with the respective coding nucleic acids controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then switched to a selective media. The selectable marker in the recombinant plasmid confers resistance to the selection and allows selection of cells which have stably integrated the plasmid into their chromosomes and grow to form foci which in turn can be cloned and expanded into cell lines.

When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Compositions

Provided herein are compositions (e.g., oral pharmaceutical compositions) comprising the bovinized and fully bovine recombinant monoclonal antibodies described herein.

Pharmaceutical compositions described herein comprise a therapeutically effective amount of a bovinized and/or fully bovine recombinant monoclonal antibody, optionally formulated together with one or more pharmaceutically acceptable carriers or excipients.

Accordingly, in some embodiments, provided herein are pharmaceutical compositions comprising or consisting essentially of bovinized and/or fully bovine recombinant monoclonal antibodies, and optionally a carrier (e.g., a pharmaceutically acceptable carrier and/or preservative). In other embodiments, the composition is substantially free, e.g., at least 90%, 95%, or 99% free, from other (i.e., non-bovine IgG1 or bovinized) antibodies. In particular embodiments, the pharmaceutical composition is formulated for oral administration.

For treating disorders of the oral cavity, the compositions can be delivered in a mouthwash, rinse, paste, gel, or other suitable formulation. The antibodies described herein can be delivered using formulations designed to increase the contact between the active antibody and the mucosal surface, such as buccal patches, buccal tape, mucoadhesive films, sublingual tablets, lozenges, wafers, chewable tablets, quick or fast dissolving tablets, effervescent tablets, or a buccal or sublingual solid. For treating disorders of the digestive tract, the antibody can be delivered by oral ingestion in the form of a capsule, tablet, liquid formulation or similar form designed to introduce drug to the digestive tract. Alternatively, antibody may be administered by suppository or enema for delivery to the lower digestive tract. Such formulations are well known to those skilled in the art. In certain embodiments, the antibody is administered prior to and/or concurrently with hydrolase inhibitors, antibiotics, and/or protease inhibitors.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are water, sterile water, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical composition may also include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Compositions for rectal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound. In one embodiment, compositions for rectal administration are in the form of an enema.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Although the antibodies described herein exhibit enhanced stability to intestinal degradation, it may be desirable under some conditions to provide additional levels of protection against intestinal degradation. If this is desired, there are many options for enteric coating (see for example U.S. Pat. Nos. 4,330,338 and 4,518,433). In one embodiment, enteric coatings take advantage of the post-intestinal change in pH to dissolve a film coating and release the active ingredient. Coatings and formulations have been developed to deliver protein therapeutics to the small intestine and these approaches could be adapted for the delivery of an antibody of the invention. For example, an enteric-coated form of insulin has been developed for oral delivery (Toorisaka et al., *J Control Release* 2005; 107:91-6). Additional options for enteric coating are described in, e.g., U.S. Pat. Nos. 5,225,202 and 6,306,900, and US2008/0020041. In addition, the solid dosage forms of tablets, dragees, capsules, pills, and granules can be prepared with other coatings and shells well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. In a preferred embodiment, the antibody is formulated in enterically-coated microparticles delivered as a liquid suspension. In another preferred embodiment, the antibody is formulated in enterically-coated microparticles delivered as a capsule.

The compositions (e.g., oral pharmaceutical compositions) described herein may also contain wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions.

In some embodiments, the pharmaceutical compositions comprising the antibodies described herein also include a preservative.

Effective doses will vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the timing of delivery of the compound relative to food intake; the duration of the treatment; drugs used in combination or contemporaneously with the specific compound employed; and like factors well known in the medical arts.

Particular embodiments of the present invention involve administering a pharmaceutical composition comprising an antibody of the invention at a dosage of from about 1 mg per day to about 1 g/day, more preferably from about 10 mg/day to about 500 mg/day, and most preferably from about 20 mg/day to about 100 mg/day, to a subject. In one embodiment, a polyclonal antibody preparation is administered at a dosage of antibody from about 100 mg to about 50 g/day, more preferably from about 500 mg/day to about 10 g/day, and most preferably from about 1 g/day to about 5 g/day, to a subject, wherein the polyclonal antibody preparation has not been enriched for antibodies specific for the target antigen.

Treatment regimens include administering an antibody composition of the invention one time per day, two times per day, or three or more times per day, to treat a medical disorder disclosed herein. In one embodiment, an antibody composition of the invention is administered four times per day, 6 times per day or 8 times per day to treat a medical disorder disclosed herein. In one embodiment, an antibody composition of the invention is administered one time per week, two times per week, or three or more times per week, to treat a medical disorder disclosed herein.

The methods and compositions of the invention include the use of an antibody of the invention in combination with one or more additional therapeutic agents useful in treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which an antibody of the invention is administered at least once during a course of treatment that involves administering at least one other therapeutic agent to the patient.

An antibody to be used for in vivo administration must be sterile. This is readily accomplished by filtration through sterile filtration membranes, prior to or following lyophilization and reconstitution. The formulation ordinarily will be stored in lyophilized form, as spray dried particles or in solution.

Methods of Use

Topical administration of antibodies to the digestive tract is challenging because the digestive tract degrades and digests the topically applied antibodies. Enzymes in the oral cavity, primarily derived from commensal and pathogenic bacteria living within the oral cavity, degrade antibody in the oral cavity. In the stomach, the low pH and the protease pepsin degrade ingested immunoglobulin. In the small intestine, the enzymes trypsin and chymotrypsin, among others, degrade ingested antibody. In the large intestine, bacterially-derived proteases degrade ingested antibody. Antibodies with improved stability in the oral cavity and improved stability to gastric and intestinal digestion (e.g., the bovinized and fully bovine recombinant monoclonal antibodies described herein) have numerous in vivo applications, for example, in the treatment of diseases involving the digestive tract (e.g., inflammatory bowel disease).

The antibodies described herein may be used in the oral cavity for the prevention of dental caries and for the treatment or prevention of periodontal disease as described in U.S. Pat. Nos. 5,759,544; 4,689,221; 4,324,782; 4,693,888; 4,725,428; 6,143,330; 5,240,704 and for the control of microorganisms, including bacteria, protozoa, parasites, viruses, and fungi, or for the control of inflammation through the use of antibodies specific for cytokines or chemokines, or receptors for cytokines or chemokines. Bovinized and fully bovine recombinant monoclonal antibodies used in the oral cavity may be specific for receptors or other antigens expressed on the apical surface of the oral cavity, against receptors or other antigens expressed on the basolateral surface of the mucosal barrier of the oral cavity, or against receptors or other antigens expressed in the mucosa, submucosa, or any other region of the body accessible to topically applied antibody. Such antibodies may be used for the treatment of infections of the oral cavity or diseases of the oral cavity, including but not limited to mucositis, cancers of the oral cavity, nicotinic stomatitis, leukoplakia, hairy tongue, recurrent aphthous stomatitis, geographic tongue, denture stomatitis, gastroesophageal reflux, eosinophilic esophagitis, and lichen planus. The antibodies may also be applied topically to the oral cavity as a diagnostic reagent as described in U.S. Pat. No. 7,175,430.

Many of the proteases present in the oral cavity are of bacterial origin. In one embodiment, a topical antibiotic is administered to the oral cavity prior to topical administration of antibody. In another embodiment, protease inhibitors are administered to the oral cavity prior to and/or concurrently with topical administration of antibody. Microbes in the oral cavity also produce hydrolases that remove carbohydrate from antibody, thus making it more susceptible to proteolytic degradation. Accordingly, in one embodiment, hydrolase inhibitors are administered to the oral cavity prior to and/or concurrently with topical administration of antibody. Antibiotics, protease inhibitors, and hydrolase inhibitors may be given in combination.

The antibodies described herein may be used in the GI tract for the treatment or prevention of diseases, including but not limited to bacterial, viral, or parasitic infections of the gastrointestinal tract, cancers of the gastrointestinal tract, and inflammation of the gastrointestinal tract as a result of injury, surgery, radiation, infection, or autoimmune disease.

The antibodies described herein are useful in the modulation of apical receptors in the digestive tract, including nutrient receptors, nutrient transporters, pattern recognition receptors, chemokine receptors, cytokine receptors, bile salt transporters, inorganic ion transporters, mineral transporters, peptidases, saccharases, and growth factor receptors.

The antibodies described herein are useful in the treatment or prevention of food allergies or intolerances, including celiac disease. In one embodiment, the antibody is specific for gluten or gluten derived peptide and is used to treat celiac disease.

The antibodies described herein are useful in modulating the function of receptors, cytokines, chemokines, or similar mediators expressed in the lumen of the digestive tract or, in the case of a disease or condition that renders the digestive tract permeable to topically applied antibodies, in modulating the function of receptors, cytokines, chemokines, or similar mediators expressed in the portions of the body below the mucosal barrier that are accessible to the antibody. The antibodies described herein are also useful in the treatment of immunodeficiency.

The antibodies described herein have minimal activity outside of the digestive tract and minimize the induction of a neutralizing immune response. The therapeutic compositions comprise antibodies that are delivered topically to the luminal face of the digestive tract. The antibodies described herein may be administered topically to the digestive tract by, for example, oral administration, rectal administration, and all forms of administration to the oral cavity such as by buccal, mucoadhesive films and the like. The antibodies may cross the mucosal barrier of the digestive tract to enter the submucosal space to interact with their targets, but do not enter the systemic circulation at levels sufficient to be clinically relevant.

In certain embodiments, the antibodies described herein bind to antigens associated with disease pathology or the treatment of disease. For example, the antibody compositions described herein may be directed at biological targets expressed on or near the luminal surface of the digestive tract as well as below the mucosal barrier such as on the basal side of the epithelium, targets expressed in the submucosa, target expressed in the lateral intercellular space, and targets expressed in the lamina propria.

In some embodiments, antibody compositions described herein cross the mucosal barrier of a patient as a result of pre-existing damage to the mucosal barrier. In one embodiment, the mucosal barrier of the digestive tract may be breached or compromised through mechanical trauma, including but not limited to dental and oral wounds, esophageal wounds, or surgically induced trauma due to partial gut resection, jejunostomy, ileostomy, colostomy or other surgical procedures. The mucosal barrier of the digestive tract may also be breached by ischemia or reperfusion injury. The mucosal barrier of the digestive tract may also be breached by damage caused by cancer chemotherapy, cancer radiation therapy, or high dose radiation exposure outside of a therapeutic setting. The mucosal barrier of the digestive tract may be breached or compromised through gross inflammation and/or ulceration, including but not limited to periodontal disease, aphthous stomatitis, bacterial, viral, fungal or parasitic infections of the digestive tract, peptic ulcers, ulcers associated with stress or *H. pylori* infection, damage caused by esophageal reflux, inflammatory bowel disease, damage caused by cancer of the digestive tract, food intolerance, including celiac disease, or ulcers induced by non-steroidal anti-inflammatory drugs (NSAIDs) or other ingested or systemically delivered drugs. The mucosal barrier of the digestive tract may also be breached by genetically-determined pre-disposition to increased intestinal permeability.

In some embodiments, the antibodies described herein cross the mucosal barrier as a result of specific aspects of the formulation that facilitate the transit of antibody across the mucosal barrier. Exemplary permeation enhancers include but are not limited to chitosan, poly-L-arginine and Carbopol.

In some embodiments, the antibodies described herein are loaded onto inflammation-targeting hydrogels (IT-hydrogel) to reduce systemic exposure and target antibodies to the inflamed colon of patients with inflammatory bowel disease (Crohn's disease and ulcerative colitis) (see Zhang et al., *Sci Transl Med* 2015; 7:300ra128). Also suitable for targeting the antibodies described herein to inflamed tissue in the colon are nanodelivery systems, for example, those described in Hua et al., *Nanomedicine: Nanotechnology, Biology, and Medicine* 2015; 11:1117-32.

In some embodiments, the antibodies described herein are specific for target antigens such as cytokines that regulate inflammation, including but not limited to TNF, TNF-kappa, IFN-gamma, IL-1 beta, IL-2, IL-6, IL-12, IL-13, IL-15, IL-17, IL-18, IL-21, IL-23, IL27, IL-32, IL-33, and IL-35. In other embodiments, the antibodies described herein are specific for target antigens that are enteric neurotransmitters or their receptors or transporters expressed below the mucosal barrier of the digestive tract, including receptors for serotonin that are expressed in the gut (5-HT1A, 5-HT1B/B, 5-HT2A, 5-HT2B, 5-HT3, 5-HT4, 5-HT7, 5-HT1P). In further embodiments, the antibodies described herein re specific for target antigens that are peptides that regulate food intake or the receptors for such peptides. Such peptides include but are not limited to CCK, GLP1, GIP, oxyntomodulin, PYY3-36, enterostatin, APOAIV, PP, amylin, GRP and NMB, gastric leptin, and ghrelin. In other embodiments, the antibodies described herein are specific for target antigens that are biological targets that enhance wound healing, that alter the function of tight junctions such as occludin, claudins, junctional adhesion molecule, ZO-1, E-cadherin, coxackie adenovirus receptor, and serine proteases such as elastase that are involved in the release of claudins.

In one embodiment, the antibodies described herein are specific for EGFR on colorectal cancer cells.

In another embodiment, the antibodies described herein are specific for Toll-like receptors expressed on the basolateral face of mucosal epithelial cells, and are applied to the mucosa of the digestive tract of a patient with an intestinal inflammatory disease.

In one embodiment, the antibodies described herein are specific for target antigens that are apical intestinal receptors. "Apical intestinal receptors" as used herein are endogenous transmembrane proteins, expressed in the cell membrane of cells facing the luminal side of the intestinal tract. Classes of apical intestinal receptors include but are not limited to: nutrient receptors and transporters (including sugar receptors and transporters, taste receptors, amino acid transporters, and free fatty acid receptors); pattern recognition receptors (including the Toll-like receptors); chemokine and cytokine receptors; bile salt transporters; transporters for calcium iron, and other ions and minerals; peptidases; disaccharidases; growth factor receptors (including epidermal growth factor receptor) and proteins expressed on the surface of cancerous cells in the GI tract. Apical intestinal receptors may be expressed in the stomach, the small intestine or the colon.

In a preferred embodiment, the antibody is specific for tumor necrosis factor-alpha (TNF). In some embodiments, compositions comprising such anti-TNF antibodies are suitable for use in the treatment of inflammation, and particularly inflammatory bowel disease, which includes Crohn's disease and ulcerative colitis.

In some embodiments, compositions comprising anti-TNF antibodies are suitable for use in the treatment of oral or intestinal mucositis. The mucositis may, for example, be caused by radiation therapy, chemotherapy or any combination thereof. Mucositis may also be caused by exposure to high doses of radiation, including total body irradiation, outside of the context of radiation therapy. Chemotherapeutic agents which may induce mucositis when used alone or in combination include, but are not limited to, platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide, and doxorubicin. Additional agents include inhibitors of mTOR (mammalian target of rapamycin), including but not limited to rapamycin, everolimus, temsirolimus, and deforolimus. In one embodiment, compositions comprising the anti-TNF antibodies are suitable for use in the treatment of recurrent aphthous stomatitis, eosinophilic esophagitis, eosinophilic gastritis, and other conditions involving hypereosinophilic activity in a part of the gastrointestinal tract. The compositions may be administered topically, for example, to the oral cavity to treat oral mucositis and aphthous stomatitis, or orally or rectally to the digestive tract, for example, to treat intestinal mucositis.

In one embodiment, for the treatment of aphthous stomatitis (RAS), the antibodies described herein can be administered at the earliest manifestation of an ulcer. Alternatively, the antibodies can be administered on a regular basis throughout the course of manifestation of the ulcer. Alternatively, the antibodies can be administered on a regular basis to prevent the recurrence of ulcer formation. In a preferred embodiment, provided herein is a method of treating recurrent aphthous stomatitis (RAS) in a patient comprising administering to the patient by topical application to the oral cavity a therapeutically effective amount of a composition comprising an antibody specific for TNF (an anti-TNF antibody). In one embodiment, the anti-TNF antibody is a bovinized or fully bovine recombinant monoclonal antibody, as described herein. In one embodiment, the anti-TNF antibody is an antibody with enhanced mucosal permeability. In another embodiment anti-TNF antibody is administered topically to the oral cavity as described herein.

In some embodiments, the anti-TNF antibodies are co-administered with additional therapeutic agents to treat, e.g., inflammatory bowel disease. Exemplary agents suitable for co-administration include, but are not limited to, oral steriods, IFN-β, budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; CDP-571/BAY-10-3356 (humanized anti-TNF antibody; Celltech/Bayer); 75 kdTNFR-IgG (75 kD TNF receptor-IgG fusion protein; Immunex; see e.g., *Arthritis & Rheumatism* 1994; 37:5295; *J Invest Med* 1996; 44:235A); 55 kdTNFR-IgG (55 kD TNF receptor-IgG fusion protein; Hoffmann-LaRoche); interleukin-10 (SCH 52000; Schering Plough); IL-4; IL-10 and/or IL-4 agonists (e.g., agonist antibodies); interleukin-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of Platelet Activating Factor (PAF); ciprofloxacin; and lignocaine.

Additional potential co-therapeutic agents suitable for treating TNF modulated disease (e.g. IBD) are commercially available or are currently in clinical development and include the following: 5-ASA (generic); MMX Mesalazine (Cosmo); MMX Budesonide (Cosmo); MMX LMW Heparin (Cosmo); ER Mesalazine (Salix); Azathioprine (generic); 6-mercaptopurine; Infliximab (Centocor, J&J); Adalimumab (Abbott); Certolizumab pegol (UCB); Atrosab (Baliopharma); Natalizumab (Elan); Golimumab (Centocor J&J); Dersalazine (Palau); HMPL-004 (Hutchinson Medi Pharma); Ozoralizumab (Ablynx); TNF-α Kinoid (Neovacs); Apilimod (Synta); Ustekinumab (Centocor J&J); Briakinumab (Abbott); SCH-900222 (Schering Plough); FM202 and FM303; MP-196; Basiliximab (Cerimon); Daclizumab (Roche); Fontolizumab (PDL); C326 (Avidia); Sirukumab (Centocor J&J); Olokizumab (UCB); Sarilumab (Centocor J&J); BMS-945429 (Alder); Tocilizumab (Chugai); Anrukinzumab (Wyeth); QAX567 (Novartis); GSK1070806 (GSK); PF-05230900 (Pfizer) Vidofludimus (4SC); Tofacitinib (Pfizer); Visilizumab (PDL); Rituximab (Genentech); Abatacept (BMS); Filgrastim (Amgen); Sargramostim (Immunex, Amgen); Vedolizumab (Takeda); Etrolizumab (Genentech); AJM-300 (Ajinimoto); ASP-2002 (Mitsubishi); Alicaforsen (Isis); PF-547659 (Pfizer); CCX282 (GSK1605786); Remestemcel-L (Osiris); PDA-001 (Celgene); OvaSave (TxCell); Secukinumab; MDX-1100 (Medarex); Tetomilast (Otsuka); LT-02 (Lipid Therapeutics); ozanimod (Receptos/Celgene); apremilast (Celgene); bertilumumab (Immune Sciences); abrilumab (AstraZeneca); ABT-494 (AbbVie); BI655066 (Boehringer Ingelheim); Mongersen (Celgene); MT-1303 (Mitsubishi Tanabe); and PF-00547659 (Pfizer).

In one embodiment, antibodies delivered to the digestive tract that are specific for soluble cytokines reduce levels of those cytokines in the digestive tract, but not in the systemic circulation. Levels of cytokine can be determined by direct measurement of the cytokine or by analysis of a surrogate marker that responds to the cytokine. In one aspect, antibodies delivered to the digestive tract that are specific for soluble cytokines reduce levels of those cytokines in both the digestive tract and systemic circulation.

In one embodiment, antibodies delivered to the digestive tract that have clinical benefit do not induce an antibody response to the administered antibody that is sufficient to inhibit the response to subsequent doses of the antibody or to cause an injurious response to subsequent doses of the antibody.

In another embodiment, the lack of an induced antibody response is seen following maintenance therapy. In a further embodiment, the lack of an induced antibody response is seen following episodic dosing. The antibody response can be measured by direct measurement of antibody specific for the therapeutic antibody or by assessment of the physiological response to repeated doses of the therapeutic antibody.

In a preferred embodiment, fewer than 2% of patients develop antibodies to the therapeutic antibodies of the invention after exposure to 3 or more doses of therapeutic antibody. In another preferred embodiment, administration of 3 or more doses of the antibody does not lower the efficacy of the antibody. In one embodiment, the efficacy of the antibody is not diminished after administration of 1, 2, 3 or more doses over a period of about 1 month from the date of first administration of the antibody, and preferably over a period of about 6 months from the date of the first administration of the antibody, more preferably over a period of about 1 year from first administration of the antibody, and even more preferably over a period of about 10 years from first administration of the antibody.

Measurements of the antibody response to the therapeutic antibody (TA) can be accomplished using standard assays as are known in the prior art, such as RIA and solid phase RIA. Assays for assessing the antibody response to a therapeutic antibody can be adapted to the specific situation and the methods and considerations are well understood (Gorovits, *The AAPS Journal*, Vol. 11, No. 1, March 2009). For assaying antibody responses to the antibodies described herein, a direct comparison of the pretreatment and post-treatment sample results for a given patient is preferred. A patient is defined as having an induced antibody response against the therapeutic antibody if the levels of anti-TA antibody significantly increase during the course of treatment with the therapeutic antibody. For therapeutic antibodies where preexisting antibody responses are not detected, a patient is defined as having an induced antibody response against the therapeutic antibody if the antibody response is greater than two-fold above background.

In addition to the digestive tract, the antibodies described herein may also be applied to other tissues with mucosal barriers, including the urogenital system and the respiratory system. The antibodies described herein may also be applied to other tissues with an epithelial system, including the eye and the skin.

Kits

Also within the scope of the invention are kits comprising the antibody compositions (pharmaceutical compositions) described herein (e.g., bovinized antibodies, fully bovine recombinant monoclonal antibodies, bispecific antibodies, or immunoconjugates) and instructions for use. In some embodiments, the kit further contains at least one additional reagent. Kits typically include a label indicating the intended use of the contents of the kit. The term label includes any writing, or recorded material supplied on or with the kit, or which otherwise accompanies the kit.

The present disclosure is further illustrated by the following examples, which should not be construed as further limiting. The contents of all figures and all references, Genbank sequences, and patents and published patent applications cited throughout this application are expressly incorporated herein by reference.

EXAMPLES

Example 1—Bovine Colostral Antibodies are Resistant to Intestinal Digestion

AVX-470 is a bovine colostral polyclonal antibody that binds to human tumor necrosis factor (TNF). Patients with ulcerative colitis (UC) were administered AVX-470 in a delayed-release, enteric-coated capsule formulation to evaluate the presence of AVX-470 in stool using a sandwich ELISA assay specific for bovine immunoglobulin (Ig).

Approximately 1 g of fecal sample (0.8 to 1.2 g) was added to 8 mL Extraction Buffer Solution (PBS with a protease inhibitor cocktail). Bovine Ig concentrations in the samples were analyzed using a colorimetric sandwich ELISA. Microtiter plates were coated with a commercially sourced polyclonal sheep anti-bovine IgG (H+L) antibody (Bethyl Laboratories, cat #A10-115A) as the capture antibody and incubated for 1.5 hours. The plate was washed and blocked with PBS-Tween 0.05% (PBST). After blocking, wells were washed, and stool samples at two different dilutions and bovine Ig standards from Bovine Reference Serum (BRS) were added in triplicate to the plate. All samples were tested with no further dilution after homogenization and at a 1:5 dilution after homogenization. After an hour, the plate was washed, and a polyclonal sheep anti-bovine Ig (H+L) antibody coupled to horseradish peroxidase (HRP) (Bethyl Laboratories, cat #A10-115P) was added for another hour-long incubation. The plate was washed again, and TMB chromogenic substrate was added to all wells. The reaction was stopped after fifteen minutes by adding diluted sulfuric acid. In the presence of bovine Ig, the wells turned blue. The optical densities (OD) were read on an Epoch Biotek Micro-plate reader with Gen5 software (Winooski, VT) at a 450 nm wavelength.

Bovine Ig was detected in six out of 32 (19%) pre-dose stool samples. An increased number of stool samples collected from patients at the end of the study, a total of 15 out of 32 (47%), were positive for bovine Ig after 28 days of dosing. Three of eight (38%) patients who received low dose AVX-470 (0.2 g/d) were positive for bovine Ig in stool, which was equivalent to the number of positive samples in the placebo group. In patients who received 1.6 g/d, six of ten (60%) stool samples were positive for bovine Ig. In the highest dose group (3.5 g/d) four of the six (67%) stool samples had detectable bovine Ig. Thus, there was a dose-dependent increase in the frequency of detectable bovine Ig in stool.

All samples were analyzed for TNF binding by direct ELISA. ELISA plates were coated with commercially available recombinant human TNF (Cell Sciences: Canton, MA, cat #CRT IOOC) at a concentration of 100 ng/well. After a one hour incubation at room temperature, ELISA plates were washed and blocked with SuperBlock™ (blocking buffer containing a single purified non-relevant protein formulated in phosphate-buffered saline (PBS): ThermoFisher, cat #37515). After an additional wash step, serial dilutions of AVX-470 (used as a positive control) or stool samples diluted at both 1:5 and 1:25 were added to ELISA plates. AVX-470 and stool samples were incubated at room temperature for one hour. After washing the plate, a polyclonal sheep anti-bovine Ig (H+L) antibody coupled to horseradish peroxidase (HRP) (Bethyl Laboratories, cat #A I0-115P) was added for another hour-long incubation. After a final wash step, TMB chromogenic substrate was added to all wells. The reaction was stopped after fifteen minutes by adding diluted sulfuric acid. The optical densities (OD) were read on an Epoch Biotek Micro-plate reader at a 450 nm wavelength and results were analyzed using the Gen5 software (Winooski, VT).

TNF binding activity was associated with bovine Ig was detected in an ELISA assay in the three stool samples with the highest levels of bovine Ig, and TNF binding activity was absent from all placebo and pre-dose samples. This demonstrates the presence of active AVX-470 in stool and confirms intestinal stability of AVX-470, and more generally that bovine colostral antibodies are resistant to intestinal digestion.

Example 2—Pancreatin Digestion of AVX-470 Compared to Human IgG and Infliximab The susceptibility of AVX-470 (a polyclonal bovine colostral antibody) to digestion by pancreatin was compared with that of human serum IgG1 (Athens Research &Technology cat #16-16-090707-1) and infliximab (a recombinant human-mouse chimeric antibody specific for human TNF).

Solutions for human IgG1, infliximab, and AVX-470 were diluted and 5 mg/mL pancreatin in simulated intestinal fluid (SIF) was prepared. AVX-470, Infliximab and Human IgG1 were added to tubes containing SIF and various points were selected to stop the reaction with Protease Inhibitor (Lot #P8340-5 mL, Sigma Aldrich). The pancreatin:substrate ratio was 10:1.

For reducing gels, 7.35 µL mixture of SDS (4×) (5.25 µL)+DTT (10×) (2.1 µL) was added. Samples were heat treated for 10 minutes at 95° C. Gels were run at 180 volts for 50 minutes, then stained with the EZBlue Commassie kit (Sigma-Aldrich). The two most prominent protein bands in these samples have apparent molecular weights of 50 kDa (corresponding to the IgG heavy chain) and 23 kDa (IgG light chain). The intensity of the 50 kDa (heavy chain) band was quantified with ImageJ software (NIH) and plotted as a function of incubation time.

As shown in FIGS. 1-4, AVX-470 was more resistant to digestion with pancreatin compared to human IgG and infliximab.

Antigen-Binding Analysis of Proteolysis Reactions by ELISA

The pancreatin digest samples described above were assessed for antigen-binding activity by ELISA. ELISA plates were coated with 10 µg/mL recombinant human TNF and blocked with SuperBlock. Samples were applied to selected wells at dilutions of either 1:10 and 1:20 (AVX-470) or 1:100,000 and 1:200,000 (infliximab) in PBS+0.05% polysorbate 20+2% SuperBlock. Reference standards of undigested AVX-470 or infliximab were added to separate wells. The samples and standards were allowed to bind to the plate for 1 hour. The plates were then washed, probed with either HRP-rabbit anti-bovine IgG (H+L) or HRP-mouse anti-human IgG secondary antibody. The plates were incubated for 1 hour, washed, and probed with TMB substrate to detect bound antibody.

Figure 5:
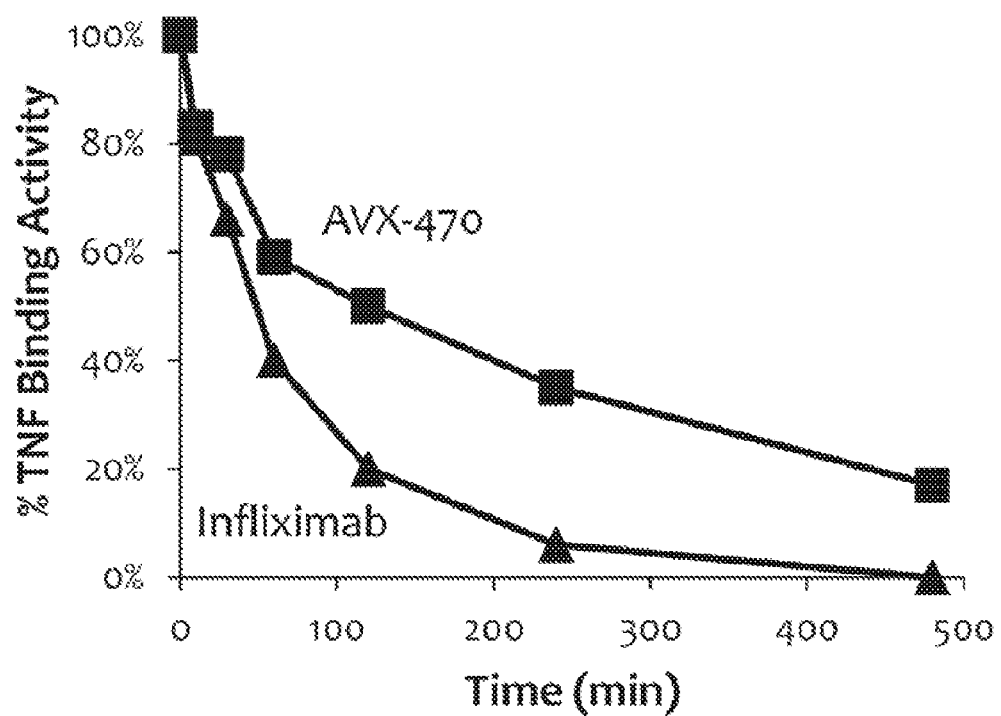
FIG. 5 is a line graph plotting the TNF-binding activity of AVX-470 and infliximab after pancreatin digestion for the indicated durations.

Compared to the TNF-binding activity of the colostral anti-TNF antibody (AVX-470), the TNF-binding activity of infliximab declined rapidly upon incubation with pancreatin (FIG. 5).

Figure 6:
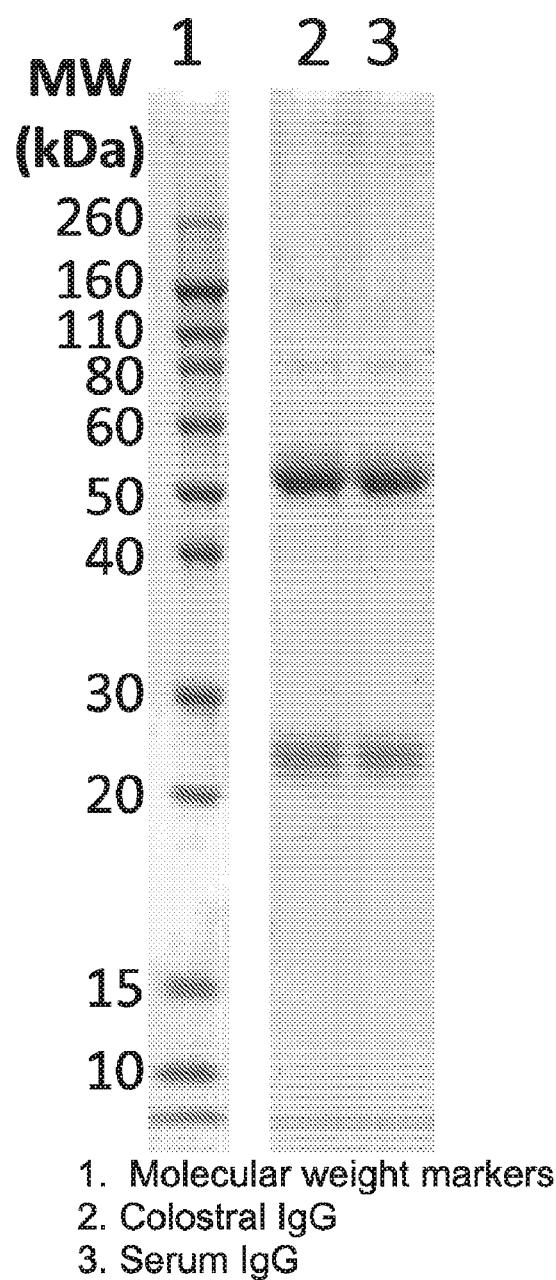
FIG. 6 is a SDS-PAGE analysis of purified colostral and serum IgG.

Example 3—Pancreatin Digests of Serum, Milk, and Colostral Bovine IgG from the Same Cow Results from Example 2 demonstrated that human IgG and inflixmab exhibit higher susceptibility to protease digestion than AVX-470, suggesting that molecular differences exist between these antibodies that restrict proteolysis of the bovine colostral antibody. To further determine the characteristics of colostral antibodies that may confer stability against proteases, a series of experiments were performed with bovine IgG from colostrum, milk, and serum. All IgG samples were purified by Protein G affinity chromatography from bodily fluids of cows that had been immunized with recombinant human TNF in the final trimester of pregnancy. Serum IgG was purified from a serum sample collected on the day of parturition. Colostral IgG was isolated from the first milking taken on the day of parturition. Milk IgG was purified from pooled milk samples taken 12-30 days post-parturition. Purified colostral IgG and serum IgG samples subjected to SDS-PAGE are shown in FIG. 6.

0.4 mg/mL IgG solutions were prepared in simulated intestinal fluid (SIF). Samples were pre-warmed to 37° C., then combined with porcine pancreatin as follows:
Mix: 1260 µL 0.4 mg/mL IgG
140 µL 10 mg/mL pancreatin in SIF
At each time point, the reaction mixture was combined with protease inhibitor:
Mix: 150 µL reaction mix
3 µL protease inhibitor cocktail
The following time points were collected for each sample:

TABLE 9

| Aliquot | Incubation time |
| --- | --- |
| 1 | 1 minute |
| 2 | 22 minutes |
| 3 | 52 minutes |
| 4 | 1 hour, 47 minutes |
| 5 | 4 hours, 17 minutes |
| 6 | 10 hours, 53 minutes |
| 7 | 23 hours, 20 minutes |

Samples were prepared for SDS-PAGE analysis as follows:
SDS Load Mix:
528 µL water
330 µL 4×LDS buffer
132 µL 10×DTT
Mix: 10 µL sample
30 µL SDS Load Mix
Samples were heated to 95° C. for 15 minutes, then spun briefly to collect condensate at the top of each tube. 10 µL of each sample was loaded onto 12% acrylamide gels (Novex) and electrophoresed for 100 minutes at 120 V. The gels were stained with EZ-Blue following the kit instructions. The two most prominent protein bands in these samples have apparent molecular weights of 50 kDa (corresponding to the IgG heavy chain) and 23 kDa (IgG light chain). The intensity of the 50 kDa (heavy chain) band was quantified with ImageJ software (NIH) and plotted as a function of incubation time.

Figure 7:
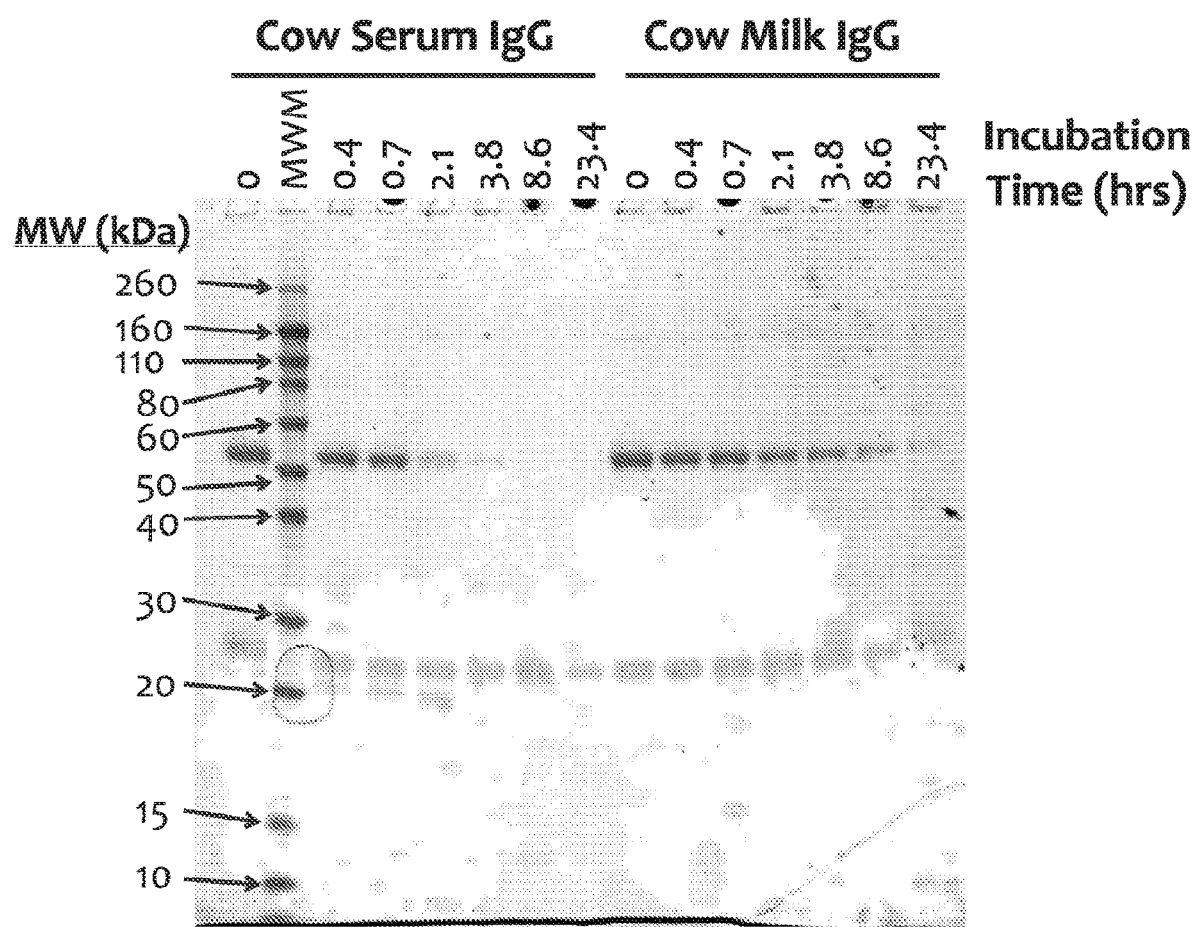
FIG. 7 is a SDS-PAGE analysis of serum IgG and milk IgG subjected to pancreatin digestion for the indicated durations.
Figure 8:
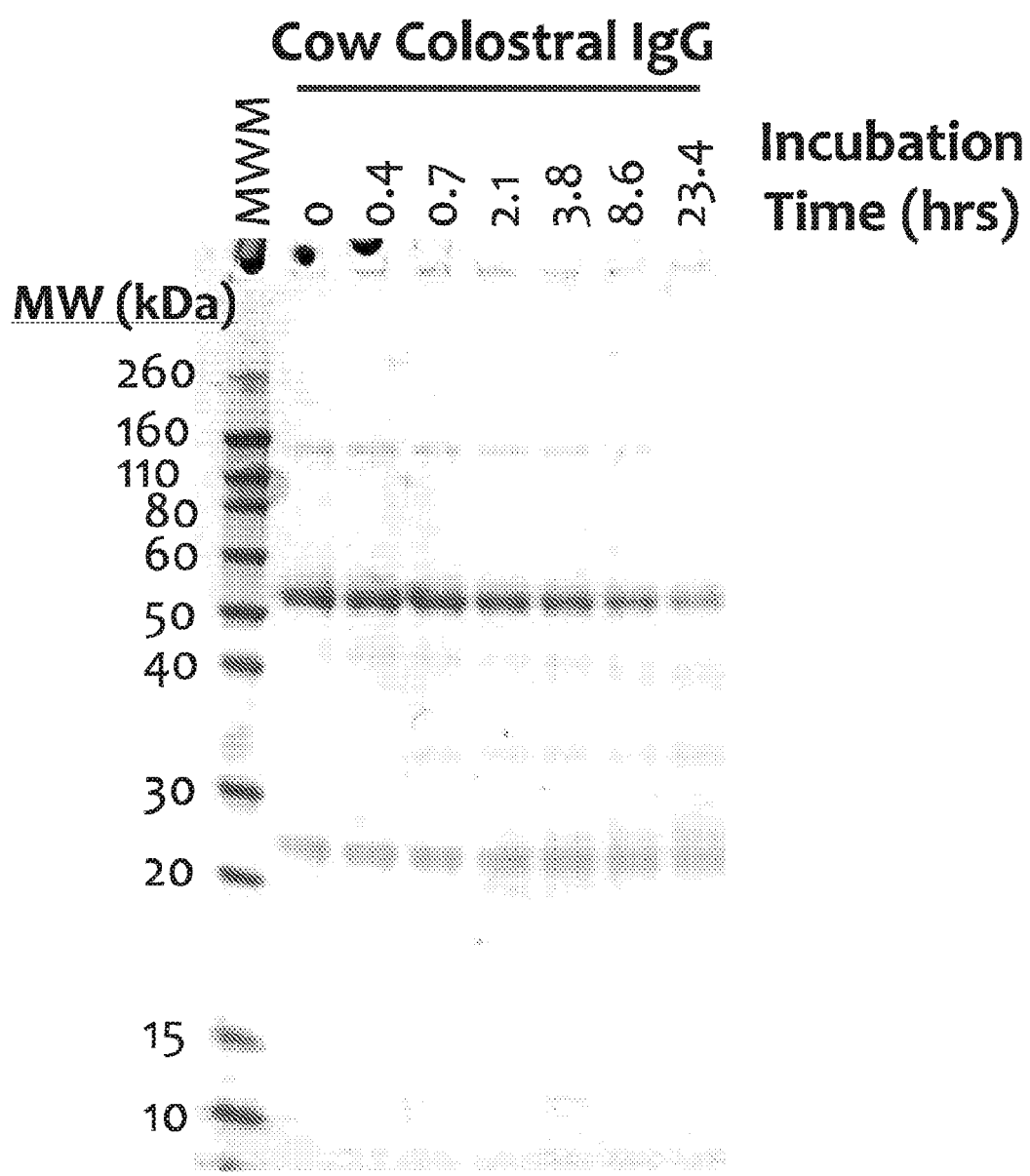
FIG. 8 is a SDS-PAGE analysis of colostral IgG subjected to pancreatin digestion for the indicated durations.
Figure 9:
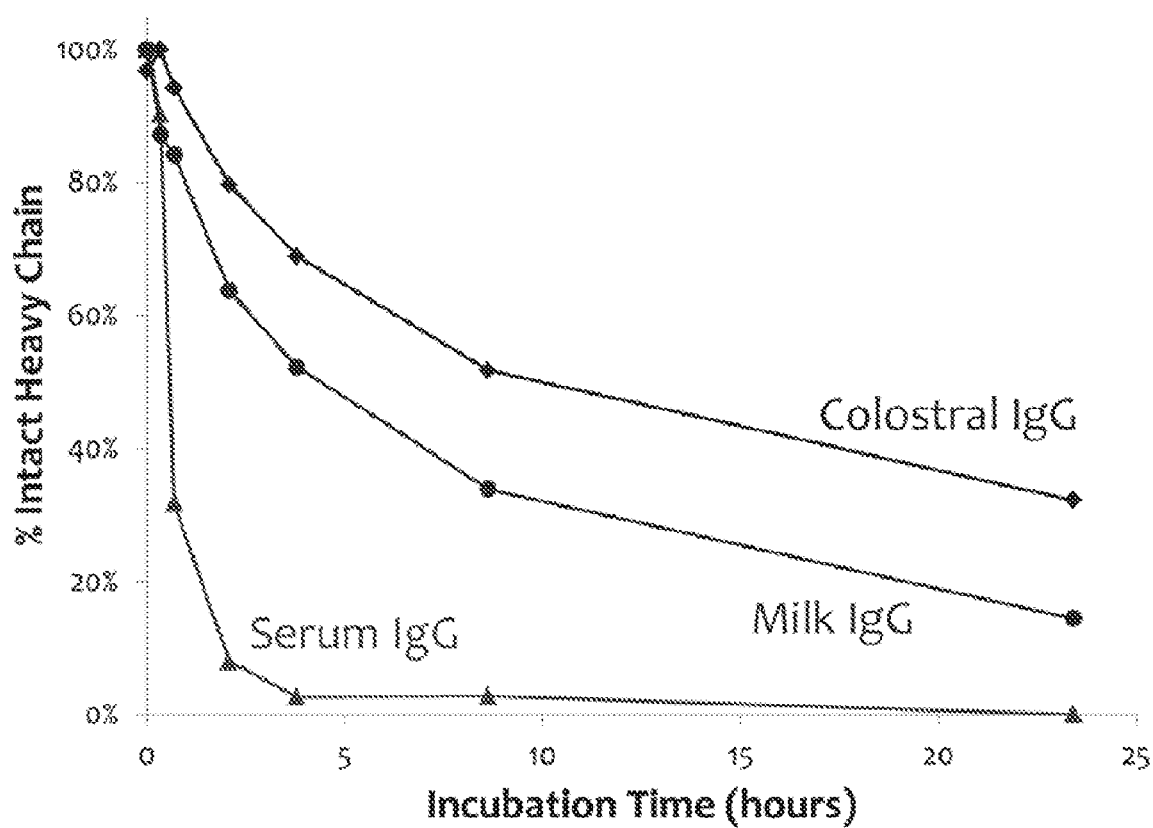
FIG. 9 is a line graph plotting the pancreatin-mediated degradation of the antibody heavy chain of serum IgG, colostral IgG, and milk IgG.

As shown in FIGS. 7-9, and Table 10, colostral IgG is the most stable against proteolysis. Milk IgG is degraded somewhat more rapidly, and serum IgG is proteolyzed significantly faster than colostral IgG and milk IgG.

TABLE 10

| IgG Source | $t_{1/2}$ (hrs) |
| --- | --- |
| Colostrum | 57.8 |
| Milk | 12.4 |
| Serum | 2.3 |

This data suggests that a factor associated only with colostral antibodies is responsible for pancreatin resistance. Potential factors that could, in theory, confer this resistance include glycosylation, a stabilizing entity present in the colostrum, and bovine immunoglobulin isotype.

Example 4—Carbohydrate Profiles of Serum, Milk, and Colostral Antibodies

Figure 10:
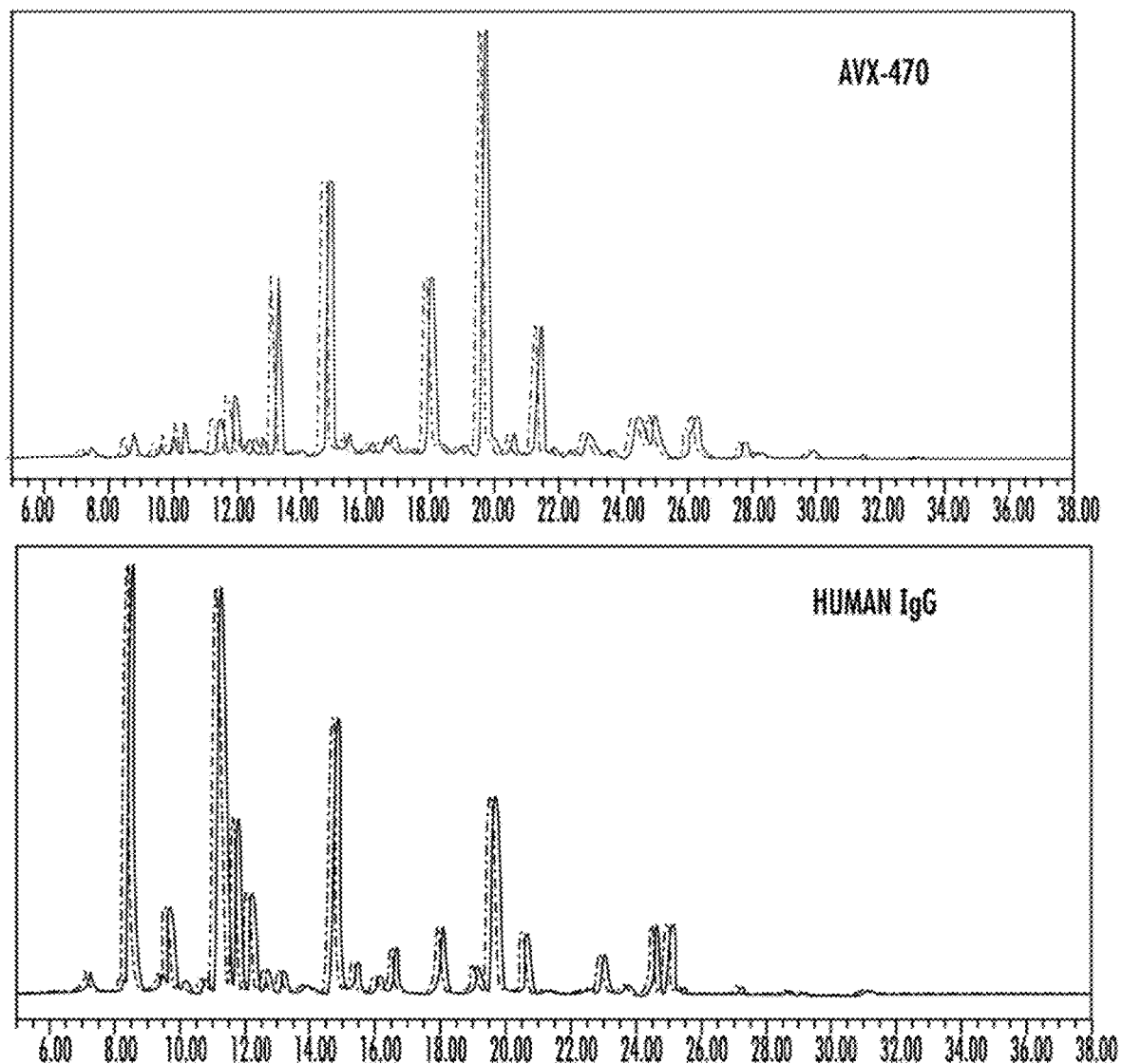
FIG. 10 is a chromatogram comparing the glycosylation patterns of AVX-470 and human IgG.
Figure 11:
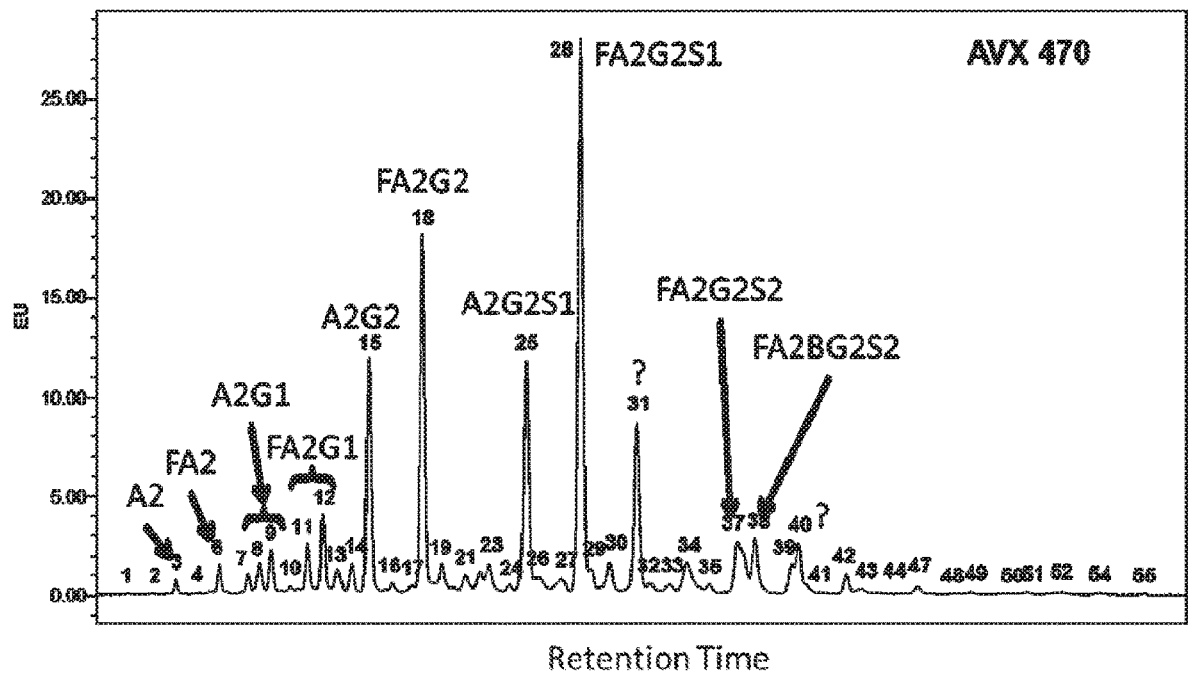
FIG. 11 is a chromatogram showing the glycosylation pattern of AVX-470, and assigning oligosaccharide species to the major peaks.

As discussed above, one factor that could confer protease resistance to colostral antibodies is glycosylation. To this end, the glycosylation pattern between AVX-470 and human IgG, and between bovine IgG from colostrum and serum were compared by hydrophilic interaction chromatography (HILIC)-ultra-high pressure liquid chromatography (UPLC) analysis. As shown in FIG. 10, AVX-470 and human IgG showed different patterns of glycosylation, with bovine colostral IgG being heavily sialylated. The identities of peaks for the most abundant species were confirmed by liquid chromatography/mass spectrometry (LC/MS) (Table 11 and FIG. 11).

The UPLC column was able to resolve 55 discrete peaks in the released sample. The retention times for each species were compared against those observed for a calibration standard consisting of glucose homopolymers to convert the peak retention times to Glucose Units (GU). The GU values are then compared to a reference database of known oligosaccharide species to identify the likely species in each peak. As shown in Table 11, most of the peaks with >10% abundance (highlighted in bold) in the chromatogram can be assigned by this method.

TABLE 11

| Peak ID | Structure | Human IgG Average GU | AVX-470 Average GU | AVX-470 % Area |
| --- | --- | --- | --- | --- |
| 1 | ND[a] | NF[b] | 4.96 | 0.04 |
| 2 | ND[a] | NF[b] | 5.25 | 0.03 |
| 3 | A2 | 5.44 | 5.45 | 0.49 |
| 4 | ND[a] | NF[b] | 5.73 | 0.08 |
| 5 | A2B | 5.81 | 5.82 | 0.13 |
| 6 | FA2 | 5.9 | 5.92 | 1 |
| 7 | Man5 | 6.2 | 6.21 | 0.77 |
| 8 | FA2B | 6.27 | 6.31 | 1.24 |
| 8 | A2[6]G1 | 6.27 | 6.31 | 1.24 |
| 9 | A2[3]G1 | 6.41 | 6.42 | 1.65 |
| 10 | A2B[6]G1 | 6.59 | 6.58 | 0.37 |
| 11 | A2B[3]G1 | 6.73 | 6.73 | 1.24 |
| 11 | FA2[6]G1 | 6.73 | 6.73 | 1.24 |
| 12 | FA2[3]G1 | 6.85 | 6.85 | 2.78 |
| 13 | FA2B[6]G1 | 6.97 | 6.97 | 1.14 |
| 14 | FA2B[3]G1 | 7.1 | 7.09 | 1.13 |
| 14 | Man6 | 7.1 | 7.09 | 1.13 |
| 15 | A2G2 | 7.23 | 7.22 | 8.33 |
| 16 | A2BG2 | 7.41 | 7.41 | 0.67 |
| 17 | ND[a] | NF[b] | 7.56 | 0.39 |
| 18 | FA2G2 | 7.66 | 7.65 | 12.96 |
| 19 | FA2BG2 | 7.81 | 7.8 | 1.54 |
| 20 | ND[a] | NF[b] | 7.9 | 0.21 |
| 21 | A2G1S(6)1 | 8 | 7.99 | 0.99 |

TABLE 11-continued

| Peak ID | Structure | Human IgG Average GU | AVX-470 Average GU | AVX-470 % Area |
|---|---|---|---|---|
| 22 | FA2G1S(6)1 | 8.12 | 8.1 | 1 |
| 23 | ND[a] | NF[b] | 8.17 | 1.49 |
| 24 | ND[a] | NF[b] | 8.33 | 0.43 |
| 25 | A2G2S(6)2 | 8.48 | 8.46 | 9.47 |
| 26 | ND[a] | NF[b] | 8.54 | 1.2 |
| 27 | A2BG2S(6)2 | 8.74 | 8.73 | 1.11 |
| 28 | FA2G2S(6)1 | 8.9 | 8.88 | 22.23 |
| 29 | ND[a] | NF[b] | 8.97 | 0.48 |
| 30 | FA2BG2S(6)1 | 9.13 | 9.11 | 1.67 |
| 31 | ND[a] | NF[b] | 9.32 | 6.87 |
| 32 | ND[a] | NF[b] | 9.43 | 0.57 |
| 33 | Man9 | 9.62 | 9.59 | 0.61 |
| 34 | A2G2S(6)2 | 9.74 | 9.72 | 2.35 |
| 35 | A2BG2S(6)2 | 9.91 | 9.9 | 0.51 |
| 36 | ND[a] | NF[b] | 9.97 | 0.03 |
| 37 | FA2G2S(6)2 | 10.15 | 10.13 | 3.6 |
| 38 | FA2BG2S(6)2 | 10.29 | 10.27 | 2.58 |
| 39 | ?S[c] | 10.39 | 10.4 | 0.03 |
| 40 | ND[a] | NF[b] | 10.57 | 1.03 |
| 41 | ND[a] | NF[b] | 10.63 | 2.5 |
| 42 | ND[a] | NF[b] | 11.04 | 0.76 |
| 43 | ND[a] | NF[b] | 11.16 | 0.35 |
| 44 | ND[a] | NF[b] | 11.29 | 0.05 |
| 45 | ND[a] | NF[b] | 11.38 | 0.02 |
| 46 | ND[a] | NF[b] | 11.49 | 0.02 |
| 47 | ND[a] | NF[b] | 11.67 | 0.32 |
| 48 | ND[a] | NF[b] | 12 | 0.02 |
| 49 | ND[a] | NF[b] | 12.13 | 0.1 |
| 50 | ND[a] | NF[b] | 12.49 | 0.08 |
| 51 | ND[a] | NF[b] | 12.66 | 0.13 |
| 52 | ND[a] | NF[b] | 12.92 | 0.09 |
| 53 | ND[a] | NF[b] | 13 | 0.12 |
| 54 | ND[a] | NF[b] | 13.36 | 0.09 |
| 55 | ND[a] | NF[b] | 13.83 | 0.04 |

Figure 12:
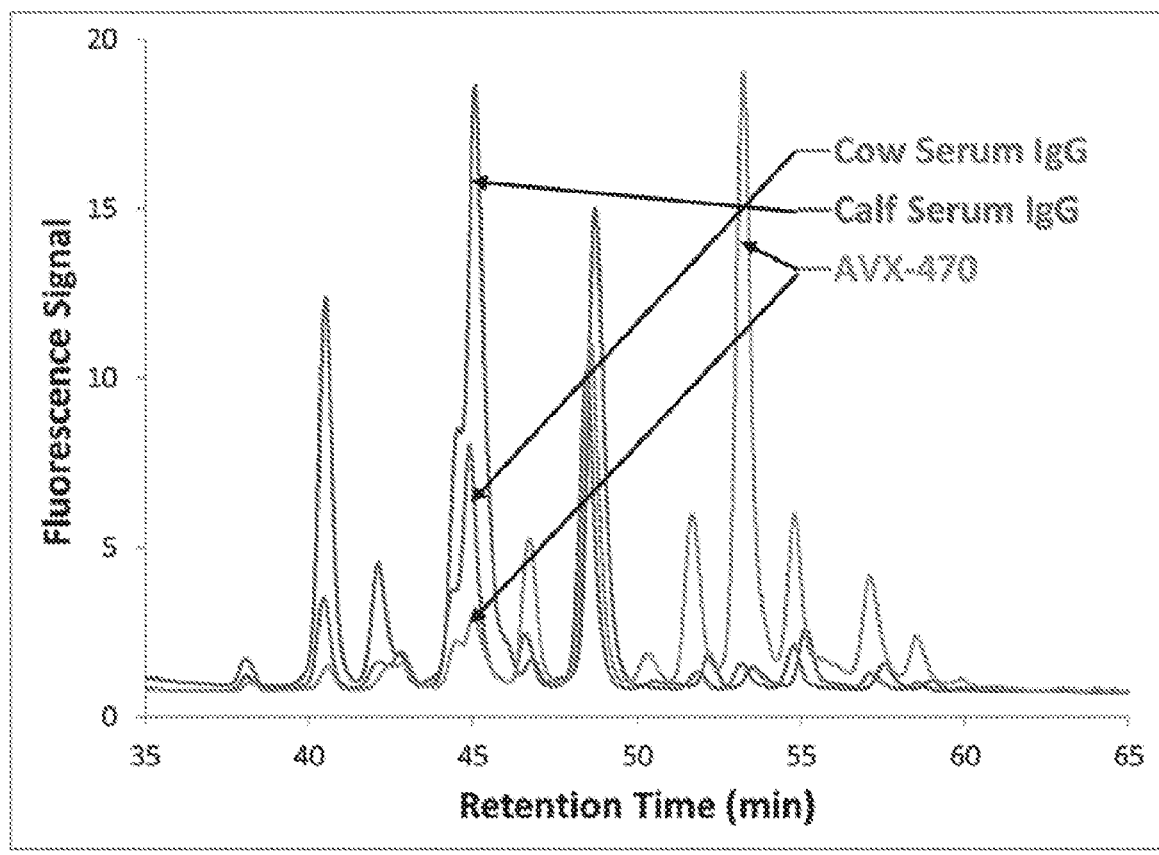
FIG. 12 is a chromatogram comparing the glycosylation patterns of AVX-470, cow serum IgG, and calf serum IgG.

[a]Not Determined
[b]Not Found
[c]GU value consistent with multiple possible sialylated species HILIC analysis was also used to assess differences in glycosylation patterns between bovine IgG derived from serum, colostrum, and milk. IgG was prepared by Protein G affinity chromatography, and the associated N-glycans from each sample were released with PNGase F, labeled with 2-AB, and separated on a GlycoSep N column. As shown in FIG. 12, the N-glycoprofile of IgG purified from the serum of a calf (which has never been pregnant) has slightly lower levels of the terminally galactosylated species G1F (rt=45 min) and G2F (rt=48 min), than IgG from the serum of a pregnant cow. Both serum IgGs have substantially less of the later-eluting species (likely mono- and disialylated oligosaccharides) than the colostral IgG sample (AVX-470).

Figure 13:
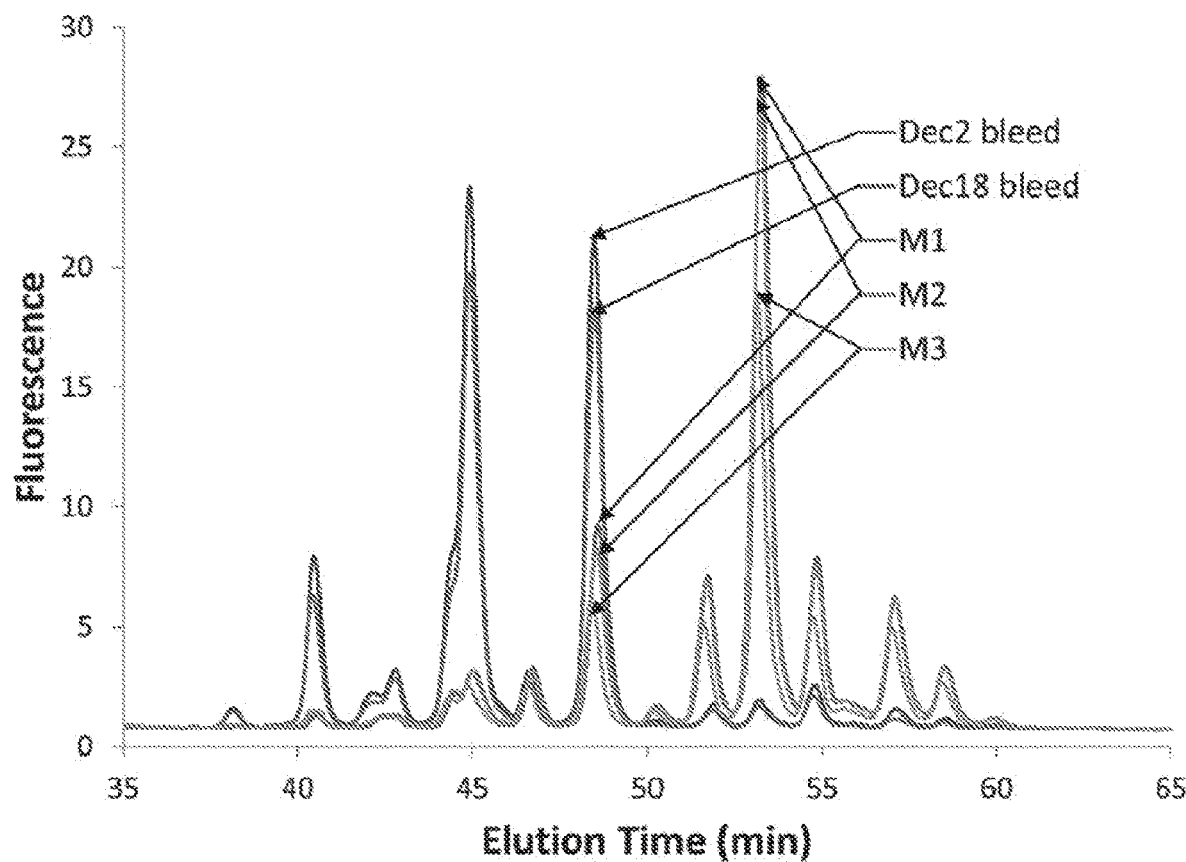
FIG. 13 is a chromatogram comparing the glycosylation patterns of serum IgG (Dec2 bleed, Dec18 bleed) and colostral IgG (M1, M2, and M3) samples.

Changes in IgG N-glycosylation over time were also assessed by HILIC on samples taken from a single cow (cow #6003 from the ACICC-2 immunization study). Two serum samples were analyzed: one sample collected on Dec. 2, 2013 (peak titer for anti-TNF binding activity) and another collected on Dec. 18, 2013 (parturition date). IgG purified from colostrum collected in the first three milkings from this cow (collected over 1.5 days post-parturition) was also analyzed. As shown in FIG. 13, the N-glycosylation patterns for the serum samples are nearly identical to each other. Likewise, the three colostral IgG samples have very similar profiles. However, the N-glycosylation patterns of serum and colostral IgG populations are clearly distinct, with a substantial increase in the abundance of the later eluting species in the colostral IgG samples. Integration of the major peaks in each chromatogram (Table 12) indicates that the primary difference between serum and colostral samples is a substantial increase in the abundance of sialic acid-containing oligosaccharides in colostral IgG. In addition, there are small changes in core fucosylation and terminal galactosylation between the serum and colostral samples.

TABLE 12

Peak integration results for serum and colostrum samples

| | Tenative | | Serum Samples | | | Colostrum samples | | |
|---|---|---|---|---|---|---|---|---|
| Peak # | assignment | RT(min) | Calf IgG | 6003Dec2 | 6003Dec18 | 6003M1 | 6003M2 | 6003M3 | AVX-470 |
| 1 | A2 | 38.1 | 1.1% | 1.0% | 1.0% | 0.1% | 0.2% | 0.2% | 0.3% |
| 2 | FA2 | 40.5 | 16.8% | 9.6% | 9.3% | 0.7% | 1.1% | 1.4% | 1.2% |
| 3 | A2G1 | 42.1 | 7.3% | 5.7% | 5.8% | 1.4% | 1.6% | 1.6% | 2.6% |
| 4 | FA2G1 | 45.1 | 41.4% | 40.2% | 41.5% | 5.9% | 6.2% | 6.7% | 6.7% |
| 5 | A2G2 | 46.8 | 1.3% | 3.4% | 3.3% | 3.7% | 3.7% | 3.5% | 7.6% |
| 6 | FA2G2 | 48.7 | 24.2% | 29.8% | 31.9% | 13.2% | 12.1% | 11.2% | 18.3% |
| 7 | A2G2S(6)1 | 52.2 | 1.5% | 1.5% | 1.5% | 9.6% | 9.6% | 9.6% | 9.4% |
| 8 | FA2G2S(6)1 | 53.5 | 1.4% | 2.0% | 1.9% | 40.8% | 40.5% | 40.2% | 32.2% |
| 9 | Unknown | 55.1 | 3.1% | 2.6% | 2.5% | 10.5% | 10.3% | 10.0% | 11.4% |
| 10 | A2G2S(6)2 | 57.5 | 1.4% | 1.4% | 0.9% | 9.7% | 10.3% | 10.9% | 7.1% |
| 11 | FA2G2S(6)2 | 59.0 | 0.6% | 2.8% | 0.5% | 4.4% | 4.6% | 4.8% | 3.2% |
| % fucosylation[a] | | | 87.1% | 86.6% | 87.2% | 72.6% | 71.8% | 71.4% | 69.5% |
| % galactosylation[b] | | | 82.1% | 89.4% | 89.7% | 99.1% | 98.8% | 98.5% | 98.4% |
| % sialylation[c] | | | 8.0% | 10.3% | 7.3% | 74.9% | 75.3% | 75.4% | 63.3% |

[a]Calculated as (sum of fucosylated species)/(sum of all identified peaks).
[b]Calculated as (sum of galactosylated species)/(sum of all peaks).
[c]Calculated as (sum of sialylated species)/(sum of all peaks)

Figure 14:
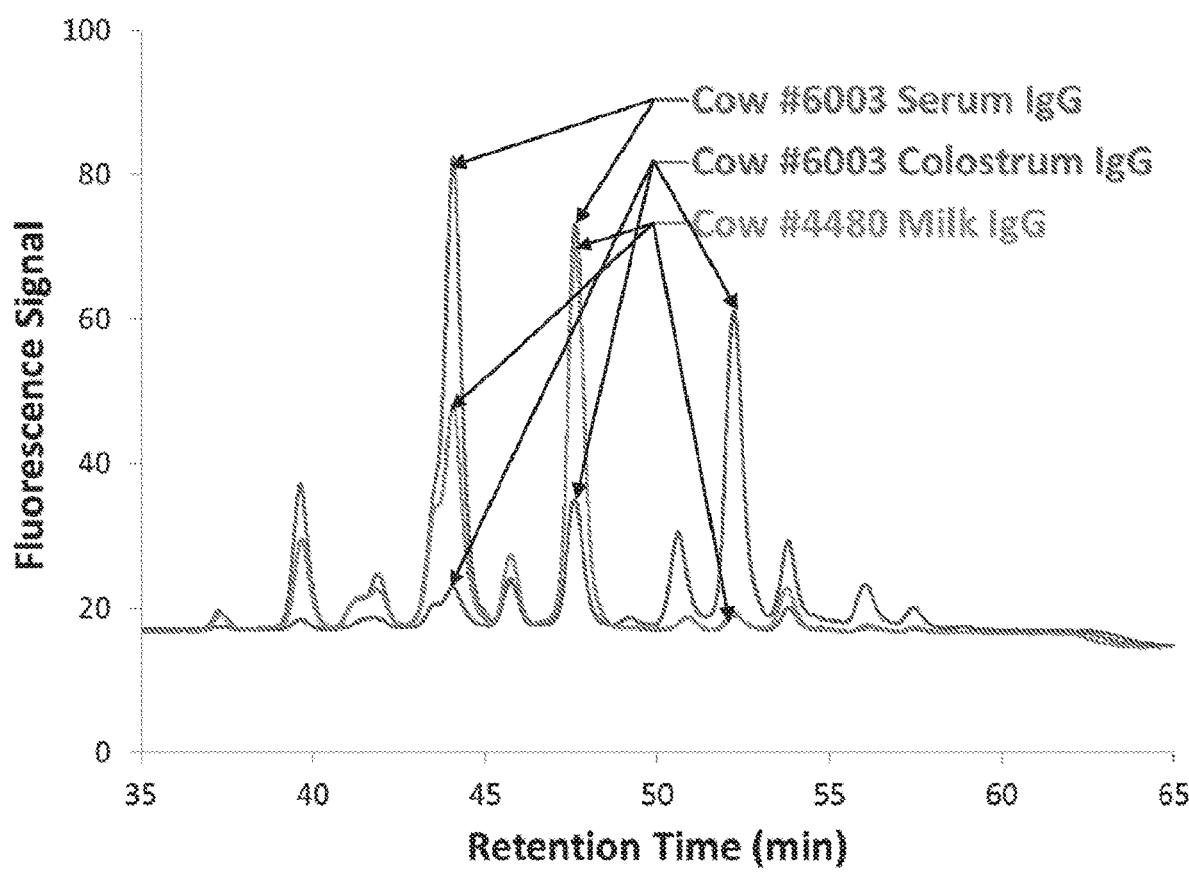
FIG. 14 is a chromatogram comparing the glycosylation patterns of serum IgG, colostral IgG, and milk IgG.

The transition from colostrum to milk is known to correspond with multiple changes in composition, including a substantial decrease in total immunoglobulin concentration and changes in N-glycosylation. As shown in FIG. 14, HILIC analysis of serum, colostrum and milk IgG samples demonstrates that colostral IgG glycosylation is the most distinct from the other fluids. Serum and milk IgG have similarly low levels of the later-eluting species which were tentatively identified as sialylated oligosaccharides.

The findings above collectively suggest that bovine colostral antibodies have a unique carbohydrate profile as compared with serum and milk antibodies.

To determine whether this unique carbohydrate profile correlated with pancreatin stability, densitometry was used to quantify the IgG heavy chain band for digestion of serum, colostral, and milk IgG. As shown in FIG. 9, colostral antibodies were more resistant to pancreatin than serum and milk IgG.

Example 5—Glycosylation does not Confer Protease Resistance to Colostral Antibodies The previous Example demonstrated differences in glycosylation pattern between bovine serum antibodies and colostral antibodies, with colostral antibodies having heavily sialylated N-linked oligosaccharides linked to the Fc domain of colostral antibodies. The present experiment was conducted to determine whether this difference is responsible for conferring the unique protease resistance characteristic of colostral antibodies.

Pancreatin digestions of colostral IgG were carried out as described in Example 2, except that the pancreatin:substrate ratio was 2.5:1. One set of samples was also treated with neuraminidase (sialidase A). N-glycan analysis of this sample confirmed the complete removal of terminal sialic acid groups.

Figure 15:
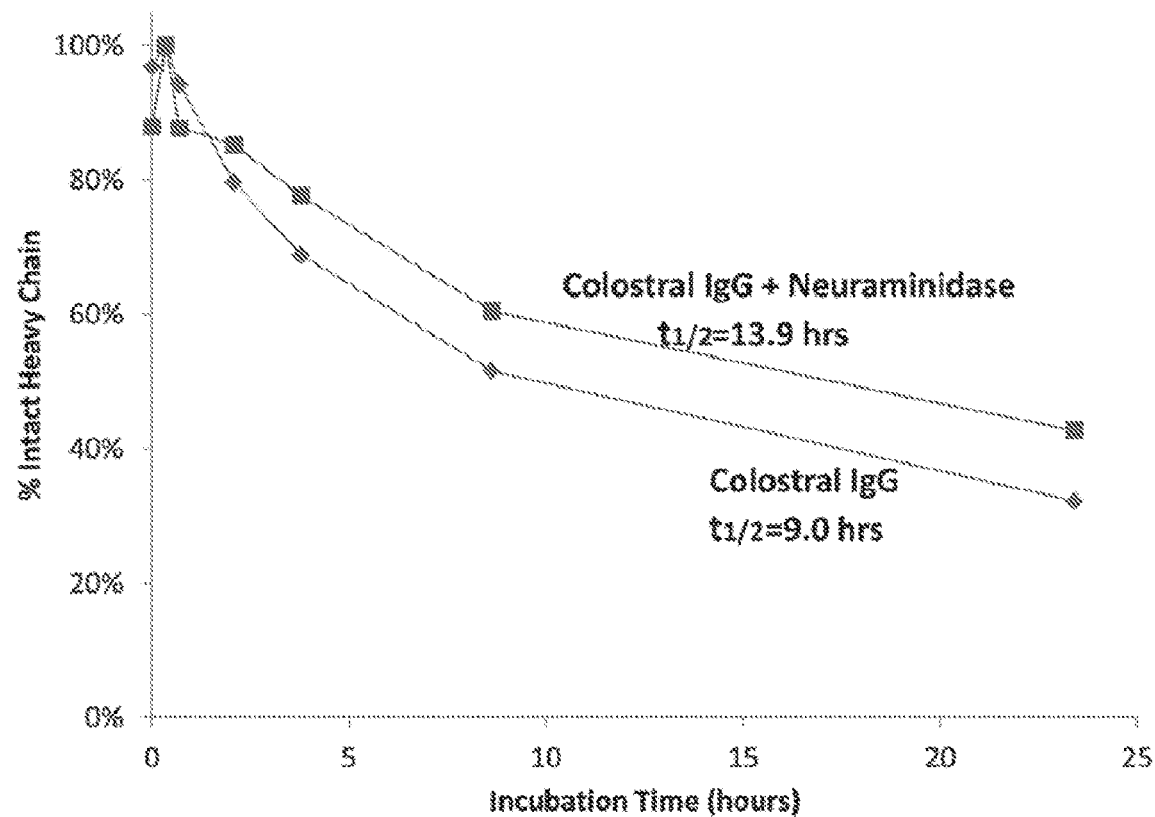
FIG. 15 is a line graph plotting the pancreatin-mediated degradation of the antibody heavy chain of colostral IgG treated with or without neuraminidase.

As shown in FIG. 15, the enhanced stability of the colostral IgG is independent of the presence of terminal sialic acid groups on the N-linked oligosaccharides, as neuraminidase treatment further stabilized the antibody (t1/2=13.9 hrs). This result suggests that sialylation is not responsible for the increase in proteolytic stability of colostral antibodies.

Example 6—Stabilizing Entity in Colostrum is not Responsible for Protease Resistance of Colostral Antibodies The hypothesis that a stabilizing entity present in the colostrum confers protease resistance to colostral antibodies was next considered.

A number of observations suggest against this possibility. First, purified colostral IgG antibodies, as shown in Example 3, are resistant to pancreatin digestion, suggesting that pancreatin resistance is likely independent of potentially stabilizing entities found in the colostrum. Second, when antibodies were purified from serum and colostrum collected from a single animal on the same day, SDS-PAGE did not detect any unique protein species in the colostral sample, i.e., there were no associated molecules (see FIG. 6). Finally, no evidence was found for a stabilizing entity in purified colostral IgG preparations by mass spectrometry that would confer protease resistance.

These findings suggest that the resistance of colostral antibodies to protease digestion is unlikely to be conferred by a stabilizing entity.

Example 7—Purification of 12G-1 and IgG2 from Colostrum and Serum

Previous studies have reported inconsistent and conflicting results regarding patterns of resistance to certain proteases of different bovine antibody isotypes. This led to the two hypotheses discussed above, i.e., the contribution of glycosylation or a stabilizing factor that conferred protease resistance to colostral antibodies.

Figure 16:
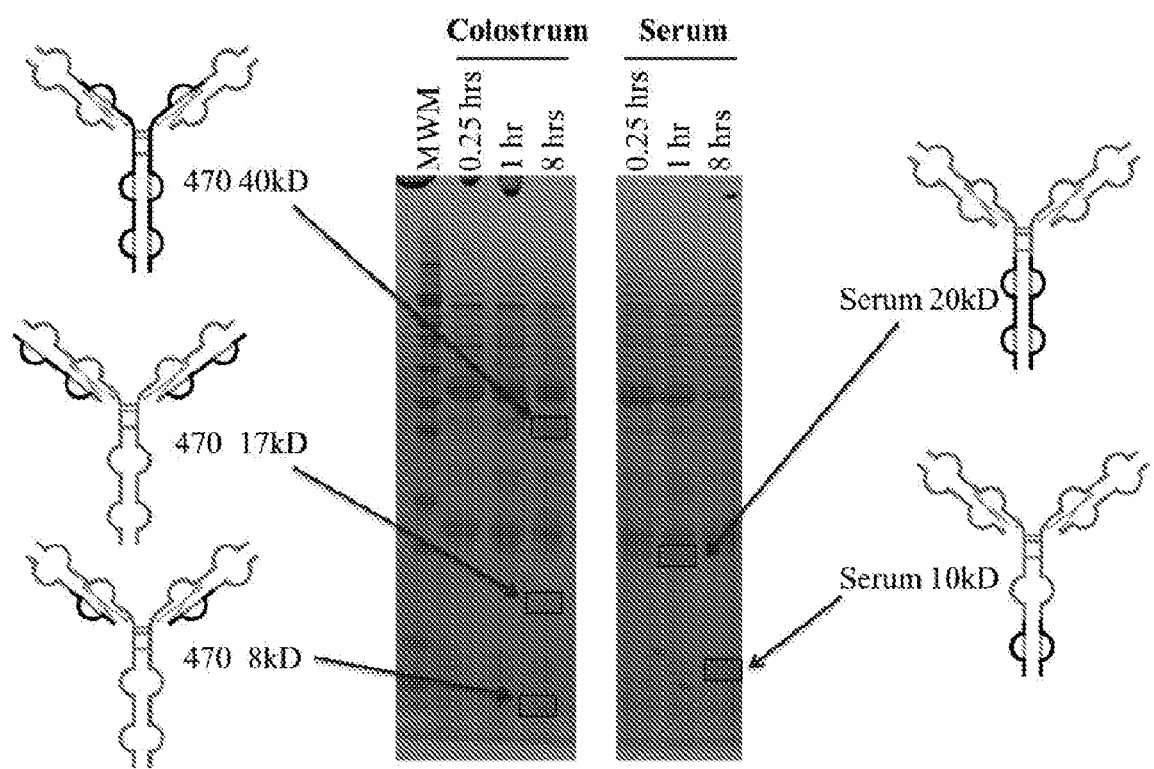
FIG. 16 is a reducing SDS-PAGE analysis of pancreatin digestion of serum IgG and colostral IgG, assigning antibody fragments to the major bands based on molecular weight of the bands and LC/MS/MS analysis.

To better understand the differences in the pancreatin digestion pathway for bovine serum and colostrum antibodies, IgG from colostrum and serum were analyzed by reducing SDS-PAGE (FIG. 16). Several bands were identified as unique at later time points of either colostral or serum IgG digestion reactions. The 1 hour time point for degradation of serum IgG had a prominent band at 20 kDa, and the 8 hour time point had a strong band at 10 kDa. These bands were excised from the gel, digested in-gel with trypsin under denaturing conditions, then subjected to LC/MS/MS analysis to identify the proteins in each band (Table 13).

TABLE 13

| Sample | WV (kDa)[a] | Top Protein Hit | Peptides Identified |
|---|---|---|---|
| AVX-470 | 8 | gi513137422[b] | SPPSVTLFPPSTEELNQNK. |
|  |  |  | YAASSYLSLTSSDWK |
| AVX-470 | 17 | gi513137422[b] | VSITQSGSSSNVQNGYVSWYQLIPGSAPR |
|  |  |  | SPPSVTLEPPSTEELNQNK |
|  |  |  | YAASSYLSUTSSDWK |
|  |  |  | QSYSCEVTHEGSTVIK |
| AVX-470 | 40 | gi108750[c] | VYPLSSCCQDK |
|  |  |  | SSSTVTLGCLVSSYMPEPVTVTWNSGALK |
|  |  |  | SGVHTFPAVLQSSGLYSLSSMVTVPGSISGQTFTQNVAHPASSTK |
|  |  |  | AVDPTCKPSPQDQPPPELPQQPSVFFPPKPK |
|  |  |  | FSWFVDDVEYNTATTKPR |
|  |  |  | VHNEGLPAPIVR |
|  |  |  | EPQVYVLAPPQEELSK |
|  |  |  | STVSLTCMYTSFYPDYIAVEWQR |
|  |  |  | NGQPESEDKYQTIPPQLDADSSYFLYSK |
| Senas IgC | 10 | gi896119[d] | EPQYYVLQPPKEELSK |
|  |  |  | TIPPQLDADR |

TABLE 13-continued

| Sample | WV (kDa)[a] | Top Protein Hit | Peptides Identified |
|---|---|---|---|
| Serut IgG | 20 | gi896119[d] | EPSVFIFFPKPK<br>VVSALPIQHQDWTGQK<br>EPQVYVLQPPKEELSK<br>TIPPQLDADR<br>GUTYTCVVMHEALHNHYMQK |

[a] Apparent molecular weight based on SDS-PAGE migration
[b] Chain L., crystal structure of bovine antibody Blvlh12 with ultralong CDRH3
[c] Ig heavy chain precursor (B/MT.4A.17.H5.AS) - bovine
[d] Ig ganima-2 chain C region (clone 32.2) - bovine (fragment)

Based on the peptides identified in Table 13, along with the apparent molecular weight of each fragment observed by reducing SDS-PAGE, each band was assigned to a fragment of the original antibody. The 8 kDa and 17 kDa bands observed in the 8 hour time point map to the light chain, while the 40 kDa band is most likely the constant domains from the heavy chain. These results suggest that the initial cleavage events occur near the N- and C-termini of the heavy and light chains, while leaving the core structure around the hinge intact. In contrast, the 20 kDa bands from the early (1 hour) time point in the serum IgG digest map to the Fc domain, consistent with cleavage in the hinge. The 10 kDa band that appears later in the serum IgG digestion reaction maps only to peptides in the CH3 domain, suggesting that the Fc is further degraded over time. These results indicate that the hinge region of colostral IgG is protected from proteolytic cleavage relative to the serum IgG antibody. In addition, the colostral IgG sequences map predominantly to the IgG1 subtype, while the serum IgG sample maps to the IgG2 sequence.

Figure 17:
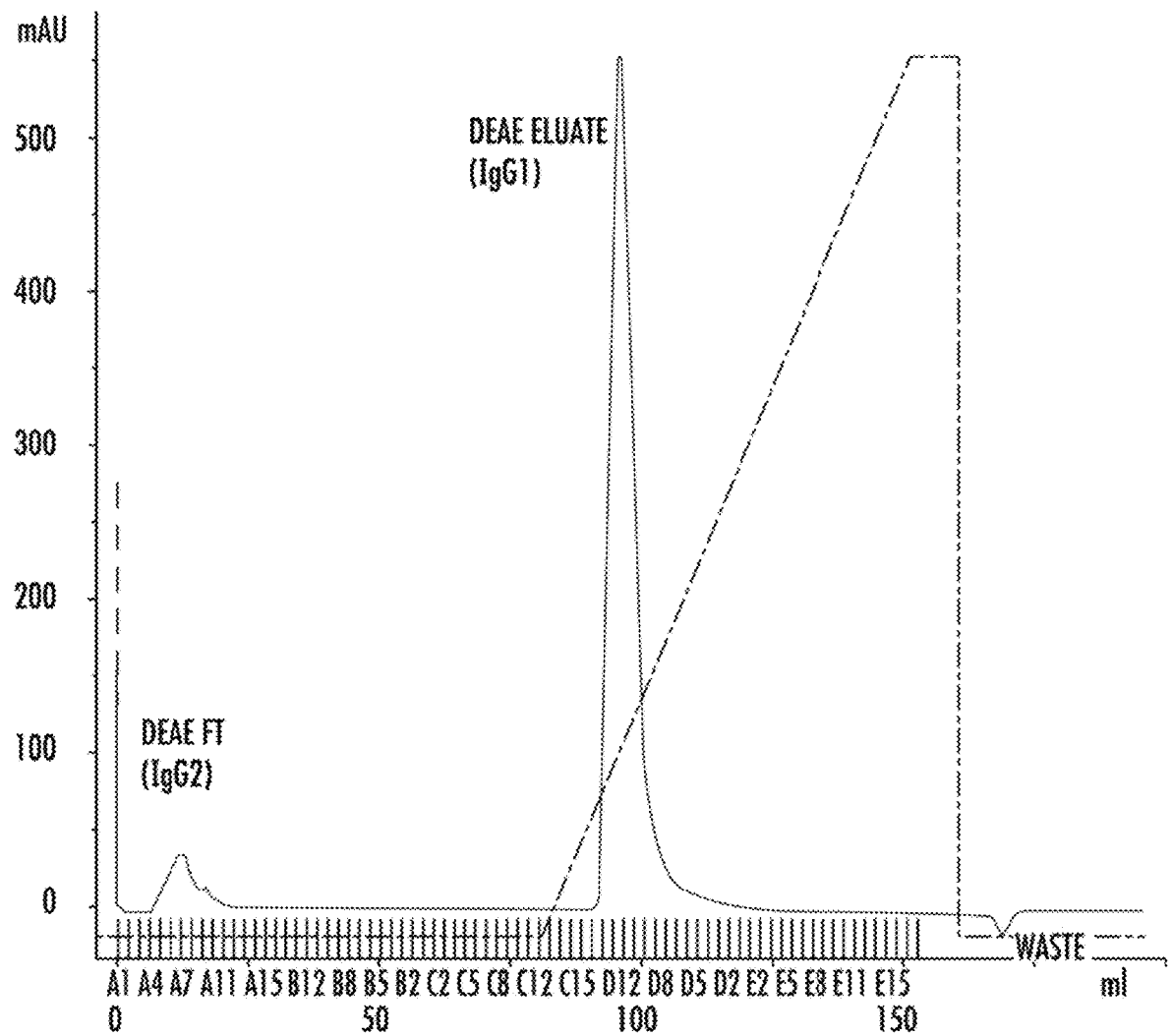
FIG. 17 is a chromatogram showing the IgG1-enriched fraction from colostrum samples.
Figure 18:
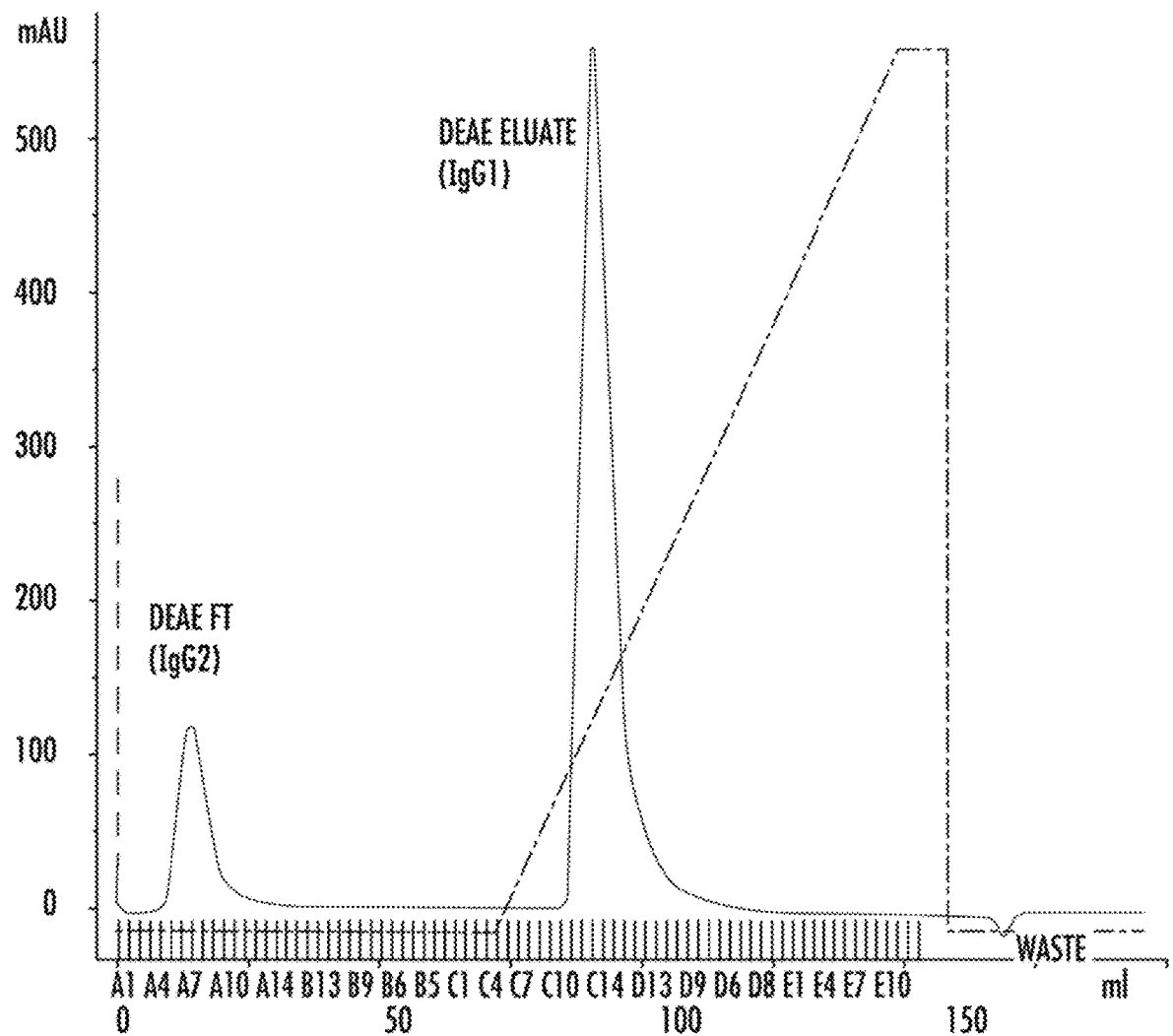
FIG. 18 is a chromatogram showing the IgG2-enriched fraction from serum samples.

To specifically investigate the impact of IgG subtype on protease susceptibility, IgG was prepared from colostrum and serum by Protein G affinity chromatography, and separated into IgG1- and IgG2-enriched fractions with a DEAE Sepharose column (FIGS. 17 and 18, respectively). As a sufficient amount of IgG1 could not be purified from the serum of pregnant cows, calf serum was used as the source of serum IgG1.

As shown in Table 14, the DEAE flow-through fraction was pure IgG2, as determined by a sandwich ELISA method with subtype-specific antibodies. The fraction eluted with the salt gradient was enriched in IgG1, but often contained trace amounts of IgG2. Others have also observed this phenomenon, and linked it to the presence of variable domains that have unusually low isoelectric points (Butler et al., 1987). To remove this contamination, the DEAE eluates were passed over a column containing immobilized anti-IgG2, which removed the contaminating IgG2 and yielded a pure IgG1 fraction (Table 14, 6003M1 DEAE+anti-IgG2 and calf #24 DEAE+anti-IgG2).

TABLE 14

Isotype ELISA results for DEAE fractions.

| Sample | ng IgG1 per µg total IgG | ng IgG2 per µg total IgG | % IgG1 |
|---|---|---|---|
| AVX-470 DEAE + anti-IgG2 | 668 | 0 | 100% |
| 6003M1 IgG | 772 | 122 | 86% |
| 6003M1 DEAE FT | 0 | 1253 | 0% |
| 6003M1 DEAE eluate | 947 | 24 | 98% |
| 6003M1 DEAE + anti-IgG2 | 845 | 0 | 100% |

TABLE 14-continued

Isotype ELISA results for DEAE fractions.

| Sample | ng IgG1 per µg total IgG | ng IgG2 per µg total IgG | % IgG1 |
|---|---|---|---|
| Call #24 serum IgG | 811 | 290 | 74% |
| Calf #24 DEAE FT | 0 | 1910 | 0% |
| Call #24 DEAE eluate | 1083 | 0 | 100% |
| Calf #124 DEAE + anti-IgG2 | 1043 | 0 | 100% |

Example 8—Pancreatin Digestion of Bovine IgG1 and IgG2

In this experiment, bovine IgG1 and IgG2 purified from serum (Calf #24) or colostrum (6003M1=early colostrum from Cow #6003; AVX-470=colostrum pooled from 20 cows) were digested with pancreatin and subjected to reducing SDS-PAGE as described in Example 3.

Figure 19:
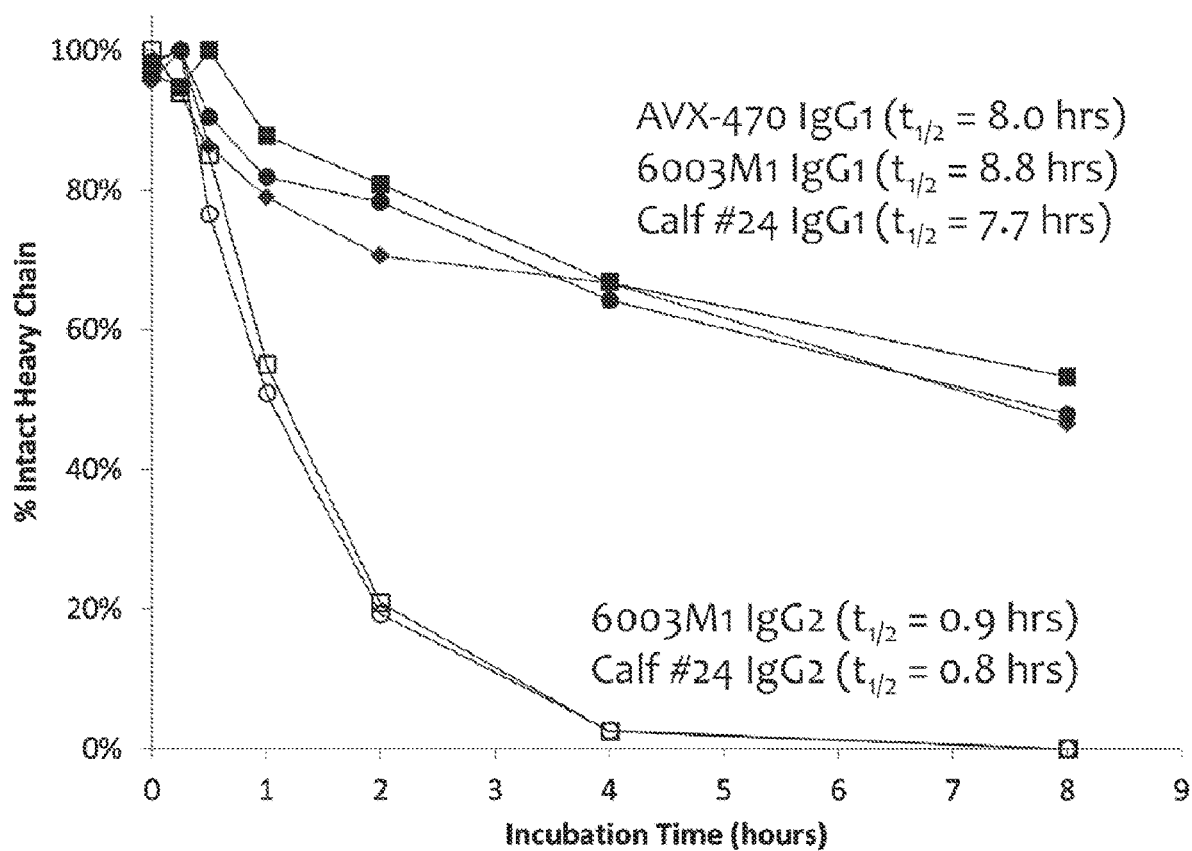
FIG. 19 is a line graph plotting the pancreatin-mediated degradation of the antibody heavy chain of AVX-470, IgG1, and IgG2 antibodies.

As shown in FIG. 19, IgG1 fractions were relatively stable against pancreatin digestion, with half-lives ranging from 7.7 to 8.8 hours. In contrast, IgG2 fractions from both serum and colostrum were rapidly degraded, with half-lives of 0.8-0.9 hours. Thus, IgG1 showed a 10-fold increase in half-life relative to IgG2. This data suggests that IgG isotype, specifically the IgG1 isotype, is the key determinant that confers protease resistance of bovine colostral antibodies.

Figure 20:
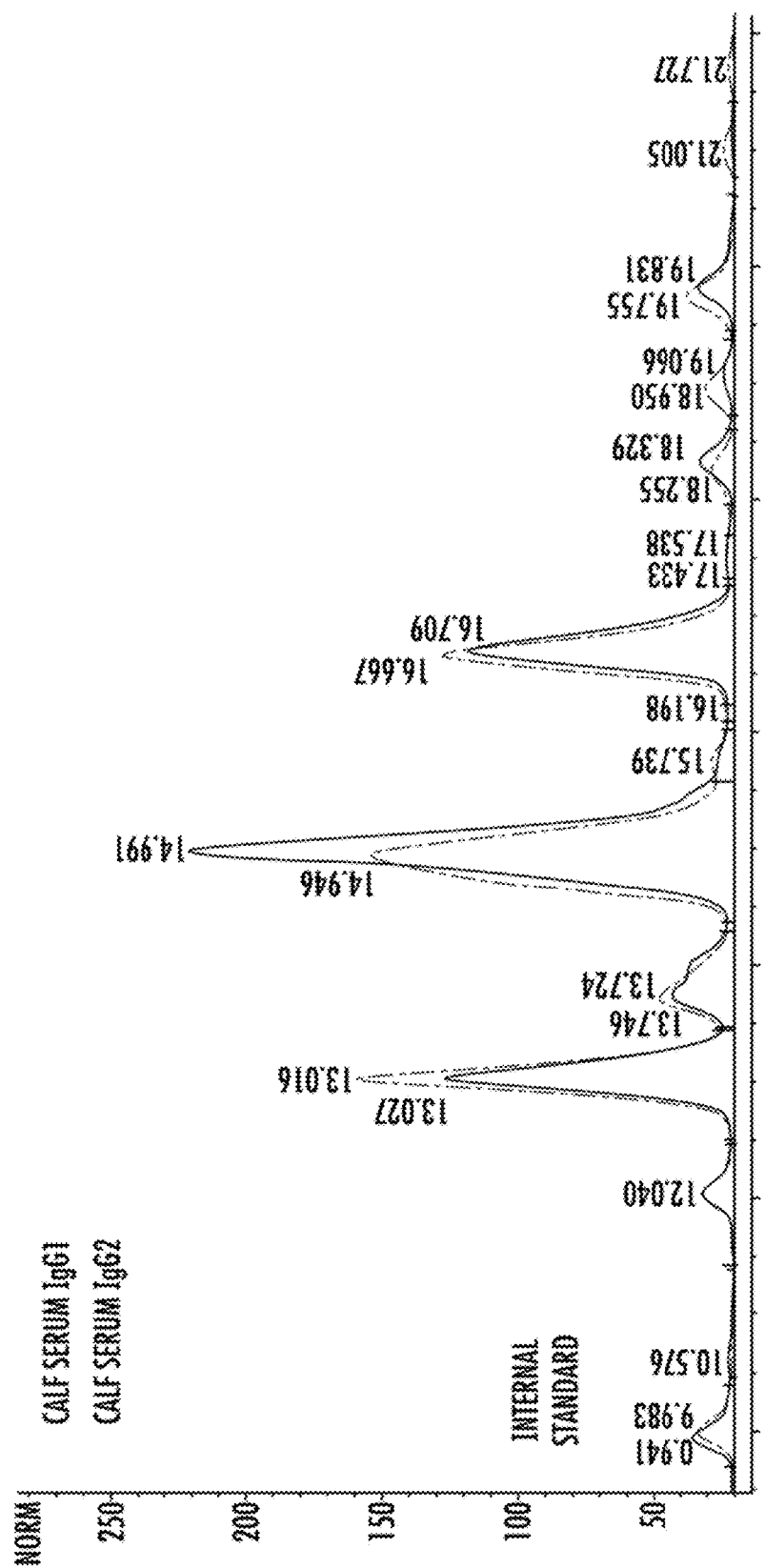
FIG. 20 is a chromatogram comparing glycosylation patterns of IgG1 and IgG2 from serum.
Figure 21:
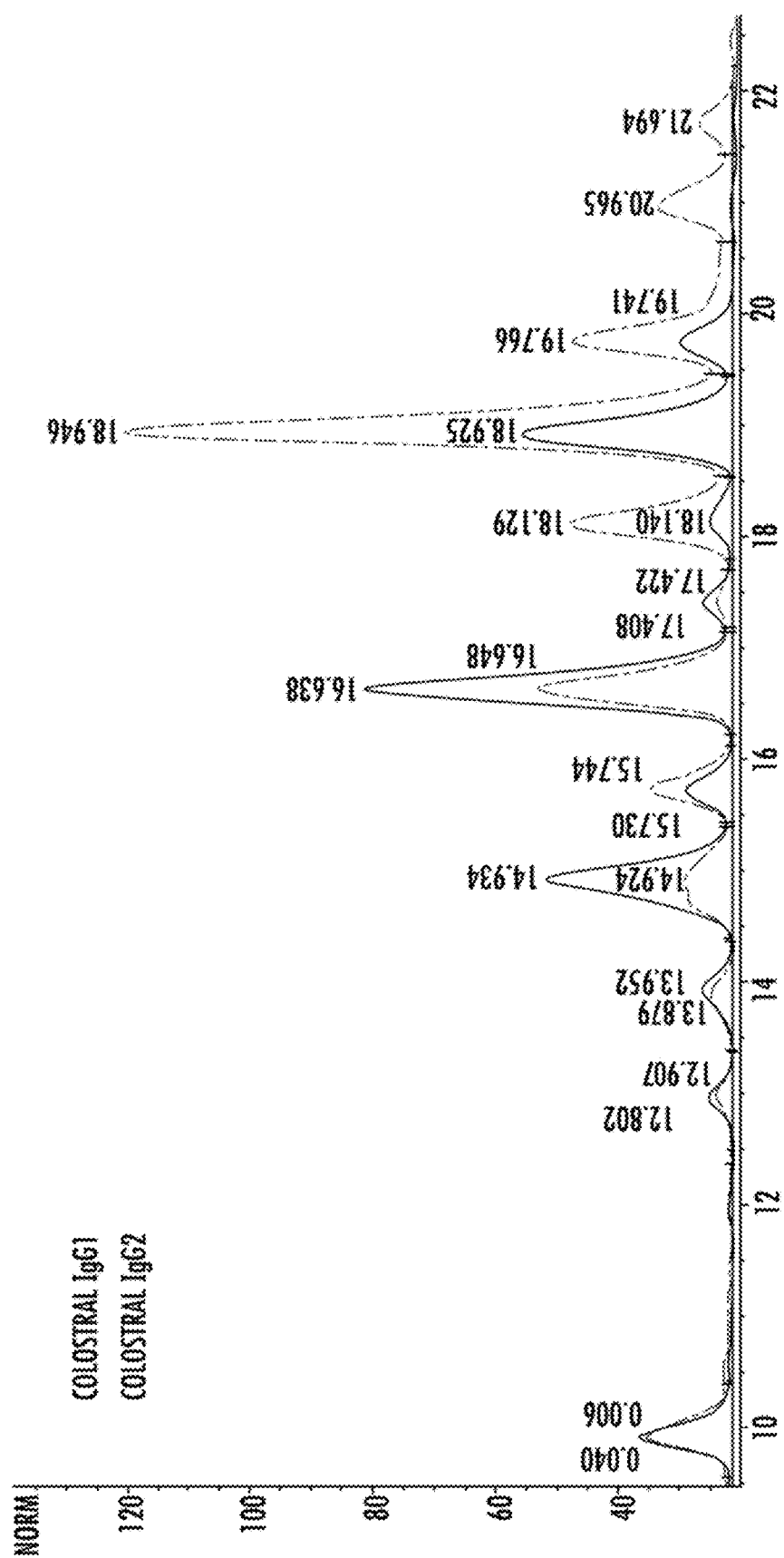
FIG. 21 is a chromatogram comparing glycosylation patterns of IgG1 and IgG2 from colostrum.

Carbohydrates on bovine isotypes from serum were also compared between IgG1 and IgG2. N-linked glycans were released enzymatically, fluorescently labeled with 2-aminobenzamidine and separated by hydrophilic interaction chromatography (HILIC) for quantitation. The oligosaccharide species present in each HILIC peak was determined by a combination of mass spectrometry and retention-time comparison with known standards. As shown in FIG. 20, there were no significant differences in fucosylation, galactosylation, and sialylation between bovine IgG1 and bovine IgG2 from serum. When comparing bovine IgG1 and bovine IgG2 from colostrum, both isotypes were sialylated, with higher sialylation and less fucosylation found in IgG1 (FIG. 21).

This result, in combination with results from the preceding Examples, suggests that the source of the antibody (i.e., colostrum or serum) determines the glycosylation pattern, while IgG isotype determines protease resistance.

Example 9—Differences in Amino Acid Sequences Between Bovine 12G1, Bovine IgG2, and Human 12G-1, and Comparisons with Other Ruminant 12G1 Sequences To gain further insight into factors that contribute to the stability of bovine IgG1 antibodies, the primary structures of bovine IgG1, bovine IgG2, and human IgG1 were compared.

FIG. 22 shows a comparison of the CH1-hinge region sequences from bovine IgG1 and bovine IgG2. Bovine IgG1 has four cysteine residues in the hinge region, whereas the A1 and A2 allotypes of bovine IgG2 have two or three cysteine residues, respectively. Moreover, bovine IgG1 has a higher incidence of proline residues than the IgG2 sequences. Proline residues are known to inhibit cleavage by many endoproteinases, and can induce a more rigid structure to the hinge. The IgG2 upper hinge also has a two-residue insertion "GV", which may introduce additional structural flexibility.

FIG. 23 shows a comparison of the CH1-hinge region of human IgG1 and bovine IgG1. Several of the sequence differences between human IgG1 and bovine IgG1 occur at sites known to be labile towards degradation by human proteases (Brerski et al., *mAbs* 2011; 3:558-67) or spontaneous peptide bond cleavage at acidic pH (Cordoba et al., *J Chromatography B* 2005; 818:115-21). The absence of these sites in the bovine IgG1 hinge may also contribute to the proteolytic stability of bovine IgG1.

The hinge sequences of other ruminant species were searched for homology to the following peptide:

```
Bovine IgG1 (AAB37381.2):
                                    (SEQ ID NO: 91)
DKAVDPRCKTTCDCCPPPELPGGP
```

This sequence was used as a query in a BLAST search against the entire non-redundant protein sequence database. The top hits from this search were as follows:

sequence contains the disulfide link between the N-terminus of the CH1 domain and the upper hinge, but only a single inter-HC disulfide bond and a significantly shorter hinge than is observed for IgG1 from other species.

Example 10—Expression and Pancreatin Stability of Bovine 12G1 Anti-Testosterone Monoclonal Antibody A bovine IgG1 anti-testosterone antibody was generated based on the anti-testosterone antibody produced by the heterohybridoma described in Jackson et al. (Molecular Immunology 1992; 29:667-76). The heavy and light chain amino acid sequences are as follows:

```
Bovine anti-testosterone IgG1 antibody (light
chain):
                                    (SEQ ID NO: 23)
QAVLGQPSSVSGSLGQRVSITCSGSSSNIGTYGVEWYQQVPGSGLRTII

YGSNSRPSGVPDRFSGSKSGNTATLTISSLQAEDEADYFCAAGDSSSRG

AVFGSGTLTALGQPKSPPSVTLFPPSTEELNGNKATLVCLISDFYPGSV

TVVWKADGSTITRNVETTRASKQSNSKYAASSYLSLTSSDWKSKGSYSC

EVTHEGSTVTKTVKPSECS
```

TABLE 15

| SEQ ID | Species | Sequence |
|---|---|---|
| 5 | *Bos taurus* (cow) IgG1a | VDK--AVDP---RCK-TTCD-C-CPPPELPGGPSVF |
| 6 | *Bos taurus* (cow) IgG1c | VDK--AVDP---RCK-RPCD-C-CPPPELPGGPSVF |
| 7 | *Bos taurus* (cow) IgG1b,d | VDK--AVDP---TCKPSPCD-C-CPPPELEGGPSVF |
| 8 | *Ovis aries* (sheep) | VDK--RVEP---GCP-DPCKHCRCPPPELPGGPSVF |
| 8 | *Ovis aries* (sheep) | VDK--RVEP---GCP-DPCKHCRCPPPELPGGPSVF |
| 8 | *Ovis aries* (sheep) | VDK--RVEP---GCP-DPCKHCRCPPPELPGGPSVF |
| 9 | *Lama glama* (llama) | VDK--RVEPHG-GCT---CP--QCPAPELPGGPSVF |
| 9 | *Vicugna pacos* (alpaca) | VDK--RVEPHG-GCT---CP--QCPAPELPGGPSVF |
| 9 | *Camelus dromedarius* (Arabian camel) | VDK--RVEPHG-GCT---CP--QCPAPELPGGPSVF |
| 10 | *Meriones unguiculatus* (gerbil) | VDK--TVEPRGTKHICPDCP--KCPAPDLSGGPSVF |
| 11 | *Felis catus* (cat) | VDKTVRKTDHP-PGP-KPCDCPKCPPPEMLGGPSIF |
| 12 | *Oryctolagus cuniculus* (rabbit) | VDK--TVAP--STCSKPT-----CPPPELLGGPSVF |

The three *Bos taurus* sequences reflect individual allotypes. The most closely related sequence is the sheep IgG1, which retains the key features of the bovine hinge (three inter-HC disulfide bonds, deletion of the known proteolysis sites). The dromedary IgG1 sequences (llama, alpaca and camel) are also very similar. The next closest hits are from gerbil and cat IgG1, which do not align as well. The cat sequence has only two inter-heavy-chain disulfide bonds. The gerbil sequence contains three cysteines, but it is unclear if the most N-terminal cysteine forms an inter-HC disulfide bond, or a HC-LC linkage. The rabbit IgG -continued

```
Bovine anti-testosterone IgG1 antibody (heavy
chain):
                                    (SEQ ID NO: 24)
QVQLRESGPSLVKPSQTLSLTCTVSGFSLSSYALTWVRQAPGKALEWVG

GITSGGTTYYNPALKSRLSITKENSKSQVSLSVSSVTPEDTATYYCARS

TYGEVGDGAIADAWGQGLLVTVSSASTTAPKVYPLSSCCGDKSSSTVTL

GCLVSSYMPEPVTVTWNSGALKSGVHTFPAVLQSSGLYSLSSMVTVPGS
```

```
TSGQTFTCNVAHPASSTKVDKAVDPTCKPSPCDCCPPPELPGGPSVFIF

PPKPKDTLTISGTPEVTCVVVDVGHDDPEVKFSWFVDDVEVNTATTKPR

EEQFNSTYRVVSALRIQHQDWTGGKEFKCKVHNEGLPAPIVRTISRTKG

PAREPQVYVLAPPQEELSKSTVSLTCMVTSFYPDYIAVEWQRNGQPESE

DKYGTTPPQLDADSSYFLYSKLRVDRNSWQEGDTYTCVVMHEALHNHYT

QKSTSKSAGK
```

DNA constructs encoding the heavy and light chains above were produced and expressed, and the resulting antibodies (50 μg/mL) were subjected to pancreatin digestion (1 mg/mL) and tested for anti-testosterone activity by ELISA. Pancreatin digestion was performed as described in Example 3.

Figure 24:
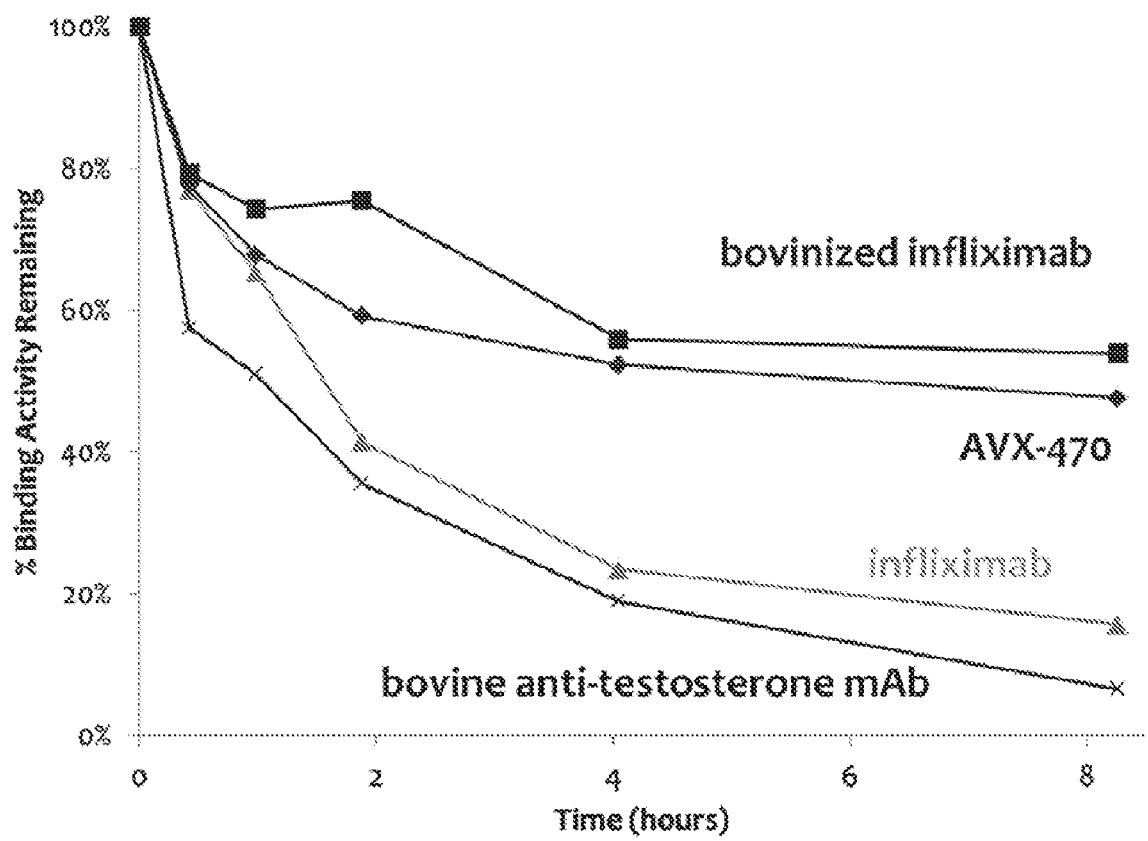
FIG. 24 is a line graph comparing antigen-binding activity of bovinized infliximab, infliximab, AVX-470, and a bovine anti-testosterone monoclonal antibody, as determined by ELISA.
Figure 25:
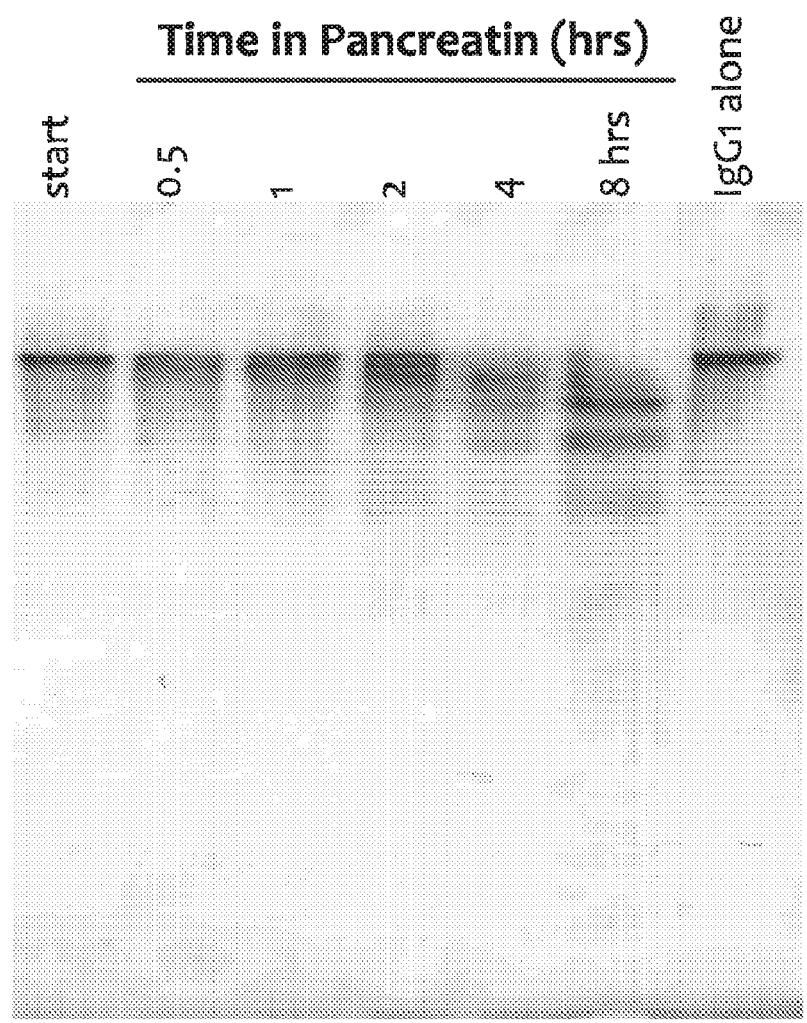
FIG. 25 is a Western blot analysis of anti-testosterone antibody digested with pancreatin (probed with anti-bovine IgG1 antibody).

As shown in FIG. 24, pancreatin-digested anti-testosterone antibody lost binding activity to testosterone at a much faster rate than AVX-470 and bovinized infliximab. This result appears to be inconsistent with bovine IgG1 being stable to digestion by intestinal proteases. However, when digested anti-testosterone antibody samples were subjected to SDS-PAGE (probed with anti-bovine IgG1) as shown in FIG. 25, multiple bands appear at slightly lower molecular weights, suggesting that small pieces of the antibody are being clipped off by the proteases, possibly in the antigen-binding region. This suggests that potential protease cut sites in the antigen-binding region is also a consideration when generating a stable bovine IgG1 antibody.

Example 11—Immunization of Cows with TNF and Adjuvants

The current immunization method used in the production of AVX-470 drug product for the Phase 1b clinical trial consists of a series of three subcutaneous injections of recombinant human TNF plus Quil A adjuvant at 2-3 week intervals in pregnant Holstein dairy cows prior to calving. These conditions were selected based on the outcome of a short series of studies conducted in calves that evaluated multiple adjuvants, antigen levels, and dosing frequency, as discussed below.

Calf Study #1

In the first study, a series of adjuvants were evaluated in male Holstein calves, aged 3-months, immunized with adjuvinized rhTNF (Cell Sciences, Canton, MA) by subcutaneous injection. Four different adjuvants were evaluated—Emulsigen-D, Carbigen, Quil A, and Seppic ISA, in combination with 0.05 mg rhTNF. Serum samples were collected prior to each immunization and 14-21 days after the final immunization.

TABLE 16

| Sample name | Inoculation | Serum collection - Date | Serum collection - Day post-inoculation |
|---|---|---|---|
| Serum sample set #1 | Pre-bleed | 1/11/11 | (—) |
| Serum sample set #2 | 1 | 2/1/11 | 21 |
| Serum sample set #3 | 2 | 2/15/11 | 14 |
| Serum sample set #4 | 3 | 3/8/11 | 21 |
| Serum sample set #5 | 4 | 3/22/11 | 14 |

Serum was prepared from pre-immunization bleeds ("pre-bleed") and after each of 4 inoculations from individual calves as shown in Table 16. Thus, 5 separate Calf Study 1 sample sets were generated for each adjuvant; however, only sample set 1 (pre-bleed), set 4 (after 3 inoculations), and set 5 (after 4 inoculations), were analyzed for rhTNF-binding activity by direct ELISA on rhTNF-coated plates and for rhTNF-neutralizing activity in the L929 cytotoxicity assay, which was carried out as described in US2012/0258118.

Individual calf sera and pools of sera for each group from set 4 (3 inoculations) and set 5 (4 inoculations) were analyzed for TNF-binding activity in anti-TNF ELISA assays at dilutions ranging from 1:10 to 1:10E6. TNF-binding titers were calculated as the inverse dilutions giving 50% of maximal binding ($1/EC_{50}$).

Figure 27:
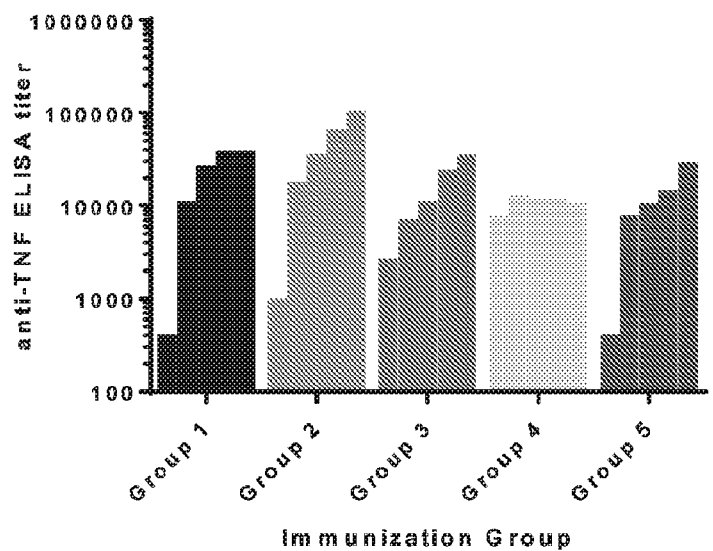
FIG. 27 is a bar graph showing titers of TNF-binding antibodies from pooled sera collected from calves of the indicated groups, as determined by ELISA.

The data in FIGS. 26 and 27, and Tables 17 and 18 (shows data from two independent experiments), show that titers of pooled sera were highest in the Quil A group, followed by Emulsigen-D, Montanide and Emulsigen-BCL. Importantly, there was little or no increase in titer after the $4^{th}$ inoculation in the Quil A and Montanide groups, whereas there was an increase in the Emulsigen-D group and a decrease in the Emulsigen-BCL group.

TABLE 17

| Adjuvant | Quil A | | | Montanide | | | Emulsigen-D | | | Emulsigen BCL | | |
|---|---|---|---|---|---|---|---|---|---|---|---|---|
| Calf # | 1 | 2 | 3 | 4 | 5 | 6 | 7 | 8 | 9 | 10 | 11 | 12 |
| Titer | 2000 | 4000 | 2000 | 1000 | 100 | 2000 | 1000 | 3000 | 5000 | 500 | 1000 | 600 |

Calf sera were then analyzed for TNF-neutralizing antibody titers in the L929 cytotoxicity assay. As shown in Table 18, Quil A showed the highest TNF-neutralizing antibody titers relative to the other adjuvant groups.

TABLE 18

| Calf Study 1 Sample | $1^{st}$ experiment | $2^{nd}$ experiment |
|---|---|---|
| Quil A, Set 4 (3 inoculations) | 53,000 | 42,000 |
| Quil A, Set 5 (4 inoculations) | 175,000 | 175,000 |
| Montanide ISA-201, Set 4 | 43,000 | 40,000 |
| Emulsigen-D, Set 4 | 16,000 | 11,000 |
| Emulsigen-BCL, Set 4 | 9,100 | 7,100 |

Another key distinction from the ELISA data is the 3-4-fold increase in potency between set 4 (3 inoculations) and set 5 (4 inoculations) of the Quil A group, whereas the ELISA data showed that the extra boost did not significantly increase binding antibody titer (from 5000 to 5500; FIG. 26 and Table 17).

Calf Study #2

In this study, 0.05 mg of rhTNF with Quil A was compared to a 10-fold higher antigen dose (0.5 mg per injection). The 0.5 mg rhTNF dose was tested with three different adjuvants—Quil A, Montanide ISA-25, and Montanide ISA-201. An additional group of calves received an even larger dose of rhTNF (1 mg) with Quil A. Three vaccinations at 3 week intervals were conducted, and an extended series of immunizations was also included, with $4^{th}$ and $5^{th}$ vaccinations.

Fifteen male Holstein (13) or Holstein-cross (2) dairy calves aged 3-5 months were used. Sera were generated by immunizing 3 calves per group 5 times by subcutaneous injection at 3 week intervals with different doses of recombinant human tumor necrosis factor (rhTNF; Cell Sciences, Canton, MA) ranging from 0.05 to 1.0 mg, plus one of three adjuvants: Quil A (Groups 1-3), Montanide ISA-201 (Group 4) or Montanide ISA-25 (Group 5) (Table 19).

TABLE 19

| Group | 1 | 2 | 3 | 4 | 5 |
|---|---|---|---|---|---|
| rhTNF antigen | 0.05 mg | 0.5 mg | 1 mg | 0.5 mg | 0.5 mg |
| Adjuvant | Quil A | Quil A | Quil A | Montanide ISA-201 | Montanide ISA-25 |

Serum was prepared from individual calves from pre-immunization bleeds ("pre-bleed") and 3 weeks after each of 5 inoculations. Sera from individual calves and pooled sera from each group were analyzed for rhTNF-binding activity by direct ELISA on rhTNF-coated plates and for rhTNF-neutralizing activity in the L929 cytotoxicity assay as in Calf Study 1.

Figure 28:
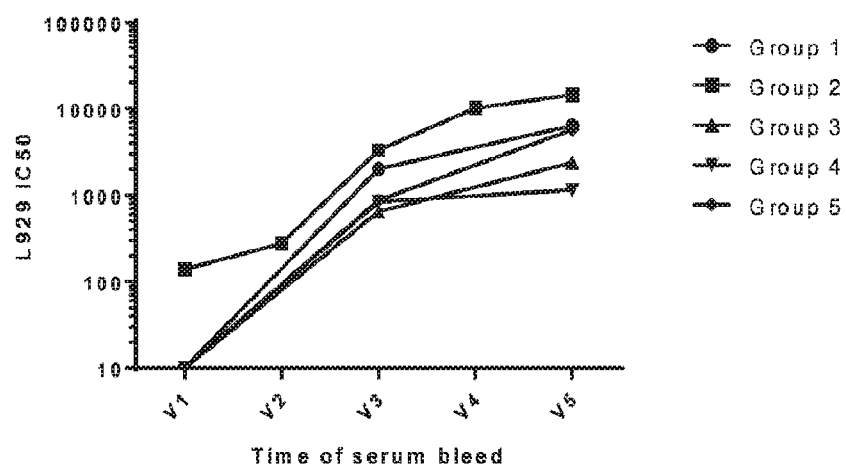
FIG. 28 is a line graph showing the TNF neutralizing activity of pooled sera collected from calves of the indicated groups, as determined by the L929 cell-based assay.

The immunization regimen used in Group 2, which consisted of 0.5 mg of rhTNF plus Quil A, was found to produce the highest peak titer of anti-TNF antibodies after each of the first three immunizations as measured in a TNF ELISA assay (FIG. 27), and the highest TNF neutralizing potency in the L929 cell-based assay (FIG. 28). A comparison among Groups 3, 4 and 5 showed that Quil A was the most effective adjuvant. The difference in both TNF binding titers and neutralization potency between Group 1 and 2 was considered insignificant after 3 vaccinations. Therefore the lower amount of antigen (0.05 mg rhTNF) was selected for immunization regimens involving three vaccinations.

Single Immunization Regimen in Pregnant Cows

This study evaluated a single immunization regimen in pregnant cows based on results from Calf Studies 1 and 2, and evaluated whether the calf data could be extrapolated to pregnant cows.

Five pregnant Holstein cows (80-85 days pre-partum) were immunized four times subcutaneously over a 75 day period with recombinant human TNF (0.5 mg per immunization) mixed with Quil-A adjuvant.

As shown in Table 20, the peak anti-TNF ELISA titers (AU/mL) for each of the 5 cow colostrum samples was seen at milking 1. Similar results were observed with 20 cows immunized 3 times with 0.05 mg rhTNF. There were no significant differences in TNF-binding antibody titers between the 5-cow (4 inoculations with 0.5 mg rhTNF) or the 20-cow (3 inoculations with 0.05 mg rhTNF) studies.

TABLE 20

| | 5 cow | | 20 cow | |
|---|---|---|---|---|
| | Average | STD | Average | STD |
| Pool | 6,479 | 6,157 | 8,140 | 5,918 |
| Milking-1 | 44,686 | 45,356 | 60,335 | 37,816 |
| Milking-2 | 15,593 | 15,521 | 28,008 | 15,810 |
| Milking-3 | 4,499 | 4,017 | 9,424 | 6,480 |
| Milking-4 | 1,806 | 1,314 | 3,663 | 3,391 |
| Milking-5 | 843 | 611 | 1,862 | 2,451 |
| Milking-6 | 602 | 480 | 845 | 1,185 |
| Milking-7 | 558 | 450 | 542 | 710 |
| Milking-8 | 609 | 387 | 426 | 619 |

Example 12—Immunization of Calves with Various Antigens

Five different antigens or antigen combinations were used to immunize male dairy calves to generate polyclonal bovine colostral antibodies for potential use as gut-targeted therapeutics. Certain antigens, such as IL-6Rα, IL-12/23p40 and MAdCAM-1, were selected based on known expression in gastrointestinal tissues, especially in patients with inflammatory bowel disease, and their promising potential as targets for antibody-based therapies (Veldman, 2006; Reenaers et al., 2012). The gluten/gliadin-derived peptide antigens PT-gliadin (van de Wal et al., 1998) and gliadin 33-mer (peptide 56-88; Shan et al., 2002) relate to the concept of generating gluten-neutralizing antibodies for reduction of trace gluten levels in the gut lumen in celiac disease patients. The gliadin 33-mer peptide has been shown to be the immunodominant peptide in the gluten/gliadin molecule in celiac disease patients (Shan et al., 2002; Matysiak-Budnik et al., 2003).

Based on the studies described in Example 11, Quil A adjuvant was used in the immunization studies described below.

Antigen Preparation

Six distinct peptide/protein antigen solutions were prepared from commercially available sources.

A Peptic/Tryptic digest of gliadin (PT-Gliadin) was prepared in house using methodology adapted from van de Wal et al, 1998. Briefly, 1 gram of gliadin (Sigma, Cat #G3375) was dissolved in 10 mL 1M acetic acid for 3 days at room temperature, then boiled for 10 minutes and treated with 10 mg pepsin (Sigma Cat #P6887) for 4 hours at 37° C. The pH was adjusted to 7.8 with NaOH and then treated with 10 mg trypsin (Sigma Cat #T1426-50) for 4 hours at 37° C. Digestion was stopped by adding 10 mg trypsin inhibitor (Sigma Cat #T6522) and incubating at 2-4° C. overnight. Particulates were removed by centrifugation and the solution was dialyzed against phosphate buffered saline (PBS) pH 7.4 using a Spectra/Por Float-a-Lyzer G2 device with an 8-10 kDal cutoff. The final PT-gliadin preparation showed bands of 20 kDal and below by SDS-PAGE, whereas the dominant bands in uundigested gliadin were 40-50 kDal. Peptide content was measured by bicinchoninic acid (BCA) assay calibrated with gliadin.

Gliadin 33-mer (H-Leu-Gln-Leu-Gln-Pro-Phe-Pro-Gln-Pro-Gln-Leu-Pro-Tyr-Pro-Gln-Pro-Gln-Leu-Pro-Tyr-Pro-Gln-Pro-Gln-Leu-Pro-Tyr-Pro-Gln-Pro-Gln-Pro-Phe-NH2; SEQ ID NO: 25) peptide was synthesized by Bachem (Torrance, CA, catalog #4077401) and represents residues 56-88 in the gliadin molecule (Shan et al., 2002).

Other protein antigens were: Recombinant Mouse IL-6Ra (carrier free) from R & D Systems (Cat #1830-SR/CF, lot #ITY141301A; Minneapolis, MN); Recombinant Mouse IL-6 from Cell Sciences (Cat #CRI130C, lot #3201610; Canton, MA); Carrier Free Recombinant Mouse IL-12/IL-23 p40 Homodimer from R& D Systems (Cat #499-ML/CF, lot #RH041212A; Minneapolis, MN) and Recombinant Mouse MAdCAM-1 Fc Chimera from R & D Systems (Cat #993-MC-050, lot #E0H1312101; Minneapolis, MN).

Animals/Immunization Groupings

Fifteen 9-11 month old neutered male Holstein dairy calves were used for the study, and they were separated into five groups with three calves each. The calf groups are summarized in Table 21.

TABLE 21

| Group Antigen | A Peptic/tryptic digest of gliadin (PT-Gliadin); 0.5 mg | B Gliadin 33-mer peptide; 0.5 mg | C IL-6 receptor (IL-6R); 0.05 mg | D IL-6 and IL-6R; 0.05 mg each | E IL-6R, IL-12/IL-23 p40 and mucosal addressin cell adhesion molecule-1 (MAdCAM-1); 0.05 mg each |
|---|---|---|---|---|---|
| Adjuvant | Quil A | Quil A | Quil A | Quil A | Quil A |
| Calf ID # | 26 | 22 | 21 | 29 | 23 |
|  | 28 | 30 | 27 | 35 | 24 |
|  | 33 | 32 | 34 | 36 | 31 |

All groups underwent the same immunization regimen. Immunizations took place on day 0 (V1), day 21 (V2), day 42 (V3), and day 63 (V4). Each dose was approximately 2 cc in volume and immunizations were delivered subcutaneously in the shoulder or neck area. Blood samples were taken before each immunization and the last sample was taken 21 days after the last immunization. Approximately 40 milliliters of blood was collected via venipuncture at each time point. Blood was allowed to clot and then centrifuged if needed to separate serum per standard procedures. The serum was aliquoted into two duplicate samples, and stored at −20° C. A large volume serum collection (40-50 ml serum from −100 ml blood) was performed at the final collection date.

ELISA and Analysis of Samples

To determine if calves produced antibodies to the antigen, serum samples were tested with direct ELISAs. ELISA conditions are shown in Table 22. Plates were washed with PBS-T (PBS pH 7.4 with 0.05% Tween-20) three times using a multi-channel matrix pipette. Wells in the plate were blocked by adding 300 uL per well of 2% Superblock solution (Thermo Fisher #37515) for 30 minutes to an hour at room temperature. Serum samples were initially diluted to a 1:200 initial dilution and tittered down 96 V-well dilution plates using serial three-fold dilutions for a seven-point curve. Reference curves were diluted to appropriate starting concentration depending on the ELISA and were tittered down the plate using serial three-fold dilutions for a seven-point curve. Dilutions were made in 2% Superblock in PBS-T. Blocking solution was removed from ELISA plates and plates were washed three times with PBS-T. Diluted Serum samples and reference curves were transferred to ELISA plates and incubated for one hour. Plates were washed three times and antibody was detected with the addition of 100 uL per well of horse radish peroxidase (HRP)-labeled secondary antibody to bovine Ig (sheep anti-bovine IgG (H+L)) for serum samples and an appropriate HRP labeled antibody for reference curves. Secondary antibody was incubated for one hour. After washing plates three times, 100 uL per well of TMB substrate was added to plates and allowed to develop for twenty minutes after which 100 uL of 1% Sulfuric Acid was added to wells. Plates were read using a Biotek Epoch (Winooski, VT) microplate reader at 450 nm. Background absorbance values from wells containing reagent buffer only were averaged and subtracted from all wells for final blanked A450 nm data. Data were analyzed using Gen5 software with a computer-generated 4-PL curve-fit for sample curves and reference curves. Antibody titer, defined as the dilution which resulted in a 0.2 OD (y=0.2), was calculated for each sample curve and the values were used to generate a curve for each calf serum and for the group pooled serum to represent progression of antibody concentration in serum through the different immunizations.

TABLE 22

| Study Group Tested | ELISA coating Antigen | Coating Concentration | Reference Curve | Reference Curve Secondary | Coating Condition |
|---|---|---|---|---|---|
| Group A | PT-Gliadin | 100 ug/mL | Rabbit anti-gliadin (Sigma #G9144) | HRP Goat anti-rabbit (Bethyl #A120-101P) | One hour at 37° C. |
| Group B | Gliadin 33-mer | 20 ug/mL | Rabbit anti-gliadin (Sigma #G9144) | HRP Goat anti-rabbit (Bethyl #A120-101P) | Two hours axe 37° C. and overnight at 4° C. |
| Group A; Group B | Gliadin in Acetic Acid | 20 ug/mL | Rabbit anti-gliadin (Sigma #G9144) | HRP Goal anti-rabbit (Bethyl #A120-101P) | One hour at 37° C. |
| Group A; Group B | Gliadin in Ures | 20 ug/mL | Rabbit anti-gliadin (Sigma #G9144) | HRP Goat anti-rabbit (Bethyl #A120-101F) | Two hours are 37° C. and overnight at 4° C. |

TABLE 22-continued

| Study Group Tested | ELISA coating Antigen | Coating Concentration | Reference Curve | Reference Curve Secondary | Coating Condition |
|---|---|---|---|---|---|
| Group C, Group D; Group E | IL-6Rα | 500 ng/mL | Goat anti-mouse IL-6R (R&DSystems #AF1830) | HRP Goat anti-rabbit (Bethyl #A120-191P) | Room temperature for one hour |
| Group D | IL-6 | 500 ng/mL | Rabbit anti-mouse IL-6 (Abcam #ab9730) | HRP Rabbit anti-goal IgG H + L (Bethyl #A50-100) | Room temperature for one hour |
| Group E | IL-12/23 p40 | 500 ng/ml | Goat anti-mouse IL-12p40 IgG (Abgent #Af1561a) | HRP Rabbit anti-goat IgG H + L (Bethyl #A50-100) | Room temperature for one hour |
| Group E | IL-23 | 500 ng/mL | #Rabbit anti-mouse IL-23 (Abbiotec #251562) | HRP Goat anti-rabbit H + L (Bethyl #A120-101P) | Room temperature for one hour |
| Group E | IL-12p70 | 500 ng/mL | Rat anti-mouse IL-12p70 (R&D systeams #MAB419) | HRP Goat anti-Rat IgG H + L (Bethyl #A50-100P) | Room temperature for one hour |
| Group E | MASCAM-I | 500 ng/mL | Goat anti-mouse MADCAM-I IgG (LSBio #LS-C150068) | HRF Rabbit anti-goat IgG H + L (Bethyl #A50-100) | Room temperature for one hour |

ELISA Development

Group A was immunized with PT-gliadin peptides and the group sera were evaluated using ELISAs for binding to PT-gliadin, gliadin in urea, and gliadin in acetic acid in order to compare different forms of gliadin that may display immunogenic epitopes to different extents. Group B was immunized with a gliadin 33-mer peptide and the group sera were also evaluated using a gliadin 33-mer, gliadin in urea, and gliadin in acetic acid ELISAs. A polyclonal Rabbit anti-gliadin (Sigma #G9144) was used as reference curve in all of the gliadin ELISA formats. All four standard curves looked similar, all had low background, showed dose-related antibody binding, reached high absorbance at high antibody concentrations, and had low variability between duplicate wells. The reference curves for IL-6, IL-6Rα, IL-12/23p40, and MAdCAM-1 used in Group C, D, and E ELISAs showed similar results. Table 23 provides a summary of the maximal antibody titers of the individual and pooled calf sera from each of the five Groups tested in various ELISAs.

TABLE 23

| Group # | Immunogen | ELISA | Maximal Antibody Titer | | | |
|---|---|---|---|---|---|---|
| | | | Calf #26 | Calf #28 | Calf #33 | Pool A |
| A | PT-Gliadin | PT-Gliadin | 1336 | 5871 | 376 | 2448 |
| | | Gliadin in Acetic acid | 823 | 1469 | 267 | 833 |
| | | Gliadin in Urea | 902 | 1528 | 218 | 826 |
| | | | Calf #22 | Calf #30 | Calf #32 | Pool B |
| B | Gliadin 33-mer | Gliadin 33-mer | 2301 | 233 | 1950 | 1410 |
| | | Gliadin in Acetic acid | 297 | 504 | 642 | 414 |
| | | Gliadin in Urea | 326 | 358 | 888 | 506 |
| | | | Calf #21 | Calf #27 | Calf #34 | Pool C |
| C | IL-6Rα | IL-6Rα | 2609 | 3163 | 9017 | 6764 |
| | | | Calf #29 | Calf #35 | Calf #36 | Pool D |
| D | IL-6 + IL-6Rα | IL-6 IL-6Rα | 2301 6007 | 233 9029 | 1950 6983 | 1410 7248 |
| | | | Calf #23 | Calf #24 | Calf #31 | Pool E |
| E | IL-6Rα + MAdCAM-1 + IL-12/23p40 | IL-6Rα MAdCAM-1 IL-12/23p40 IL-12p70 IL-23 | 752 4520 7724 7325 5280 | 1557 6368 8878 4694 2674 | 3926 13651 22828 5663 3569 | 1490 7789 13097 3619 2747 |

In Group A, calf 28 was a high responder after the second, third and fourth immunizations, while calf 33 did not show a clear response to PT-gliadin immunization at any time point. Calf 26 was a weak responder to PTgliadin, with antibody titers slightly elevated after 2 immunizations. Pooled sera of calves 26, 28 and 33 had intermediate antibody titers relative to the individual calves as would be expected.

Group B sera was analyzed to determine if antibodies would bind to the Gliadin 33-mer peptide coated plates, as well as whole gliadin prepared in acetic acid and in urea. There were significantly higher titers for calves 22 and 32 to gliadin 33-mer compared to gliadin in either acetic acid or urea, suggesting that the dominant immunogenic epitopes on the 33-mer peptide may not be exposed or conformationally present on either form of the gliadin molecule. Calf 30 sera had little or no antibody titers vs any of the three gliadin preparations.

Group C sera were analyzed using a direct ELISA to IL-6Rα, using the same antigen in the ELISA as was used in the immunization of the calves. Calf 34 was a high responder in the ELISA while calves 21 and 27 showed lower antibody titers.

Group D calves were immunized with both IL-6 and IL-6Rα, and sera were analyzed using separate direct ELISAs to IL-6 and IL-6Ra using the same antigens in the ELISAs as were used in the immunization of the calves. Calf 36 had the highest peak antibody response among the three calves after the second immunization for both IL-6 and IL-6Rα, but the antibody response decreased with subsequent immunizations, particularly vs IL-6. The antibody responses of the three calves vs IL-6 had a greater range than those vs IL-6Rα, although all three calves clearly responded to both antigens when they were administered together. The antibody titers of the pooled Group D sera vs IL-6Ra were comparable to those from pooled Group C sera, suggesting that the presence of IL-6 in Group D did not greatly affect the response to IL-6Rα.

Group E calves were immunized with a cocktail of IL-6Rα, IL-12/IL-23p40, and MAdCAM-1. The sera were analyzed in separate direct ELISAs for binding to IL-6Rα, IL-12/IL-23p40, MAdCAM-1, IL-12p70, and IL-23. Calf 31 had the highest antibody response to IL-6Rα, IL-12/IL-23p40, and MAdCAM-1. However, the magnitude of the responses to IL-6Ra was generally smaller than those vs IL-6Ra in Groups C and D. Given the variability in immune responses between individual animals, these lower titers to IL-6Ra may simply reflect that variability. All 3 calves had comparable antibody titers to the heterodimeric molecules IL-12p70 and IL-23, although the titers were lower than vs the IL-12/23p40 chain alone.

These results collectively show the feasibility of generating therapeutic bovine antibodies to Gliadin, IL-6Rα, IL-6 and MAdCAM-1 for evaluation in animal models or human therapy of celiac disease, IBD or other GI indications.

Example 13—DNA Vaccination for Generation of Bovine Antibodies

A strong antibody response to a protein antigen can be induced by vaccination of cattle with a DNA vector containing a gene encoding the desired antigen (see, e.g., van Drunen Little-van den Hurk et al., *Clin Vaccine Immunol* 2013; 20:166-73). Individual animals are injected in the right gluteus maximus muscle with 1.5 mg of plasmid DNA in 1 mL, followed by application of a 250-V/cm electrical field for 400 ms at a 10% duty cycle, using a TriGrid electrode array (Ichor Medical Systems). The immunizations are repeated two or three times, 21 days apart, and are expected to induce a significant antibody response.

Example 14—Generation of Hybridomas Producing Monoclonal Bovine Antibodies Following Immunization Hybridomas can be generated from immunized cows to establish bovine antibody-secreting cell lines, essentially as described in U.S. Pat. No. 5,026,646.

Right prescapular, left prescapular, and right prefemoral superficial lymph nodes of cows immunized as described in Examples 11 and 12 are surgically removed under general anesthesia, sectioned, and passed through a 80-mesh sieve. Extracted cells are washed and used for fusion. Fusions are performed with modified version of the PEG protocol (Van Deusen et al., *Am Assoc Vet Lab Diagnost* 24$^{th}$ *Annual Proc* 1981:211-228) using myeloma cell:lymph node cell ratios of approximately 1, and seeded onto 96-well plates. Cells are cultured at a 1:1 ratio of DMEM and high glucose with 10% horse serum to conditioned media from fusion partner cultures. Fusion partner selection for methotrexate sensitivity is achieved by passage in media containing 6-thioguanine and 8-azaguanine.

SP2/0 murine myeloma cell s are fused with right prescapular calf lymph nodes cells in a 3:1 mixture to generate bovine Ig secreting primary cell lines. After secretion ceases, the lines are selected for methotrexate sensitivity by passage in media containing 6-thioguanine and 8-azaguanine. Methotrexate-sensitive bovine:murine heterohybridomas are combined in a 1:1 ratio and mixed with lymph node cells from the immunized and extracted left prescapular lymph node from the same calf used previously at a 1:1 ratio. This fusion results in transiently bovine Ig secreting cell lines, which are then selected for methotrexate sensitivity once secretion ceases. Cells from the methotrexate-sensitive bovine x murine heterohybridomas are combined in a 1:1 ratio and fused with fresh lymph node cells from an immunized, right prefemoral lymph node from the same calf as before at a 1:2 mixture, respectively. The fusion results in bovine x murine primary heterohybridomas that secrete bovine antibodies. Stable heterohybridomas secreting antibodies having the function of interest (e.g., binding to TNF) e identified, cloned, and subcloned.

The heterohybridomas can be further screened for those which produce IgG1 antibodies by sequencing using routine methods.

Example 15—Single B Cell Sequencing and Recombinant Antibody Production

Single B cells are sequenced essentially as described by Tiller et al. (*J Immunol Methods* 2008; 329:122-4). Mononuclear cells are isolated from peripheral venous blood or serum of cows immunized as described in Examples 11 and 12, purified by Ficoll-Paque density gradient centrifugation, and optionally followed by enrichment of B cells using anti-CD19 magnetic beads. Single mononuclear cells are sorted by flow cytometry into 96-well PCR plates. cDNA is synthesized directly in each well. Total RNA from single cells are reverse transcribed with random hexamers using the Superscript III reverse transcriptase kit, and IgG, Igλ and Igκ V transcripts are amplified with gene-specific primers using the isolated cDNA as template. Aliquots of the $V_H$, Vκ and Vλ chain PCR products are purified and sequenced. Sequences are analyzed by IgBLAST comparison with GenBank to identify germline V(D)J gene segments with highest identity.

PCR products are purified using the Qia-Quick 96 PCR Purification Kit (Qiagen). PCR samples are digested and ligated into the multiple cloning site of human Igγ1, Igκ and Igλ expression vectors. Ligation products are transformed into competent DH10B bacteria cells, and colonies are PCR screened for the presence of bands of the expected size. Plasmid DNA is isolated from bacterial cultures using QIAprep Spin columns (Qiagen) and purified. Antibodies are produced by transiently transfecting the purified plasmids into HEK293 cells or 293T cells cultured in 150 mm plates. Six days after transfection, culture supernatants are harvested and antibodies are purified using Protein G beads. Recombinant antibody concentrations are then determined by ELISA.

Example 16—Selection of Recombinant Bovine Monoclonal IgG1 Antibodies

Antibodies produced according to Example 14 or 15 are sequenced to determine whether they have the structural properties that confer resistance to proteases as described herein, and tested for functional activity (e.g., binding to target antigen) and stability using methods described in the preceding Examples. Further, as discussed supra, potential protease cut sites in the antigen-binding region are also considered when generating stable bovine IgG1 antibodies. Thus, the antibodies are tested for both antigen binding and pancreatin stability using the methods described in Examples 2 and 10 to confirm they retain antigen binding and stability from pancreatin digestion.

The heavy and light chains of antibodies found to have the desired properties (both structural and functional) are cloned into expression vectors, expressed, harvested, and purified using standard recombinant methods.

Figure 29:
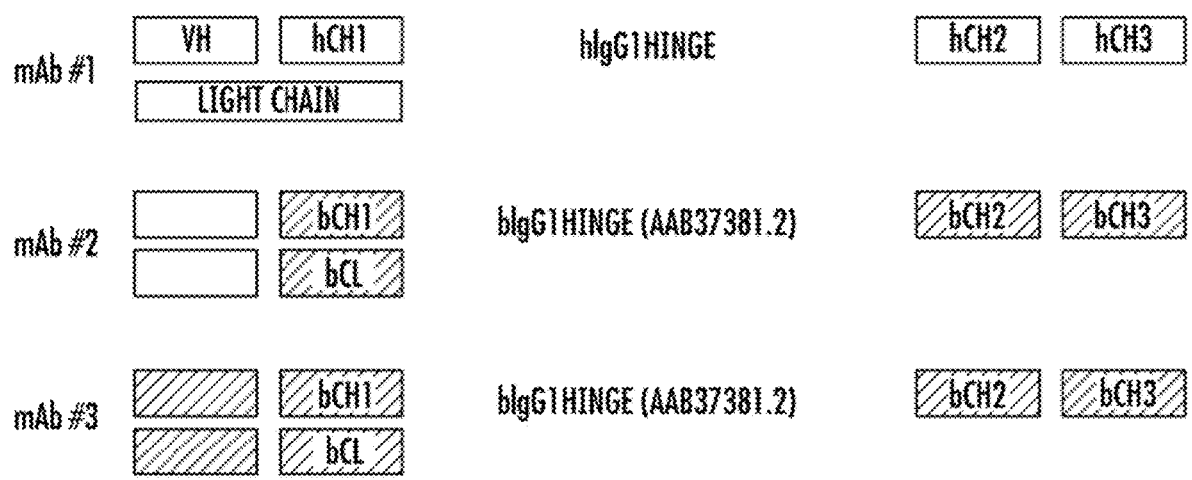
FIG. 29 is a schematic of bovinized constructs using infliximab as the parent antibody.

Example 17—Construct Design for Fully Bovine Recombinant Monoclonal Antibodies and Bovinized Antibodies A parent antibody may be modified to impart the features of a bovine early colostral antibody such that the modified antibody has enhanced resistance to protease digestion. FIG. 29 shows the various constructs that can made (using infliximab as an exemplary parent antibody) and inserted into expression vectors in host cells that may be any mammalian host cell or a ruminant mammary epithelial cell line such as MAC-T for expression.

TABLE 24

| Description | Amino acid sequence |
|---|---|
| Infliximab Fab sequence - light chain (SEQ ID NO: 26) | DILLTQSPAILSVSPGERVSFSCRASQFVGSSIHWYQQRINGSPRLLIKYASESMSG IPSRFSGSGSGTDFTLSINTVESEDIADYYCQQSHSWPFTFGSGTNLEVKRTVAAPS VFIFPPSDEQLKSGTASVVCLLNNFYPREAKVQWKVDNALQSGNSQESVTEQDSKDS TYSLSSTLTLSKADYEKHKVYACEVTHQGLSSPVTKSENRGEC |
| Infliximab Fab sequence - heavy chain (SEQ ID NO: 27) | EVKLEESGGGLVQPGGSMKLSCVASGFIFSNHWMNWVRQSPEKGLEWVAEIRSKSIN SATHYAESVKGRFTISRDDSKSAVYLQMTDLRTEDTGVYYCSRNYYGSTYDYWGQGT TLTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKSCDKT |
| Infliximab sequence heavy chain construct #1 (SEQ ID NO: 28) | EVKLEESGGGLVQPGGSMKLSCVASGFIFSNHWMNWVRQSPEKGLEWVAEIRSKSIN SATHYAESVKGRFTISRDDSKSAVYLQMTDLRTEDTGVYYCSRNYYGSTYDYWGQGT TLTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKSCDKTHT CPPCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTISKA KGQPREPQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPGK |
| Infliximab w/Bovine Fc Heavy chain construct #2 (SEQ ID NO: 29) | EVKLEESGGGLVQPGGSMKLSCVASGFIFSNHWMNWVRQSPEKGLEWVAEIRSKSIN SATHYAESVKGRFTISRDDSKSAVYLQMTDLRTEDTGVYYCSRNYYGSTYDYWGQGT TLTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKSCDK<u>THT CPPCPAPELLGGP</u>SVFIFPPKPKDTLTISGTPEVTCVVVDVGHDDPEVKFSWFVDDV EVNTATTKPREEQFNSTYRVVSALRIQHQDWTGGKEFKCKVHNEGLPAPIVRTISRT KGPAREPQVYVLAPPQEELSKSTVSLTCMVTSFYPDYIAVEWQRNGQPESEDKYGTT PPQLDADGSYFLYSRLRVDRNSWQEGDTYTCVVMHEALHNHYTQKSTSKSAGK |
| Infliximab with Bovine Fc IgG1 hinge Heavy chain construct #3 (SEQ ID NO: 30) | EVKLEESGGGLVQPGGSMKLSCVASGFIFSNHWMNWVRQSPEKGLEWVAEIRSKSIN SATHYAESVKGRFTISRDDSKSAVYLQMTDLRTEDTGVYYCSRNYYGSTYDYWGQGT TLTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKS<u>CKTTCD CCPPPELPGG</u>PSVFIFPPKPKDTLTISGTPEVTCVVVDVGHDDPEVKFSWFVDDVEV NTATTKPREEQFNSTYRVVSALRIQHQDWTGGKEFKCKVHNEGLPAPIVRTISRTKG PAREPQVYVLAPPQEELSKSTVSLTCMVTSFYPDYIAVEWQRNGQPESEDKYGTTPP QLDADGSYFLYSRLRVDRNSWQEGDTYTCVVMHEALHNHYTQKSTSKSAGK |
| Infliximab with bovine Fc, IgG2 hinge Heavy Chain construct #5 (SEQ ID NO: 31) | EVKLEESGGGLVQPGGSMKLSCVASGFIFSNHWMNWVRQSPEKGLEWVAEIRSKSIN SATHYAESVKGRFTISRDDSKSAVYLQMTDLRTEDTGVYYCSRNYYGSTYDYWGQGT TLTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKS<u>CKIDCS KCHNQPCVREP</u>SVFIFPPKPKDTLTISGTPEVTCVVVDVGHDDPEVKFSWFVDDVEV NTATTKPREEQFNSTYRVVSALRIQHQDWTGGKEFKCKVHNEGLPAPIVRTISRTKG PAREPQVYVLAPPQEELSKSTVSLTCMVTSFYPDYIAVEWQRNGQPESEDKYGTTPP QLDADGSYFLYSRLRVDRNSWQEGDTYTCVVMHEALHNHYTQKSTSKSAGK |
| Infliximab w/bovine Fc, IgG3 hinge Heavy Chain construct #6 (SEQ ID NO: 32) | EVKLEESGGGLVQPGGSMKLSCVASGFIFSNHWMNWVRQSPEKGLEWVAEIRSKSIN SATHYAESVKGRFTISRDDSKSAVYLQMTDLRTEDTGVYYCSRNYYGSTYDYWGQGT TLTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKS<u>CRPVPT TPKTTIPPGKPTTQESEVEKTPCQCSKCPEPLGGL</u>SVFIFPPKPKDTLTISGTPEVT CVVVDVGHDDPEVKFSWFVDDVEVNTATTKPREEQFNSTYRVVSALRIQHQDWTGGK EFKCKVHNEGLPAPIVRTISRTKGPAREPQVYVLAPPQEELSKSTVSLTCMVTSFYP DYIAVEWQRNGQPESEDKYGTTPPQLDADGSYFLYSRLRVDRNSWQEGDTYTCVVMH EALHNHYTQKSTSKSAGK |

TABLE 24-continued

| Description | Amino acid sequence |
|---|---|
| Infliximab sequence light chain with bovine kappa constant light domain (bovine constant light chain (~75%) with highest homology to infliximab constant light chain was chosen) (SEQ ID NO: 33) | DILLTQSPAILSVSPGERVSFSCRASQFVGSSIHWYQQRINGSPRLLIKYASESMSG IPSRFSGSGSGTDFTLSINTVESEDIADYYCQQSHSWPFTFGSGTNLEVKRTVAAPS VFLFKPSDEQLKTGTVSVVCLVNDFYPKDINVKWKVDGVTQSSSNFQNSFTDQDSKK STYSLSSILTLPSSEYQSHNAYTCEVSHKSLTTALVKSFSKNEC |
| Infliximab sequence light chain with bovine lambda constant light chain domain (bovine constant light chain domain with the highest abundance in AVX-470 and other colostral IgG preparations was chosen) (SEQ ID NO: 34) | DILLTQSPAILSVSPGERVSFSCRASQFVGSSIHWYQQRINGSPRLLIKYASESMSG IPSRFSGSGSGTDFTLSINTVESEDIADYYCQQSHSWPFTFGSGTNLEVKGQPKSPP SVTLFPPSTEELNGNKATLVCLISDFYPGSVTVVWKADGSTITRNVETTRASKQSNS KYAASSYLSLTSSDWKSKGSYSCEVTHEGSTVTKTVKPSECS |
| Chimeric infliximab with bovine IgG1 constant region (CH1, hinge, and Fc domain sequences) (bovine sequences are underlined)-heavy chain (SEQ ID NO: 35) | EVKLEESGGGLVQPGGSMKLSCVASGFIFSNHWMNWVRQSPEKGLEWVAEIRSKSIN SATHYAESVKGRFTISRDDSKSAVYLQMTDLRTEDTGVYYCSRNYYGSTYDYWGQGT TLTVSS<u>ASTTAPKVYPLSSCCGDKSSSTVTLGCLVSSYMPEPVTVTWNSGALKSGVH TFPAVLQSSGLYSLSSMVTVPGSTSGQTFTCNVAHPASSTKVDKAVDPTCKPSPCDC CPPPELPGGPSVFIFPPKPKDTLTISGTPEVTCVVVDVGHDDPEVKFSWFVDDVEVN TATTKPREEQFNSTYRVVSALRIQHQDWTGGKEFKCKVHNEGLPAPIVRTISRTKGP AREPQVYVLAPPQEELSKSTVSLTCMVTSFYPDYIAVEWQRNGQPESEDKYGTTPPQ LDADSSYFLYSKLRVDRNSWQEGDTYTCVVMHEALHNHYTQKSTSKSAGK</u> |
| Chimeric infliximab with bovine IgG1 constant region (CH1, hinge, and Fc domain sequences) (bovine sequences are underlined)-light chain (SEQ ID NO: 36) | DILLTQSPAILSVSPGERVSFSCRASQFVGSSIHWYQQRINGSPRLLIKYASESMSG IPSRFSGSGSGTDFTLSINTVESEDIADYYCQQSHSWPFTFGSGTNLEVK<u>RSDAEPS VFLFKPSDEQLKTGTVSVVCLVNDFYPKDINVKWKVDGVTQSSSNFQNSFTDQDSKK STYSLSSILTLPSSEYQSHNAYTCEVSHKSLTTALVKSFSKNEC</u> |

Heavy and light chain sequences of exemplary bovinized antibodies are provided below (bovine sequences are underlined).

TABLE 25

| Description | Sequence |
|---|---|
| Bovinized anti-a4b7 integrin antibody (cross-reacts with mouse and human a4b7 integrin; PDB ID: 3V4P, V domain pI = 6.72)-heavy chain (SEQ ID NO: 37) | QVQLQQPGAELVKPGTSVKLSCKGYGYTFTSYWMHWVKQRPGQGLEWIGEIDPSESNT NYNQKFKGKATLTVDISSSTAYMQLSSLTSEDSAVYYCARGGYDGWDYAIDYWGQGTS VTVSS<u>ASTTAPKVYPLSSCCGDKSSSTVTLGCLVSSYMPEPVTVTWNSGALKSGVHTF PAVLQSSGLYSLSSMVTVPGSTSGQTFTCNVAHPASSTKVDKAVDPTCKPSPCDCCPPP ELPGGPSVFIFPPKPKDTLTISGTPEVTCVVVDVGHDDPEVKFSWFVDDVEVNTATT KPREEQFNSTYRVVSALRIQHQDWTGGKEFKCKVHNEGLPAPIVRTISRTKGPAREPQ VYVLAPPQEELSKSTVSLTCMVTSFYPDYIAVEWQRNGQPESEDKYGTTPPQLDADSS YFLYSKLRVDRNSWQEGDTYTCVVMHEALHNHYTQKSTSKSAGK</u> |
| Bovinized anti-a4b7 integrin antibody (cross-reacts with mouse and human a4b7 integrin; PDB ID: 3V4P, V domain pI = 6.72)-light chain (SEQ ID NO: 38) | DVVVTQTPLSLPVSFGDQVSISCRSSQSLAKSYGNTYLSWYLHKPGQSPQLLIYGISN RFSGVPDRFSGSGSGTDFTLKISTIKPEDLGMYYCLQGTHQPYTFGGGTKLEIKRSDA <u>EPSVFLFKPSDEQLKTGTVSVVCLVNDFYPKDINVKWKVDGVTQSSSNFQNSFTDQDS KKSTYSLSSILTLPSSEYQSHNAYTCEVSHKSLTTALVKSFSKNEC</u> |
| Bovinized anti-IL-12 antibody (PBD ID: 3HMW, V domain pI = 8.74)-heavy chain (SEQ ID NO: 39) | EVQLVQSGAEVKKPGESLKISCKGSGYSFTTYWLGWVRQMPGKGLDWIGIMSPVDSDI RYSPSFQGQVTMSVDKSITTAYLQWNSLKASDTAMYYCARRRPGQGYFDFWGQGTLVT VSS<u>ASTTAPKVYPLSSCCGDKSSSTVTLGCLVSSYMPEPVTVTWNSGALKSGVHTFPA VLQSSGLYSLSSMVTVPGSTSGQTFTCNVAHPASSTKVDKAVDPTCKPSPCDCCPPPE LPGGPSVFIFPPKPKDTLTISGTPEVTCVVVDVGHDDPEVKFSWFVDDVEVNTATTKP REEQFNSTYRVVSALRIQHQDWTGGKEFKCKVHNEGLPAPIVRTISRTKGPAREPQVY VLAPPQEELSKSTVSLTCMVTSFYPDYIAVEWQRNGQPESEDKYGTTPPQLDADSSYF LYSKLRVDRNSWQEGDTYTCVVMHEALHNHYTQKSTSKSAGK</u> |
| Bovinized anti-IL-12 antibody (PBD ID: 3HMW, V domain pI = 8.74)-light chain (SEQ ID NO: 40) | DIQMTQSPSSLSASVGDRVTITCRASQGISSWLAWYQQKPEKAPKSLIYAASSLQSGV PSRFSGSGSGTDFTLTISSLQPEDFATYYCQQYNIYPYTFGQGTKLEIK<u>RSDAEPSVF LFKPSDEQLKTGTVSVVCLVNDFYPKDINVKWKVDGVTQSSSNFQNSFTDQDSKKSTY SLSSILTLPSSEYQSHNAYTCEVSHKSLTTALVKSFSKNEC</u> |
| Bovinized anti-MAdCAM-1 antibody (PBD ID: 4HCR, V domain pI = 7.6)-heavy chain (SEQ ID NO: 41) | QVQLVQSGAEVKKPGASVKVSCKASGYTFTSYGINWVRQAPGQGLEWMGWISVYSGNT NYAQKVQGRVTMTADTSTSTAYMDLRSLRSDDTAVYYCAREGSSSSGDYYYGMDVWGQ GTTVTVSS<u>ASTTAPKVYPLSSCCGDKSSSTVTLGCLVSSYMPEPVTVTWNSGALKSGV HTFPAVLQSSGLYSLSSMVTVPGSTSGQTFTCNVAHPASSTKVDKAVDPTCKPSPCDC CPPPELPGGPSVFIFPPKPKDTLTISGTPEVTCVVVDVGHDDPEVKFSWFVDDVEVNT</u> |

TABLE 25-continued

| Description | Sequence |
|---|---|
| | ATTKPREEQFNSTYRVVSALRIQHQDWTGGKEFKCKVHNEGLPAPIVRTISRTKGPAR<br>EPQVYVLAPPQEELSKSTVSLTCMVTSFYPDYIAVEWQRNGQPESEDKYGTTPPQLDA<br>DSSYFLYSKLRVDRNSWQEGDTYTCVVMHEALHNHYTQKSTSKSAGK |
| Bovinized anti-MAdCAM-1 antibody (PBD ID: 4HCR, V domain pI = 7.6)-light chain (SEQ ID NO: 42) | DIVMTQTPLSLSVTPGQPASISCKSSQSLLHTDGTTYLYWYLQKPGQPPQLLIYEVSN<br>RFSGVPDRFSGSGSGTDFTLKISRVEAEDVGIYYCMQNIQLPWTFGQGTKVEIKRSDA<br>EPSVFLFKPSDEQLKTGTVSVVCLVNDFYPKDINVKWKVDGVTQSSSNFQNSFTDQDS<br>KKSTYSLSSILTLPSSEYQSHNAYTCEVSHKSLTTALVKSFSKNEC |
| Bovinized anti-IL-23 antibody (PBD ID: 3D85, V domain pI = 8.38)-heavy chain (SEQ ID NO: 43) | EVQLQQSGPELVKPGASVKMSCKASGYTFTSNVMHWVKQKPGQGLEWIGYINPYNDGT<br>KYNEKFKGKATLTSDKSSSTAYMELSSLTSEDSAVYYCARNWDVAYWGQGTLVTVSAA<br>STTAPKVYPLSSCCGDKSSSTVTLGCLVSSYMPEPVTVTWNSGALKSGVHTFPAVLQS<br>SGLYSLSSMVTVPGSTSGQTFTCNVAHPASSTKVDKAVDPTCKPSPCDCCPPPELPGG<br>PSVFIFPPKPKDTLTISGTPEVTCVVVDVGHDDPEVKFSWFVDDVEVNTATTKPREEQ<br>FNSTYRVVSALRIQHQDWTGGKEFKCKVHNEGLPAPIVRTISRTKGPAREPQVYVLAP<br>PQEELSKSTVSLTCMVTSFYPDYIAVEWQRNGQPESEDKYGTTPPQLDADSSYFLYSK<br>LRVDRNSWQEGDTYTCVVMHEALHNHYTQKSTSKSAGK |
| Bovinized anti-IL-23 antibody (PBD ID: 3D85, V domain pI = 8.38)-light chain (SEQ ID NO: 44) | DIVMTQSPATLSVTPGDRVSLSCRASQSISDYLHWYRQKSHESPRLLIKYASQSISGI<br>PSRFSGSGSGSDFTLSINSVEPEDVGVYYCQNGHSFPFTFGSGTKLEIKRSDAEPSVF<br>LFKPSDEQLKTGTVSVVCLVNDFYPKDINVKWKVDGVTQSSSNFQNSFTDQDSKKSTY<br>SLSSILTLPSSEYQSHNAYTCEVSHKSLTTALVKSFSKNEC |
| Bovinized anti-EGFR/HER3 bispecific antibody (PBD ID: 3P0V, V domain pI = 6.13)-heavy chain (SEQ ID NO: 45) | EVQLVESGGGLVQPGGSLRLSCAASGFTLSGDWIHWVRQAPGKGLEWLGEISAAGGYT<br>DYADSVKGRFTISADTSKNTAYLQMNSLRAEDTAVYYCARESRVSFEAAMDYWGQGTL<br>VTVSSASTTAPKVYPLSSCCGDKSSSTVTLGCLVSSYMPEPVTVTWNSGALKSGVHTF<br>PAVLQSSGLYSLSSMVTVPGSTSGQTFTCNVAHPASSTKVDKAVDPTCKPSPCDCCPP<br>PELPGGPSVFIFPPKPKDTLTISGTPEVTCVVVDVGHDDPEVKFSWFVDDVEVNTATT<br>KPREEQFNSTYRVVSALRIQHQDWTGGKEFKCKVHNEGLPAPIVRTISRTKGPAREPQ<br>VYVLAPPQEELSKSTVSLTCMVTSFYPDYIAVEWQRNGQPESEDKYGTTPPQLDADSS<br>YFLYSKLRVDRNSWQEGDTYTCVVMHEALHNHYTQKSTSKSAGK |
| Bovinized anti-EGFR/HER3 bispecific antibody (PBD ID: 3P0V, V domain pI = 6.13)-light chain (SEQ ID NO: 46) | DIQMTQSPSSLSASVGDRVTITCRASQDLATDVAWYQQKPGKAPKLLIYSASFLYSGV<br>PSRFSGSGSGTDFTLTISSLQPEDFATYYCQQSEPEPYTFGQGTKVEIKRSDAEPSVF<br>LFKPSDEQLKTGTVSVVCLVNDFYPKDINVKWKVDGVTQSSSNFQNSFTDQDSKKSTY<br>SLSSILTLPSSEYQSHNAYTCEVSHKSLTTALVKSFSKNEC |
| Bovinized anti-CD25 antibody (PBD ID: 3P0V, V domain pI = 6.13)-heavy chain (SEQ ID NO: 47) | EVQLQQSGTVLARPGASVKMSCKASGYSFTRYWMHWIKQRPGQGLEWIGAIYPGNSDT<br>SYNQKFEGKAKLTAVTSASTAYMELSSLTHEDSAVYYCSRDYGYYFDFWGQGTTLTVS<br>SASTTAPKVYPLSSCCGDKSSSTVTLGCLVSSYMPEPVTVTWNSGALKSGVHTFPAVL<br>QSSGLYSLSSMVTVPGSTSGQTFTCNVAHPASSTKVDKAVDPTCKPSPCDCCPPPELP<br>GGPSVFIFPPKPKDTLTISGTPEVTCVVVDVGHDDPEVKFSWFVDDVEVNTATTKPRE<br>EQFNSTYRVVSALRIQHQDWTGGKEFKCKVHNEGLPAPIVRTISRTKGPAREPQVYVL<br>APPQEELSKSTVSLTCMVTSFYPDYIAVEWQRNGQPESEDKYGTTPPQLDADSSYFLY<br>SKLRVDRNSWQEGDTYTCVVMHEALHNHYTQKSTSKSAGK |
| Bovinized anti-CD25 antibody (PBD ID: 3P0V, V domain pI = 6.13)-light chain (SEQ ID NO: 48) | QIVSTQSPAIMSASPGEKVTMTCSASSSRSYMQWYQQKPGTSPKRWIYDTSKLASGVP<br>ARFSGSGSGTSYSLTISSMEAEDAATYYCHQRSSYTFGGGTKLEIKRSDAEPSVFLFK<br>PSDEQLKTGTVSVVCLVNDFYPKDINVKWKVDGVTQSSSNFQNSFTDQDSKKSTYSLS<br>SILTLPSSEYQSHNAYTCEVSHKSLTTALVKSFSKNEC |
| Bovinized anti-IL-6R_antibody-heavy chain (SEQ ID NO: 49) | EVQLVESGGGLVQPGRSLRLSCAASRFTFDDYAMHWVRQAPGKGLEWVSGISWNSGRI<br>GYADSVKGRFTISRDNAENSLFLQMNGLRAEDTALYYCAKGRDSFDIWGQGTMVTVSS<br>ASTTAPKVYPLSSCCGDKSSSTVTLGCLVSSYMPEPVTVTWNSGALKSGVHTFPAVLQ<br>SSGLYSLSSMVTVPGSTSGQTFTCNVAHPASSTKVDKAVDPTCKPSPCDCCPPPELPG<br>GPSVFIFPPKPKDTLTISGTPEVTCVVVDVGHDDPEVKFSWFVDDVEVNTATTKPREE<br>QFNSTYRVVSALRIQHQDWTGGKEFKCKVHNEGLPAPIVRTISRTKGPAREPQVYVLA<br>PPQEELSKSTVSLTCMVTSFYPDYIAVEWQRNGQPESEDKYGTTPPQLDADSSYFLYS<br>KLRVDRNSWQEGDTYTCVVMHEALHNHYTQKSTSKSAGK |
| Bovinized anti-IL-6R_antibody-light chain (SEQ ID NO: 50) | DIQMTQSPSSVSASVGDRVTITCRASQGISSWLAWYQQKPGKAPKLLIYGASSLESGV<br>PSRFSGSGSGTDFTLTISSLQPEDFASYYCQQANSFPYTFGQGTKLEIKRSDAEPSVF<br>LFKPSDEQLKTGTVSVVCLVNDFYPKDINVKWKVDGVTQSSSNFQNSFTDQDSKKSTY<br>SLSSILTLPSSEYQSHNAYTCEVSHKSLTTALVKSFSKNEC |

Minimal Bovinization

Figure 30:
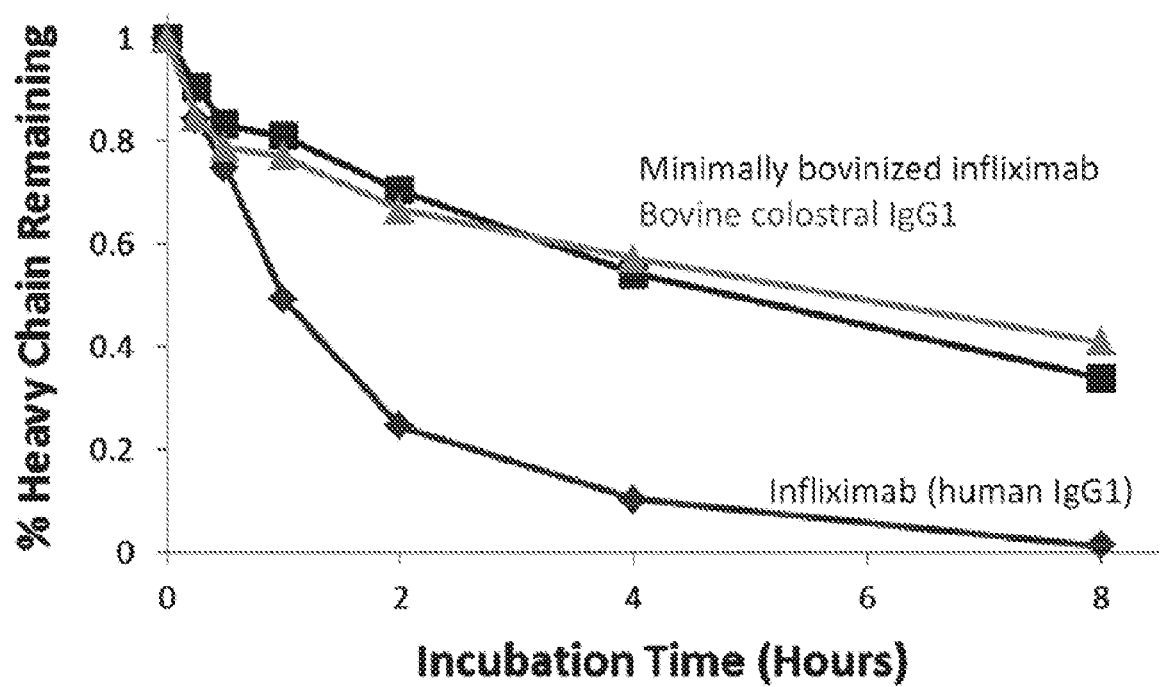
FIG. 30 is a line graph plotting the pancreatin-mediated degradation of the antibody heavy chain of infliximab, minimally bovinized infliximab, and bovine colostral IgG1.

Presented below are minimally bovinized human IgG1, 2, and 4 constant region sequences which exhibit protease resistance and be incorporated into parent antibodies (e.g., combined with the variable regions of the parent antibody) to create highly stable, digestion resistant antibodies which can be administered orally. The constant regions of the parent antibody are replaced with the minimally bovinized sequences using routine recombinant techniques. Protease resistance can then be tested using the art-recognized methods described herein. For instance, the minimally bovinized human IgG1 construct was purified and tested by pancreatin digestion, as described in Example 3, and shown to have comparable protease stability to bovine colostral IgG1 and significantly greater protease stability than the parent human IgG1 molecule (infliximab) (FIG. 30).

TABLE 26

| Minimally bovinized human IgG1 | |
|---|---|
| Human IgG1 (SEQ ID NO: 51) | ASTKGPSVFPLAPSSKSTSGGTAALGCLVKDYFPEPVTVSWNSGALTSGVHTFPAVLQSSGLYSLSSVVTVPSSSLGT |
| Bovine IgG1d (CAA44699.1) (SEQ ID NO: 52) | ASTTAPKVYPLSSCCGDKSSSTVTLGCLVSSYMPEPVTVTWNSGALKSGVHTFPAVLQSSGLYSLSSMVTVPGSTSG |
| Minimally bovinized IgG1 (SEQ ID NO: 53) | ASTKGPSVFPLSSCCGDKSGGTAALGCLVKDYFPEPVTVSWNSGALTSGVHTFPAVLQSSGLYSLSSVVTVPSSSLGT |
| Human IgG1 (SEQ ID NO: 54) | QTYICNVNHKPSNTKVDKKVEPKSCDKTHTCPPCPAPELLGGPSVFLFPPKPKDTLMISRTPEVTCVVVDVSHEDPEV |
| Bovine IgG1d (CAA44699.1) (SEQ ID NO: 55) | QTFTCNVAHPASSTKVDKAVDP.TC.KPSPCDCCPPPELPGGPSVFIFPPKPKDTLTISGTPEVTCVVVDVGHDDPEV |
| Minimally bovinized IgG1 (SEQ ID NO: 56) | QTYICNVNHKPSNTKVDKAVDP.TC.KPSPCDCCPPPELLGGPSVFLFPPKPKDTLMISRTPEVTCVVVDVSHEDPEV |

TABLE 27

| Minimally bovinized human IgG2 | |
|---|---|
| Human IgG2 (AAB59393.1) (SEQ ID NO: 57) | ASTKGPSVFPLAPCSRSTSESTAALGCLVKDYFPEPVTVSWNSGALTSGVHTFPAVLQSSGLYSLSSVVTVPSSNFGT |
| Bovine IgG1d (CAA44699.1) (SEQ ID NO: 58) | ASTTAPKVYPLSSCCGDKSSSTVTLGCLVSSYMPEPVTVTWNSGALKSGVHTFPAVLQSSGLYSLSSMVTVPGSTSG |
| Minimally bovinized IgG2 (SEQ ID NO: 59) | ASTKGPSVFPLSSCCGDKSESTAALGCLVKDYFPEPVTVSWNSGALTSGVHTFPAVLQSSGLYSLSSVVTVPSSNFGT |
| Human IgG2 (AAB59393.1) (SEQ ID NO: 60) | QTYTCNVDHKPSNTKVDKTVERKCCVE.CPPCPAP.PVAGPSVFLFPPKPKDTLMISRTPEVTCVVVDVSHEDPEV |
| Bovine IgG1d (CAA44699.1) (SEQ ID NO: 61) | QTFTCNVAHPASSTKVDKAVDPTCKPSPCDCCPPPELPGGPSVFIFPPKPKDTLTISGTPEVTCVVVDVGHDDPEV |
| Minimally bovinized IgG2 (SEQ ID NO: 62) | QTYTCNVDHKPSNTKVDKAVDPTCKPSPCDCCPPPELPAGPSVFLFPPKPKDTLMISRTPEVTCVVVDVSHEDPEV |

TABLE 28

| Minimally bovinized human IgG4 | |
|---|---|
| Human IgG4 (AAB59394.1) (SEQ ID NO: 63) | ASTKGPSVFPLAPCSRSTSESTAALGCLVKDYFPEPVTVSWNSGALTSGVHTFPAVLQSSGLYSLSSVVTVPSSSLGT |
| Bovine IgG1d (CAA44699.1) (SEQ ID NO: 64) | ASTTAPKVYPLSSCCGDKSSSTVTLGCLVSSYMPEPVTVTWNSGALKSGVHTFPAVLQSSGLYSLSSMVTVPGSTSG |
| Minimally bovinized IgG4 (SEQ ID NO: 65) | ASTKGPSVFPLSSCCGDKSESTAALGCLVKDYFPEPVTVSWNSGALTSGVHTFPAVLQSSGLYSLSSVVTVPSSSLGT |
| Human IgG4 (AAB59394.1) (SEQ ID NO: 66) | KTYTCNVDHKPSNTKVDKRVESKYGP.PCPSCPAPEFLGGPSVFLFPPKPKDTLMISRTPEVTCVVVDVSQEDPEV |

TABLE 28-continued

Minimally bovinized human IgG4

```
Bovine IgG1d      QTFTCNVAHPASSTKVDKAVDPTCKPSPCDCCPPPELPGGPSVFIFPPKPKDTLTISGTPEVTCVVVDVGHD
(CAA44699.1)      DPEV
(SEQ ID NO: 67)

Minimally         KTYTCNVDHKPSNTKVDKAVDPTCKPSPCDCCPAPEFLGGPSVFLFPPKPKDTLMISRTPEVTCVVVDVSQE
bovinized IgG4    DPEV
(SEQ ID NO: 68)
```

Figure 31:
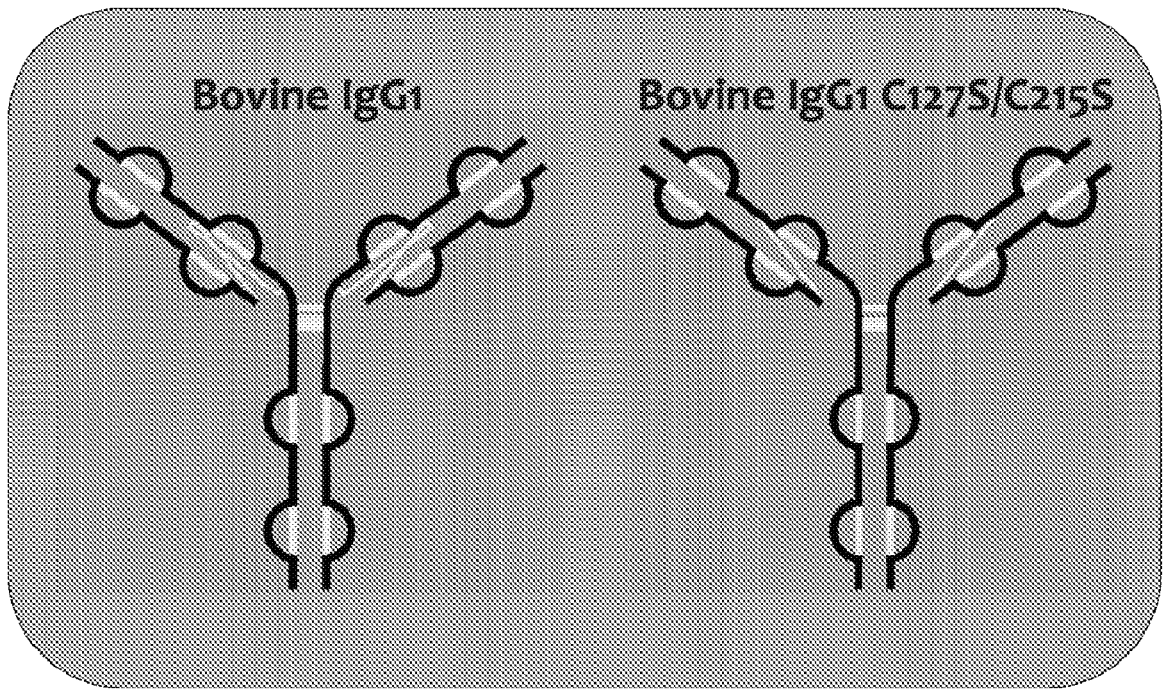
FIG. 31 is schematic representation of the predicted disulfide bond structure of wild-type bovine IgG1 and the C127S/C215S variant.
Figure 32:
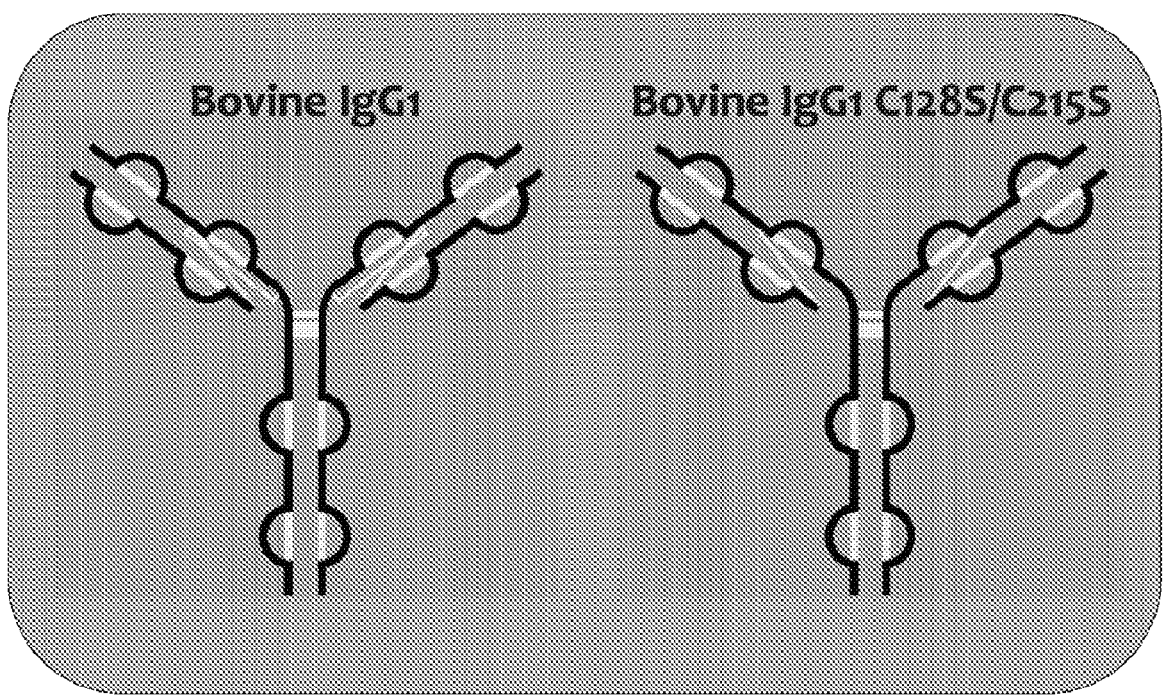
FIG. 32 is schematic representation of the predicted disulfide bond structure of wild-type bovine IgG1 and the C128S/C215S variant.
Figure 33:
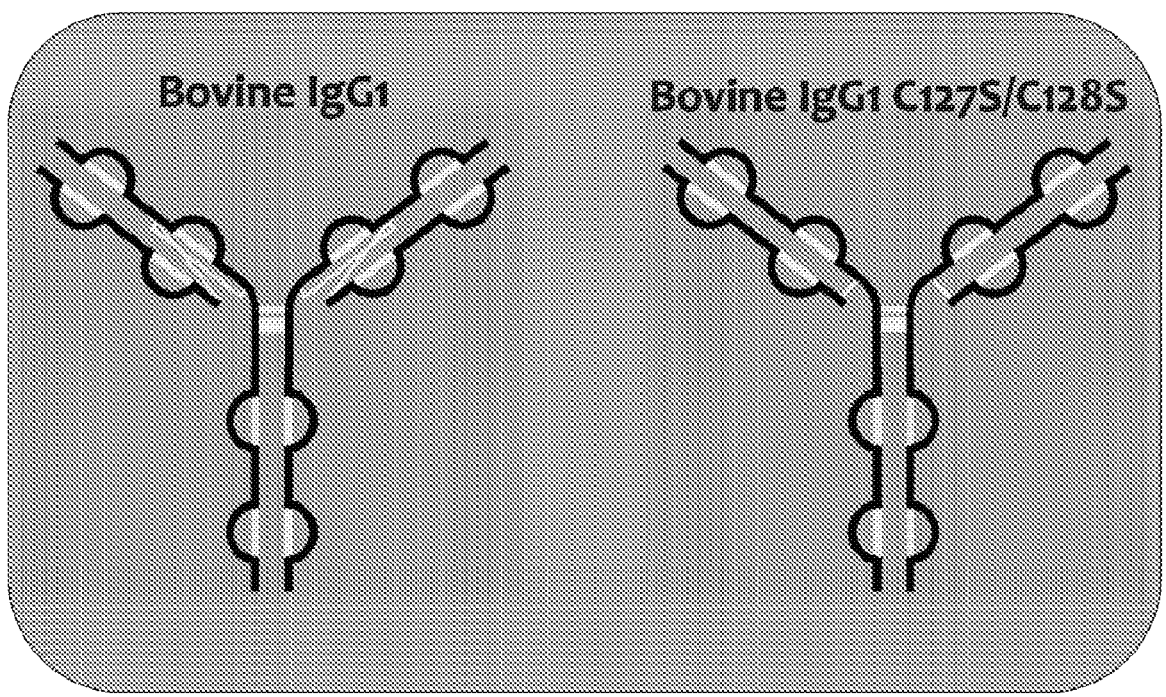
FIG. 33 is schematic representation of the predicted disulfide bond structure of wild-type bovine IgG1 and the C127S/C128S variant.
Figure 34:
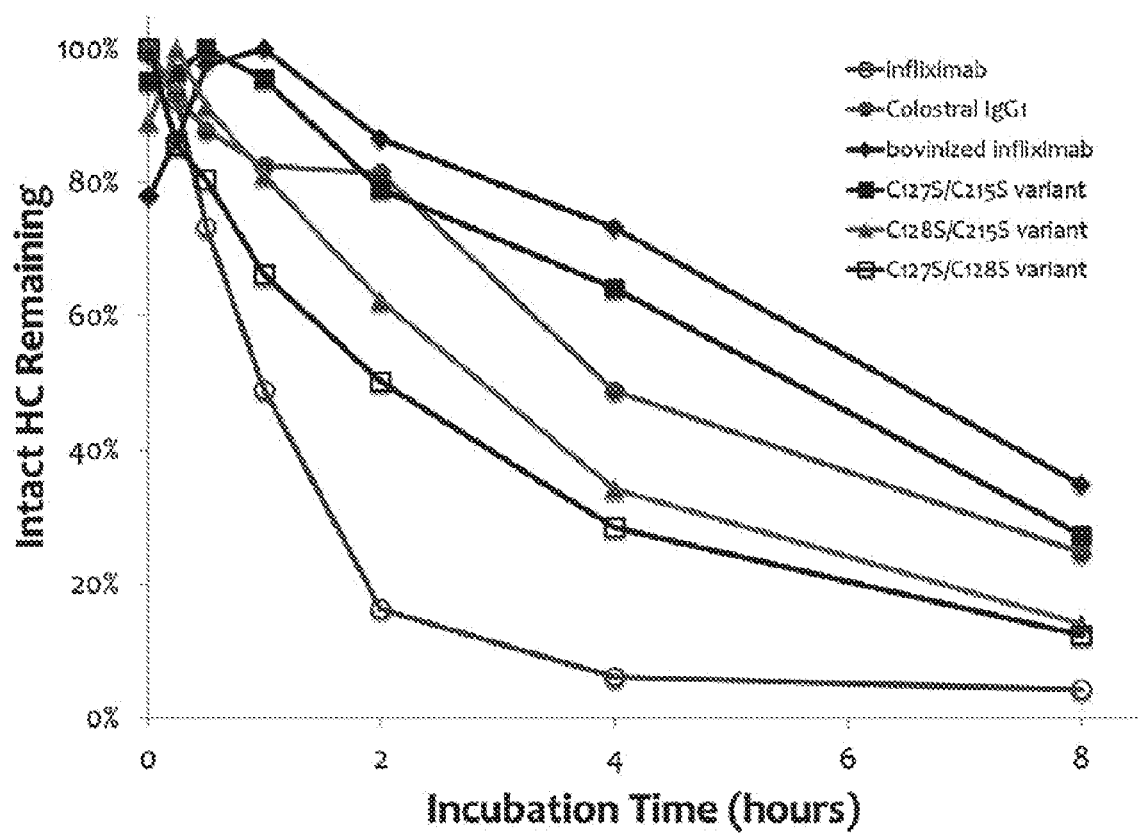
FIG. 34 is a line graph plotting the pancreatin-mediated degradation of the antibody heavy chain of infliximab, bovine colostral IgG1, wild-type bovinized infliximab, and bovinized infliximab with the C127S/C215S, C128S/C215S or C127S/C128S substitutions.

Also provided are bovinized antibodies comprising a bovine constant region, wherein the heavy chain comprises amino acid substitutions that remove particular disulfide bond linkages. Such antibodies are useful for testing the contribution of the CH1-hinge disulfide linkage and CH1-light chain disulfide linkage for conferring protease resistance to the parent antibody. As shown in FIG. 34, the bovinized infliximab construct is degraded more slowly by intestinal proteases than infliximab. The C127S/C215S, C128S/C215S and C127S/C128S variants (all of which are depicted in FIGS. 31-33) have intermediate stabilities between that of infliximab and bovinized infliximab. This supports the hypothesis that bovine IgG1 antibodies are stabilized by the combination of the CH1-hinge and CH1-LC disulfide bonds, as removing either disulfide bond destabilizes the molecule.

TABLE 29

| Description | Sequence |
| --- | --- |
| Bovinized infliximab (C127S/C215S)-removes CH1-hinge linkage, resembles bovine IgG2 A2 allotype (see FIG. 31)- heavy chain (SEQ ID NO: 69) | EVKLEESGGGLVQPGGSMKLSCVASGFIFSNHWMNWVRQSPEKGLEWVAEIRSKSINS ATHYAESVKGRFTISRDDSKSAVYLQMTDLRTEDTGVYYCSRNYYGSTYDYWGQGTTL TVSSASTTAPKVYPLSSSCGDKSSSTVTLGCLVSSYMPEPVTVTWNSGALKSGVHTFP AVLQSSGLYSLSSMVTVPGSTSGQTFTCNVAHPASSTKVDKAVDPTSKPSPCDCCPPP ELPGGPSVFIFPPKPKDTLTISGTPEVTCVVVDVGHDDPEVKFSWFVDDVEVNTATTK PREEQFNSTYRVVSALRIQHQDWTGGKEFKCKVHNEGLPAPIVRTISRTKGPAREPQV YVLAPPQEELSKSTVSLTCMVTSFYPDYIAVEWQRNGQPESEDKYGTTPPQLDADSSY FLYSKLRVDRNSWQEGDTYTCVVMHEALHNHYTQKSTSKSAGK |
| Bovinized infliximab (C127S/C215S)-removes CH1-hinge linkage, resembles bovine IgG2 A2 allotype (see FIG. 31)- light chain (SEQ ID NO: 70) | DILLTQSPAILSVSPGERVSFSCRASQFVGSSIHWYQQRINGSPRLLIKYASESMSGI PSRFSGSGSGTDFTLSINTVESEDIADYYCQQSHSWPFTFGSGTNLEVKRSDAEPSVF LFKPSDEQLKTGTVSVVCLVNDFYPKDINVKWKVDGVTQSSSNFQNSFTDQDSKKSTY SLSSILTLPSSEYQSHNAYTCEVSHKSLTTALVKSFSKNEC |
| Bovinized infliximab (C128S/C215S)-removes CH1-hinge linkage, retains IgG1/CH1 loop structure (see FIG. 32)- heavy chain (SEQ ID NO: 71) | EVKLEESGGGLVQPGGSMKLSCVASGFIFSNHWMNWVRQSPEKGLEWVAEIRSKSINS ATHYAESVKGRFTISRDDSKSAVYLQMTDLRTEDTGVYYCSRNYYGSTYDYWGQGTTL TVSSASTTAPKVYPLSSCSGDKSSSTVTLGCLVSSYMPEPVTVTWNSGALKSGVHTFP AVLQSSGLYSLSSMVTVPGSTSGQTFTCNVAHPASSTKVDKAVDPTSKPSPCDCCPPP ELPGGPSVFIFPPKPKDTLTISGTPEVTCVVVDVGHDDPEVKFSWFVDDVEVNTATTK PREEQFNSTYRVVSALRIQHQDWTGGKEFKCKVHNEGLPAPIVRTISRTKGPAREPQV YVLAPPQEELSKSTVSLTCMVTSFYPDYIAVEWQRNGQPESEDKYGTTPPQLDADSSY FLYSKLRVDRNSWQEGDTYTCVVMHEALHNHYTQKSTSKSAGK |
| Bovinized infliximab (C128S/C215S)-removes CH1-hinge linkage, retains IgG1/CH1 loop structure (see FIG. 32)- light chain (SEQ ID NO: 72) | DILLTQSPAILSVSPGERVSFSCRASQFVGSSIHWYQQRINGSPRLLIKYASESMSGI PSRFSGSGSGTDFTLSINTVESEDIADYYCQQSHSWPFTFGSGTNLEVKRSDAEPSVF LFKPSDEQLKTGTVSVVCLVNDFYPKDINVKWKVDGVTQSSSNFQNSFTDQDSKKSTY SLSSILTLPSSEYQSHNAYTCEVSHKSLTTALVKSFSKNEC |
| Bovinized infliximab (C127S/C128S)-removes both CH1-LC and CH1-hinge linkages (see FIG. 33)-heavy chain (SEQ ID NO: 73) | EVKLEESGGGLVQPGGSMKLSCVASGFIFSNHWMNWVRQSPEKGLEWVAEIRSKSINS ATHYAESVKGRFTISRDDSKSAVYLQMTDLRTEDTGVYYCSRNYYGSTYDYWGQGTTL TVSSASTTAPKVYPLSSSSGDKSSSTVTLGCLVSSYMPEPVTVTWNSGALKSGVHTFP AVLQSSGLYSLSSMVTVPGSTSGQTFTCNVAHPASSTKVDKAVDPTCKPSPCDCCPPP ELPGGPSVFIFPPKPKDTLTISGTPEVTCVVVDVGHDDPEVKFSWFVDDVEVNTATTK PREEQFNSTYRVVSALRIQHQDWTGGKEFKCKVHNEGLPAPIVRTISRTKGPAREPQV YVLAPPQEELSKSTVSLTCMVTSFYPDYIAVEWQRNGQPESEDKYGTTPPQLDADSSY FLYSKLRVDRNSWQEGDTYTCVVMHEALHNHYTQKSTSKSAGK |
| Bovinized infliximab (C127S/C128S)-removes both CH1-LC and CH1-hinge linkages (see FIG. 33)-light chain (SEQ ID NO: 74) | DILLTQSPAILSVSPGERVSFSCRASQFVGSSIHWYQQRINGSPRLLIKYASESMSGI PSRFSGSGSGTDFTLSINTVESEDIADYYCQQSHSWPFTFGSGTNLEVKRSDAEPSVF LFKPSDEQLKTGTVSVVCLVNDFYPKDINVKWKVDGVTQSSSNFQNSFTDQDSKKSTY SLSSILTLPSSEYQSHNAYTCEVSHKSLTTALVKSFSKNEC |

Chimeric (Human/Ruminant and Human/Rabbit) Antibodies

Also provided herein are chimeric antibodies (e.g., chimeric infliximab) that fuse a parent variable region to a IgG1 constant region from other ruminants (e.g., sheep, goat) or rabbit.

The heavy chain sequences for the constructs below were designed by fusing the VH domain of infliximab with the CH1-hinge-CH2-CH3 sequences of the closest sequence match to the bovine IgG1d sequence used in Example 8. The light chain sequence contains the VL domain for infliximab fused to the CL domain with the closest sequence match to the infliximab CL domain, in order to maximize favorable interactions between the VL and CL domains of each construct.

TABLE 30

Combination of infliximab variable domain with sheep constant domain (Genbank: CAA49451.1 for heavy chain, CAA38046.1 for light chain)

| | |
|---|---|
| Heavy Chain (SEQ ID NO: 75) | EVKLEESGGGLVQPGGSMKLSCVASGFIFSNHWMNWVRQSPEKGLEWVAEIRSKSINSATHYAESVKGRFTI SRDDSKSAVYLQMTDLRTEDTGVYYCSRNYYGSTYDYWGQGTTLTVSSASTTPPKVYPLTSCCGDTSSSIVT LGCLVSSYMPEPVTVTWNSGALTSGVHTFPAILQSSGLYSLSSVVTVPASTSGAQTFICNVAHPASSTKVDK RVEPGCPDPCKHCRCPPPELPGGPSVFIFPPKPKDTLTISGTPEVTCVVVDVGQDDPEVQFSWFVDNVEVRT ARTKPREEQFNSTFRVVSALPIQHQDWTGGKEFKCKVHNEALPAPIVRTISRTKGQAREPQVYVLAPPQEEL SKSTLSVTCLVTGFYPDYIAVEWQKNGQPESEDKYGTTTSQLDADGSYFLYSRLRVDKNSWQEGDTYACVVM HEALHNHYTQKSISKPPGK |
| Light Chain (SEQ ID NO: 76) | DILLTQSPAILSVSPGERVSFSCRASQFVGSSIHWYQQRINGSPRLLIKYASESMSGIPSRFSGSGSGTDFT LSINTVESEDIADYYCQQSHSWPFTFGSGTNLEVKRSDAQPSVLFLFKPSEEQLRTGTVSVVCLVNDFYPKDI NVKVKVDGVTQNSNFQNSFTDQDSKKSTYSLSSTLTLSSSEYQSHNAYACEVSHKSLPTALVKSENKNEC |

TABLE 31

Combination of infliximab variable domain with goat constant domain (Genbank: AAX45026.1 + CAA44699.1 for heavy chain, AAX45027.1 for light chain)

| | |
|---|---|
| Heavy Chain* (SEQ ID NO: 77) | EVKLEESGGGLVQPGGSMKLSCVASGFIFSNHWMNWVRQSPEKGLEWVAEIRSKSINSATHYAESVKGRFTI SRDDSKSAVYLQMTDLRTEDTGVYYCSRNYYGSTYDYWGQGTTLTVSSASTTPPKVYPLTSCCGDTSSSIVT LGCLVSSYMPEPVTVTWNSGALTSGVHTFPAVLQSSGLYSLSSMVTVPASTSGAQTFICNVAHPASSTKVDK RVEPGCKPSPCDCCPPPELPGGPSVFIFPPKPKDTLTISGTPEVTCVVVDVGHDDPEVKFSWFVDDVEVNTA TTKPREEQFNSTYRVVSALRIQHQDWTGGKEFKCKVHNEGLPAPIVRTISRTKGPAREPQVYVLAPPQEELS KSTVSLTCMVTSFYPDYIAVEWQRNGQPESEDKYGTTPPQLDADSSYFLYSKLRVDRNSWQEGDTYTCVVMH EALHNHYTQKSTSKSAGK |
| Light Chain (SEQ ID NO: 78) | DILLTQSPAILSVSPGERVSFSCRASQFVGSSIHWYQQRINGSPRLLIKYASESMSGIPSRFSGSGSGTDFT LSINTVESEDIADYYCQQSHSWPFTFGSGTNLEVKGQPKSAPSVTLFPPSTEELNANKATVVCLISDFYPGS VTVVWKADGSTINQNVKTTQASKQSNSKYAASSYLTLTGSEWKSKSSYSCEVTHEGSTVKKTVKPSEC |

*The goat CH1 and upper hinge sequence from AAX45026.1 was used, and fused to the lower hinge, CH2, and CH3 domains from the bovine IgG1d sequence (CAA44699.1)

TABLE 32

Combination of infliximab variable domain with rabbit constant domain (Genbank: ABD64612.1 for heavy chain, 0507224A for light chain) (mAb#5)-rabbit IgG1 retains bovine CH1 structure but with weaker hinge (equivalent to human IgG1 hinge)

| | |
|---|---|
| Heavy Chain (SEQ ID NO: 79) | EVKLEESGGGLVQPGGSMKLSCVASGFIFSNHWMNWVRQSPEKGLEWVAEIRSKSINSATHYAESVKGRFTI SRDDSKSAVYLQMTDLRTEDTGVYYCSRNYYGSTYDYWGQGTTLTVSSGSFKAPSVFPLAPCCGDTPSSTVT LGCLVKGYLPEPVTVTWNSGTLINGVRTFPSVRQSSGLYSLSSVVSVTSSSQPVTCNVAHPATNTKVDKTVA PSTCSKPTCPPPELLGGPSVFIFPPKPKDTLMISRTPEVTCVVVDVSQDDPEVQFTWYINNEQVRTARPPLR EQQFNSTIRVVSTLPIAHQDWLRGKEFKCKVHNKALPAPIEKTISKARGQPLEPKVYTMGPPREELSSRSVS LTCMINGFYPSDISVEWEKNGKAEDNYKTTPAVLDSDGSYFLYSKLSVPTSEWQRGDVFTCSVMHEALHNHY TQKSISRSPGK |
| Light Chain (SEQ ID NO: 80) | DILLTQSPAILSVSPGERVSFSCRASQFVGSSIHWYQQRINGSPRLLIKYASESMSGIPSRFSGSGSGTDFT LSINTVESEDIADYYCQQSHSWPFTFGSGTNLEVKGDPVAPTVLIFPPAADQVATGTVTIVCVANKYFPDVT VTWEVDGTTQTTGIENSKTPQDSADCTYNLSSTLTLTSTQYNSHKEYTCKVTQGGTTSVVQSFNRGDC |

Bovinized Antibodies with Modifications to Modulate Biological Activity

Also provide are bovinized antibodies with amino acid substitutions that modulate biological activity. Specifically, shown below are amino acid substitutions to the bovine IgG1 hinge region for modulating FcR binding activity.

TABLE 33

| | |
|---|---|
| Human (SEQ ID NO: 81) | CPPCPAPELLGGPSVFLFPPKPKDTLMISRTPE VTCVVVDVSHED...VSNKALPAPIEK |
| Bovine (SEQ ID NO: 82) | CDCCPPPELPGGPSVFIFPPKPKDTLTISGTPE VTCVVVDVGHDD...VHNEGLPAPIVR |
| Mutant (SEQ ID NO: 83) | CDCCPPPELLGGPSVFIFPPKPKDTLTISGTPE VTCVVVDVSHDD...VHNEALPAPIVR |

Pepsin cleavage can be prevented by adding a bovine IgG3 hinge domain having a putative O-glycosylation site to the bovine IgG1 constant region.

TABLE 34

| | |
|---|---|
| bIgG3 (SEQ ID NO: 84) | VDKAVTARRPVPTTPKTTIPPGKPTTPKSEVEK TPCQ...CSKCPEP.L.GGLSVF |
| bIgG1 (SEQ ID NO: 85) | VDKAV........................DP R.CKPSPCDCCPPPELPGGPSVF |
| Mutant (SEQ ID NO: 86) | VDKAVTARRPVPTTPKTTIPPGKPTTPKSEVEP R.CKPSPCDCCPPPELPGGPSVF |

Additional stabilization against proteolysis may be achieved by amino-acid substitutions in the lower hinge, as described in Table 35. Alternative hinge #1 contains a shorter sequence for the lower hinge, mimicking the bovine IgG2 sequence. Alternative hinge #2 has the same length as the bovine IgG1 hinge, but replaces the lower hinge sequence with proline residues, which inhibit degradation by most proteases. Alternative hinge #3 replaces the lower hinge sequence with alternating glycine and serine residues, which provide a hydrophilic, flexible sequence that maintains the conformational flexibility of the original sequence while removing potential proteolysis sites.

TABLE 35

| | |
|---|---|
| Bovine IgG1d hinge (SEQ ID NO: 87) | AVDPTCKPSPCDCCPPPELPGGPSVF |
| Alternate hinge #1 (SEQ ID NO: 88) | AVDPTCKPSPCDCC.VRE....PSVF |
| Alternate hinge #2 (SEQ ID NO: 89) | AVDPTCKPSPCDCCPPPPPPPPPSVF |
| Alternate hinge #3 (SEQ ID NO: 90) | AVDPTCKPSPCDCCPPPGSGSGPSVF |

Recombinant IgG therapeutics are commonly purified by a Protein A affinity chromatography step. However, bovine IgG1 sequences do not bind to Protein A resins, due to differences in the amino-acid sequences of the CH2 and CH3 domains. Protein A binding may be reinstated by introducing amino-acid substitutions in the bovine CH2 and CH3 domains that re-create the binding interface between Protein A and human IgG1. Preferably, the substitutions made should avoid introducing strong binding to the human neonatal Fc receptor, as this would impact the biodistribution of the antibody in vivo. Exemplary amino acid substitutions to the bovine IgG1 sequence that may enhance Protein A binding, but not binding to human FcRn, include T252M, G255R, Q309L, T314L, G315N, or any combination thereof.

Example 18—Expression of Bovinized Infliximab

Figure 35:
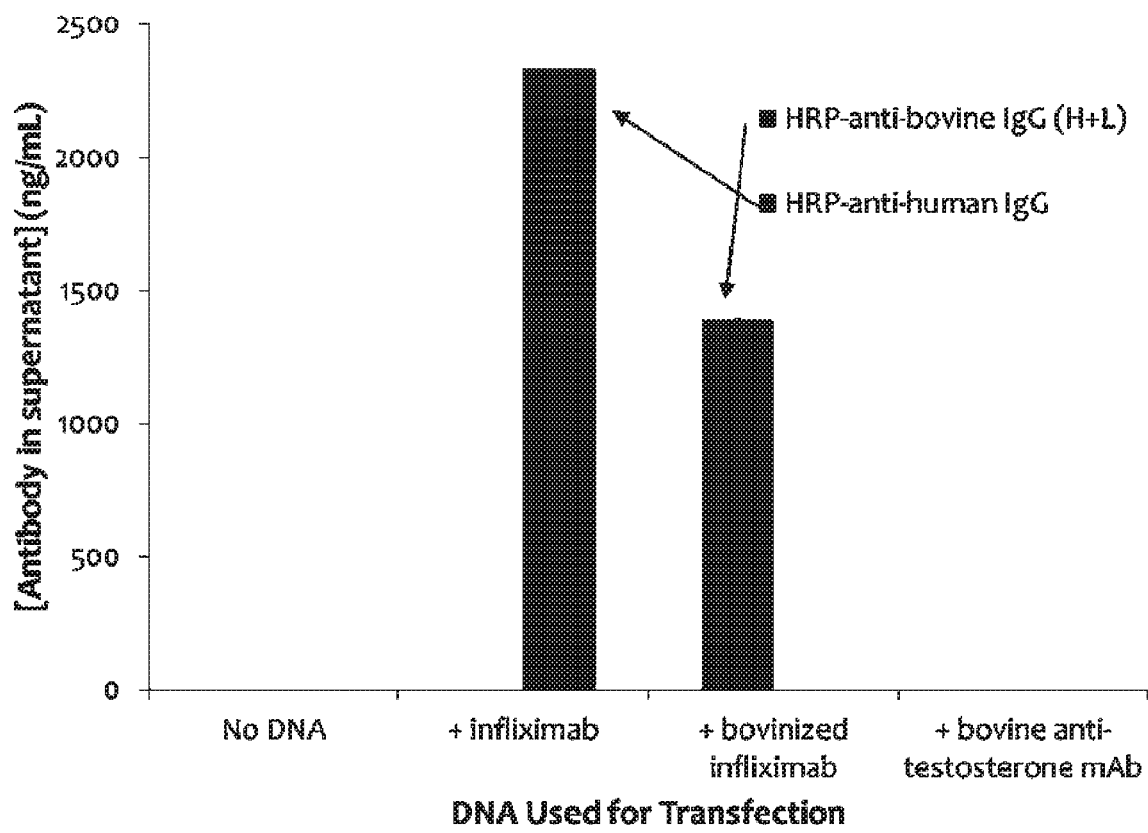
FIG. 35 is a bar graph showing the levels of expression of infliximab, bovinized infliximab, and bovine anti-testosterone antibody.

The expression of bovinized infliximab and infliximab expressed in HEK293 cells was compared. As shown in FIG. 35, the expression of bovinized infliximab and infliximab in HEK293 cells was comparable.

Example 19—Large-Scale Production of Bovine IgG1 Monoclonal and Bovinized Antibodies Bovine monoclonal and chimeric antibodies (e.g., bovine anti-TNF antibodies), such as those described in Examples 16 and 17, can be recombinantly produced in large-scale in various host organisms for use in research and clinical settings, as described below.

Production in Yeast

Nucleic acids encoding the heavy and light chain of an antibody of interest (e.g., anti-TNF antibody) are cloned into appropriate yeast expression vectors. Yeast cells are grown in YEPD medium containing 2% glucose at 30° C. in a shaker for 4-6 hours to create a stock. 100 ml of the same media is inoculated with the stock and grown to an OD600 of 1.3-1.5. Cells are harvested by centrifugation, washed with water, and washed with sterile 1M sorbitol at 4° C. The cells are resuspended in 100 ul of 1M sorbitol, and 40 ul of cell suspension is added. Approximately 1 μg of plasmid DNA (two plasmids: one encoding the heavy chain and the other encoding the light chain, or alternatively one plasmid comprising sequences encoding both heavy and light chains) are added to the cells. The cells and plasmid DNA are incubated on ice for 5 min and transferred to 0.2 cm electroporation cuvettes. A Bio-Rad Gene Pulser (Richmond, Calif.) is used to perform the electroporation. Transformants are selected on YNB media lacking uracil.

A preculture is grown in 100 ml YNB media (ura−, leu+)+2% glucose for 24 hrs at followed by inoculation in 200 ml fermentation media, (ura−, leu−)+2% glucose, at 0.5 OD. Cultures are grown and harvested and samples taken at various time points and induced with 2% galactose. Cells are separated from the culture media by centrifugation, and culture supernatants are concentrated with Centricon 30 filters by ultrafiltration and used for SDS-PAGE analysis. Antibody purity and yield can be detected by running concentrated supernatant on SDS-PAGE.

The procedure above can be up-scaled using 2-10 L fermenters for large-scale fermentations.

Production in *Aspergillus*

Nucleic acids encoding the heavy and light chain of an antibody of interest (e.g., anti-TNF antibody) are cloned into separate expression vectors with selectable markers known in the art (e.g., pGAMpR, or those described for filamentous fungi in Sambrook et al., 1989 and Ausubel F M et al., 1989).

*Aspergillus niger* or *Aspergillus niger* var. *awamori* strain (which has a deletion in the gene encoding a major secreted aspartyl protease) are used as host cells. Transformations and large-scale fermentations are carried out as described in Ward et al. (*Appl Environ Microb* 2004; 70:2567-576). Yields using the protocol described in Ward et al. can reach 0.2-0.9 g/L.

Briefly, cells are incubated at 37° C. in flasks on a shaker for 2 days. 2-day-old medium is transferred and incubated at 30° C. on a shaker for 5 days. Transformants producing high levels of antibody and balanced amounts of light and heavy chains are identified by SDS-PAGE or ELISAs, and subsequently used for large-scale production.

Selected transformants are grown in large (i.e., 14-liter) fermentors. After 48 to 60 hours of incubation at 30° C. on a shaker, cultures are transferred and incubated overnight on a shaker at 30° C. Antibodies in culture supernatants are quantified by ELISA. Antibodies are purified from the culture supernatant by removal of the fungal cells by filtration through a cellulose pad and filtration of the supernatant. Hydrophobic charge induction chromatography (HCIC) and high-performance liquid chromatography (HPLC) are used to purify the supernatant. Antibody purity and yield are detected by running concentrated supernatant on SDS-PAGE.

Production in Mammalian Cells

Mammalian cells (e.g., Chinese hamster ovary (CHO) cells, and NSO murine myeloma cells) are used for large-scale production of antibodies. Nucleic acids encoding the heavy and light chain of an antibody of interest (e.g., anti-TNF antibody) are cloned into appropriate mammalian expression vectors and transfected into cells. If necessary, adherent cell lines are adapted to suspension culture formats for large-scale production (see, e.g., Sinacore et al., Biotechnol Bioeng 1996; 52: 518-28).

Cultures are grown in media (e.g., DMEM) without serum at 37° C. Stable cell line clones are selected using methods known in the art, such as through metabolic markers, including methotrexate (MTX). To identify high-producing clones, cells are separated from the culture media by centrifugation, and culture supernatants are concentrated by ultrafiltration and used for SDS-PAGE analysis. Antibody purity and yield can be detected by running concentrated supernatant on SDS-PAGE. The top yielding clones are selected for further evaluation in large-scale bioreactors (e.g., 2,000 liters) to determine the final production clone.

Production in Insect Cells

Insect cells (e.g., Sf-9 cells) can be used in the large-scale production of antibodies of interest. Nucleic acids encoding the heavy and light chain of an antibody of interest (e.g., anti-TNF antibody) are cloned into a baculovirus expression vector. Cells are cultured at 25° C.-30° C. in Grace's Supplemented (TNM-FH) medium and grown overnight. Cells are infected with the baculovirus and harvested at various time points to measure antibody production.

To measure antibody production, supernatants are clarified before further processing with cartridge membranes or ultrafiltration membranes. Membrane filtration or chromatographic techniques are used to remove baculoviruses from the supernatant. The resulting supernatants are concentrated by ultrafiltration and used for SDS-PAGE analysis. Antibody purity and yield can be detected by running concentrated supernatant on SDS-PAGE.

Example 20—Antibody Purification

The antibodies described herein may be purified by several procedures commonly used in the production of recombinant antibodies, including precipitation by ammonium sulfate, antigen affinity chromatography, thioaffinity chromatography, or binding to bacterial proteins that have high affinity for mammalian immunoglobulins. Beads coupled to recombinant Streptococcus Protein G have been used to purify the IgG molecules described herein. A 5 mL Protein G Sepharose HiTrap column (GE Healthcare cat #17-0405-01) was equilibrated with 1×PBS (10 mM sodium phosphate, 150 mM sodium chloride, pH 7.4). The sample was loaded onto the column, washed with PBS, and the antibody was eluted with 5 column volumes of 100 mM glycine, pH 2.7. The fraction collection tubes contained 100 µL 1 M TrisCl, pH 9 to neutralize the eluate fractions. The elution fractions were pooled and concentrated with an Amicon 10k MWCO spin filter to purify the antibodies.

Example 21—Treatment of DSS and DNBS Mouse Colitis Model with Bovine Recombinant Monoclonal 12G1 or Bovinized Anti-TNF Antibodies C57BL/6 mice are used to induce artificial colitis, essentially as described in WO2012/058769.

For dextran sulfate sodium (DSS)-induced colitis, DSS is added to drinking water for a final concentration of 5% (wt/volume) for a total of 5 days. Mice are administered a bovinized or fully bovine recombinant monoclonal anti-TNF antibody (selected and produced as described in Examples 14-16) or an isotype control antibody (e.g., IgG1 antibody) for 6 days starting one day prior to exposure to DSS. Onset of colitis is assessed using the disease activity index (DAI). The DAI is a combined score of weight loss, stool consistency, and fecal bleeding. The scoring system is as follows: weight loss: 0, no loss; 1, 1-5%; 2, 5-10%; 3, 4, 20%+; stool: 0, normal; 2, loose stool; 4, diarrhea; and bleeding: 0, no blood, 2, Hemoccult positive; and 4, gross blood (blood around anus). DAI is measured on all 5 days of DSS treatment.

For DNBS-induced colitis, C57BL/6 mice are anesthetized, and a 10-cm long tubing attached to a tuberculin syringe is intrarectally inserted 3.5 cm into the colon and in order to induce colitis. 100 µL of 5 mg of DNBS solution dissolved in 50% ethanol is administered and left for 3 days. Controls receive vehicle (50% ethanol) for the same duration.

To assess macroscopic damage, mice are sacrificed 5 days post-DSS or 3 days post-DNBS administration, the abdominal cavity is opened, and observations on colonic distension, fluid content, hyperemia, and erythema are recorded. The colon is removed and macroscopic damage assessed on the full section of the colon. Macroscopic scores are performed using previously described scoring systems for DSS colitis (Cooper et al. Lab Invest 1993; 69:238-49) and DNBS (Khan et al., Infect Immun 2002; 70:5931-5937).

For colonic histology assessments, colon segments are fixed in formalin and embedded in paraffin, followed by sectioning and staining with hematoxylin and eosin. Colonic damage is blindly scored based on the DSS colitis scoring system described above. The scoring system considers loss of architecture (0, normal—3, severe), cellular infiltration (0, normal—3, severe), muscle thickening (0, normal—3, severe), goblet cell depletion (0, absent; 1, present), crypt abscess (0, absent; 1, present).

MPO activity measurements are carried out as described in Khan et al. (Infect Immun 2002; 70:5931-7). Colonic tissue samples are homogenized in ice-cold 50 mmol/L potassium phosphate buffer (pH=6.0) containing 0.5% hexadecyl trimethyl ammonium bromide, homogenates are centrifuged, the supernatant is removed, and an aliquot is added to a solution containing potassium phosphate buffer, O-dianisidine, and hydrogen peroxide. Absorbance is measured at 450 mm using a spectrophotogram. MPO activity is expressed in units per milligram of wet tissue, where 1 unit is the quantity of enzyme able to convert 1 µmol of hydrogen peroxide to water in 1 minute at room temperature.

DAI scores, histology, and MPO activity are compared between treatment groups.

Example 22—Treatment of Mouse Model of TNBS-Induced Colitis with Oral Fully Bovine Recombinant Monoclonal 12G1 or Bovinized Anti-TNF Antibodies C57B 16 mice ((8-9 weeks old) Charles River Laboratories, Wilmington, Mass.) are administered 0.1 mL TNBS (trinitrobenzene sulfonate) (4 mg) in 50% ethanol intrarectally. The TNBS model is a well-accepted model of inflammatory bowel disease. Control animals are dosed with ethanol alone. Twelve animals are used in TNBS-treated group and eight animals in each of the other groups. Animals are dosed with 0.05 mg, 0.015 mg, or 0.005 mg of a bovinized or fully bovine recombinant monoclonal anti-TNF IgG1 antibody (selected and produced as described in Examples 14-16), 0.015 mg of an isotype control antibody (e.g., IgG1 antibody), or saline twice per day by oral gavage in 0.1 ml. All samples contain 0.2 mg ovalbumin as an excipient. Antibody is administered from day −1 to day 3.

Each mouse is analyzed using video endoscopy, under isoflurane anesthesia, on day 5 just prior to being sacrificed. During each endoscopic procedure still images as well as video are recorded to evaluate the extent of colitis and the response to treatment. Colitis severity is scored by a blinded observer using a 0-4 scale (0=normal; 1=loss of vascularity; 2=loss of vascularity and friability; 3=friability and erosions; 4=ulcerations and bleeding). Differences between groups are analyzed.

Example 23—Treatment of Adoptive-Transfer Model of Chronic Colitis with Fully Bovine Recombinant Monoclonal IgG1 or Bovinized Anti-TNF Antibodies Chronic CD45Rb$^{high}$ transfer colitis is induced essentially as described in U.S. Pat. No. 8,119,401. Briefly, BALB/c splenocytes are first enriched for CD4$^+$ cells by red cell lysis and negative selection using the following rat anti-mouse mAbs to B220 (clone RA3-6B2), Mac-1 (clone M1/70), and CD8α. MAb-stained cells are removed in a magnetic field using sheep anti rat IgG coated magnetic beads (Dynal, Hamburg, Germany). The resulting CD4 enriched cells are stained with cychrome (Cy)-conjugated CD4 and fluorescein isothiocyanate (FITC)-conjugated CD45RB mAbs. Subpopulations of CD4 cells are generated by two color sorting on the FACS sorter (Becton Dickinson).

C.B-17 SCID mice are injected intraperitoneally with sorted CD4$^+$ cell subpopulations in PBS. To induce colitis, CD45RB$^{high}$ CD4$^+$ cells (1-4×10$^5$) are transferred to the SCID mice. Starting on the day of transfer, the mice are administered 0.1 mg of a bovinized or fully bovine recombinant monoclonal anti-TNF IgG1 antibody (selected and produced as described in Examples 14-16), or an isotype control antibody (e.g., IgG1) in saline buffer once a day. Antibodies are formulated in 10 mg bovine serum albumin.

Mice are weighed twice a week and wasting disease is determined by percentage of weight loss from baseline body weight. Peripheral blood is drawn at different time points by retro-orbital sinus puncture for plasma cytokine measurements.

Mice are scarified approximately 4-6 weeks after transfer, colons are isolated and fixed in 4% formalin, embedded in paraffin, sectioned, and stained with hematoxylin and eosin for histological grading. Inflammation is scored by an experienced pathologist blinded to treatment allocation on a scale of 0-4, representing no change to severe changes, as described in Powrie et al. (Induction of inflammatory bowel disease in immunodeficient mice by depletion of regulatory T cells. In: Coico R, ed. Current protocols in immunology. Vol. 4: John Wiley & Sons, Inc., 1999:15.3.1-0.3.0).

Example 24—Antibody Efficacy

Efficacy of the antibodies described herein can be tested in vitro using the ELISA, TNF neutralization, and pancreatin digestion assays described in Examples 2, 3, and 11. The in vivo efficacy of the antibodies can be tested using animal models relevant to the target of interest. For instance, for bovinized and fully bovine recombinant monoclonal anti-TNF IgG1 antibodies, the animal model systems described in Examples 21-23 can be used. The efficacy of these antibodies can be determined in parallel with that of AVX-470 and/or infliximab and compared. Antibodies having the desired properties (e.g., ELISA binding, TNF neutralizing potency, and pancreatin resistance) are selected.

Example 25—Antibody Biodistribution

Bovinized and fully bovine recombinant monoclonal antibodies described herein are conjugated to a detectable label (e.g., a radioactive label such as $^{99m}$Tc) using standard methods (see, e.g., D'Alessandria et al., *Q J Nucl Med Mol Imaging* 2007; 51:334-42) in order evaluate their biodistribution in mice. Briefly, mice are orally dosed with the labeled antibodies, and sacrificed at different time points after antibody dosing (e.g., 30 min, 1, 2, 4, 6, 8, 12, and 24 hours after injection). Serum is collected after sacrifice. The gastrointestinal tract is removed, lavaged with a fixed volume of saline, sectioned, and weighed, and, if the label is radioactive, assessed for radioactivity. Organ activity is expressed as a percentage of administered activity (% AD)/ gram tissue or /mL of serum or gut lavage fluid. The biodistribution of the antibodies described herein can be determined in parallel with a known antibody. For instance, for bovinized and fully bovine recombinant monoclonal anti-TNF IgG1 antibodies, the biodistribution of these antibodies can be determined and compared in parallel with that of AVX-470 and/or infliximab.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

EQUIVALENTS

Those skilled in the art will recognize, or be able to ascertain using no more than routine experimentation, many equivalents of the specific embodiments disclosed herein.

I claim:

1. An isolated recombinant monoclonal antibody comprising (a) heavy and light chain CDRs from a non-bovine antibody and (b) a constant region comprising all or a portion of a bovine IgG1 constant region, wherein the constant region or portion thereof comprises all or a portion of a bovine IgG1 hinge region, said all or a portion of the bovine IgG1 hinge region comprising a cluster of three disulfide bonds linking the hinge regions of two heavy chains together, and/or a hinge region amino acid sequence that is less susceptible to common proteases.

2. The antibody of claim 1, wherein the non-bovine antibody is a human antibody.

3. The antibody of claim 1, wherein the constant region comprises all or a portion of a bovine IgG1 hinge region.

4. The antibody claim 1, wherein the constant region comprises all or a portion of a bovine IgG1 CH1 domain, all or a portion of a bovine IgG1 CH2 domain, and/or all or a portion of a bovine IgG1 CH3 domain.

5. The antibody of claim 1, wherein the antibody comprises one or both of the following features found in bovine IgG1:
   a) a disulfide bond linking the N-terminus of the CH1 domain to the N-terminus of the hinge region, and
   b) a disulfide bond linking the N-terminus of the CH1 domain to the C-terminus of the light chain.

6. The antibody of claim 1, wherein the bovine IgG1 constant region is selected from any of SEQ ID NOs: 1-3.

7. The antibody of claim 5, wherein the antibody binds to a biological antigen.

8. The antibody of claim 7, wherein the antigen is TNF-α.

9. The antibody of claim 8, wherein the antibody comprises the heavy and light chain variable region sequences of infliximab.

10. The antibody of claim 1, wherein the antibody retains antigen binding after protease digestion.

11. The antibody of claim 1, wherein the antibody comprises a constant region comprising one or more of the following substitutions (Kabat numbering) to the bovine Fc domain: threonine at position 252 is substituted with methionine; glycine at position 255 is substituted with arginine; glutamine at position 309 is substituted with leucine; threonine at position 314 is substituted with leucine; and glycine at position 315 is substituted with asparagine.

12. A recombinant fully bovine monoclonal IgG1 antibody according to claim 1.

13. A polynucleotide encoding the antibody of claim 1.

14. An expression vector comprising the polynucleotide of claim 13.

15. An isolated host cell comprising the polynucleotide of claim 13.

16. A pharmaceutical composition comprising the antibody of claim 1 and a carrier.

17. The composition of claim 16 which is formulated for oral administration.

18. A method of treating a disease of the digestive tract comprising orally administering to an individual in need thereof the antibody of claim 1.

19. The method of claim 18, wherein the disease is inflammatory bowel disease or Crohn's disease.

20. The antibody of claim 1 which has enhanced resistance to degradation during intestinal digestion by common proteases selected from the group of simulated intestinal fluid, papain, pepsin, a matrix metalloproteinase including MMP-7, neutrophil elastase (HNE), stromelysin (MMP-3), macrophage elastase (MMP-12), trypsin, chymotrypsin and combinations of two of more of the foregoing.

* * * * *

SEQUENCE LISTING

<160> NUMBER OF SEQ ID NOS: 118

<210> SEQ ID NO 1
<211> LENGTH: 329
<212> TYPE: PRT
<213> ORGANISM: Bos taurus

<400> SEQUENCE: 1

```
Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Thr Gln Thr
65                  70                  75                  80

Phe Thr Cys Asn Val Ala His Pro Ala Ser Ser Thr Lys Val Asp Lys
                85                  90                  95

Ala Val Asp Pro Arg Cys Lys Thr Thr Cys Asp Cys Cys Pro Pro Pro
            100                 105                 110

Glu Leu Pro Gly Gly Pro Ser Val Phe Ile Phe Pro Pro Lys Pro Lys
        115                 120                 125

Asp Thr Leu Thr Ile Ser Gly Thr Pro Glu Val Thr Cys Val Val Val
    130                 135                 140

Asp Val Gly His Asp Asp Pro Glu Val Lys Phe Ser Trp Phe Val Asp
145                 150                 155                 160

Asp Val Glu Val Asn Thr Ala Thr Lys Pro Arg Glu Glu Gln Phe
                165                 170                 175

Asn Ser Thr Tyr Arg Val Val Ser Ala Leu Arg Ile Gln His Gln Asp
            180                 185                 190

Trp Thr Gly Gly Lys Glu Phe Lys Cys Lys Val His Asn Glu Gly Leu
        195                 200                 205

Pro Ala Pro Ile Val Arg Thr Ile Ser Arg Thr Lys Gly Pro Ala Arg
    210                 215                 220

Glu Pro Gln Val Tyr Val Leu Ala Pro Pro Gln Glu Glu Leu Ser Lys
225                 230                 235                 240

Ser Thr Val Ser Leu Thr Cys Met Val Thr Ser Phe Tyr Pro Asp Tyr
                245                 250                 255

Ile Ala Val Glu Trp Gln Arg Asn Gly Gln Pro Glu Ser Glu Asp Lys
            260                 265                 270

Tyr Gly Thr Thr Pro Pro Gln Leu Asp Ala Asp Gly Ser Tyr Phe Leu
        275                 280                 285

Tyr Ser Arg Leu Arg Val Asp Arg Asn Ser Trp Gln Glu Gly Asp Thr
    290                 295                 300

Tyr Thr Cys Val Val Met His Glu Ala Leu His Asn His Tyr Thr Gln
305                 310                 315                 320

Lys Ser Thr Ser Lys Ser Ala Gly Lys
                325
```

<210> SEQ ID NO 2
<211> LENGTH: 329
<212> TYPE: PRT
<213> ORGANISM: Bos taurus

<400> SEQUENCE: 2

```
Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Asp Pro Thr Cys Lys Pro Ser Pro Cys Asp Cys Cys Pro Pro Pro
                100                 105                 110

Glu Leu Pro Gly Gly Pro Ser Val Phe Ile Phe Pro Pro Lys Pro Lys
            115                 120                 125

Asp Thr Leu Thr Ile Ser Gly Thr Pro Glu Val Thr Cys Val Val Val
130                 135                 140

Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
                165                 170                 175

Asn Ser Thr Tyr Arg Val Val Ser Ala Leu Arg Ile Gln His Gln Asp
            180                 185                 190

Trp Thr Gly Gly Lys Glu Phe Lys Cys Lys Val His Asn Glu Gly Leu
        195                 200                 205

Pro Ala Pro Ile Val Arg Thr Ile Ser Arg Thr Lys Gly Pro Ala Arg
    210                 215                 220

Glu Pro Gln Val Tyr Val Leu Ala Pro Pro Gln Glu Glu Leu Ser Lys
225                 230                 235                 240

Ser Thr Val Ser Leu Thr Cys Met Val Thr Ser Phe Tyr Pro Asp Tyr
                245                 250                 255

Ile Ala Val Glu Trp Gln Arg Asn Gly Gln Pro Glu Ser Glu Asp Lys
                260                 265                 270

Tyr Gly Thr Thr Pro Pro Gln Leu Asp Ala Asp Ser Ser Tyr Phe Leu
            275                 280                 285

Tyr Ser Lys Leu Arg Val Asp Arg Asn Ser Trp Gln Glu Gly Asp Thr
        290                 295                 300

Tyr Thr Cys Val Val Met His Glu Ala Leu His Asn His Tyr Thr Gln
305                 310                 315                 320

Lys Ser Thr Ser Lys Ser Ala Gly Lys
                325
```

<210> SEQ ID NO 3
<211> LENGTH: 329
<212> TYPE: PRT
<213> ORGANISM: Bos taurus

<400> SEQUENCE: 3

```
Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30
```

Met Pro Glu Pro Val Thr Val Thr Trp Asn Ser Gly Ala Leu Lys Ser
            35                  40                  45

Gly Val His Thr Phe Pro Ala Val Leu Gln Ser Ser Gly Leu Tyr Ser
 50                  55                  60

Leu Ser Ser Met Val Thr Val Pro Ala Ser Ser Gly Thr Gln Thr
 65                  70                  75                  80

Phe Thr Cys Asn Val Ala His Pro Ala Ser Ser Thr Lys Val Asp Lys
                 85                  90                  95

Ala Val Asp Pro Arg Cys Lys Arg Pro Cys Asp Cys Cys Pro Pro
                100                 105                 110

Glu Leu Pro Gly Gly Pro Ser Val Phe Ile Phe Pro Pro Lys Pro Lys
            115                 120                 125

Asp Thr Leu Thr Ile Ser Gly Thr Pro Glu Val Thr Cys Val Val Val
            130                 135                 140

Asp Val Gly His Asp Asp Pro Glu Val Lys Phe Ser Trp Phe Val Asp
145                 150                 155                 160

Asn Val Glu Val Asn Thr Ala Thr Thr Lys Pro Arg Glu Glu Gln Phe
                165                 170                 175

Asn Ser Thr Tyr Arg Val Val Ser Ala Leu Arg Ile Gln His Gln Asp
                180                 185                 190

Trp Thr Gly Gly Lys Glu Phe Lys Cys Lys Val His Asn Glu Gly Leu
            195                 200                 205

Pro Ala Pro Ile Val Arg Thr Ile Ser Arg Thr Lys Gly Pro Ala Arg
            210                 215                 220

Glu Pro Gln Val Tyr Val Leu Ala Pro Pro Gln Glu Glu Leu Ser Lys
225                 230                 235                 240

Ser Thr Val Ser Leu Thr Cys Met Val Thr Ser Phe Tyr Pro Asp Tyr
                245                 250                 255

Ile Ala Val Glu Trp Gln Arg Asn Gly Gln Pro Glu Ser Glu Asp Lys
                260                 265                 270

Tyr Gly Thr Thr Pro Pro Gln Leu Asp Ala Asp Ser Ser Tyr Phe Leu
            275                 280                 285

Tyr Ser Lys Leu Arg Val Asp Arg Asn Ser Trp Gln Glu Gly Asp Thr
290                 295                 300

Tyr Thr Cys Val Val Met His Glu Ala Leu His Asn His Tyr Thr Gln
305                 310                 315                 320

Lys Ser Thr Ser Lys Ser Ala Gly Lys
                325

<210> SEQ ID NO 4
<211> LENGTH: 25
<212> TYPE: PRT
<213> ORGANISM: Bos taurus

<400> SEQUENCE: 4

Asp Lys Ala Val Asp Pro Arg Cys Lys Pro Ser Pro Cys Asp Cys Cys
 1               5                  10                  15

Pro Pro Pro Glu Leu Pro Gly Gly Pro
                20                  25

<210> SEQ ID NO 5
<211> LENGTH: 28
<212> TYPE: PRT
<213> ORGANISM: Bos taurus

<400> SEQUENCE: 5

Val Asp Lys Ala Val Asp Pro Arg Cys Lys Thr Thr Cys Asp Cys Cys
1               5                   10                  15

Pro Pro Pro Glu Leu Pro Gly Gly Pro Ser Val Phe
                20                  25

<210> SEQ ID NO 6
<211> LENGTH: 28
<212> TYPE: PRT
<213> ORGANISM: Bos taurus

<400> SEQUENCE: 6

Val Asp Lys Ala Val Asp Pro Arg Cys Lys Arg Pro Cys Asp Cys Cys
1               5                   10                  15

Pro Pro Pro Glu Leu Pro Gly Gly Pro Ser Val Phe
                20                  25

<210> SEQ ID NO 7
<211> LENGTH: 29
<212> TYPE: PRT
<213> ORGANISM: Bos taurus

<400> SEQUENCE: 7

Val Asp Lys Ala Val Asp Pro Thr Cys Lys Pro Ser Pro Cys Asp Cys
1               5                   10                  15

Cys Pro Pro Pro Glu Leu Pro Gly Gly Pro Ser Val Phe
                20                  25

<210> SEQ ID NO 8
<211> LENGTH: 30
<212> TYPE: PRT
<213> ORGANISM: Ovis aries

<400> SEQUENCE: 8

Val Asp Lys Arg Val Glu Pro Gly Cys Pro Asp Pro Cys Lys His Cys
1               5                   10                  15

Arg Cys Pro Pro Pro Glu Leu Pro Gly Gly Pro Ser Val Phe
                20                  25                  30

<210> SEQ ID NO 9
<211> LENGTH: 28
<212> TYPE: PRT
<213> ORGANISM: Lama glama

<400> SEQUENCE: 9

Val Asp Lys Arg Val Glu Pro His Gly Gly Cys Thr Cys Pro Gln Cys
1               5                   10                  15

Pro Ala Pro Glu Leu Pro Gly Gly Pro Ser Val Phe
                20                  25

<210> SEQ ID NO 10
<211> LENGTH: 32
<212> TYPE: PRT
<213> ORGANISM: Meriones unguiculatus

<400> SEQUENCE: 10

Val Asp Lys Thr Val Glu Pro Arg Gly Thr Lys His Ile Cys Pro Asp
1               5                   10                  15

Cys Pro Lys Cys Pro Ala Pro Asp Leu Ser Gly Gly Pro Ser Val Phe
                20                  25                  30

<210> SEQ ID NO 11
<211> LENGTH: 34

```
<212> TYPE: PRT
<213> ORGANISM: Felis catus

<400> SEQUENCE: 11

Val Asp Lys Thr Val Arg Lys Thr Asp His Pro Pro Gly Pro Lys Pro
1               5                   10                  15

Cys Asp Cys Pro Lys Cys Pro Pro Glu Met Leu Gly Gly Pro Ser
            20                  25                  30

Ile Phe

<210> SEQ ID NO 12
<211> LENGTH: 12
<212> TYPE: PRT
<213> ORGANISM: Bos taurus

<400> SEQUENCE: 12

Asp Pro Arg Cys Lys Thr Thr Cys Asp Cys Pro
1               5                   10

<210> SEQ ID NO 13
<211> LENGTH: 13
<212> TYPE: PRT
<213> ORGANISM: Bos taurus

<400> SEQUENCE: 13

Asp Pro Thr Cys Lys Pro Ser Pro Cys Asp Cys Pro
1               5                   10

<210> SEQ ID NO 14
<211> LENGTH: 12
<212> TYPE: PRT
<213> ORGANISM: Bos taurus

<400> SEQUENCE: 14

Asp Pro Arg Cys Lys Arg Pro Cys Asp Cys Cys Pro
1               5                   10

<210> SEQ ID NO 15
<211> LENGTH: 98
<212> TYPE: PRT
<213> ORGANISM: Bos taurus

<400> SEQUENCE: 15

Ala Ser Thr Thr Ala Pro Lys Val Tyr Pro Leu Ser Cys Cys Gly
1               5                   10                  15

Asp Lys Ser Ser Ser Thr Val Thr Leu Gly Cys Leu Val Ser Ser Tyr
                20                  25                  30

Met Pro Glu Pro Val Thr Val Thr Trp Asn Ser Gly Ala Leu Lys Ser
            35                  40                  45

Gly Val His Thr Phe Pro Ala Val Leu Gln Ser Ser Gly Leu Tyr Ser
        50                  55                  60

Leu Ser Ser Met Val Thr Val Pro Gly Ser Thr Ser Gly Thr Gln Thr
65                  70                  75                  80

Phe Thr Cys Asn Val Ala His Pro Ala Ser Ser Thr Lys Val Asp Lys
                85                  90                  95

Ala Val

<210> SEQ ID NO 16
<211> LENGTH: 97
<212> TYPE: PRT
<213> ORGANISM: Bos taurus
```

<400> SEQUENCE: 16

```
Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val
```

<210> SEQ ID NO 17
<211> LENGTH: 98
<212> TYPE: PRT
<213> ORGANISM: Bos taurus

<400> SEQUENCE: 17

```
Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Ser Gly Thr Gln Thr
65                  70                  75                  80

Phe Thr Cys Asn Val Ala His Pro Ala Ser Ser Thr Lys Val Asp Lys
                85                  90                  95

Ala Val
```

<210> SEQ ID NO 18
<211> LENGTH: 110
<212> TYPE: PRT
<213> ORGANISM: Bos taurus

<400> SEQUENCE: 18

```
Pro Pro Glu Leu Pro Gly Gly Pro Ser Val Phe Ile Phe Pro Pro Lys
1               5                   10                  15

Pro Lys Asp Thr Leu Thr Ile Ser Gly Thr Pro Glu Val Thr Cys Val
            20                  25                  30

Val Val Asp Val Gly His Asp Asp Pro Glu Val Lys Phe Ser Trp Phe
        35                  40                  45

Val Asp Asp Val Glu Val Asn Thr Ala Thr Thr Lys Pro Arg Glu Glu
    50                  55                  60

Gln Phe Asn Ser Thr Tyr Arg Val Val Ser Ala Leu Arg Ile Gln His
65                  70                  75                  80

Gln Asp Trp Thr Gly Gly Lys Glu Phe Lys Cys Lys Val His Asn Glu
                85                  90                  95

Gly Leu Pro Ala Pro Ile Val Arg Thr Ile Ser Arg Thr Lys
                100                 105                 110
```

```
<210> SEQ ID NO 19
<211> LENGTH: 110
<212> TYPE: PRT
<213> ORGANISM: Bos taurus

<400> SEQUENCE: 19

Pro Pro Glu Leu Pro Gly Gly Pro Ser Val Phe Ile Phe Pro Pro Lys
1               5                   10                  15

Pro Lys Asp Thr Leu Thr Ile Ser Gly Thr Pro Glu Val Thr Cys Val
            20                  25                  30

Val Val Asp Val Gly His Asp Asp Pro Glu Val Lys Phe Ser Trp Phe
        35                  40                  45

Val Asp Asn Val Glu Val Asn Thr Ala Thr Thr Lys Pro Arg Glu Glu
    50                  55                  60

Gln Phe Asn Ser Thr Tyr Arg Val Val Ser Ala Leu Arg Ile Gln His
65                  70                  75                  80

Gln Asp Trp Thr Gly Gly Lys Glu Phe Lys Cys Lys Val His Asn Glu
                85                  90                  95

Gly Leu Pro Ala Pro Ile Val Arg Thr Ile Ser Arg Thr Lys
            100                 105                 110

<210> SEQ ID NO 20
<211> LENGTH: 109
<212> TYPE: PRT
<213> ORGANISM: Bos taurus

<400> SEQUENCE: 20

Gly Pro Ala Arg Glu Pro Gln Val Tyr Val Leu Ala Pro Pro Gln Glu
1               5                   10                  15

Glu Leu Ser Lys Ser Thr Val Ser Leu Thr Cys Met Val Thr Ser Phe
            20                  25                  30

Tyr Pro Asp Tyr Ile Ala Val Glu Trp Gln Arg Asn Gly Gln Pro Glu
        35                  40                  45

Ser Glu Asp Lys Tyr Gly Thr Thr Pro Pro Gln Leu Asp Ala Asp Gly
    50                  55                  60

Ser Tyr Phe Leu Tyr Ser Arg Leu Arg Val Asp Arg Asn Ser Trp Gln
65                  70                  75                  80

Glu Gly Asp Thr Tyr Thr Cys Val Val Met His Glu Ala Leu His Asn
                85                  90                  95

His Tyr Thr Gln Lys Ser Thr Ser Lys Ser Ala Gly Lys
            100                 105

<210> SEQ ID NO 21
<211> LENGTH: 109
<212> TYPE: PRT
<213> ORGANISM: Bos taurus

<400> SEQUENCE: 21

Gly Pro Ala Arg Glu Pro Gln Val Tyr Val Leu Ala Pro Pro Gln Glu
1               5                   10                  15

Glu Leu Ser Lys Ser Thr Val Ser Leu Thr Cys Met Val Thr Ser Phe
            20                  25                  30

Tyr Pro Asp Tyr Ile Ala Val Glu Trp Gln Arg Asn Gly Gln Pro Glu
        35                  40                  45

Ser Glu Asp Lys Tyr Gly Thr Thr Pro Pro Gln Leu Asp Ala Asp Ser
    50                  55                  60
```

```
Ser Tyr Phe Leu Tyr Ser Lys Leu Arg Val Asp Arg Asn Ser Trp Gln
 65                  70                  75                  80

Glu Gly Asp Thr Tyr Thr Cys Val Val Met His Glu Ala Leu His Asn
                 85                  90                  95

His Tyr Thr Gln Lys Ser Thr Ser Lys Ser Ala Gly Lys
            100                 105
```

<210> SEQ ID NO 22

<400> SEQUENCE: 22

000

<210> SEQ ID NO 23
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Gln Ala Val Leu Gly Gln Pro Ser Ser Val Ser Gly Ser Leu Gly Gln
 1               5                   10                  15

Arg Val Ser Ile Thr Cys Ser Gly Ser Ser Ser Asn Ile Gly Thr Tyr
                 20                  25                  30

Gly Val Glu Trp Tyr Gln Gln Val Pro Gly Ser Gly Leu Arg Thr Ile
             35                  40                  45

Ile Tyr Gly Ser Asn Ser Arg Pro Ser Gly Val Pro Asp Arg Phe Ser
 50                  55                  60

Gly Ser Lys Ser Gly Asn Thr Ala Thr Leu Thr Ile Ser Ser Leu Gln
 65                  70                  75                  80

Ala Glu Asp Glu Ala Asp Tyr Phe Cys Ala Ala Gly Asp Ser Ser Ser
                 85                  90                  95

Arg Gly Ala Val Phe Gly Ser Gly Thr Leu Thr Ala Leu Gly Gln Pro
            100                 105                 110

Lys Ser Pro Pro Ser Val Thr Leu Phe Pro Pro Ser Thr Glu Glu Leu
        115                 120                 125

Asn Gly Asn Lys Ala Thr Leu Val Cys Leu Ile Ser Asp Phe Tyr Pro
130                 135                 140

Gly Ser Val Thr Val Val Trp Lys Ala Asp Gly Ser Thr Ile Thr Arg
145                 150                 155                 160

Asn Val Glu Thr Thr Arg Ala Ser Lys Gln Ser Asn Ser Lys Tyr Ala
                165                 170                 175

Ala Ser Ser Tyr Leu Ser Leu Thr Ser Ser Asp Trp Lys Ser Lys Gly
            180                 185                 190

Ser Tyr Ser Cys Glu Val Thr His Glu Gly Ser Thr Val Thr Lys Thr
        195                 200                 205

Val Lys Pro Ser Glu Cys Ser
    210                 215
```

<210> SEQ ID NO 24
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

-continued

```
Gln Val Gln Leu Arg Glu Ser Gly Pro Ser Leu Val Lys Pro Ser Gln
1               5                   10                  15

Thr Leu Ser Leu Thr Cys Thr Val Ser Gly Phe Ser Leu Ser Ser Tyr
            20                  25                  30

Ala Leu Thr Trp Val Arg Gln Ala Pro Gly Lys Ala Leu Glu Trp Val
        35                  40                  45

Gly Gly Ile Thr Ser Gly Gly Thr Thr Tyr Tyr Asn Pro Ala Leu Lys
50                  55                  60

Ser Arg Leu Ser Ile Thr Lys Glu Asn Ser Lys Ser Gln Val Ser Leu
65                  70                  75                  80

Ser Val Ser Ser Val Thr Pro Glu Asp Thr Ala Thr Tyr Tyr Cys Ala
                85                  90                  95

Arg Ser Thr Tyr Gly Glu Val Gly Asp Gly Ala Ile Ala Asp Ala Trp
            100                 105                 110

Gly Gln Gly Leu Leu Val Thr Val Ser Ser Ala Ser Thr Thr Ala Pro
        115                 120                 125

Lys Val Tyr Pro Leu Ser Ser Cys Cys Gly Asp Lys Ser Ser Ser Thr
130                 135                 140

Val Thr Leu Gly Cys Leu Val Ser Ser Tyr Met Pro Glu Pro Val Thr
145                 150                 155                 160

Val Thr Trp Asn Ser Gly Ala Leu Lys Ser Gly Val His Thr Phe Pro
                165                 170                 175

Ala Val Leu Gln Ser Ser Gly Leu Tyr Ser Leu Ser Ser Met Val Thr
            180                 185                 190

Val Pro Gly Ser Thr Ser Gly Gln Thr Phe Thr Cys Asn Val Ala His
        195                 200                 205

Pro Ala Ser Ser Thr Lys Val Asp Lys Ala Val Asp Pro Thr Cys Lys
210                 215                 220

Pro Ser Pro Cys Asp Cys Cys Pro Pro Glu Leu Pro Gly Gly Pro
225                 230                 235                 240

Ser Val Phe Ile Phe Pro Pro Lys Pro Lys Asp Thr Leu Thr Ile Ser
                245                 250                 255

Gly Thr Pro Glu Val Thr Cys Val Val Val Asp Val Gly His Asp Asp
            260                 265                 270

Pro Glu Val Lys Phe Ser Trp Phe Val Asp Asp Val Glu Val Asn Thr
        275                 280                 285

Ala Thr Thr Lys Pro Arg Glu Glu Gln Phe Asn Ser Thr Tyr Arg Val
290                 295                 300

Val Ser Ala Leu Arg Ile Gln His Gln Asp Trp Thr Gly Gly Lys Glu
305                 310                 315                 320

Phe Lys Cys Lys Val His Asn Glu Gly Leu Pro Ala Pro Ile Val Arg
                325                 330                 335

Thr Ile Ser Arg Thr Lys Gly Pro Ala Arg Glu Pro Gln Val Tyr Val
            340                 345                 350

Leu Ala Pro Pro Gln Glu Glu Leu Ser Lys Ser Thr Val Ser Leu Thr
        355                 360                 365

Cys Met Val Thr Ser Phe Tyr Pro Asp Tyr Ile Ala Val Glu Trp Gln
370                 375                 380

Arg Asn Gly Gln Pro Glu Ser Glu Asp Lys Tyr Gly Thr Thr Pro Pro
385                 390                 395                 400

Gln Leu Asp Ala Asp Ser Ser Tyr Phe Leu Tyr Ser Lys Leu Arg Val
                405                 410                 415
```

```
Asp Arg Asn Ser Trp Gln Glu Gly Asp Thr Tyr Thr Cys Val Val Met
            420                 425                 430

His Glu Ala Leu His Asn His Tyr Thr Gln Lys Ser Thr Ser Lys Ser
            435                 440                 445

Ala Gly Lys
    450

<210> SEQ ID NO 25
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 26
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
            35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65              70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
```

<210> SEQ ID NO 27
<211> LENGTH: 226
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 27

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr
225
```

<210> SEQ ID NO 28
<211> LENGTH: 450
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 28

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
```

```
                   50                  55                  60
Ser Val Lys Gly Arg Phe Thr Ile Ser Arg Asp Asp Ser Lys Ser Ala
 65                  70                  75                  80

Val Tyr Leu Gln Met Thr Asp Leu Arg Thr Glu Asp Thr Gly Val Tyr
                     85                  90                  95

Tyr Cys Ser Arg Asn Tyr Tyr Gly Ser Thr Tyr Asp Tyr Trp Gly Gln
                100                 105                 110

Gly Thr Thr Leu Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450

<210> SEQ ID NO 29
```

```
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Ile Phe Pro Pro Lys Pro Lys Asp Thr Leu Thr Ile
                245                 250                 255

Ser Gly Thr Pro Glu Val Thr Cys Val Val Asp Val Gly His Asp
            260                 265                 270

Asp Pro Glu Val Lys Phe Ser Trp Phe Val Asp Val Glu Val Asn
        275                 280                 285

Thr Ala Thr Thr Lys Pro Arg Glu Glu Gln Phe Asn Ser Thr Tyr Arg
    290                 295                 300

Val Val Ser Ala Leu Arg Ile Gln His Gln Asp Trp Thr Gly Gly Lys
305                 310                 315                 320

Glu Phe Lys Cys Lys Val His Asn Glu Gly Leu Pro Ala Pro Ile Val
                325                 330                 335

Arg Thr Ile Ser Arg Thr Lys Gly Pro Ala Arg Glu Pro Gln Val Tyr
            340                 345                 350

Val Leu Ala Pro Pro Gln Glu Glu Leu Ser Lys Ser Thr Val Ser Leu
        355                 360                 365

Thr Cys Met Val Thr Ser Phe Tyr Pro Asp Tyr Ile Ala Val Glu Trp

```
                 370                 375                 380
Gln Arg Asn Gly Gln Pro Glu Ser Glu Asp Lys Tyr Gly Thr Thr Pro
385                 390                 395                 400

Pro Gln Leu Asp Ala Asp Gly Ser Tyr Phe Leu Tyr Ser Arg Leu Arg
                405                 410                 415

Val Asp Arg Asn Ser Trp Gln Glu Gly Asp Thr Tyr Thr Cys Val Val
            420                 425                 430

Met His Glu Ala Leu His Asn His Tyr Thr Gln Lys Ser Thr Ser Lys
        435                 440                 445

Ser Ala Gly Lys
    450

<210> SEQ ID NO 30
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Lys
    210                 215                 220

Thr Thr Cys Asp Cys Cys Pro Pro Glu Leu Pro Gly Gly Pro Ser
225                 230                 235                 240

Val Phe Ile Phe Pro Pro Lys Pro Lys Asp Thr Leu Thr Ile Ser Gly
                245                 250                 255

Thr Pro Glu Val Thr Cys Val Val Asp Val Gly His Asp Asp Pro
            260                 265                 270
```

Glu Val Lys Phe Ser Trp Phe Val Asp Asp Val Glu Val Asn Thr Ala
            275                 280                 285

Thr Thr Lys Pro Arg Glu Glu Gln Phe Asn Ser Thr Tyr Arg Val Val
290                 295                 300

Ser Ala Leu Arg Ile Gln His Gln Asp Trp Thr Gly Gly Lys Glu Phe
305                 310                 315                 320

Lys Cys Lys Val His Asn Glu Gly Leu Pro Ala Pro Ile Val Arg Thr
                325                 330                 335

Ile Ser Arg Thr Lys Gly Pro Ala Arg Glu Pro Gln Val Tyr Val Leu
            340                 345                 350

Ala Pro Pro Gln Glu Glu Leu Ser Lys Ser Thr Val Ser Leu Thr Cys
            355                 360                 365

Met Val Thr Ser Phe Tyr Pro Asp Tyr Ile Ala Val Glu Trp Gln Arg
            370                 375                 380

Asn Gly Gln Pro Glu Ser Glu Asp Lys Tyr Gly Thr Thr Pro Pro Gln
385                 390                 395                 400

Leu Asp Ala Asp Gly Ser Tyr Phe Leu Tyr Ser Arg Leu Arg Val Asp
                405                 410                 415

Arg Asn Ser Trp Gln Glu Gly Asp Thr Tyr Thr Cys Val Val Met His
            420                 425                 430

Glu Ala Leu His Asn His Tyr Thr Gln Lys Ser Thr Ser Lys Ser Ala
            435                 440                 445

Gly Lys
    450

<210> SEQ ID NO 31
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Lys
210                 215                 220

Ile Asp Cys Ser Lys Cys His Asn Gln Pro Cys Val Arg Glu Pro Ser
225                 230                 235                 240

Val Phe Ile Phe Pro Pro Lys Pro Lys Asp Thr Leu Thr Ile Ser Gly
                245                 250                 255

Thr Pro Glu Val Thr Cys Val Val Val Asp Val Gly His Asp Asp Pro
            260                 265                 270

Glu Val Lys Phe Ser Trp Phe Val Asp Asp Val Glu Val Asn Thr Ala
            275                 280                 285

Thr Thr Lys Pro Arg Glu Glu Gln Phe Asn Ser Thr Tyr Arg Val Val
290                 295                 300

Ser Ala Leu Arg Ile Gln His Gln Asp Trp Thr Gly Gly Lys Glu Phe
305                 310                 315                 320

Lys Cys Lys Val His Asn Glu Gly Leu Pro Ala Pro Ile Val Arg Thr
                325                 330                 335

Ile Ser Arg Thr Lys Gly Pro Ala Arg Glu Pro Gln Val Tyr Val Leu
            340                 345                 350

Ala Pro Pro Gln Glu Glu Leu Ser Lys Ser Thr Val Ser Leu Thr Cys
            355                 360                 365

Met Val Thr Ser Phe Tyr Pro Asp Tyr Ile Ala Val Glu Trp Gln Arg
            370                 375                 380

Asn Gly Gln Pro Glu Ser Glu Asp Lys Tyr Gly Thr Thr Pro Pro Gln
385                 390                 395                 400

Leu Asp Ala Asp Gly Ser Tyr Phe Leu Tyr Ser Arg Leu Arg Val Asp
                405                 410                 415

Arg Asn Ser Trp Gln Glu Gly Asp Thr Tyr Thr Cys Val Val Met His
            420                 425                 430

Glu Ala Leu His Asn His Tyr Thr Gln Lys Ser Thr Ser Lys Ser Ala
            435                 440                 445

Gly Lys
    450

<210> SEQ ID NO 32
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala

```
                65                  70                  75                  80
        Val Tyr Leu Gln Met Thr Asp Leu Arg Thr Glu Asp Thr Gly Val Tyr
                        85                  90                  95

Tyr Cys Ser Arg Asn Tyr Tyr Gly Ser Thr Tyr Asp Tyr Trp Gly Gln
                        100                 105                 110

Gly Thr Thr Leu Thr Val Ser Ser Ala Ser Thr Lys Gly Pro Ser Val
                        115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                        180                 185                 190

Ser Ser Ser Leu Gly Thr Gln Thr Tyr Ile Cys Asn Val Asn His Lys
                        195                 200                 205

Pro Ser Asn Thr Lys Val Asp Lys Lys Val Glu Pro Lys Ser Cys Arg
                210                 215                 220

Pro Val Pro Thr Thr Pro Lys Thr Thr Ile Pro Pro Gly Lys Pro Thr
        225                 230                 235                 240

Thr Gln Glu Ser Glu Val Glu Lys Thr Pro Cys Gln Cys Ser Lys Cys
                        245                 250                 255

Pro Glu Pro Leu Gly Gly Leu Ser Val Phe Ile Phe Pro Pro Lys Pro
                        260                 265                 270

Lys Asp Thr Leu Thr Ile Ser Gly Thr Pro Glu Val Thr Cys Val Val
                        275                 280                 285

Val Asp Val Gly His Asp Asp Pro Glu Val Lys Phe Trp Phe Val
                290                 295                 300

Asp Asp Val Glu Val Asn Thr Ala Thr Thr Lys Pro Arg Glu Glu Gln
        305                 310                 315                 320

Phe Asn Ser Thr Tyr Arg Val Val Ser Ala Leu Arg Ile Gln His Gln
                        325                 330                 335

Asp Trp Thr Gly Gly Lys Glu Phe Lys Cys Lys Val His Asn Glu Gly
                        340                 345                 350

Leu Pro Ala Pro Ile Val Arg Thr Ile Ser Arg Thr Lys Gly Pro Ala
                        355                 360                 365

Arg Glu Pro Gln Val Tyr Val Leu Ala Pro Pro Gln Glu Glu Leu Ser
                370                 375                 380

Lys Ser Thr Val Ser Leu Thr Cys Met Val Thr Ser Phe Tyr Pro Asp
        385                 390                 395                 400

Tyr Ile Ala Val Glu Trp Gln Arg Asn Gly Gln Pro Glu Ser Glu Asp
                        405                 410                 415

Lys Tyr Gly Thr Thr Pro Pro Gln Leu Asp Ala Asp Gly Ser Tyr Phe
                        420                 425                 430

Leu Tyr Ser Arg Leu Arg Val Asp Arg Asn Ser Trp Gln Glu Gly Asp
                        435                 440                 445

Thr Tyr Thr Cys Val Val Met His Glu Ala Leu His Asn His Tyr Thr
                450                 455                 460

Gln Lys Ser Thr Ser Lys Ser Ala Gly Lys
        465                 470

<210> SEQ ID NO 33
```

<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Thr Val Ala Ala
            100                 105                 110

Pro Ser Val Phe Leu Phe Lys Pro Ser Asp Glu Gln Leu Lys Thr Gly
        115                 120                 125

Thr Val Ser Val Val Cys Leu Val Asn Asp Phe Tyr Pro Lys Asp Ile
130                 135                 140

Asn Val Lys Trp Lys Val Asp Gly Val Thr Gln Ser Ser Ser Asn Phe
145                 150                 155                 160

Gln Asn Ser Phe Thr Asp Gln Asp Ser Lys Lys Ser Thr Tyr Ser Leu
                165                 170                 175

Ser Ser Ile Leu Thr Leu Pro Ser Ser Glu Tyr Gln Ser His Asn Ala
            180                 185                 190

Tyr Thr Cys Glu Val Ser His Lys Ser Leu Thr Thr Ala Leu Val Lys
        195                 200                 205

Ser Phe Ser Lys Asn Glu Cys
    210                 215

<210> SEQ ID NO 34
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

```
Thr Phe Gly Ser Gly Thr Asn Leu Glu Val Lys Gly Gln Pro Lys Ser
                100                 105                 110

Pro Pro Ser Val Thr Leu Phe Pro Pro Ser Thr Glu Glu Leu Asn Gly
            115                 120                 125

Asn Lys Ala Thr Leu Val Cys Leu Ile Ser Asp Phe Tyr Pro Gly Ser
        130                 135                 140

Val Thr Val Val Trp Lys Ala Asp Gly Ser Thr Ile Thr Arg Asn Val
145                 150                 155                 160

Glu Thr Thr Arg Ala Ser Lys Gln Ser Asn Ser Lys Tyr Ala Ala Ser
                165                 170                 175

Ser Tyr Leu Ser Leu Thr Ser Ser Asp Trp Lys Ser Lys Gly Ser Tyr
            180                 185                 190

Ser Cys Glu Val Thr His Glu Gly Ser Thr Val Thr Lys Thr Val Lys
        195                 200                 205

Pro Ser Glu Cys Ser
    210

<210> SEQ ID NO 35
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Thr Ala Pro Lys Val
        115                 120                 125

Tyr Pro Leu Ser Ser Cys Cys Gly Asp Lys Ser Ser Ser Thr Val Thr
    130                 135                 140

Leu Gly Cys Leu Val Ser Ser Tyr Met Pro Glu Pro Val Thr Val Thr
145                 150                 155                 160

Trp Asn Ser Gly Ala Leu Lys Ser Gly Val His Thr Phe Pro Ala Val
                165                 170                 175

Leu Gln Ser Ser Gly Leu Tyr Ser Leu Ser Ser Met Val Thr Val Pro
            180                 185                 190

Gly Ser Thr Ser Gly Gln Thr Phe Thr Cys Asn Val Ala His Pro Ala
        195                 200                 205

Ser Ser Thr Lys Val Asp Lys Ala Val Asp Pro Thr Cys Lys Pro Ser
    210                 215                 220

Pro Cys Asp Cys Cys Pro Pro Glu Leu Pro Gly Gly Pro Ser Val
```

```
                225                 230                 235                 240
        Phe Ile Phe Pro Pro Lys Pro Lys Asp Thr Leu Thr Ile Ser Gly Thr
                        245                 250                 255

Pro Glu Val Thr Cys Val Val Val Asp Val Gly His Asp Asp Pro Glu
                        260                 265                 270

Val Lys Phe Ser Trp Phe Val Asp Asp Val Glu Val Asn Thr Ala Thr
                        275                 280                 285

Thr Lys Pro Arg Glu Glu Gln Phe Asn Ser Thr Tyr Arg Val Val Ser
                290                 295                 300

Ala Leu Arg Ile Gln His Gln Asp Trp Thr Gly Gly Lys Glu Phe Lys
        305                 310                 315                 320

Cys Lys Val His Asn Glu Gly Leu Pro Ala Pro Ile Val Arg Thr Ile
                        325                 330                 335

Ser Arg Thr Lys Gly Pro Ala Arg Glu Pro Gln Val Tyr Val Leu Ala
                        340                 345                 350

Pro Pro Gln Glu Glu Leu Ser Lys Ser Thr Val Ser Leu Thr Cys Met
                        355                 360                 365

Val Thr Ser Phe Tyr Pro Asp Tyr Ile Ala Val Glu Trp Gln Arg Asn
                370                 375                 380

Gly Gln Pro Glu Ser Glu Asp Lys Tyr Gly Thr Thr Pro Pro Gln Leu
        385                 390                 395                 400

Asp Ala Asp Ser Ser Tyr Phe Leu Tyr Ser Lys Leu Arg Val Asp Arg
                        405                 410                 415

Asn Ser Trp Gln Glu Gly Asp Thr Tyr Thr Cys Val Val Met His Glu
                        420                 425                 430

Ala Leu His Asn His Tyr Thr Gln Lys Ser Thr Ser Lys Ser Ala Gly
                        435                 440                 445

Lys

<210> SEQ ID NO 36
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Leu Leu Thr Gln Ser Pro Ala Ile Leu Ser Val Ser Pro Gly
        1               5                   10                  15

Glu Arg Val Ser Phe Ser Cys Arg Ala Ser Gln Phe Val Gly Ser Ser
                        20                  25                  30

Ile His Trp Tyr Gln Gln Arg Thr Asn Gly Ser Pro Arg Leu Leu Ile
                        35                  40                  45

Lys Tyr Ala Ser Glu Ser Met Ser Gly Ile Pro Ser Arg Phe Ser Gly
                50                  55                  60

Ser Gly Ser Gly Thr Asp Phe Thr Leu Ser Ile Asn Thr Val Glu Ser
        65                  70                  75                  80

Glu Asp Ile Ala Asp Tyr Tyr Cys Gln Gln Ser His Ser Trp Pro Phe
                        85                  90                  95

Thr Phe Gly Ser Gly Thr Asn Leu Glu Val Lys Arg Ser Asp Ala Glu
                        100                 105                 110

Pro Ser Val Phe Leu Phe Lys Pro Ser Asp Glu Gln Leu Lys Thr Gly
                        115                 120                 125

Thr Val Ser Val Val Cys Leu Val Asn Asp Phe Tyr Pro Lys Asp Ile
```

```
                130               135                 140
Asn Val Lys Trp Lys Val Asp Gly Val Thr Gln Ser Ser Asn Phe
145                 150                 155                 160

Gln Asn Ser Phe Thr Asp Gln Asp Ser Lys Lys Ser Thr Tyr Ser Leu
                165                 170                 175

Ser Ser Ile Leu Thr Leu Pro Ser Ser Glu Tyr Gln Ser His Asn Ala
            180                 185                 190

Tyr Thr Cys Glu Val Ser His Lys Ser Leu Thr Ala Leu Val Lys
        195                 200                 205

Ser Phe Ser Lys Asn Glu Cys
    210                 215

<210> SEQ ID NO 37
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Gln Pro Gly Ala Glu Leu Val Lys Pro Gly Thr
1               5                   10                  15

Ser Val Lys Leu Ser Cys Lys Gly Tyr Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Glu Ser Asn Thr Asn Tyr Asn Gln Lys Phe
    50                  55                  60

Lys Gly Lys Ala Thr Leu Thr Val Asp Ile Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Tyr Asp Gly Trp Asp Tyr Ala Ile Asp Tyr Trp Gly
            100                 105                 110

Gln Gly Thr Ser Val Thr Val Ser Ser Ala Ser Thr Thr Ala Pro Lys
        115                 120                 125

Val Tyr Pro Leu Ser Ser Cys Cys Gly Asp Lys Ser Ser Ser Thr Val
    130                 135                 140

Thr Leu Gly Cys Leu Val Ser Ser Tyr Met Pro Glu Pro Val Thr Val
145                 150                 155                 160

Thr Trp Asn Ser Gly Ala Leu Lys Ser Gly Val His Thr Phe Pro Ala
                165                 170                 175

Val Leu Gln Ser Ser Gly Leu Tyr Ser Leu Ser Ser Met Val Thr Val
            180                 185                 190

Pro Gly Ser Thr Ser Gly Gln Thr Phe Thr Cys Asn Val Ala His Pro
        195                 200                 205

Ala Ser Ser Thr Lys Val Asp Lys Ala Val Asp Pro Thr Cys Lys Pro
    210                 215                 220

Ser Pro Cys Asp Cys Cys Pro Pro Glu Leu Pro Gly Gly Pro Ser
225                 230                 235                 240

Val Phe Ile Phe Pro Pro Lys Pro Lys Asp Thr Leu Thr Ile Ser Gly
            245                 250                 255

Thr Pro Glu Val Thr Cys Val Val Val Asp Val Gly His Asp Asp Pro
        260                 265                 270
```

```
Glu Val Lys Phe Ser Trp Phe Val Asp Asp Val Glu Val Asn Thr Ala
            275                 280                 285

Thr Thr Lys Pro Arg Glu Glu Gln Phe Asn Ser Thr Tyr Arg Val Val
    290                 295                 300

Ser Ala Leu Arg Ile Gln His Gln Asp Trp Thr Gly Gly Lys Glu Phe
305                 310                 315                 320

Lys Cys Lys Val His Asn Glu Gly Leu Pro Ala Pro Ile Val Arg Thr
                325                 330                 335

Ile Ser Arg Thr Lys Gly Pro Ala Arg Glu Pro Gln Val Tyr Val Leu
            340                 345                 350

Ala Pro Pro Gln Glu Glu Leu Ser Lys Ser Thr Val Ser Leu Thr Cys
            355                 360                 365

Met Val Thr Ser Phe Tyr Pro Asp Tyr Ile Ala Val Glu Trp Gln Arg
            370                 375                 380

Asn Gly Gln Pro Glu Ser Glu Asp Lys Tyr Gly Thr Thr Pro Pro Gln
385                 390                 395                 400

Leu Asp Ala Asp Ser Ser Tyr Phe Leu Tyr Ser Lys Leu Arg Val Asp
                405                 410                 415

Arg Asn Ser Trp Gln Glu Gly Asp Thr Tyr Thr Cys Val Val Met His
            420                 425                 430

Glu Ala Leu His Asn His Tyr Thr Gln Lys Ser Thr Ser Lys Ser Ala
            435                 440                 445

Gly Lys
    450

<210> SEQ ID NO 38
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Val Val Val Thr Gln Thr Pro Leu Ser Leu Pro Val Ser Phe Gly
1               5                   10                  15

Asp Gln Val Ser Ile Ser Cys Arg Ser Ser Gln Ser Leu Ala Lys Ser
            20                  25                  30

Tyr Gly Asn Thr Tyr Leu Ser Trp Tyr Leu His Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Thr Ile Lys Pro Glu Asp Leu Gly Met Tyr Tyr Cys Leu Gln Gly
                85                  90                  95

Thr His Gln Pro Tyr Thr Phe Gly Gly Gly Thr Lys Leu Glu Ile Lys
            100                 105                 110

Arg Ser Asp Ala Glu Pro Ser Val Phe Leu Phe Lys Pro Ser Asp Glu
        115                 120                 125

Gln Leu Lys Thr Gly Thr Val Ser Val Val Cys Leu Val Asn Asp Phe
    130                 135                 140

Tyr Pro Lys Asp Ile Asn Val Lys Trp Lys Val Asp Gly Val Thr Gln
145                 150                 155                 160

Ser Ser Ser Asn Phe Gln Asn Ser Phe Thr Asp Gln Asp Ser Lys Lys
                165                 170                 175
```

```
Ser Thr Tyr Ser Leu Ser Ser Ile Leu Thr Leu Pro Ser Ser Glu Tyr
                180                 185                 190

Gln Ser His Asn Ala Tyr Thr Cys Glu Val Ser His Lys Ser Leu Thr
        195                 200                 205

Thr Ala Leu Val Lys Ser Phe Ser Lys Asn Glu Cys
    210                 215                 220

<210> SEQ ID NO 39
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
            100                 105                 110

Thr Leu Val Thr Val Ser Ser Ala Ser Thr Thr Ala Pro Lys Val Tyr
        115                 120                 125

Pro Leu Ser Ser Cys Cys Gly Asp Lys Ser Ser Ser Thr Val Thr Leu
    130                 135                 140

Gly Cys Leu Val Ser Ser Tyr Met Pro Glu Pro Val Thr Val Thr Trp
145                 150                 155                 160

Asn Ser Gly Ala Leu Lys Ser Gly Val His Thr Phe Pro Ala Val Leu
                165                 170                 175

Gln Ser Ser Gly Leu Tyr Ser Leu Ser Ser Met Val Thr Val Pro Gly
            180                 185                 190

Ser Thr Ser Gly Gln Thr Phe Thr Cys Asn Val Ala His Pro Ala Ser
        195                 200                 205

Ser Thr Lys Val Asp Lys Ala Val Asp Pro Thr Cys Lys Pro Ser Pro
    210                 215                 220

Cys Asp Cys Cys Pro Pro Glu Leu Pro Gly Gly Pro Ser Val Phe
225                 230                 235                 240

Ile Phe Pro Pro Lys Pro Lys Asp Thr Leu Thr Ile Ser Gly Thr Pro
                245                 250                 255

Glu Val Thr Cys Val Val Val Asp Val Gly His Asp Asp Pro Glu Val
            260                 265                 270

Lys Phe Ser Trp Phe Val Asp Asp Val Glu Val Asn Thr Ala Thr Thr
        275                 280                 285

Lys Pro Arg Glu Glu Gln Phe Asn Ser Thr Tyr Arg Val Val Ser Ala
    290                 295                 300

Leu Arg Ile Gln His Gln Asp Trp Thr Gly Gly Lys Glu Phe Lys Cys
```

```
               305                 310                 315                 320
Lys Val His Asn Glu Gly Leu Pro Ala Pro Ile Val Arg Thr Ile Ser
                325                 330                 335

Arg Thr Lys Gly Pro Ala Arg Glu Pro Gln Val Tyr Val Leu Ala Pro
                340                 345                 350

Pro Gln Glu Glu Leu Ser Lys Ser Thr Val Ser Leu Thr Cys Met Val
                355                 360                 365

Thr Ser Phe Tyr Pro Asp Tyr Ile Ala Val Glu Trp Gln Arg Asn Gly
                370                 375                 380

Gln Pro Glu Ser Glu Asp Lys Tyr Gly Thr Thr Pro Pro Gln Leu Asp
385                 390                 395                 400

Ala Asp Ser Ser Tyr Phe Leu Tyr Ser Lys Leu Arg Val Asp Arg Asn
                405                 410                 415

Ser Trp Gln Glu Gly Asp Thr Tyr Thr Cys Val Val Met His Glu Ala
                420                 425                 430

Leu His Asn His Tyr Thr Gln Lys Ser Thr Ser Lys Ser Ala Gly Lys
                435                 440                 445

<210> SEQ ID NO 40
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
                35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg Ser Asp Ala Glu
                100                 105                 110

Pro Ser Val Phe Leu Phe Lys Pro Ser Asp Glu Gln Leu Lys Thr Gly
            115                 120                 125

Thr Val Ser Val Val Cys Leu Val Asn Asp Phe Tyr Pro Lys Asp Ile
        130                 135                 140

Asn Val Lys Trp Lys Val Asp Gly Val Thr Gln Ser Ser Ser Asn Phe
145                 150                 155                 160

Gln Asn Ser Phe Thr Asp Gln Asp Ser Lys Lys Ser Thr Tyr Ser Leu
                165                 170                 175

Ser Ser Ile Leu Thr Leu Pro Ser Ser Glu Tyr Gln Ser His Asn Ala
            180                 185                 190

Tyr Thr Cys Glu Val Ser His Lys Ser Leu Thr Thr Ala Leu Val Lys
        195                 200                 205

Ser Phe Ser Lys Asn Glu Cys
        210                 215
```

<210> SEQ ID NO 41
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Asn Trp Val Arg Gln Ala Pro Gly Gln Gly Leu Glu Trp Met
        35                  40                  45

Gly Trp Ile Ser Val Tyr Ser Gly Asn Thr Asn Tyr Ala Gln Lys Val
50                  55                  60

Gln Gly Arg Val Thr Met Thr Ala Asp Thr Ser Thr Ser Thr Ala Tyr
65                  70                  75                  80

Met Asp Leu Arg Ser Leu Arg Ser Asp Thr Ala Val Tyr Tyr Cys
                85                  90                  95

Ala Arg Glu Gly Ser Ser Ser Gly Asp Tyr Tyr Gly Met Asp
                100                 105                 110

Val Trp Gly Gln Gly Thr Thr Val Thr Val Ser Ser Ala Ser Thr Thr
            115                 120                 125

Ala Pro Lys Val Tyr Pro Leu Ser Ser Cys Cys Gly Asp Lys Ser Ser
        130                 135                 140

Ser Thr Val Thr Leu Gly Cys Leu Val Ser Ser Tyr Met Pro Glu Pro
145                 150                 155                 160

Val Thr Val Thr Trp Asn Ser Gly Ala Leu Lys Ser Gly Val His Thr
                165                 170                 175

Phe Pro Ala Val Leu Gln Ser Ser Gly Leu Tyr Ser Leu Ser Ser Met
            180                 185                 190

Val Thr Val Pro Gly Ser Thr Ser Gly Gln Thr Phe Thr Cys Asn Val
        195                 200                 205

Ala His Pro Ala Ser Ser Thr Lys Val Asp Lys Ala Val Asp Pro Thr
210                 215                 220

Cys Lys Pro Ser Pro Cys Asp Cys Cys Pro Pro Glu Leu Pro Gly
225                 230                 235                 240

Gly Pro Ser Val Phe Ile Phe Pro Pro Lys Pro Lys Asp Thr Leu Thr
                245                 250                 255

Ile Ser Gly Thr Pro Glu Val Thr Cys Val Val Val Asp Val Gly His
            260                 265                 270

Asp Asp Pro Glu Val Lys Phe Ser Trp Phe Val Asp Asp Val Glu Val
        275                 280                 285

Asn Thr Ala Thr Thr Lys Pro Arg Glu Glu Gln Phe Asn Ser Thr Tyr
        290                 295                 300

Arg Val Val Ser Ala Leu Arg Ile Gln His Gln Asp Trp Thr Gly Gly
305                 310                 315                 320

Lys Glu Phe Lys Cys Lys Val His Asn Glu Gly Leu Pro Ala Pro Ile
                325                 330                 335

Val Arg Thr Ile Ser Arg Thr Lys Gly Pro Ala Arg Glu Pro Gln Val
            340                 345                 350

Tyr Val Leu Ala Pro Pro Gln Glu Glu Leu Ser Lys Ser Thr Val Ser
        355                 360                 365
```

```
Leu Thr Cys Met Val Thr Ser Phe Tyr Pro Asp Tyr Ile Ala Val Glu
        370                 375                 380

Trp Gln Arg Asn Gly Gln Pro Glu Ser Glu Asp Lys Tyr Gly Thr Thr
385                 390                 395                 400

Pro Pro Gln Leu Asp Ala Asp Ser Ser Tyr Phe Leu Tyr Ser Lys Leu
                405                 410                 415

Arg Val Asp Arg Asn Ser Trp Gln Glu Gly Asp Thr Tyr Thr Cys Val
                420                 425                 430

Val Met His Glu Ala Leu His Asn His Tyr Thr Gln Lys Ser Thr Ser
            435                 440                 445

Lys Ser Ala Gly Lys
        450

<210> SEQ ID NO 42
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Thr
            20                  25                  30

Asp Gly Thr Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Asn
                85                  90                  95

Ile Gln Leu Pro Trp Thr Phe Gly Gln Gly Thr Lys Val Glu Ile Lys
            100                 105                 110

Arg Ser Asp Ala Glu Pro Ser Val Phe Leu Phe Lys Pro Ser Asp Glu
        115                 120                 125

Gln Leu Lys Thr Gly Thr Val Ser Val Val Cys Leu Val Asn Asp Phe
    130                 135                 140

Tyr Pro Lys Asp Ile Asn Val Lys Trp Lys Val Asp Gly Val Thr Gln
145                 150                 155                 160

Ser Ser Ser Asn Phe Gln Asn Ser Phe Thr Asp Gln Asp Ser Lys Lys
                165                 170                 175

Ser Thr Tyr Ser Leu Ser Ser Ile Leu Thr Leu Pro Ser Ser Glu Tyr
            180                 185                 190

Gln Ser His Asn Ala Tyr Thr Cys Glu Val Ser His Lys Ser Leu Thr
        195                 200                 205

Thr Ala Leu Val Lys Ser Phe Ser Lys Asn Glu Cys
    210                 215                 220

<210> SEQ ID NO 43
<211> LENGTH: 444
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 43

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Asn
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Asn Trp Asp Val Ala Tyr Trp Gly Gln Gly Thr Leu Val Thr
            100                 105                 110

Val Ser Ala Ala Ser Thr Thr Ala Pro Lys Val Tyr Pro Leu Ser Ser
        115                 120                 125

Cys Cys Gly Asp Lys Ser Ser Thr Val Thr Leu Gly Cys Leu Val
130                 135                 140

Ser Ser Tyr Met Pro Glu Pro Val Thr Val Thr Trp Asn Ser Gly Ala
145                 150                 155                 160

Leu Lys Ser Gly Val His Thr Phe Pro Ala Val Leu Gln Ser Ser Gly
                165                 170                 175

Leu Tyr Ser Leu Ser Ser Met Val Thr Val Pro Gly Ser Thr Ser Gly
            180                 185                 190

Gln Thr Phe Thr Cys Asn Val Ala His Pro Ala Ser Ser Thr Lys Val
        195                 200                 205

Asp Lys Ala Val Asp Pro Thr Cys Lys Pro Ser Pro Cys Asp Cys Cys
    210                 215                 220

Pro Pro Pro Glu Leu Pro Gly Gly Pro Ser Val Phe Ile Phe Pro Pro
225                 230                 235                 240

Lys Pro Lys Asp Thr Leu Thr Ile Ser Gly Thr Pro Glu Val Thr Cys
                245                 250                 255

Val Val Val Asp Val Gly His Asp Asp Pro Glu Val Lys Phe Ser Trp
            260                 265                 270

Phe Val Asp Asp Val Glu Val Asn Thr Ala Thr Thr Lys Pro Arg Glu
        275                 280                 285

Glu Gln Phe Asn Ser Thr Tyr Arg Val Val Ser Ala Leu Arg Ile Gln
    290                 295                 300

His Gln Asp Trp Thr Gly Gly Lys Glu Phe Lys Cys Lys Val His Asn
305                 310                 315                 320

Glu Gly Leu Pro Ala Pro Ile Val Arg Thr Ile Ser Arg Thr Lys Gly
                325                 330                 335

Pro Ala Arg Glu Pro Gln Val Tyr Val Leu Ala Pro Gln Glu Glu
            340                 345                 350

Leu Ser Lys Ser Thr Val Ser Leu Thr Cys Met Val Thr Ser Phe Tyr
        355                 360                 365

Pro Asp Tyr Ile Ala Val Glu Trp Gln Arg Asn Gly Gln Pro Glu Ser
    370                 375                 380

Glu Asp Lys Tyr Gly Thr Thr Pro Pro Gln Leu Asp Ala Asp Ser Ser
385                 390                 395                 400
```

Tyr Phe Leu Tyr Ser Lys Leu Arg Val Asp Arg Asn Ser Trp Gln Glu
                405                 410                 415

Gly Asp Thr Tyr Thr Cys Val Val Met His Glu Ala Leu His Asn His
            420                 425                 430

Tyr Thr Gln Lys Ser Thr Ser Lys Ser Ala Gly Lys
        435                 440

<210> SEQ ID NO 44
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Arg Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Phe
                85                  90                  95

Thr Phe Gly Ser Gly Thr Lys Leu Glu Ile Lys Arg Ser Asp Ala Glu
            100                 105                 110

Pro Ser Val Phe Leu Phe Lys Pro Ser Asp Glu Gln Leu Lys Thr Gly
        115                 120                 125

Thr Val Ser Val Val Cys Leu Val Asn Asp Phe Tyr Pro Lys Asp Ile
    130                 135                 140

Asn Val Lys Trp Lys Val Asp Gly Val Thr Gln Ser Ser Ser Asn Phe
145                 150                 155                 160

Gln Asn Ser Phe Thr Asp Gln Asp Ser Lys Lys Ser Thr Tyr Ser Leu
                165                 170                 175

Ser Ser Ile Leu Thr Leu Pro Ser Ser Glu Tyr Gln Ser His Asn Ala
            180                 185                 190

Tyr Thr Cys Glu Val Ser His Lys Ser Leu Thr Thr Ala Leu Val Lys
        195                 200                 205

Ser Phe Ser Lys Asn Glu Cys
    210                 215

<210> SEQ ID NO 45
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

-continued

```
Trp Ile His Trp Val Arg Gln Ala Pro Gly Lys Gly Leu Glu Trp Leu
             35                  40                  45

Gly Glu Ile Ser Ala Ala Gly Gly Tyr Thr Asp Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Ser Arg Val Ser Phe Glu Ala Ala Met Asp Tyr Trp Gly
                100                 105                 110

Gln Gly Thr Leu Val Thr Val Ser Ser Ala Ser Thr Thr Ala Pro Lys
            115                 120                 125

Val Tyr Pro Leu Ser Ser Cys Cys Gly Asp Lys Ser Ser Ser Thr Val
        130                 135                 140

Thr Leu Gly Cys Leu Val Ser Ser Tyr Met Pro Glu Pro Val Thr Val
145                 150                 155                 160

Thr Trp Asn Ser Gly Ala Leu Lys Ser Gly Val His Thr Phe Pro Ala
                165                 170                 175

Val Leu Gln Ser Ser Gly Leu Tyr Ser Leu Ser Ser Met Val Thr Val
            180                 185                 190

Pro Gly Ser Thr Ser Gly Gln Thr Phe Thr Cys Asn Val Ala His Pro
        195                 200                 205

Ala Ser Ser Thr Lys Val Asp Lys Ala Val Asp Pro Thr Cys Lys Pro
    210                 215                 220

Ser Pro Cys Asp Cys Cys Pro Pro Glu Leu Pro Gly Gly Pro Ser
225                 230                 235                 240

Val Phe Ile Phe Pro Pro Lys Pro Lys Asp Thr Leu Thr Ile Ser Gly
                245                 250                 255

Thr Pro Glu Val Thr Cys Val Val Asp Val Gly His Asp Asp Pro
            260                 265                 270

Glu Val Lys Phe Ser Trp Phe Val Asp Asp Val Glu Val Asn Thr Ala
        275                 280                 285

Thr Thr Lys Pro Arg Glu Glu Gln Phe Asn Ser Thr Tyr Arg Val Val
    290                 295                 300

Ser Ala Leu Arg Ile Gln His Gln Asp Trp Thr Gly Gly Lys Glu Phe
305                 310                 315                 320

Lys Cys Lys Val His Asn Glu Gly Leu Pro Ala Pro Ile Val Arg Thr
                325                 330                 335

Ile Ser Arg Thr Lys Gly Pro Ala Arg Glu Pro Gln Val Tyr Val Leu
            340                 345                 350

Ala Pro Pro Gln Glu Glu Leu Ser Lys Ser Thr Val Ser Leu Thr Cys
        355                 360                 365

Met Val Thr Ser Phe Tyr Pro Asp Tyr Ile Ala Val Glu Trp Gln Arg
    370                 375                 380

Asn Gly Gln Pro Glu Ser Glu Asp Lys Tyr Gly Thr Thr Pro Pro Gln
385                 390                 395                 400

Leu Asp Ala Asp Ser Ser Tyr Phe Leu Tyr Ser Lys Leu Arg Val Asp
                405                 410                 415

Arg Asn Ser Trp Gln Glu Gly Asp Thr Tyr Thr Cys Val Val Met His
            420                 425                 430

Glu Ala Leu His Asn His Tyr Thr Gln Lys Ser Thr Ser Lys Ser Ala
        435                 440                 445

Gly Lys
```

<210> SEQ ID NO 46
<211> LENGTH: 215
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Leu Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg Ser Asp Ala Glu
            100                 105                 110

Pro Ser Val Phe Leu Phe Lys Pro Ser Asp Glu Gln Leu Lys Thr Gly
        115                 120                 125

Thr Val Ser Val Val Cys Leu Val Asn Asp Phe Tyr Pro Lys Asp Ile
    130                 135                 140

Asn Val Lys Trp Lys Val Asp Gly Val Thr Gln Ser Ser Ser Asn Phe
145                 150                 155                 160

Gln Asn Ser Phe Thr Asp Gln Asp Ser Lys Lys Ser Thr Tyr Ser Leu
                165                 170                 175

Ser Ser Ile Leu Thr Leu Pro Ser Ser Glu Tyr Gln Ser His Asn Ala
            180                 185                 190

Tyr Thr Cys Glu Val Ser His Lys Ser Leu Thr Thr Ala Leu Val Lys
        195                 200                 205

Ser Phe Ser Lys Asn Glu Cys
    210                 215
```

<210> SEQ ID NO 47
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Arg Tyr
            20                  25                  30

Trp Met His Trp Ile Lys Gln Arg Pro Gly Gln Gly Leu Glu Trp Ile
        35                  40                  45

Gly Ala Ile Tyr Pro Gly Asn Ser Asp Thr Ser Tyr Asn Gln Lys Phe
    50                  55                  60

Glu Gly Lys Ala Lys Leu Thr Ala Val Thr Ser Ala Ser Thr Ala Tyr
```

```
                65                  70                  75                  80
Met Glu Leu Ser Ser Leu Thr His Glu Asp Ser Ala Val Tyr Tyr Cys
                    85                  90                  95

Ser Arg Asp Tyr Gly Tyr Tyr Phe Asp Phe Trp Gly Gln Gly Thr Thr
                100                 105                 110

Leu Thr Val Ser Ser Ala Ser Thr Ala Pro Lys Val Tyr Pro Leu
            115                 120                 125

Ser Ser Cys Cys Gly Asp Lys Ser Ser Thr Val Thr Leu Gly Cys
130                 135                 140

Leu Val Ser Ser Tyr Met Pro Glu Pro Val Thr Val Thr Trp Asn Ser
145                 150                 155                 160

Gly Ala Leu Lys Ser Gly Val His Thr Phe Pro Ala Val Leu Gln Ser
                165                 170                 175

Ser Gly Leu Tyr Ser Leu Ser Ser Met Val Thr Val Pro Gly Ser Thr
                180                 185                 190

Ser Gly Gln Thr Phe Thr Cys Asn Val Ala His Pro Ala Ser Ser Thr
                195                 200                 205

Lys Val Asp Lys Ala Val Asp Pro Thr Cys Lys Pro Ser Pro Cys Asp
            210                 215                 220

Cys Cys Pro Pro Pro Glu Leu Pro Gly Gly Pro Ser Val Phe Ile Phe
225                 230                 235                 240

Pro Pro Lys Pro Lys Asp Thr Leu Thr Ile Ser Gly Thr Pro Glu Val
                245                 250                 255

Thr Cys Val Val Val Asp Val Gly His Asp Asp Pro Glu Val Lys Phe
                260                 265                 270

Ser Trp Phe Val Asp Asp Val Glu Val Asn Thr Ala Thr Thr Lys Pro
            275                 280                 285

Arg Glu Glu Gln Phe Asn Ser Thr Tyr Arg Val Val Ser Ala Leu Arg
290                 295                 300

Ile Gln His Gln Asp Trp Thr Gly Gly Lys Glu Phe Lys Cys Lys Val
305                 310                 315                 320

His Asn Glu Gly Leu Pro Ala Pro Ile Val Arg Thr Ile Ser Arg Thr
                325                 330                 335

Lys Gly Pro Ala Arg Glu Pro Gln Val Tyr Val Leu Ala Pro Pro Gln
                340                 345                 350

Glu Glu Leu Ser Lys Ser Thr Val Ser Leu Thr Cys Met Val Thr Ser
            355                 360                 365

Phe Tyr Pro Asp Tyr Ile Ala Val Glu Trp Gln Arg Asn Gly Gln Pro
370                 375                 380

Glu Ser Glu Asp Lys Tyr Gly Thr Thr Pro Pro Gln Leu Asp Ala Asp
385                 390                 395                 400

Ser Ser Tyr Phe Leu Tyr Ser Lys Leu Arg Val Asp Arg Asn Ser Trp
                405                 410                 415

Gln Glu Gly Asp Thr Tyr Thr Cys Val Val Met His Glu Ala Leu His
                420                 425                 430

Asn His Tyr Thr Gln Lys Ser Thr Ser Lys Ser Ala Gly Lys
                435                 440                 445

<210> SEQ ID NO 48
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 48

```
Gln Ile Val Ser Thr Gln Ser Pro Ala Ile Met Ser Ala Ser Pro Gly
1               5                   10                  15

Glu Lys Val Thr Met Thr Cys Ser Ala Ser Ser Arg Ser Tyr Met
            20                  25                  30

Gln Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Thr Phe Gly
                85                  90                  95

Gly Gly Thr Lys Leu Glu Ile Lys Arg Ser Asp Ala Glu Pro Ser Val
            100                 105                 110

Phe Leu Phe Lys Pro Ser Asp Glu Gln Leu Lys Thr Gly Thr Val Ser
        115                 120                 125

Val Val Cys Leu Val Asn Asp Phe Tyr Pro Lys Asp Ile Asn Val Lys
    130                 135                 140

Trp Lys Val Asp Gly Val Thr Gln Ser Ser Ser Asn Phe Gln Asn Ser
145                 150                 155                 160

Phe Thr Asp Gln Asp Ser Lys Lys Ser Thr Tyr Ser Leu Ser Ser Ile
                165                 170                 175

Leu Thr Leu Pro Ser Ser Glu Tyr Gln Ser His Asn Ala Tyr Thr Cys
            180                 185                 190

Glu Val Ser His Lys Ser Leu Thr Thr Ala Leu Val Lys Ser Phe Ser
        195                 200                 205

Lys Asn Glu Cys
    210
```

<210> SEQ ID NO 49
<211> LENGTH: 445
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 49

```
Glu Val Gln Leu Val Glu Ser Gly Gly Leu Val Gln Pro Gly Arg
1               5                   10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser Ala Ser Thr Thr Ala Pro Lys Val Tyr Pro Leu Ser
        115                 120                 125
```

Ser Cys Cys Gly Asp Lys Ser Ser Thr Val Thr Leu Gly Cys Leu
130                 135                 140

Val Ser Ser Tyr Met Pro Glu Pro Val Thr Val Thr Trp Asn Ser Gly
145                 150                 155                 160

Ala Leu Lys Ser Gly Val His Thr Phe Pro Ala Val Leu Gln Ser Ser
                165                 170                 175

Gly Leu Tyr Ser Leu Ser Ser Met Val Thr Val Pro Gly Ser Thr Ser
            180                 185                 190

Gly Gln Thr Phe Thr Cys Asn Val Ala His Pro Ala Ser Ser Thr Lys
        195                 200                 205

Val Asp Lys Ala Val Asp Pro Thr Cys Lys Pro Ser Pro Cys Asp Cys
210                 215                 220

Cys Pro Pro Pro Glu Leu Pro Gly Gly Pro Ser Val Phe Ile Phe Pro
225                 230                 235                 240

Pro Lys Pro Lys Asp Thr Leu Thr Ile Ser Gly Thr Pro Glu Val Thr
                245                 250                 255

Cys Val Val Val Asp Val Gly His Asp Asp Pro Glu Val Lys Phe Ser
            260                 265                 270

Trp Phe Val Asp Asp Val Glu Val Asn Thr Ala Thr Thr Lys Pro Arg
        275                 280                 285

Glu Glu Gln Phe Asn Ser Thr Tyr Arg Val Val Ser Ala Leu Arg Ile
290                 295                 300

Gln His Gln Asp Trp Thr Gly Gly Lys Glu Phe Lys Cys Lys Val His
305                 310                 315                 320

Asn Glu Gly Leu Pro Ala Pro Ile Val Arg Thr Ile Ser Arg Thr Lys
                325                 330                 335

Gly Pro Ala Arg Glu Pro Gln Val Tyr Val Leu Ala Pro Pro Gln Glu
            340                 345                 350

Glu Leu Ser Lys Ser Thr Val Ser Leu Thr Cys Met Val Thr Ser Phe
        355                 360                 365

Tyr Pro Asp Tyr Ile Ala Val Glu Trp Gln Arg Asn Gly Gln Pro Glu
370                 375                 380

Ser Glu Asp Lys Tyr Gly Thr Thr Pro Pro Gln Leu Asp Ala Asp Ser
385                 390                 395                 400

Ser Tyr Phe Leu Tyr Ser Lys Leu Arg Val Asp Arg Asn Ser Trp Gln
                405                 410                 415

Glu Gly Asp Thr Tyr Thr Cys Val Val Met His Glu Ala Leu His Asn
            420                 425                 430

His Tyr Thr Gln Lys Ser Thr Ser Lys Ser Ala Gly Lys
        435                 440                 445

<210> SEQ ID NO 50
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile

```
                35                  40                  45
Tyr Gly Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ala Asn Ser Phe Pro Tyr
                85                  90                  95

Thr Phe Gly Gln Gly Thr Lys Leu Glu Ile Lys Arg Ser Asp Ala Glu
            100                 105                 110

Pro Ser Val Phe Leu Phe Lys Pro Ser Asp Glu Gln Leu Lys Thr Gly
        115                 120                 125

Thr Val Ser Val Val Cys Leu Val Asn Asp Phe Tyr Pro Lys Asp Ile
    130                 135                 140

Asn Val Lys Trp Lys Val Asp Gly Val Thr Gln Ser Ser Ser Asn Phe
145                 150                 155                 160

Gln Asn Ser Phe Thr Asp Gln Asp Ser Lys Lys Ser Thr Tyr Ser Leu
                165                 170                 175

Ser Ser Ile Leu Thr Leu Pro Ser Ser Glu Tyr Gln Ser His Asn Ala
            180                 185                 190

Tyr Thr Cys Glu Val Ser His Lys Ser Leu Thr Thr Ala Leu Val Lys
        195                 200                 205

Ser Phe Ser Lys Asn Glu Cys
    210                 215

<210> SEQ ID NO 51
<211> LENGTH: 78
<212> TYPE: PRT
<213> ORGANISM: Homo sapiens

<400> SEQUENCE: 51

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr
65                  70                  75

<210> SEQ ID NO 52
<211> LENGTH: 77
<212> TYPE: PRT
<213> ORGANISM: Bos taurus

<400> SEQUENCE: 52

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly
65                  70                  75
```

```
65                  70                  75

<210> SEQ ID NO 53
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Ser Thr Lys Gly Pro Ser Val Phe Pro Leu Ser Ser Cys Cys Gly
1               5                   10                  15

Asp Lys Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr
65                  70                  75

<210> SEQ ID NO 54
<211> LENGTH: 78
<212> TYPE: PRT
<213> ORGANISM: Homo sapiens

<400> SEQUENCE: 54

Gln Thr Tyr Ile Cys Asn Val Asn His Lys Pro Ser Asn Thr Lys Val
1               5                   10                  15

Asp Lys Lys Val Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val
65                  70                  75

<210> SEQ ID NO 55
<211> LENGTH: 76
<212> TYPE: PRT
<213> ORGANISM: Bos taurus

<400> SEQUENCE: 55

Gln Thr Phe Thr Cys Asn Val Ala His Pro Ala Ser Ser Thr Lys Val
1               5                   10                  15

Asp Lys Ala Val Asp Pro Thr Cys Lys Pro Ser Pro Cys Asp Cys Cys
            20                  25                  30

Pro Pro Pro Glu Leu Pro Gly Gly Pro Ser Val Phe Ile Phe Pro Pro
        35                  40                  45

Lys Pro Lys Asp Thr Leu Thr Ile Ser Gly Thr Pro Glu Val Thr Cys
    50                  55                  60

Val Val Val Asp Val Gly His Asp Asp Pro Glu Val
65                  70                  75

<210> SEQ ID NO 56
<211> LENGTH: 76
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 56

Gln Thr Tyr Ile Cys Asn Val Asn His Lys Pro Ser Asn Thr Lys Val
1               5                   10                  15

Asp Lys Ala Val Asp Pro Thr Cys Lys Pro Ser Pro Cys Asp Cys Cys
            20                  25                  30

Pro Pro Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val
65                  70                  75

<210> SEQ ID NO 57
<211> LENGTH: 78
<212> TYPE: PRT
<213> ORGANISM: Homo sapiens

<400> SEQUENCE: 57

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr
65                  70                  75

<210> SEQ ID NO 58
<211> LENGTH: 77
<212> TYPE: PRT
<213> ORGANISM: Bos taurus

<400> SEQUENCE: 58

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
50                  55                  60

Leu Ser Ser Met Val Thr Val Pro Gly Ser Thr Ser Gly
65                  70                  75

<210> SEQ ID NO 59
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Ala Ser Thr Lys Gly Pro Ser Val Phe Pro Leu Ser Ser Cys Cys Gly
```

```
                1               5                  10                  15
Asp Lys Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr
65                  70                  75

<210> SEQ ID NO 60
<211> LENGTH: 74
<212> TYPE: PRT
<213> ORGANISM: Homo sapiens

<400> SEQUENCE: 60

Gln Thr Tyr Thr Cys Asn Val Asp His Lys Pro Ser Asn Thr Lys Val
1               5                   10                  15

Asp Lys Thr Val Glu Arg Lys Cys Cys Val Glu Cys Pro Pro Cys Pro
                20                  25                  30

Ala Pro Pro Val Ala Gly Pro Ser Val Phe Leu Phe Pro Pro Lys Pro
            35                  40                  45

Lys Asp Thr Leu Met Ile Ser Arg Thr Pro Glu Val Thr Cys Val Val
        50                  55                  60

Val Asp Val Ser His Glu Asp Pro Glu Val
65                  70

<210> SEQ ID NO 61
<211> LENGTH: 76
<212> TYPE: PRT
<213> ORGANISM: Bos taurus

<400> SEQUENCE: 61

Gln Thr Phe Thr Cys Asn Val Ala His Pro Ala Ser Ser Thr Lys Val
1               5                   10                  15

Asp Lys Ala Val Asp Pro Thr Cys Lys Pro Ser Pro Cys Asp Cys Cys
                20                  25                  30

Pro Pro Pro Glu Leu Pro Gly Gly Pro Ser Val Phe Ile Phe Pro Pro
            35                  40                  45

Lys Pro Lys Asp Thr Leu Thr Ile Ser Gly Thr Pro Glu Val Thr Cys
        50                  55                  60

Val Val Val Asp Val Gly His Asp Asp Pro Glu Val
65                  70                  75

<210> SEQ ID NO 62
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Thr Tyr Thr Cys Asn Val Asp His Lys Pro Ser Asn Thr Lys Val
1               5                   10                  15

Asp Lys Ala Val Asp Pro Thr Cys Lys Pro Ser Pro Cys Asp Cys Cys
                20                  25                  30

Pro Pro Pro Glu Leu Pro Ala Gly Pro Ser Val Phe Leu Phe Pro Pro
            35                  40                  45
```

```
Lys Pro Lys Asp Thr Leu Met Ile Ser Arg Thr Pro Glu Val Thr Cys
 50                  55                  60
Val Val Val Asp Val Ser His Glu Asp Pro Glu Val
 65                  70                  75

<210> SEQ ID NO 63
<211> LENGTH: 78
<212> TYPE: PRT
<213> ORGANISM: Homo sapiens

<400> SEQUENCE: 63

Ala Ser Thr Lys Gly Pro Ser Val Phe Pro Leu Ala Pro Cys Ser Arg
 1               5                  10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
     50                  55                  60
Leu Ser Ser Val Val Thr Val Pro Ser Ser Ser Leu Gly Thr
 65                  70                  75

<210> SEQ ID NO 64
<211> LENGTH: 77
<212> TYPE: PRT
<213> ORGANISM: Bos taurus

<400> SEQUENCE: 64

Ala Ser Thr Thr Ala Pro Lys Val Tyr Pro Leu Ser Ser Cys Cys Gly
 1               5                  10                  15
Asp Lys Ser Ser Ser Thr Val Thr Leu Gly Cys Leu Val Ser Ser Tyr
                20                  25                  30
Met Pro Glu Pro Val Thr Val Thr Trp Asn Ser Gly Ala Leu Lys Ser
            35                  40                  45
Gly Val His Thr Phe Pro Ala Val Leu Gln Ser Ser Gly Leu Tyr Ser
     50                  55                  60
Leu Ser Ser Met Val Thr Val Pro Gly Ser Thr Ser Gly
 65                  70                  75

<210> SEQ ID NO 65
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Ala Ser Thr Lys Gly Pro Ser Val Phe Pro Leu Ser Ser Cys Cys Gly
 1               5                  10                  15
Asp Lys Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
     50                  55                  60
Leu Ser Ser Val Val Thr Val Pro Ser Ser Ser Leu Gly Thr
 65                  70                  75
```

<210> SEQ ID NO 66
<211> LENGTH: 75
<212> TYPE: PRT
<213> ORGANISM: Homo sapiens

<400> SEQUENCE: 66

Lys Thr Tyr Thr Cys Asn Val Asp His Lys Pro Ser Asn Thr Lys Val
1               5                   10                  15

Asp Lys Arg Val Glu Ser Lys Tyr Gly Pro Pro Cys Pro Ser Cys Pro
            20                  25                  30

Ala Pro Glu Phe Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser Gln Glu Asp Pro Glu Val
65                  70                  75

<210> SEQ ID NO 67
<211> LENGTH: 76
<212> TYPE: PRT
<213> ORGANISM: Bos taurus

<400> SEQUENCE: 67

Gln Thr Phe Thr Cys Asn Val Ala His Pro Ala Ser Ser Thr Lys Val
1               5                   10                  15

Asp Lys Ala Val Asp Pro Thr Cys Lys Pro Ser Pro Cys Asp Cys Cys
            20                  25                  30

Pro Pro Pro Glu Leu Pro Gly Gly Pro Ser Val Phe Ile Phe Pro Pro
        35                  40                  45

Lys Pro Lys Asp Thr Leu Thr Ile Ser Gly Thr Pro Glu Val Thr Cys
    50                  55                  60

Val Val Val Asp Val Gly His Asp Asp Pro Glu Val
65                  70                  75

<210> SEQ ID NO 68
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Lys Thr Tyr Thr Cys Asn Val Asp His Lys Pro Ser Asn Thr Lys Val
1               5                   10                  15

Asp Lys Ala Val Asp Pro Thr Cys Lys Pro Ser Pro Cys Asp Cys Cys
            20                  25                  30

Pro Ala Pro Glu Phe Leu Gly Gly Pro Ser Val Phe Leu Phe Pro Pro
        35                  40                  45

Lys Pro Lys Asp Thr Leu Met Ile Ser Arg Thr Pro Glu Val Thr Cys
    50                  55                  60

Val Val Val Asp Val Ser Gln Glu Asp Pro Glu Val
65                  70                  75

<210> SEQ ID NO 69
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Thr Ala Pro Lys Val
        115                 120                 125

Tyr Pro Leu Ser Ser Cys Gly Asp Lys Ser Ser Thr Val Thr
    130                 135                 140

Leu Gly Cys Leu Val Ser Ser Tyr Met Pro Glu Pro Val Thr Val Thr
145                 150                 155                 160

Trp Asn Ser Gly Ala Leu Lys Ser Gly Val His Thr Phe Pro Ala Val
                165                 170                 175

Leu Gln Ser Ser Gly Leu Tyr Ser Leu Ser Ser Met Val Thr Val Pro
            180                 185                 190

Gly Ser Thr Ser Gly Gln Thr Phe Thr Cys Asn Val Ala His Pro Ala
        195                 200                 205

Ser Ser Thr Lys Val Asp Lys Ala Val Asp Pro Thr Ser Lys Pro Ser
    210                 215                 220

Pro Cys Asp Cys Cys Pro Pro Glu Leu Pro Gly Gly Pro Ser Val
225                 230                 235                 240

Phe Ile Phe Pro Pro Lys Pro Lys Asp Thr Leu Thr Ile Ser Gly Thr
                245                 250                 255

Pro Glu Val Thr Cys Val Val Asp Val Gly His Asp Asp Pro Glu
            260                 265                 270

Val Lys Phe Ser Trp Phe Val Asp Asp Val Glu Val Asn Thr Ala Thr
        275                 280                 285

Thr Lys Pro Arg Glu Glu Gln Phe Asn Ser Thr Tyr Arg Val Val Ser
    290                 295                 300

Ala Leu Arg Ile Gln His Gln Asp Trp Thr Gly Gly Lys Glu Phe Lys
305                 310                 315                 320

Cys Lys Val His Asn Glu Gly Leu Pro Ala Pro Ile Val Arg Thr Ile
                325                 330                 335

Ser Arg Thr Lys Gly Pro Ala Arg Glu Pro Gln Val Tyr Val Leu Ala
            340                 345                 350

Pro Pro Gln Glu Glu Leu Ser Lys Ser Thr Val Ser Leu Thr Cys Met
        355                 360                 365

Val Thr Ser Phe Tyr Pro Asp Tyr Ile Ala Val Glu Trp Gln Arg Asn
    370                 375                 380

Gly Gln Pro Glu Ser Glu Asp Lys Tyr Gly Thr Thr Pro Pro Gln Leu
385                 390                 395                 400
```

-continued

```
Asp Ala Asp Ser Ser Tyr Phe Leu Tyr Ser Lys Leu Arg Val Asp Arg
            405                 410                 415

Asn Ser Trp Gln Glu Gly Asp Thr Tyr Thr Cys Val Val Met His Glu
        420                 425                 430

Ala Leu His Asn His Tyr Thr Gln Lys Ser Thr Ser Lys Ser Ala Gly
    435                 440                 445

Lys

<210> SEQ ID NO 70
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Ser Asp Ala Glu
            100                 105                 110

Pro Ser Val Phe Leu Phe Lys Pro Ser Asp Glu Gln Leu Lys Thr Gly
        115                 120                 125

Thr Val Ser Val Val Cys Leu Val Asn Asp Phe Tyr Pro Lys Asp Ile
    130                 135                 140

Asn Val Lys Trp Lys Val Asp Gly Val Thr Gln Ser Ser Ser Asn Phe
145                 150                 155                 160

Gln Asn Ser Phe Thr Asp Gln Asp Ser Lys Lys Ser Thr Tyr Ser Leu
                165                 170                 175

Ser Ser Ile Leu Thr Leu Pro Ser Ser Glu Tyr Gln Ser His Asn Ala
            180                 185                 190

Tyr Thr Cys Glu Val Ser His Lys Ser Leu Thr Thr Ala Leu Val Lys
        195                 200                 205

Ser Phe Ser Lys Asn Glu Cys
    210                 215

<210> SEQ ID NO 71
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
```

```
                 20                  25                  30
Trp Met Asn Trp Val Arg Gln Ser Pro Glu Lys Gly Leu Glu Trp Val
             35                  40                  45
Ala Glu Ile Arg Ser Lys Ser Ile Asn Ser Ala Thr His Tyr Ala Glu
 50                  55                  60
Ser Val Lys Gly Arg Phe Thr Ile Ser Arg Asp Asp Ser Lys Ser Ala
 65                  70                  75                  80
Val Tyr Leu Gln Met Thr Asp Leu Arg Thr Glu Asp Thr Gly Val Tyr
             85                  90                  95
Tyr Cys Ser Arg Asn Tyr Tyr Gly Ser Thr Tyr Asp Tyr Trp Gly Gln
             100                 105                 110
Gly Thr Thr Leu Thr Val Ser Ser Ala Ser Thr Thr Ala Pro Lys Val
             115                 120                 125
Tyr Pro Leu Ser Ser Cys Ser Gly Asp Lys Ser Ser Thr Val Thr
             130                 135                 140
Leu Gly Cys Leu Val Ser Ser Tyr Met Pro Glu Pro Val Thr Val Thr
145                 150                 155                 160
Trp Asn Ser Gly Ala Leu Lys Ser Gly Val His Thr Phe Pro Ala Val
                 165                 170                 175
Leu Gln Ser Ser Gly Leu Tyr Ser Leu Ser Ser Met Val Thr Val Pro
             180                 185                 190
Gly Ser Thr Ser Gly Gln Thr Phe Thr Cys Asn Val Ala His Pro Ala
             195                 200                 205
Ser Ser Thr Lys Val Asp Lys Ala Val Asp Pro Thr Ser Lys Pro Ser
             210                 215                 220
Pro Cys Asp Cys Cys Pro Pro Glu Leu Pro Gly Gly Pro Ser Val
225                 230                 235                 240
Phe Ile Phe Pro Pro Lys Pro Lys Asp Thr Leu Thr Ile Ser Gly Thr
                 245                 250                 255
Pro Glu Val Thr Cys Val Val Asp Val Gly His Asp Asp Pro Glu
             260                 265                 270
Val Lys Phe Ser Trp Phe Val Asp Asp Val Glu Val Asn Thr Ala Thr
             275                 280                 285
Thr Lys Pro Arg Glu Glu Gln Phe Asn Ser Thr Tyr Arg Val Val Ser
 290                 295                 300
Ala Leu Arg Ile Gln His Gln Asp Trp Thr Gly Gly Lys Glu Phe Lys
305                 310                 315                 320
Cys Lys Val His Asn Glu Gly Leu Pro Ala Pro Ile Val Arg Thr Ile
                 325                 330                 335
Ser Arg Thr Lys Gly Pro Ala Arg Glu Pro Gln Val Tyr Val Leu Ala
                 340                 345                 350
Pro Pro Gln Glu Glu Leu Ser Lys Ser Thr Val Ser Leu Thr Cys Met
             355                 360                 365
Val Thr Ser Phe Tyr Pro Asp Tyr Ile Ala Val Glu Trp Gln Arg Asn
             370                 375                 380
Gly Gln Pro Glu Ser Glu Asp Lys Tyr Gly Thr Thr Pro Pro Gln Leu
385                 390                 395                 400
Asp Ala Asp Ser Ser Tyr Phe Leu Tyr Ser Lys Leu Arg Val Asp Arg
                 405                 410                 415
Asn Ser Trp Gln Glu Gly Asp Thr Tyr Thr Cys Val Val Met His Glu
             420                 425                 430
Ala Leu His Asn His Tyr Thr Gln Lys Ser Thr Ser Lys Ser Ala Gly
             435                 440                 445
```

Lys

<210> SEQ ID NO 72
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
                20                  25                  30

Ile His Trp Tyr Gln Gln Arg Thr Asn Gly Ser Pro Arg Leu Leu Ile
            35                  40                  45

Lys Tyr Ala Ser Glu Ser Met Ser Gly Ile Pro Ser Arg Phe Ser Gly
50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Ser Asp Ala Glu
            100                 105                 110

Pro Ser Val Phe Leu Phe Lys Pro Ser Asp Glu Gln Leu Lys Thr Gly
        115                 120                 125

Thr Val Ser Val Val Cys Leu Val Asn Asp Phe Tyr Pro Lys Asp Ile
130                 135                 140

Asn Val Lys Trp Lys Val Asp Gly Val Thr Gln Ser Ser Ser Asn Phe
145                 150                 155                 160

Gln Asn Ser Phe Thr Asp Gln Asp Ser Lys Lys Ser Thr Tyr Ser Leu
                165                 170                 175

Ser Ser Ile Leu Thr Leu Pro Ser Ser Glu Tyr Gln Ser His Asn Ala
            180                 185                 190

Tyr Thr Cys Glu Val Ser His Lys Ser Leu Thr Thr Ala Leu Val Lys
        195                 200                 205

Ser Phe Ser Lys Asn Glu Cys
        210                 215

<210> SEQ ID NO 73
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
                20                  25                  30

Trp Met Asn Trp Val Arg Gln Ser Pro Glu Lys Gly Leu Glu Trp Val
            35                  40                  45

Ala Glu Ile Arg Ser Lys Ser Ile Asn Ser Ala Thr His Tyr Ala Glu
50                  55                  60

```
Ser Val Lys Gly Arg Phe Thr Ile Ser Arg Asp Asp Ser Lys Ser Ala
 65                  70                  75                  80

Val Tyr Leu Gln Met Thr Asp Leu Arg Thr Glu Asp Thr Gly Val Tyr
             85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Thr Ala Pro Lys Val
            115                 120                 125

Tyr Pro Leu Ser Ser Ser Ser Gly Asp Lys Ser Ser Ser Thr Val Thr
        130                 135                 140

Leu Gly Cys Leu Val Ser Ser Tyr Met Pro Glu Pro Val Thr Val Thr
145                 150                 155                 160

Trp Asn Ser Gly Ala Leu Lys Ser Gly Val His Thr Phe Pro Ala Val
                165                 170                 175

Leu Gln Ser Ser Gly Leu Tyr Ser Leu Ser Ser Met Val Thr Val Pro
            180                 185                 190

Gly Ser Thr Ser Gly Gln Thr Phe Thr Cys Asn Val Ala His Pro Ala
            195                 200                 205

Ser Ser Thr Lys Val Asp Lys Ala Val Asp Pro Thr Cys Lys Pro Ser
        210                 215                 220

Pro Cys Asp Cys Cys Pro Pro Glu Leu Pro Gly Gly Pro Ser Val
225                 230                 235                 240

Phe Ile Phe Pro Pro Lys Pro Lys Asp Thr Leu Thr Ile Ser Gly Thr
                245                 250                 255

Pro Glu Val Thr Cys Val Val Asp Val Gly His Asp Asp Pro Glu
            260                 265                 270

Val Lys Phe Ser Trp Phe Val Asp Asp Val Glu Val Asn Thr Ala Thr
        275                 280                 285

Thr Lys Pro Arg Glu Glu Gln Phe Asn Ser Thr Tyr Arg Val Val Ser
        290                 295                 300

Ala Leu Arg Ile Gln His Gln Asp Trp Thr Gly Gly Lys Glu Phe Lys
305                 310                 315                 320

Cys Lys Val His Asn Glu Gly Leu Pro Ala Pro Ile Val Arg Thr Ile
                325                 330                 335

Ser Arg Thr Lys Gly Pro Ala Arg Glu Pro Gln Val Tyr Val Leu Ala
            340                 345                 350

Pro Pro Gln Glu Glu Leu Ser Lys Ser Thr Val Ser Leu Thr Cys Met
            355                 360                 365

Val Thr Ser Phe Tyr Pro Asp Tyr Ile Ala Val Glu Trp Gln Arg Asn
        370                 375                 380

Gly Gln Pro Glu Ser Glu Asp Lys Tyr Gly Thr Thr Pro Pro Gln Leu
385                 390                 395                 400

Asp Ala Asp Ser Ser Tyr Phe Leu Tyr Ser Lys Leu Arg Val Asp Arg
                405                 410                 415

Asn Ser Trp Gln Glu Gly Asp Thr Tyr Thr Cys Val Val Met His Glu
            420                 425                 430

Ala Leu His Asn His Tyr Thr Gln Lys Ser Thr Ser Lys Ser Ala Gly
            435                 440                 445

Lys

<210> SEQ ID NO 74
<211> LENGTH: 215
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 74

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Ser Asp Ala Glu
            100                 105                 110

Pro Ser Val Phe Leu Phe Lys Pro Ser Asp Glu Gln Leu Lys Thr Gly
            115                 120                 125

Thr Val Ser Val Val Cys Leu Val Asn Asp Phe Tyr Pro Lys Asp Ile
130                 135                 140

Asn Val Lys Trp Lys Val Asp Gly Val Thr Gln Ser Ser Ser Asn Phe
145                 150                 155                 160

Gln Asn Ser Phe Thr Asp Gln Asp Ser Lys Lys Ser Thr Tyr Ser Leu
                165                 170                 175

Ser Ser Ile Leu Thr Leu Pro Ser Ser Glu Tyr Gln Ser His Asn Ala
            180                 185                 190

Tyr Thr Cys Glu Val Ser His Lys Ser Leu Thr Thr Ala Leu Val Lys
        195                 200                 205

Ser Phe Ser Lys Asn Glu Cys
    210                 215

<210> SEQ ID NO 75
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110
```

Gly Thr Thr Leu Thr Val Ser Ser Ala Ser Thr Thr Pro Pro Lys Val
            115                 120                 125

Tyr Pro Leu Thr Ser Cys Cys Gly Asp Thr Ser Ser Ser Ile Val Thr
        130                 135                 140

Leu Gly Cys Leu Val Ser Ser Tyr Met Pro Glu Pro Val Thr Val Thr
145                 150                 155                 160

Trp Asn Ser Gly Ala Leu Thr Ser Gly Val His Thr Phe Pro Ala Ile
                165                 170                 175

Leu Gln Ser Ser Gly Leu Tyr Ser Leu Ser Ser Val Val Thr Val Pro
            180                 185                 190

Ala Ser Thr Ser Gly Ala Gln Thr Phe Ile Cys Asn Val Ala His Pro
        195                 200                 205

Ala Ser Ser Thr Lys Val Asp Lys Arg Val Glu Pro Gly Cys Pro Asp
210                 215                 220

Pro Cys Lys His Cys Arg Cys Pro Pro Glu Leu Pro Gly Gly Pro
225                 230                 235                 240

Ser Val Phe Ile Phe Pro Pro Lys Pro Lys Asp Thr Leu Thr Ile Ser
                245                 250                 255

Gly Thr Pro Glu Val Thr Cys Val Val Val Asp Val Gly Gln Asp Asp
            260                 265                 270

Pro Glu Val Gln Phe Ser Trp Phe Val Asp Asn Val Glu Val Arg Thr
        275                 280                 285

Ala Arg Thr Lys Pro Arg Glu Glu Gln Phe Asn Ser Thr Phe Arg Val
290                 295                 300

Val Ser Ala Leu Pro Ile Gln His Gln Asp Trp Thr Gly Gly Lys Glu
305                 310                 315                 320

Phe Lys Cys Lys Val His Asn Glu Ala Leu Pro Ala Pro Ile Val Arg
                325                 330                 335

Thr Ile Ser Arg Thr Lys Gly Gln Ala Arg Glu Pro Gln Val Tyr Val
            340                 345                 350

Leu Ala Pro Pro Gln Glu Glu Leu Ser Lys Ser Thr Leu Ser Val Thr
        355                 360                 365

Cys Leu Val Thr Gly Phe Tyr Pro Asp Tyr Ile Ala Val Glu Trp Gln
370                 375                 380

Lys Asn Gly Gln Pro Glu Ser Glu Asp Lys Tyr Gly Thr Thr Thr Ser
385                 390                 395                 400

Gln Leu Asp Ala Asp Gly Ser Tyr Phe Leu Tyr Ser Arg Leu Arg Val
                405                 410                 415

Asp Lys Asn Ser Trp Gln Glu Gly Asp Thr Tyr Ala Cys Val Val Met
            420                 425                 430

His Glu Ala Leu His Asn His Tyr Thr Gln Lys Ser Ile Ser Lys Pro
        435                 440                 445

Pro Gly Lys
    450

<210> SEQ ID NO 76
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Leu Leu Thr Gln Ser Pro Ala Ile Leu Ser Val Ser Pro Gly

```
1               5                  10                 15
Glu Arg Val Ser Phe Ser Cys Arg Ala Ser Gln Phe Val Gly Ser Ser
                20                 25                 30
Ile His Trp Tyr Gln Gln Arg Thr Asn Gly Ser Pro Arg Leu Leu Ile
                35                 40                 45
Lys Tyr Ala Ser Glu Ser Met Ser Gly Ile Pro Ser Arg Phe Ser Gly
                50                 55                 60
Ser Gly Ser Gly Thr Asp Phe Thr Leu Ser Ile Asn Thr Val Glu Ser
65                 70                 75                 80
Glu Asp Ile Ala Asp Tyr Tyr Cys Gln Gln Ser His Ser Trp Pro Phe
                85                 90                 95
Thr Phe Gly Ser Gly Thr Asn Leu Glu Val Lys Arg Ser Asp Ala Gln
                100                105                110
Pro Ser Val Phe Leu Phe Lys Pro Ser Glu Glu Gln Leu Arg Thr Gly
                115                120                125
Thr Val Ser Val Val Cys Leu Val Asn Asp Phe Tyr Pro Lys Asp Ile
        130                135                140
Asn Val Lys Val Lys Val Asp Gly Val Thr Gln Asn Ser Asn Phe Gln
145                150                155                160
Asn Ser Phe Thr Asp Gln Asp Ser Lys Lys Ser Thr Tyr Ser Leu Ser
                165                170                175
Ser Thr Leu Thr Leu Ser Ser Ser Glu Tyr Gln Ser His Asn Ala Tyr
                180                185                190
Ala Cys Glu Val Ser His Lys Ser Leu Pro Thr Ala Leu Val Lys Ser
                195                200                205
Phe Asn Lys Asn Glu Cys
        210

<210> SEQ ID NO 77
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Lys Leu Glu Glu Ser Gly Gly Gly Leu Val Gln Pro Gly Gly
1               5                  10                 15
Ser Met Lys Leu Ser Cys Val Ala Ser Gly Phe Ile Phe Ser Asn His
                20                 25                 30
Trp Met Asn Trp Val Arg Gln Ser Pro Glu Lys Gly Leu Glu Trp Val
                35                 40                 45
Ala Glu Ile Arg Ser Lys Ser Ile Asn Ser Ala Thr His Tyr Ala Glu
                50                 55                 60
Ser Val Lys Gly Arg Phe Thr Ile Ser Arg Asp Asp Ser Lys Ser Ala
65                 70                 75                 80
Val Tyr Leu Gln Met Thr Asp Leu Arg Thr Glu Asp Thr Gly Val Tyr
                85                 90                 95
Tyr Cys Ser Arg Asn Tyr Tyr Gly Ser Thr Tyr Asp Tyr Trp Gly Gln
                100                105                110
Gly Thr Thr Leu Thr Val Ser Ser Ala Ser Thr Thr Pro Pro Lys Val
                115                120                125
Tyr Pro Leu Thr Ser Cys Cys Gly Asp Thr Ser Ser Ser Ile Val Thr
        130                135                140
```

Leu Gly Cys Leu Val Ser Ser Tyr Met Pro Glu Pro Val Thr Val Thr
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Met Val Thr Val Pro
            180                 185                 190

Ala Ser Thr Ser Gly Ala Gln Thr Phe Ile Cys Asn Val Ala His Pro
        195                 200                 205

Ala Ser Ser Thr Lys Val Asp Lys Arg Val Glu Pro Gly Cys Lys Pro
210                 215                 220

Ser Pro Cys Asp Cys Cys Pro Pro Glu Leu Pro Gly Gly Pro Ser
225                 230                 235                 240

Val Phe Ile Phe Pro Pro Lys Pro Lys Asp Thr Leu Thr Ile Ser Gly
                245                 250                 255

Thr Pro Glu Val Thr Cys Val Val Asp Val Gly His Asp Asp Pro
            260                 265                 270

Glu Val Lys Phe Ser Trp Phe Val Asp Asp Val Glu Val Asn Thr Ala
        275                 280                 285

Thr Thr Lys Pro Arg Glu Glu Gln Phe Asn Ser Thr Tyr Arg Val Val
290                 295                 300

Ser Ala Leu Arg Ile Gln His Gln Asp Trp Thr Gly Gly Lys Glu Phe
305                 310                 315                 320

Lys Cys Lys Val His Asn Glu Gly Leu Pro Ala Pro Ile Val Arg Thr
                325                 330                 335

Ile Ser Arg Thr Lys Gly Pro Ala Arg Glu Pro Gln Val Tyr Val Leu
            340                 345                 350

Ala Pro Pro Gln Glu Glu Leu Ser Lys Ser Thr Val Ser Leu Thr Cys
        355                 360                 365

Met Val Thr Ser Phe Tyr Pro Asp Tyr Ile Ala Val Glu Trp Gln Arg
370                 375                 380

Asn Gly Gln Pro Glu Ser Glu Asp Lys Tyr Gly Thr Thr Pro Pro Gln
385                 390                 395                 400

Leu Asp Ala Asp Ser Ser Tyr Phe Leu Tyr Ser Lys Leu Arg Val Asp
                405                 410                 415

Arg Asn Ser Trp Gln Glu Gly Asp Thr Tyr Thr Cys Val Val Met His
            420                 425                 430

Glu Ala Leu His Asn His Tyr Thr Gln Lys Ser Thr Ser Lys Ser Ala
        435                 440                 445

Gly Lys
450

<210> SEQ ID NO 78
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

```
Lys Tyr Ala Ser Glu Ser Met Ser Gly Ile Pro Ser Arg Phe Ser Gly
         50                  55                  60

Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys Gly Gln Pro Lys Ser
            100                 105                 110

Ala Pro Ser Val Thr Leu Phe Pro Pro Ser Thr Glu Glu Leu Asn Ala
            115                 120                 125

Asn Lys Ala Thr Val Val Cys Leu Ile Ser Asp Phe Tyr Pro Gly Ser
130                 135                 140

Val Thr Val Val Trp Lys Ala Asp Gly Ser Thr Ile Asn Gln Asn Val
145                 150                 155                 160

Lys Thr Thr Gln Ala Ser Lys Gln Ser Asn Ser Lys Tyr Ala Ala Ser
                165                 170                 175

Ser Tyr Leu Thr Leu Thr Gly Ser Glu Trp Lys Ser Lys Ser Ser Tyr
            180                 185                 190

Ser Cys Glu Val Thr His Glu Gly Ser Thr Val Lys Lys Thr Val Lys
            195                 200                 205

Pro Ser Glu Cys
    210
```

<210> SEQ ID NO 79
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

```
Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Ile Phe Ser Asn His
             20                  25                  30

Trp Met Asn Trp Val Arg Gln Ser Pro Glu Lys Gly Leu Glu Trp Val
         35                  40                  45

Ala Glu Ile Arg Ser Lys Ser Ile Asn Ser Ala Thr His Tyr Ala Glu
     50                  55                  60

Ser Val Lys Gly Arg Phe Thr Ile Ser Arg Asp Asp Ser Lys Ser Ala
 65                  70                  75                  80

Val Tyr Leu Gln Met Thr Asp Leu Arg Thr Glu Asp Thr Gly Val Tyr
                 85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Gly Ser Phe Lys Ala Pro Ser Val
            115                 120                 125

Phe Pro Leu Ala Pro Cys Cys Gly Asp Thr Pro Ser Ser Thr Val Thr
130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                165                 170                 175

Arg Gln Ser Ser Gly Leu Tyr Ser Leu Ser Ser Val Val Ser Val Thr
```

```
                180                 185                 190
Ser Ser Ser Gln Pro Val Thr Cys Asn Val Ala His Pro Ala Thr Asn
            195                 200                 205

Thr Lys Val Asp Lys Thr Val Ala Pro Ser Thr Cys Ser Lys Pro Thr
        210                 215                 220

Cys Pro Pro Glu Leu Leu Gly Gly Pro Ser Val Phe Ile Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Asp Asp Pro Glu Val Gln Phe Thr
            260                 265                 270

Trp Tyr Ile Asn Asn Glu Gln Val Arg Thr Ala Arg Pro Pro Leu Arg
        275                 280                 285

Glu Gln Gln Phe Asn Ser Thr Ile Arg Val Val Ser Thr Leu Pro Ile
    290                 295                 300

Ala His Gln Asp Trp Leu Arg Gly Lys Glu Phe Lys Cys Lys Val His
305                 310                 315                 320

Asn Lys Ala Leu Pro Ala Pro Ile Glu Lys Thr Ile Ser Lys Ala Arg
                325                 330                 335

Gly Gln Pro Leu Glu Pro Lys Val Tyr Thr Met Gly Pro Pro Arg Glu
            340                 345                 350

Glu Leu Ser Ser Arg Ser Val Ser Leu Thr Cys Met Ile Asn Gly Phe
        355                 360                 365

Tyr Pro Ser Asp Ile Ser Val Glu Trp Glu Lys Asn Gly Lys Ala Glu
    370                 375                 380

Asp Asn Tyr Lys Thr Thr Pro Ala Val Leu Asp Ser Asp Gly Ser Tyr
385                 390                 395                 400

Phe Leu Tyr Ser Lys Leu Ser Val Pro Thr Ser Glu Trp Gln Arg Gly
                405                 410                 415

Asp Val Phe Thr Cys Ser Val Met His Glu Ala Leu His Asn His Tyr
            420                 425                 430

Thr Gln Lys Ser Ile Ser Arg Ser Pro Gly Lys
        435                 440

<210> SEQ ID NO 80
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95
```

Thr Phe Gly Ser Gly Thr Asn Leu Glu Val Lys Gly Asp Pro Val Ala
            100                 105                 110

Pro Thr Val Leu Ile Phe Pro Pro Ala Ala Asp Gln Val Ala Thr Gly
        115                 120                 125

Thr Val Thr Ile Val Cys Val Ala Asn Lys Tyr Phe Pro Asp Val Thr
    130                 135                 140

Val Thr Trp Glu Val Asp Gly Thr Thr Gln Thr Thr Gly Ile Glu Asn
145                 150                 155                 160

Ser Lys Thr Pro Gln Asp Ser Ala Asp Cys Thr Tyr Asn Leu Ser Ser
                165                 170                 175

Thr Leu Thr Leu Thr Ser Thr Gln Tyr Asn Ser His Lys Glu Tyr Thr
            180                 185                 190

Cys Lys Val Thr Gln Gly Thr Thr Ser Val Val Gln Ser Phe Asn Arg
        195                 200                 205

Gly Asp Cys
    210

<210> SEQ ID NO 81
<211> LENGTH: 57
<212> TYPE: PRT
<213> ORGANISM: Homo sapiens

<400> SEQUENCE: 81

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Val Ser Asn
        35                  40                  45

Lys Ala Leu Pro Ala Pro Ile Glu Lys
    50                  55

<210> SEQ ID NO 82
<211> LENGTH: 57
<212> TYPE: PRT
<213> ORGANISM: Bos taurus

<400> SEQUENCE: 82

Cys Asp Cys Cys Pro Pro Pro Glu Leu Pro Gly Gly Pro Ser Val Phe
1               5                   10                  15

Ile Phe Pro Pro Lys Pro Lys Asp Thr Leu Thr Ile Ser Gly Thr Pro
            20                  25                  30

Glu Val Thr Cys Val Val Val Asp Val Gly His Asp Asp Val His Asn
        35                  40                  45

Glu Gly Leu Pro Ala Pro Ile Val Arg
    50                  55

<210> SEQ ID NO 83
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Cys Asp Cys Cys Pro Pro Pro Glu Leu Leu Gly Gly Pro Ser Val Phe
1               5                   10                  15

Ile Phe Pro Pro Lys Pro Lys Asp Thr Leu Thr Ile Ser Gly Thr Pro

```
                20                  25                  30

Glu Val Thr Cys Val Val Val Asp Val Ser His Asp Asp Val His Asn
            35                  40                  45

Glu Ala Leu Pro Ala Pro Ile Val Arg
        50                  55

<210> SEQ ID NO 84
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Val Asp Lys Ala Val Thr Ala Arg Arg Pro Val Pro Thr Thr Pro Lys
1               5                   10                  15

Thr Thr Ile Pro Pro Gly Lys Pro Thr Thr Pro Lys Ser Glu Val Glu
            20                  25                  30

Lys Thr Pro Cys Gln Cys Ser Lys Cys Pro Glu Pro Leu Gly Gly Leu
        35                  40                  45

Ser Val Phe
    50

<210> SEQ ID NO 85
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Val Asp Lys Ala Val Asp Pro Arg Cys Lys Pro Ser Pro Cys Asp Cys
1               5                   10                  15

Cys Pro Pro Pro Glu Leu Pro Gly Gly Pro Ser Val Phe
            20                  25

<210> SEQ ID NO 86
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Val Asp Lys Ala Val Thr Ala Arg Arg Pro Val Pro Thr Thr Pro Lys
1               5                   10                  15

Thr Thr Ile Pro Pro Gly Lys Pro Thr Thr Pro Lys Ser Glu Val Glu
            20                  25                  30

Pro Arg Cys Lys Pro Ser Pro Cys Asp Cys Cys Pro Pro Pro Glu Leu
        35                  40                  45

Pro Gly Gly Pro Ser Val Phe
    50                  55

<210> SEQ ID NO 87
<211> LENGTH: 26
<212> TYPE: PRT
<213> ORGANISM: Bos taurus

<400> SEQUENCE: 87
```

```
Ala Val Asp Pro Thr Cys Lys Pro Ser Pro Cys Asp Cys Cys Pro Pro
1               5                   10                  15

Pro Glu Leu Pro Gly Gly Pro Ser Val Phe
            20                  25
```

<210> SEQ ID NO 88
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

```
Ala Val Asp Pro Thr Cys Lys Pro Ser Pro Cys Asp Cys Cys Val Arg
1               5                   10                  15

Glu Pro Ser Val Phe
            20
```

<210> SEQ ID NO 89
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

```
Ala Val Asp Pro Thr Cys Lys Pro Ser Pro Cys Asp Cys Cys Pro Pro
1               5                   10                  15

Pro Pro Pro Pro Pro Pro Pro Ser Val Phe
            20                  25
```

<210> SEQ ID NO 90
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Ala Val Asp Pro Thr Cys Lys Pro Ser Pro Cys Asp Cys Cys Pro Pro
1               5                   10                  15

Pro Gly Ser Gly Ser Gly Pro Ser Val Phe
            20                  25
```

<210> SEQ ID NO 91
<211> LENGTH: 24
<212> TYPE: PRT
<213> ORGANISM: Bos taurus

<400> SEQUENCE: 91

```
Asp Lys Ala Val Asp Pro Arg Cys Lys Thr Thr Cys Asp Cys Cys Pro
1               5                   10                  15

Pro Pro Glu Leu Pro Gly Gly Pro
            20
```

<210> SEQ ID NO 92
<211> LENGTH: 28
<212> TYPE: PRT
<213> ORGANISM: Vicugna pacos

<400> SEQUENCE: 92

```
Val Asp Lys Arg Val Glu Pro His Gly Gly Cys Thr Cys Pro Gln Cys
1               5                   10                  15

Pro Ala Pro Glu Leu Pro Gly Gly Pro Ser Val Phe
            20                  25

<210> SEQ ID NO 93
<211> LENGTH: 28
<212> TYPE: PRT
<213> ORGANISM: Camelus dromedarius

<400> SEQUENCE: 93

Val Asp Lys Arg Val Glu Pro His Gly Gly Cys Thr Cys Pro Gln Cys
1               5                   10                  15

Pro Ala Pro Glu Leu Pro Gly Gly Pro Ser Val Phe
            20                  25

<210> SEQ ID NO 94
<211> LENGTH: 27
<212> TYPE: PRT
<213> ORGANISM: Oryctolagus cuniculus

<400> SEQUENCE: 94

Val Asp Lys Thr Val Ala Pro Ser Thr Cys Ser Lys Pro Thr Cys Pro
1               5                   10                  15

Pro Pro Glu Leu Leu Gly Gly Pro Ser Val Phe
            20                  25

<210> SEQ ID NO 95
<211> LENGTH: 53
<212> TYPE: PRT
<213> ORGANISM: Bos taurus

<400> SEQUENCE: 95

Val Thr Val Pro Gly Ser Thr Ser Gly Gln Thr Phe Thr Cys Asn Val
1               5                   10                  15

Ala His Pro Ala Ser Ser Thr Lys Val Asp Lys Ala Val Asp Pro Thr
            20                  25                  30

Cys Lys Pro Ser Pro Cys Asp Cys Cys Pro Pro Pro Glu Leu Pro Gly
        35                  40                  45

Gly Pro Ser Val Phe
    50

<210> SEQ ID NO 96
<211> LENGTH: 50
<212> TYPE: PRT
<213> ORGANISM: Bos taurus

<400> SEQUENCE: 96

Val Thr Val Pro Gly Ser Thr Ser Gly Gln Thr Phe Thr Cys Asn Val
1               5                   10                  15

Ala His Pro Ala Ser Ser Thr Lys Val Asp Lys Ala Val Gly Val Ser
            20                  25                  30

Ser Asp Cys Ser Lys Pro Asn Asn Gln His Cys Val Arg Glu Pro Ser
        35                  40                  45

Val Phe
    50

<210> SEQ ID NO 97
<211> LENGTH: 50
<212> TYPE: PRT
<213> ORGANISM: Bos taurus
```

```
<400> SEQUENCE: 97

Val Thr Val Pro Ala Ser Ser Gly Gln Thr Phe Thr Cys Asn Val
1               5                   10                  15

Ala His Pro Ala Ser Ser Thr Lys Val Asp Lys Ala Val Gly Val Ser
            20                  25                  30

Ile Asp Cys Ser Lys Cys His Asn Gln Pro Cys Val Arg Glu Pro Ser
        35                  40                  45

Val Phe
    50

<210> SEQ ID NO 98
<211> LENGTH: 53
<212> TYPE: PRT
<213> ORGANISM: Homo sapiens

<400> SEQUENCE: 98

Pro Ser Ser Ser Leu Gly Thr Gln Thr Tyr Ile Cys Asn Val Asn His
1               5                   10                  15

Lys Pro Ser Asn Thr Lys Val Asp Lys Lys Val Glu Pro Lys Ser Cys
            20                  25                  30

Asp Lys Thr His Thr Cys Pro Pro Cys Pro Ala Pro Glu Leu Leu Gly
        35                  40                  45

Gly Pro Ser Val Phe
    50

<210> SEQ ID NO 99
<211> LENGTH: 50
<212> TYPE: PRT
<213> ORGANISM: Bos taurus

<400> SEQUENCE: 99

Pro Gly Ser Thr Ser Gly Thr Gln Thr Phe Thr Cys Asn Val Ala His
1               5                   10                  15

Pro Ala Ser Ser Thr Lys Val Asp Lys Ala Val Asp Pro Arg Cys Lys
            20                  25                  30

Thr Thr Cys Asp Cys Cys Pro Pro Pro Glu Leu Pro Gly Gly Pro Ser
        35                  40                  45

Val Phe
    50

<210> SEQ ID NO 100
<211> LENGTH: 19
<212> TYPE: PRT
<213> ORGANISM: Bos taurus

<400> SEQUENCE: 100

Ser Pro Pro Ser Val Thr Leu Phe Pro Pro Ser Thr Glu Glu Leu Asn
1               5                   10                  15

Gly Asn Lys

<210> SEQ ID NO 101
<211> LENGTH: 15
<212> TYPE: PRT
<213> ORGANISM: Bos taurus

<400> SEQUENCE: 101

Tyr Ala Ala Ser Ser Tyr Leu Ser Leu Thr Ser Ser Asp Trp Lys
1               5                   10                  15
```

```
<210> SEQ ID NO 102
<211> LENGTH: 29
<212> TYPE: PRT
<213> ORGANISM: Bos taurus

<400> SEQUENCE: 102

Val Ser Ile Thr Cys Ser Gly Ser Ser Ser Asn Val Gly Asn Gly Tyr
1               5                   10                  15

Val Ser Trp Tyr Gln Leu Ile Pro Gly Ser Ala Pro Arg
            20                  25

<210> SEQ ID NO 103
<211> LENGTH: 16
<212> TYPE: PRT
<213> ORGANISM: Bos taurus

<400> SEQUENCE: 103

Gly Ser Tyr Ser Cys Glu Val Thr His Glu Gly Ser Thr Val Thr Lys
1               5                   10                  15

<210> SEQ ID NO 104
<211> LENGTH: 11
<212> TYPE: PRT
<213> ORGANISM: Bos taurus

<400> SEQUENCE: 104

Val Tyr Pro Leu Ser Ser Cys Cys Gly Asp Lys
1               5                   10

<210> SEQ ID NO 105
<211> LENGTH: 29
<212> TYPE: PRT
<213> ORGANISM: Bos taurus

<400> SEQUENCE: 105

Ser Ser Ser Thr Val Thr Leu Gly Cys Leu Val Ser Ser Tyr Met Pro
1               5                   10                  15

Glu Pro Val Thr Val Thr Trp Asn Ser Gly Ala Leu Lys
            20                  25

<210> SEQ ID NO 106
<211> LENGTH: 45
<212> TYPE: PRT
<213> ORGANISM: Bos taurus

<400> SEQUENCE: 106

Ser Gly Val His Thr Phe Pro Ala Val Leu Gln Ser Ser Gly Leu Tyr
1               5                   10                  15

Ser Leu Ser Ser Met Val Thr Val Pro Gly Ser Thr Ser Gly Gln Thr
            20                  25                  30

Phe Thr Cys Asn Val Ala His Pro Ala Ser Ser Thr Lys
        35                  40                  45

<210> SEQ ID NO 107
<211> LENGTH: 33
<212> TYPE: PRT
<213> ORGANISM: Bos taurus

<400> SEQUENCE: 107

Ala Val Asp Pro Thr Cys Lys Pro Ser Pro Cys Asp Cys Cys Pro Pro
1               5                   10                  15

Pro Glu Leu Pro Gly Gly Pro Ser Val Phe Ile Phe Pro Pro Lys Pro
```

```
            20                  25                  30
Lys

<210> SEQ ID NO 108
<211> LENGTH: 25
<212> TYPE: PRT
<213> ORGANISM: Bos taurus

<400> SEQUENCE: 108

Asp Thr Leu Thr Ile Ser Gly Thr Pro Glu Val Thr Cys Val Val Asp
1               5                   10                  15

Val Gly His Asp Asp Pro Glu Val Lys
            20                  25

<210> SEQ ID NO 109
<211> LENGTH: 18
<212> TYPE: PRT
<213> ORGANISM: Bos taurus

<400> SEQUENCE: 109

Phe Ser Trp Phe Val Asp Asp Val Glu Val Asn Thr Ala Thr Thr Lys
1               5                   10                  15

Pro Arg

<210> SEQ ID NO 110
<211> LENGTH: 12
<212> TYPE: PRT
<213> ORGANISM: Bos taurus

<400> SEQUENCE: 110

Val His Asn Glu Gly Leu Pro Ala Pro Ile Val Arg
1               5                   10

<210> SEQ ID NO 111
<211> LENGTH: 16
<212> TYPE: PRT
<213> ORGANISM: Bos taurus

<400> SEQUENCE: 111

Glu Pro Gln Val Tyr Val Leu Ala Pro Pro Gln Glu Glu Leu Ser Lys
1               5                   10                  15

<210> SEQ ID NO 112
<211> LENGTH: 23
<212> TYPE: PRT
<213> ORGANISM: Bos taurus

<400> SEQUENCE: 112

Ser Thr Val Ser Leu Thr Cys Met Val Thr Ser Phe Tyr Pro Asp Tyr
1               5                   10                  15

Ile Ala Val Glu Trp Gln Arg
            20

<210> SEQ ID NO 113
<211> LENGTH: 28
<212> TYPE: PRT
<213> ORGANISM: Bos taurus

<400> SEQUENCE: 113

Asn Gly Gln Pro Glu Ser Glu Asp Lys Tyr Gly Thr Thr Pro Pro Gln
1               5                   10                  15

Leu Asp Ala Asp Ser Ser Tyr Phe Leu Tyr Ser Lys
```

```
<210> SEQ ID NO 114
<211> LENGTH: 16
<212> TYPE: PRT
<213> ORGANISM: Bos taurus

<400> SEQUENCE: 114

Glu Pro Gln Val Tyr Val Leu Asp Pro Pro Lys Glu Glu Leu Ser Lys
1               5                   10                  15

<210> SEQ ID NO 115
<211> LENGTH: 10
<212> TYPE: PRT
<213> ORGANISM: Bos taurus

<400> SEQUENCE: 115

Thr Thr Pro Pro Gln Leu Asp Ala Asp Arg
1               5                   10

<210> SEQ ID NO 116
<211> LENGTH: 12
<212> TYPE: PRT
<213> ORGANISM: Bos taurus

<400> SEQUENCE: 116

Glu Pro Ser Val Phe Ile Phe Pro Pro Lys Pro Lys
1               5                   10

<210> SEQ ID NO 117
<211> LENGTH: 16
<212> TYPE: PRT
<213> ORGANISM: Bos taurus

<400> SEQUENCE: 117

Val Val Ser Ala Leu Pro Ile Gln His Gln Asp Trp Thr Gly Gly Lys
1               5                   10                  15

<210> SEQ ID NO 118
<211> LENGTH: 20
<212> TYPE: PRT
<213> ORGANISM: Bos taurus

<400> SEQUENCE: 118

Gly Asp Thr Tyr Thr Cys Val Val Met His Glu Ala Leu His Asn His
1               5                   10                  15

Tyr Met Gln Lys
            20
```